(12) United States Patent
Smolinski et al.

(10) Patent No.: US 10,899,747 B2
(45) Date of Patent: Jan. 26, 2021

(54) BIARYL PIPERIDINE AMIDE COMPOUNDS AND METHODS OF USE THEREOF

(71) Applicant: Athenex, Inc., Buffalo, NY (US)

(72) Inventors: Michael P. Smolinski, Amherst, NY (US); Sameer Urgaonkar, Amherst, NY (US); James Lindsay Clements, East Aurora, NY (US); David G. Hangauer, Jr., Lancaster, NY (US)

(73) Assignee: Athenex, Inc., Buffalo, NY (US)

( * ) Notice: Subject to any disclaimer, the term of this patent is extended or adjusted under 35 U.S.C. 154(b) by 0 days.

(21) Appl. No.: 16/567,300

(22) Filed: Sep. 11, 2019

(65) Prior Publication Data

US 2020/0071305 A1    Mar. 5, 2020

Related U.S. Application Data

(62) Division of application No. 15/921,890, filed on Mar. 15, 2018, now Pat. No. 10,450,303.

(60) Provisional application No. 62/471,496, filed on Mar. 15, 2017.

(51) Int. Cl.
| | | |
|---|---|---|
| *C07D 403/14* | (2006.01) | |
| *C07D 403/12* | (2006.01) | |
| *A61P 37/08* | (2006.01) | |
| *A61P 37/02* | (2006.01) | |
| *C07D 211/40* | (2006.01) | |

(52) U.S. Cl.
CPC ............ *C07D 403/14* (2013.01); *A61P 37/02* (2018.01); *A61P 37/08* (2018.01); *C07D 403/12* (2013.01); *C07D 211/40* (2013.01)

(58) Field of Classification Search
CPC .................................................. C07D 403/14
See application file for complete search history.

(56) References Cited

U.S. PATENT DOCUMENTS

| 5,112,859 A | 5/1992 | Commons et al. |
|---|---|---|
| 10,450,303 B2 | 10/2019 | Smolinski et al. |
| 2002/0034728 A1 | 3/2002 | Normant et al. |

FOREIGN PATENT DOCUMENTS

| WO | WO 01-64676 A2 | 9/2001 |
|---|---|---|
| WO | WO 2008-134547 A1 | 11/2008 |
| WO | WO 2009-078932 A1 | 6/2009 |

OTHER PUBLICATIONS

Banker et al. eds. "Modern Pharmaceutics", 3$^{rd}$ edition, 1997, 3 pages.
Funaba et al. "Degranulation in RBL-2H3 cells: regulation by calmodulin pathway", Cell Biology International, vol. 27, p. 879-885, 2003.
Liou J. et al. "STIM Is a Ca2+ Sensor Essential for Ca$^{2+}$-Store-Depletion-Triggered Ca$^{2+}$Influx", Current Biology, vol. 15, p. 1235-1241, 2005.
Partiseti et al. "The Calcium Current Activated by T Cell Receptor and Store Depiction in Human Lymphocytes Is Absent in a Primary Immunodeficiency", The Journal of Biological Chemistry, vol. 269, No. 51, p. 32327-32335, 1994.
Trevillyan et al. "Potent Inhibition of NFAT Activation and T Cell Cytokine Production by Novel Low Molecular Weight Pyrazole Compounds", The Journal of Biological Chemistry, vol. 276, No. 51, p. 48118-48126, 2001.
Vippagunta et al. "Crystalline Solids", Advanced Drug Delivery Reviews, 2001, vol. 48, p. 3-26.
Westaway, S. M. et al., "The discovery of biaryl carboxamides as novel small molecule agonists of the motilin receptor", Bioorganic & Medicinal Chemistry Letters, 2008, vol. 18, No. 24, p. 6429-6436.

*Primary Examiner* — Paul V Ward
(74) *Attorney, Agent, or Firm* — Cooley LLP; Heidi A. Erlacher; Chen Chen

(57) ABSTRACT

The present application is directed to biaryl piperidine amide compounds, or pharmaceutically acceptable salts, solvates, and prodrugs thereof, and methods of use thereof.

22 Claims, 1 Drawing Sheet

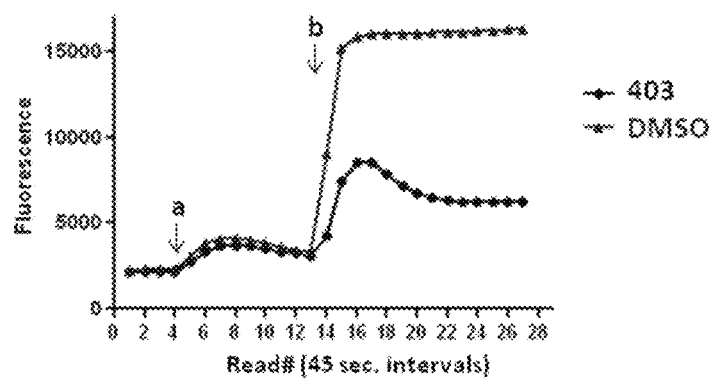

BIARYL PIPERIDINE AMIDE COMPOUNDS AND METHODS OF USE THEREOF

RELATED APPLICATION

This application is a division of U.S. application Ser. No. 15/921,890, filed on Mar. 15, 2018, which claims priority to, and the benefit of, U.S. Provisional Application No. 62/471, 496, filed on Mar. 15, 2017, the entire contents of each of which are incorporated herein by reference.

BACKGROUND

Calcium ($Ca^{2+}$) plays an important role in the transduction of signals into and within cells. Many cell types depend on the generation of calcium signals to regulate numerous cell functions or to trigger specific responses. For example, cytosolic calcium signals control cellular functions such as short-term responses (e.g. contraction and secretion) and long term regulation of cell growth and proliferation. These signals generally involve some combination of release of calcium from intracellular stores, such as the endoplasmic reticulum (ER), and influx of calcium across the plasma membrane. For example, cell activation may begin with a ligand binding to a surface membrane receptor, coupled to phospholipase C (PLC) and/or a G-protein regulated mechanism. PLC activation leads to the production of inositol 1,4,5-triphosphate ($IP_3$), which may activate the $IP_3$ receptor causing release of calcium from the ER. The decrease in ER calcium may signal the plasma membrane store-operated calcium (SOC) channels.

Store-operated calcium (SOC) influx is a process that controls many diverse functions including e.g., refilling of intracellular calcium stores, activation of enzymatic activity, gene transcription, cell proliferation, and release of cytokines. In certain nonexcitable cells (e.g., blood cells, immune cells, hematopoietic cells, T lymphocytes and mast cells), SOC influx occurs through calcium release-activated calcium (CRAC) channels, a type of SOC channel.

Since calcium plays an important role in cell function, differentiation and survival, dysregulation of calcium in cells can have adverse effects on cell structure and function. Numerous diseases (e.g., immune disorders, inflammatory disorders, and allergic disorders) are linked with calcium dysregulation. Accordingly, new compounds and methods for modulating calcium in cells are needed to treat or prevent these diseases. The present application addresses these needs.

SUMMARY

In one aspect, the present application relates to a compound of formula (I):

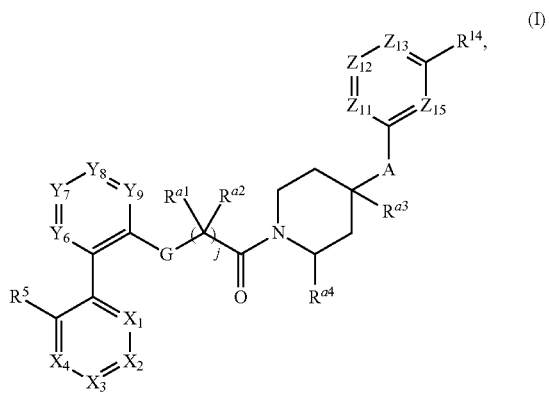

(I)

or a pharmaceutically acceptable salt, solvate, or prodrug thereof, wherein $X_1$ is selected from $CR^1$, N, and N—O;
$X_2$ is selected from $CR^2$, N, and N—O;
$X_3$ is selected from $CR^3$, N, and N—O;
$X_4$ is selected from $CR^4$, N, and N—O;
$R^1$, $R^2$, $R^3$, $R^4$, and $R^5$ are independently selected from hydrogen; halogen; $C_1$-$C_6$ alkyl; $C_2$-$C_6$ alkenyl; $C_2$-$C_6$ alkynyl; $C_1$-$C_6$ haloalkyl; ($C_1$-$C_6$ alkyl)-$OR^{20}$; OH; O($C_1$-$C_6$ alkyl); $OCF_3$; $OCF_2H$; $OCFH_2$; CN; $N_3$; $NO_2$; $NH_2$; NH($C_1$-$C_6$ alkyl); N($C_1$-$C_6$ alkyl)$_2$; $NR^{20}C(O)R^{20}$; $C(O)NR^{20}R^{20}$; $COR^{20}$; CO($C_1$-$C_6$ alkyl); $S(O)_pR^{20}$; $NR^{20}S(O)_pR^{20}$; $S(O)_pNR^{20}R^{20}$; $SR^{20}$; $SCF_3$; $COOR^{20}$; $OR^{20}$; ($C_1$-$C_6$ alkyl)-$R^{20}$; 3-7 membered saturated, partially saturated, or unsaturated carbocycle; and 3-7 membered saturated, partially saturated, or unsaturated heterocycle containing one or more heteroatoms selected from the group consisting of nitrogen, oxygen, and sulfur;

alternatively, two substituents selected from $R^1$, $R^2$, $R^3$, $R^4$, and $R^5$ on two adjacent carbon atoms taken together form a 3-7 membered saturated, partially saturated, or unsaturated carbocycle; or a 3-7 membered saturated, partially saturated, or unsaturated heterocycle containing one or more heteroatoms selected from the group consisting of nitrogen, oxygen, and sulfur; where the carbocycle or heterocycle is optionally substituted with one or more $R^{20}$;

$R^{20}$ is independently selected from hydrogen; $C_1$-$C_6$ alkyl; CN; ($C_1$-$C_6$ alkyl)-$NR^{21}R^{21}$; ($C_1$-$C_6$ alkyl)-$OR^{21}$; 3-7 membered saturated, partially saturated, or unsaturated carbocycle; 3-7 membered saturated, partially saturated, or unsaturated heterocycle containing one or more heteroatoms selected from the group consisting of nitrogen, oxygen, and sulfur; ($C_1$-$C_6$ alkyl)-3-7 membered saturated, partially saturated, or unsaturated carbocycle; ($C_1$-$C_6$ alkyl)-3-7 membered saturated, partially saturated, or unsaturated heterocycle containing one or more heteroatoms selected from the group consisting of nitrogen, oxygen, and sulfur; where the carbocycle or heterocycle is optionally substituted with one or more $R^{21}$;

or two $R^{20}$ taken together with the carbon atom to which they are attached form a carbonyl;

$R^{21}$ is independently selected from hydrogen, $C_1$-$C_6$ alkyl, $C_2$-$C_6$ alkenyl, $C_2$-$C_6$ alkynyl; OH, O—($C_1$-$C_6$ alkyl), O—($C_2$-$C_6$ alkenyl), and O—($C_2$-$C_6$ alkynyl);

$Y_6$ is independently selected from $CR^6$, N, and N—O;
$Y_7$ is independently selected from $CR^7$, N, and N—O;
$Y_8$ is independently selected from $CR^8$, N, and N—O;
$Y_9$ is independently selected from $CR^9$, N, and N—O;
$R^6$, $R^7$, $R^8$, and $R^9$ are independently selected from hydrogen; halogen; $C_1$-$C_6$ alkyl; $C_2$-$C_6$ alkenyl; $C_2$-$C_6$ alkynyl; $C_1$-$C_6$ haloalkyl; ($C_1$-$C_6$ alkyl)-$R^{30}$; ($C_1$-$C_6$ alkyl)-$OR^{30}$; OH; O($C_1$-$C_6$ alkyl); $OCF_3$; $OCF_2H$; $OCFH_2$; CN; $N_3$; $NO_2$; $NH_2$; NH($C_1$-$C_6$ alkyl); N($C_1$-$C_6$ alkyl)$_2$; $NR^{30}C(O)R^{30}$; $C(O)NR^{30}R^{30}$; $COR^{30}$; CO($C_1$-$C_6$ alkyl); $S(O)_qR^{30}$; $NR^{30}S(O)_qR^{30}$; $S(O)_qNR^{30}R^{30}$; $SR^{30}$; $SCF_3$; and $COOR^{30}$;

alternatively, two substituents selected from $R^6$, $R^7$, $R^8$, and $R^9$ on two adjacent carbon atoms taken together form a 3-7 membered saturated, partially saturated, or unsaturated carbocycle; or a 3-7 membered saturated, partially saturated, or unsaturated heterocycle containing one or more heteroatoms selected from the group consisting of nitrogen, oxygen, and sulfur; where the carbocycle or heterocycle is optionally substituted with one or more $R^{30}$;

$R^{30}$ is independently selected from hydrogen; $C_1$-$C_6$ alkyl; ($C_1$-$C_6$ alkyl)-$R^{31}$; ($C_1$-$C_6$ alkyl)-$OR^{31}$; ($C_1$-$C_6$ alkyl)-$NR^{31}R^{31}$; 3-7 membered saturated, partially saturated, or unsaturated carbocycle; and 3-7 membered saturated, partially saturated, or unsaturated heterocycle containing one or more heteroatoms selected from the group consisting of nitrogen, oxygen, and sulfur; where the carbocycle or heterocycle is optionally substituted with one or more $R^{31}$;

$R^{31}$ is independently selected from hydrogen; $C_1$-$C_6$ alkyl; 3-7 membered saturated, partially saturated, or unsaturated carbocycle; and 3-7 membered saturated, partially saturated, or unsaturated heterocycle containing one or more heteroatoms selected from the group consisting of nitrogen, oxygen, and sulfur;

G is selected from a bond, O, S, S(O), S(O)$_2$, CH$_2$, CH$_2$CH$_2$, and CHCH;

alternatively, G and $R^{a1}$ together form a 3-7 membered saturated, partially saturated, or unsaturated carbocycle; or a 3-7 membered saturated, partially saturated, or unsaturated heterocycle containing one or more heteroatoms selected from the group consisting of nitrogen, oxygen, and sulfur;

A is selected from a bond, CH$_2$, CH$_2$CH$_2$, CH$_2$CH$_2$CH$_2$, CHCH, and CC;

$R^{a1}$ and $R^{a2}$ are independently selected from hydrogen; halogen; $C_1$-$C_6$ alkyl; $C_2$-$C_6$ alkenyl; $C_2$-$C_6$ alkynyl; $C_1$-$C_6$ haloalkyl; OH; O($C_1$-$C_6$ alkyl); ($C_1$-$C_6$ alkyl)-OH; ($C_1$-$C_6$ alkyl)-O($C_1$-$C_6$ alkyl); ($C_1$-$C_6$ alkyl)-3-7 membered saturated, partially saturated, or unsaturated carbocycle; and ($C_1$-$C_6$ alkyl)-3-7 membered saturated, partially saturated, or unsaturated heterocycle containing one or more heteroatoms selected from the group consisting of nitrogen, oxygen, and sulfur;

$R^{a3}$ is selected from hydrogen, halogen, OH, O($C_1$-$C_6$ alkyl), and $C_1$-$C_6$ alkyl;

$R^{a4}$ is selected from hydrogen, halogen, and $C_1$-$C_6$ alkyl;

$Z_{11}$ is selected from $CR^{11}$, N, and N—O;
$Z_{12}$ is selected from $CR^{12}$, N, and N—O;
$Z_{13}$ is selected from $CR^{13}$, N, and N—O;
$Z_{15}$ is selected from $CR^{15}$, N, and N—O;

$R^{11}$, $R^{12}$, $R^{13}$, $R^{14}$, and $R^{15}$ are independently selected from hydrogen, halogen, $C_1$-$C_6$ alkyl, $C_2$-$C_6$ alkenyl, $C_2$-$C_6$ alkynyl, $C_1$-$C_6$ haloalkyl, ($C_1$-$C_6$ alkyl)-OR$^{40}$, OH, O($C_1$-$C_6$ alkyl), OCF$_3$, OCF$_2$H, OCFH$_2$, CN, N$_3$, NO$_2$, NH$_2$, NH($C_1$-$C_6$ alkyl), N($C_1$-$C_6$ alkyl)$_2$, NR$^{40}$C(O)R$^{40}$, C(O)NR$^{40}$R$^{40}$, COH, CO($C_1$-$C_6$ alkyl), S(O)$_t$R$^{40}$, NR$^{40}$S(O)$_t$R$^{40}$, S(O)$_t$NR$^{40}$R$^{40}$, SR$^{40}$, SCF$_3$, COOR$^{40}$, COR$^{40}$, and OR$^{40}$; 3-7 membered saturated, partially saturated, or unsaturated carbocycle; and 3-7 membered saturated, partially saturated, or unsaturated heterocycle containing one or more heteroatoms selected from the group consisting of nitrogen, oxygen, and sulfur;

alternatively, two substituents selected from $R^{11}$, $R^{12}$, $R^{13}$, $R^{14}$, and $R^{15}$ on two adjacent carbon atoms taken together form a 3-7 membered saturated, partially saturated, or unsaturated carbocycle; or a 3-7 membered saturated, partially saturated, or unsaturated heterocycle containing one or more heteroatoms selected from the group consisting of nitrogen, oxygen, and sulfur; where the carbocycle or heterocycle is optionally substituted with one or more $R^{40}$;

$R^{40}$ is independently selected from hydrogen; halogen; $C_1$-$C_6$ alkyl; $C_2$-$C_6$ alkenyl, $C_2$-$C_6$ alkynyl; 3-7 membered saturated, partially saturated, or unsaturated carbocycle; 3-7 membered saturated, partially saturated, or unsaturated heterocycle containing one or more heteroatoms selected from the group consisting of nitrogen, oxygen, and sulfur; ($C_1$-$C_6$ alkyl)-3-7 membered saturated, partially saturated, or unsaturated carbocycle; and ($C_1$-$C_6$ alkyl)-3-7 membered saturated, partially saturated, or unsaturated heterocycle containing one or more heteroatoms selected from the group consisting of nitrogen, oxygen, and sulfur;

or two $R^{40}$ taken together with the carbon atom to which they are attached form a carbonyl;

j is 0, 1, or 2;

p is 0, 1, or 2;

q is 0, 1, or 2; and t is 0, 1, or 2.

In one aspect, the present application relates to a compound of formula (II):

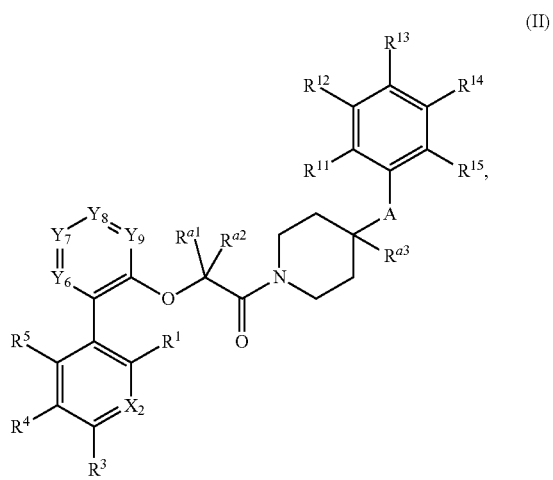

(II)

or a pharmaceutically acceptable salt, solvate, or prodrug thereof, where A, $X_2$, $Y_6$, $Y_7$, $Y_8$, $Y_9$, $R^1$, $R^3$, $R^4$, $R^5$, $R^{11}$, $R^{12}$, $R^{13}$, $R^{14}$, $R^{15}$, $R^{a1}$, $R^{a2}$, and $R^{a3}$ are as described herein.

In one aspect the present application relates to a compound of formula (III):

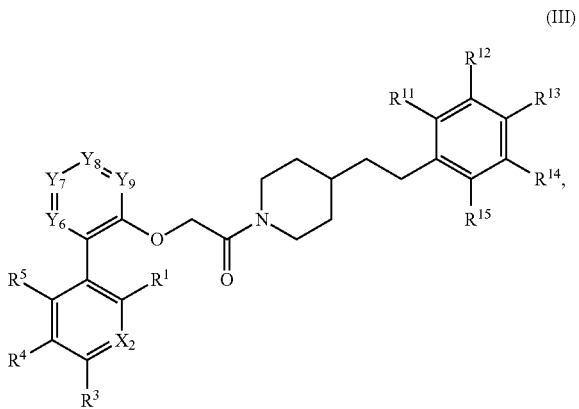

(III)

or a pharmaceutically acceptable salt, solvate, or prodrug thereof, where $X_2$, $Y_6$, $Y_7$, $Y_8$, $Y_9$, $R^1$, $R^3$, $R^4$, $R^5$, $R^{11}$, $R^{12}$, $R^{13}$, $R^{14}$ and $R^{15}$ are as described herein.

In one aspect, the present application relates to a compound of a formula selected from:

(IVa)

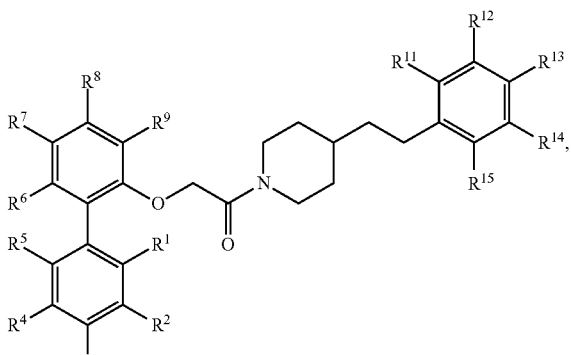

(IVb)

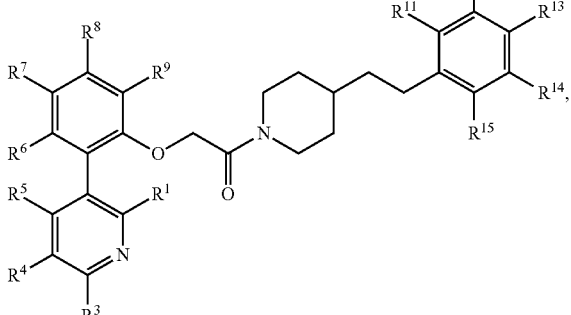

(IVc)

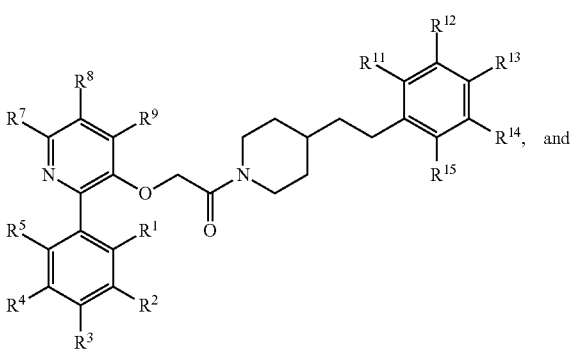

(IVd)

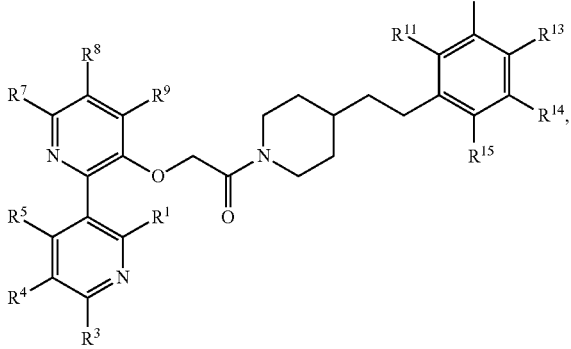

or a pharmaceutically acceptable salt, solvate, or prodrug thereof, where $R^1$, $R^3$, $R^4$, $R^5$, $R^6$, $R^7$, $R^8$, $R^9$, $R^{11}$, $R^{12}$, $R^{13}$, $R^{14}$ and $R^{15}$ are as described herein.

In one aspect, the present application relates to a compound of formula (V):

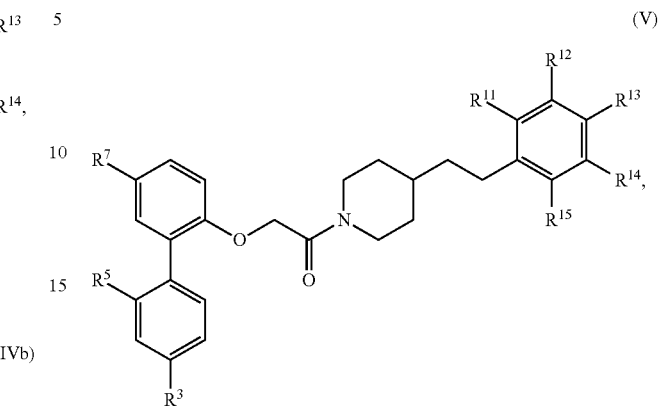

(V)

or a pharmaceutically acceptable salt, solvate, or prodrug thereof, where $R^3$, $R^5$, $R^7$, $R^{11}$, $R^{12}$, $R^{13}$, $R^{14}$, and $R^{15}$ are as described herein.

In one aspect, the present application relates to a compound of any one of formulae I, II, III, IVa, IVb, IVc, IVd, or V, wherein $R^3$ is selected from hydrogen, halogen, $C_1$-$C_6$ alkyl, $C_1$-$C_6$ haloalkyl, OH, O($C_1$-$C_6$ alkyl), $OCF_3$, $OCF_2H$, $OCFH_2$, CN, $N_3$, $NO_2$, $NH_2$, NH($C_1$-$C_6$ alkyl), and N($C_1$-$C_6$ alkyl)$_2$. In another aspect, $R^3$ is selected from hydrogen, halogen, and CN. In one aspect, $R^3$ is hydrogen. In one aspect, $R^3$ is halogen. In one aspect, $R^3$ is fluoro or chloro. In one aspect, $R^3$ is CN.

In one aspect, the present application relates to a compound of any one of formulae I, II, III, IVa, IVb, IVc, IVd, or V, wherein $R^5$ is selected from hydrogen, halogen, $C_1$-$C_6$ alkyl, $C_1$-$C_6$ haloalkyl, OH, O($C_1$-$C_6$ alkyl), $OCF_3$, $OCF_2H$, $OCFH_2$, CN, $NH_2$, NH($C_1$-$C_6$ alkyl), and N($C_1$-$C_6$ alkyl)$_2$. In one aspect, $R^5$ is selected from hydrogen, halogen, $C_1$-$C_6$ alkyl, OH, and O($C_1$-$C_6$ alkyl). In one aspect, $R^5$ is hydrogen. In one aspect, $R^5$ is halogen. In one aspect, $R^5$ is fluoro. In one aspect, $R^5$ is OH. In one aspect, $R^5$ is $OCH_3$.

In one aspect, the present application relates to a compound of any one of formulae I, II, III, IVa, IVb, IVc, IVd, or V, wherein $R^7$ is selected from hydrogen, halogen, $C_1$-$C_6$ alkyl, $C_1$-$C_6$ haloalkyl, OH, O($C_1$-$C_6$ alkyl), $OCF_3$, $OCF_2H$, $OCFH_2$, CN, $NH_2$, NH($C_1$-$C_6$ alkyl), N($C_1$-$C_6$ alkyl)$_2$, $S(O)_q$$NR^{30}R^{30}$, $C(O)NR^{30}R^{30}$, $COR^{30}$, and $COOR^{30}$. In one aspect, $R^7$ is selected from hydrogen, halogen, $C_1$-$C_6$ alkyl, $C_1$-$C_6$ haloalkyl, OH, O($C_1$-$C_6$ alkyl), CN, $S(O)_q NR^{30}R^{30}$, $C(O)NR^{30}R^{30}$, $COR^{30}$, and $COOR^{30}$. In one aspect, $R^7$ is selected from hydrogen, $CF_3$, OH, CN, $S(O)_2NR^{30}R^{30}$, and $C(O)NR^{30}R^{30}$. In one aspect, $R^7$ is hydrogen.

In one aspect, the present application relates to a pharmaceutical composition comprising a compound of the application, or a pharmaceutically acceptable salt, solvate, or prodrug thereof, and a pharmaceutically acceptable excipient.

In one aspect, the present application relates to a method of preventing or treating an immune disorder, an inflammatory disorder, or an allergic disorder in a subject comprising administering to the subject an effective amount of a compound or composition of the application.

In one aspect, the immune disorder is selected from multiple sclerosis, myasthenia gravis, Guillain-Barre, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, psoriasis, dermatitis herpetiformis, pemphigus vulgaris, vitiligo, Crohn's disease, ulcerative colitis, primary biliary cirrhosis, autoimmune hepatitis, Type 1 diabetes mellitus, immune-mediated diabetes mellitus, Grave's disease, Hashimoto's thyroiditis, autoimmune oophoritis disorder of the adrenal gland, orchitis, autoimmune disorder of the adrenal gland, rheumatoid arthritis, systemic lupus erythematosus, scleroderma, polymyositis, dermatomyositis, ankylosing spondylitis, and Sjogren's syndrome.

In one aspect, the inflammatory disorder is selected from transplant rejection, skin graft rejection, arthritis, rheumatoid arthritis, osteoarthritis, bone diseases associated with increased bone resorption, inflammatory bowel disease, ileitis, ulcerative colitis, Barrett's syndrome, Crohn's disease, asthma, adult respiratory distress syndrome, chronic obstructive airway disease, corneal dystrophy, trachoma, onchocerciasis, uveitis, sympathetic ophthalmitis, endophthalmitis, gingivitis, periodontitis, tuberculosis, leprosy, uremic complications, glomerulonephritis, nephrosis, sclerodermatitis, psoriasis, eczema, chronic demyelinating diseases of the nervous system, multiple sclerosis, AIDS-related neurodegeneration, Alzheimer's disease, infectious meningitis, encephalomyelitis, Parkinson's disease, Huntington's disease, amyotrophic lateral sclerosis, viral encephalitis, autoimmune encephalitis, autoimmune disorders, immune-complex vasculitis, systemic lupus erythematosus (SLE), cardiomyopathy, ischemic heart disease, hypercholesterolemia, atherosclerosis, preeclampsia, chronic liver failure, brain trauma, spinal cord trauma, and cancer.

In one aspect, the allergic disorder is selected from allergic rhinitis, sinusitis, rhinosinusitis, chronic otitis media, recurrent otitis media, drug reactions, insect sting reactions, latex reactions, conjunctivitis, urticaria, anaphylaxis reactions, anaphylactoid reactions, atopic dermatitis, asthma, or food allergies.

In one aspect the present application relates to a method of modulating antigen receptor signaling comprising administering a compound or composition of the application. In another aspect, the method of modulating antigen receptor further comprises modulating subsequent biochemical pathways culminating in cellular activation. In another aspect, the method of modulating antigen receptor further comprises modulating subsequent biochemical pathways culminating in cellular activation and production of a responsive cytokine. In one aspect, the antigen receptor is a T cell receptor. In another aspect, the cytokine is selected from IL-2, IL-4, IL-5, IL-7, IL-10, IL-17, IL-21, IFNγ, and TNFα. In one aspect, the modulating occurs in vitro. In another aspect, the modulating occurs in vivo.

In one aspect, the present application relates to a method of modulating the store-operated calcium (SOC) channel comprising contacting the SOC channel complex, or part thereof, with a compound or composition of the application. In one aspect, the SOC channel complex is calcium-release activated calcium (CRAC) channel complex. In one aspect, the contacting occurs in vitro. In another aspect, the contacting occurs in vivo.

BRIEF DESCRIPTION OF THE FIGURES

FIG. 1 is graph showing changes in intracellular calcium levels at various time intervals in Jurkat T cells following calcium store depletion (see example 4 for details).

DETAILED DESCRIPTION

The present application provides novel biaryl piperidine amide compounds, pharmaceutical compositions containing them, various uses of these compounds, and synthetic methods for making the compounds.

1. Compounds of the Application

In one aspect, the present application relates to a compound of formula (I):

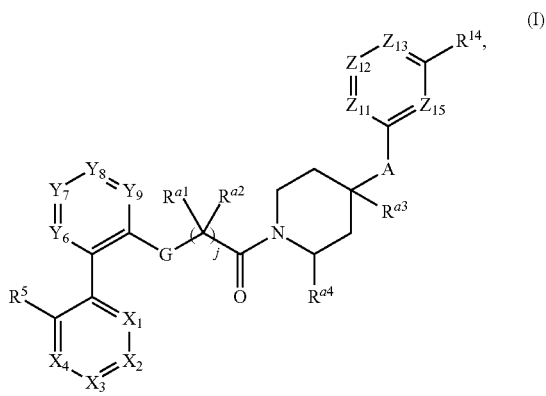

or a pharmaceutically acceptable salt, solvate, or prodrug thereof, wherein
$X_1$ is selected from $CR^1$, N, and N—O;
$X_2$ is selected from $CR^2$, N, and N—O;
$X_3$ is selected from $CR^3$, N, and N—O;
$X_4$ is selected from $CR^4$, N, and N—O;
$R^1$, $R^2$, $R^3$, $R^4$, and $R^5$ are independently selected from hydrogen; halogen; $C_1$-$C_6$ alkyl; $C_2$-$C_6$ alkenyl; $C_2$-$C_6$ alkynyl; $C_1$-$C_6$ haloalkyl; ($C_1$-$C_6$ alkyl)-$OR^{20}$; OH; O($C_1$-$C_6$ alkyl); $OCF_3$; $OCF_2H$; $OCFH_2$; CN; $N_3$; $NO_2$; $NH_2$; NH($C_1$-$C_6$ alkyl); N($C_1$-$C_6$ alkyl)$_2$; $NR^{20}C(O)R^{20}$; $C(O)NR^{20}R^{20}$; $COR^{20}$; CO($C_1$-$C_6$ alkyl); $S(O)_pR^{20}$; $NR^{20}S(O)_pR^{20}$; $S(O)_pNR^{20}R^{20}$; $SR^{20}$; $SCF_3$; $COOR^M$; $OR^{20}$; ($C_1$-$C_6$ alkyl)-$R^{20}$; 3-7 membered saturated, partially saturated, or unsaturated carbocycle; and 3-7 membered saturated, partially saturated, or unsaturated heterocycle containing one or more heteroatoms selected from the group consisting of nitrogen, oxygen, and sulfur;
alternatively, two substituents selected from $R^1$, $R^2$, $R^3$, $R^4$, and $R^5$ on two adjacent carbon atoms taken together form a 3-7 membered saturated, partially saturated, or unsaturated carbocycle; or a 3-7 membered saturated, partially saturated, or unsaturated heterocycle containing one or more heteroatoms selected from the group consisting of nitrogen, oxygen, and sulfur; where the carbocycle or heterocycle is optionally substituted with one or more $R^{20}$;
$R^{20}$ is independently selected from hydrogen; $C_1$-$C_6$ alkyl; CN; ($C_1$-$C_6$ alkyl)-$NR^{21}R^{21}$; ($C_1$-$C_6$ alkyl)-$OR^{21}$; 3-7 membered saturated, partially saturated, or unsaturated carbocycle; 3-7 membered saturated, partially saturated, or unsaturated heterocycle containing one or more heteroatoms selected from the group consisting of nitrogen, oxygen, and sulfur; ($C_1$-$C_6$ alkyl)-3-7 membered saturated, partially saturated, or unsaturated carbocycle; ($C_1$-$C_6$ alkyl)-3-7 membered saturated, partially saturated, or unsaturated heterocycle containing one or more heteroatoms selected from the group consisting of nitrogen, oxygen, and sulfur; where the carbocycle or heterocycle is optionally substituted with one or more $R^{21}$;
or two $R^{20}$ taken together with the carbon atom to which they are attached form a carbonyl;

$R^{21}$ is independently selected from hydrogen, $C_1$-$C_6$ alkyl, $C_2$-$C_6$ alkenyl, $C_2$-$C_6$ alkynyl; OH, O—($C_1$-$C_6$ alkyl), O—($C_2$-$C_6$ alkenyl), and O—($C_2$-$C_6$ alkynyl);

$Y_6$ is independently selected from $CR^6$, N, and N—O;
$Y_7$ is independently selected from $CR^7$, N, and N—O;
$Y_8$ is independently selected from $CR^8$, N, and N—O;
$Y_9$ is independently selected from $CR^9$, N, and N—O;
$R^6$, $R^7$, $R^8$, and $R^9$ are independently selected from hydrogen; halogen; $C_1$-$C_6$ alkyl; $C_2$-$C_6$ alkenyl; $C_2$-$C_6$ alkynyl; $C_1$-$C_6$ haloalkyl; ($C_1$-$C_6$ alkyl)-$R^{30}$; ($C_1$-$C_6$ alkyl)-$OR^{30}$; OH; O($C_1$-$C_6$ alkyl); $OCF_3$; $OCF_2H$; $OCFH_2$; CN; $N_3$; $NO_2$; $NH_2$; NH($C_1$-$C_6$ alkyl); N($C_1$-$C_6$ alkyl)$_2$; $NR^{30}C(O)R^{30}$; $C(O)NR^{30}R^{30}$; $COR^{30}$; $CO(C_1$-$C_6$ alkyl); $S(O)_qR^{30}$; $NR^{30}S(O)_qR^{30}$; $S(O)_qNR^{30}R^{30}$; $SR^{30}$; $SCF_3$; and $COOR^{30}$;

alternatively, two substituents selected from $R^6$, $R^7$, $R^8$, and $R^9$ on two adjacent carbon atoms taken together form a 3-7 membered saturated, partially saturated, or unsaturated carbocycle; or a 3-7 membered saturated, partially saturated, or unsaturated heterocycle containing one or more heteroatoms selected from the group consisting of nitrogen, oxygen, and sulfur; where the carbocycle or heterocycle is optionally substituted with one or more $R^{30}$;

$R^{30}$ is independently selected from hydrogen; $C_1$-$C_6$ alkyl; ($C_1$-$C_6$ alkyl)-$R^{31}$; ($C_1$-$C_6$ alkyl)-$OR^{31}$; ($C_1$-$C_6$ alkyl)-$NR^{31}R^{31}$; 3-7 membered saturated, partially saturated, or unsaturated carbocycle; and 3-7 membered saturated, partially saturated, or unsaturated heterocycle containing one or more heteroatoms selected from the group consisting of nitrogen, oxygen, and sulfur; where the carbocycle or heterocycle is optionally substituted with one or more $R^{31}$;

$R^{31}$ is independently selected from hydrogen; $C_1$-$C_6$ alkyl; 3-7 membered saturated, partially saturated, or unsaturated carbocycle; and 3-7 membered saturated, partially saturated, or unsaturated heterocycle containing one or more heteroatoms selected from the group consisting of nitrogen, oxygen, and sulfur;

G is selected from a bond, O, S, S(O), $S(O)_2$, $CH_2$, $CH_2CH_2$, and CHCH;

alternatively, G and $R^{a1}$ together form a 3-7 membered saturated, partially saturated, or unsaturated carbocycle; or a 3-7 membered saturated, partially saturated, or unsaturated heterocycle containing one or more heteroatoms selected from the group consisting of nitrogen, oxygen, and sulfur;

A is selected from a bond, $CH_2$, $CH_2CH_2$, $CH_2CH_2CH_2$, CHCH, and C≡C;

$R^{a1}$ and $R^{a2}$ are independently selected from hydrogen; halogen; $C_1$-$C_6$ alkyl; $C_2$-$C_6$ alkenyl; $C_2$-$C_6$ alkynyl; $C_1$-$C_6$ haloalkyl; OH; O($C_1$-$C_6$ alkyl); ($C_1$-$C_6$ alkyl)-OH; ($C_1$-$C_6$ alkyl)-O($C_1$-$C_6$ alkyl); ($C_1$-$C_6$ alkyl)-3-7 membered saturated, partially saturated, or unsaturated carbocycle; and ($C_1$-$C_6$ alkyl)-3-7 membered saturated, partially saturated, or unsaturated heterocycle containing one or more heteroatoms selected from the group consisting of nitrogen, oxygen, and sulfur;

$R^{a3}$ is selected from hydrogen, halogen, OH, O($C_1$-$C_6$ alkyl), and $C_1$-$C_6$ alkyl;

$R^{a4}$ is selected from hydrogen, halogen, and $C_1$-$C_6$ alkyl;

$Z_{11}$ is selected from $CR^{11}$, N, and N—O;
$Z_{12}$ is selected from $CR^{12}$, N, and N—O;
$Z_{13}$ is selected from $CR^{13}$, N, and N—O;
$Z_{15}$ is selected from $CR^{15}$, N, and N—O;

$R^{11}$, $R^{12}$, $R^{13}$, $R^{14}$, and $R^{15}$ are independently selected from hydrogen, halogen, $C_1$-$C_6$ alkyl, $C_2$-$C_6$ alkenyl, $C_2$-$C_6$ alkynyl, $C_1$-$C_6$ haloalkyl, ($C_1$-$C_6$ alkyl)-$OR^{40}$, OH, O($C_1$-$C_6$ alkyl), $OCF_3$, $OCF_2H$, $OCFH_2$, CN, $N_3$, $NO_2$, $NH_2$, NH($C_1$-$C_6$ alkyl), N($C_1$-$C_6$ alkyl)$_2$, $NR^{40}C(O)R^{40}$, $C(O)NR^{40}R^{40}$, COH, $CO(C_1$-$C_6$ alkyl), $S(O)_tR^{40}$, $NR^{40}S(O)_tR^{40}$, $S(O)_tNR^{40}R^{40}$, $SR^{40}$, $SCF_3$, $COOR^{40}$, $COR^{40}$, and $OR^{40}$; 3-7 membered saturated, partially saturated, or unsaturated carbocycle; and 3-7 membered saturated, partially saturated, or unsaturated heterocycle containing one or more heteroatoms selected from the group consisting of nitrogen, oxygen, and sulfur;

alternatively, two substituents selected from $R^{11}$, $R^{12}$, $R^{13}$, $R^{14}$, and $R^{15}$ on two adjacent carbon atoms taken together form a 3-7 membered saturated, partially saturated, or unsaturated carbocycle; or a 3-7 membered saturated, partially saturated, or unsaturated heterocycle containing one or more heteroatoms selected from the group consisting of nitrogen, oxygen, and sulfur; where the carbocycle or heterocycle is optionally substituted with one or more $R^{40}$;

$R^{40}$ is independently selected from hydrogen; halogen; $C_1$-$C_6$ alkyl; $C_2$-$C_6$ alkenyl, $C_2$-$C_6$ alkynyl; 3-7 membered saturated, partially saturated, or unsaturated carbocycle; 3-7 membered saturated, partially saturated, or unsaturated heterocycle containing one or more heteroatoms selected from the group consisting of nitrogen, oxygen, and sulfur; ($C_1$-$C_6$ alkyl)-3-7 membered saturated, partially saturated, or unsaturated carbocycle; and ($C_1$-$C_6$ alkyl)-3-7 membered saturated, partially saturated, or unsaturated heterocycle containing one or more heteroatoms selected from the group consisting of nitrogen, oxygen, and sulfur;

or two $R^{40}$ taken together with the carbon atom to which they are attached form a carbonyl;

j is 0, 1, or 2;
p is 0, 1, or 2;
q is 0, 1, or 2; and
t is 0, 1, or 2.

In one aspect, the present application relates to a compound of formula (II):

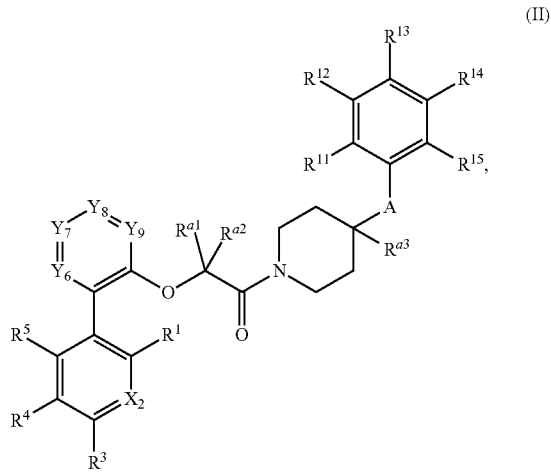

or a pharmaceutically acceptable salt, solvate, or prodrug thereof, where A, $X_2$, $Y_6$, $Y_7$, $Y_8$, $Y_9$, $R^1$, $R^3$, $R^4$, $R^5$, $R^{11}$, $R^{12}$, $R^{13}$, $R^{14}$, $R^{15}$, $R^{a1}$, $R^{a2}$, and $R^{a3}$ are as described herein.

In one aspect the present application relates to a compound of formula (III):

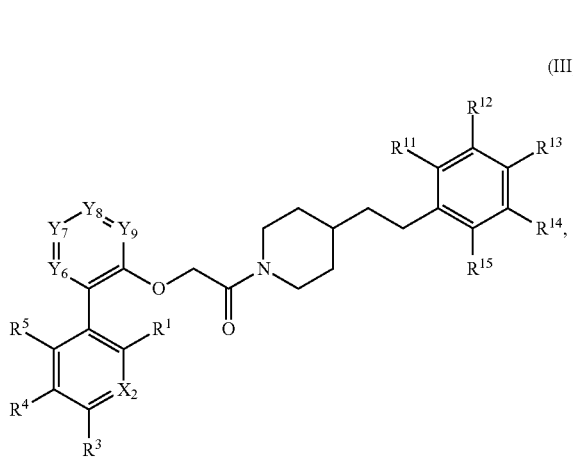
(III)

or a pharmaceutically acceptable salt, solvate, or prodrug thereof, where $X_2$, $Y_6$, $Y_7$, $Y_8$, $Y_9$, $R^1$, $R^3$, $R^4$, $R^5$, $R^{11}$, $R^{12}$, $R^{13}$, $R^{14}$ and $R^{15}$ are as described herein.

In one aspect, the present application relates to a compound of a formula selected from:

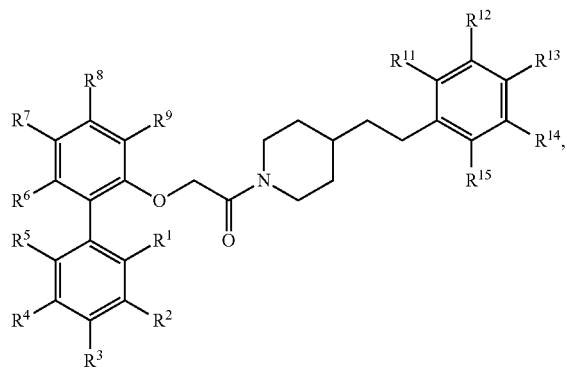
(IVa)

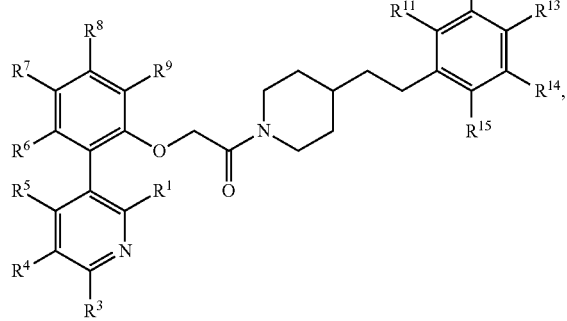
(IVb)

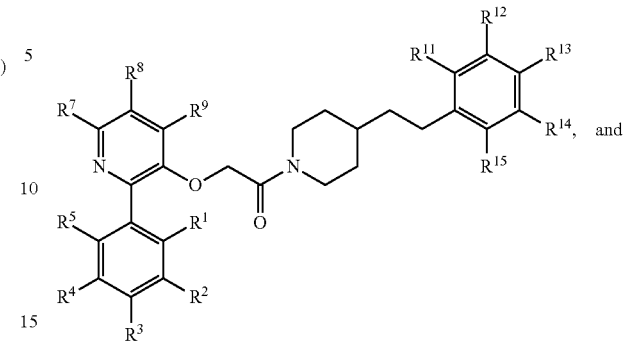
(IVc)

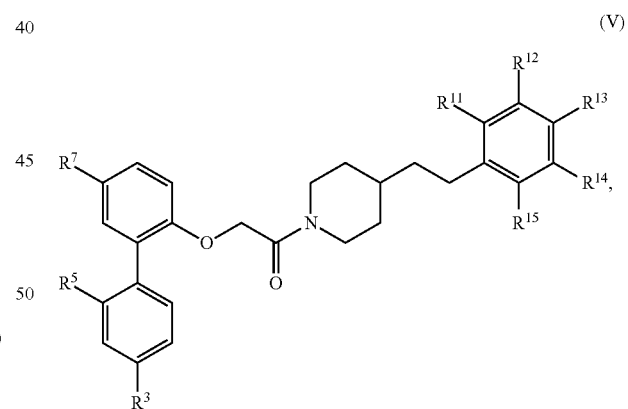
(IVd)

or a pharmaceutically acceptable salt, solvate, or prodrug thereof, where $R^1$, $R^3$, $R^4$, $R^5$, $R^6$, $R^7$, $R^8$, $R^9$, $R^{11}$, $R^{12}$, $R^{13}$, $R^{14}$ and $R^{15}$ are as described herein.

In one aspect, the present application relates to a compound of formula (V):

(V)

or a pharmaceutically acceptable salt, solvate, or prodrug thereof, where $R^3$, $R^5$, $R^7$, $R^{11}$, $R^{12}$, $R^{13}$, $R^{14}$, and $R^{15}$ are as described herein.

In one aspect, the present application relates to a compound of any one of formulae I, II, III, IVa, IVb, IVc, IVd, or V, wherein $R^3$ is selected from hydrogen, halogen, $C_1$-$C_6$ alkyl, $C_1$-$C_6$ haloalkyl, OH, O($C_1$-$C_6$ alkyl), $OCF_3$, $OCF_2H$, $OCFH_2$, CN, $N_3$, $NO_2$, $NH_2$, NH($C_1$-$C_6$ alkyl), and N($C_1$-$C_6$ alkyl)$_2$. In another aspect, $R^3$ is selected from hydrogen, halogen, and CN. In one aspect, $R^3$ is hydrogen. In one aspect, $R^3$ is halogen. In one aspect, $R^3$ is fluoro or chloro. In one aspect, $R^3$ is CN.

In one aspect, the present application relates to a compound of any one of formulae I, II, III, IVa, IVb, IVc, IVd, or V, wherein $R^5$ is selected from hydrogen, halogen, $C_1$-$C_6$ alkyl, $C_1$-$C_6$ haloalkyl, OH, O($C_1$-$C_6$ alkyl), $OCF_3$, $OCF_2H$, $OCFH_2$, CN, $NH_2$, NH($C_1$-$C_6$ alkyl), and N($C_1$-$C_6$ alkyl)$_2$. In one aspect, $R^5$ is selected from hydrogen, halogen, $C_1$-$C_6$ alkyl, OH, and O($C_1$-$C_6$ alkyl). In one aspect, $R^5$ is hydrogen. In one aspect, $R^5$ is halogen. In one aspect, $R^5$ is fluoro. In one aspect, $R^5$ is OH. In one aspect, $R^5$ is $OCH_3$.

In one aspect, the present application relates to a compound of any one of formulae I, II, III, IVa, IVb, IVc, IVd, or V, wherein $R^7$ is selected from hydrogen, halogen, $C_1$-$C_6$ alkyl, $C_1$-$C_6$ haloalkyl, OH, O($C_1$-$C_6$ alkyl), $OCF_3$, $OCF_2H$, $OCFH_2$, CN, $NH_2$, NH($C_1$-$C_6$ alkyl), N($C_1$-$C_6$ alkyl)$_2$, S(O)$_q$ $NR^{30}R^{30}$, C(O)$NR^{30}R^{30}$, $COR^{30}$, and $COOR^{30}$. In one aspect, $R^7$ is selected from hydrogen, halogen, $C_1$-$C_6$ alkyl, $C_1$-$C_6$ haloalkyl, OH, O($C_1$-$C_6$ alkyl), CN, S(O)$_q$$NR^{30}R^{30}$, C(O)$NR^{30}R^{30}$, $COR^{30}$, and $COOR^{30}$. In one aspect, $R^7$ is selected from hydrogen, $CF_3$, OH, CN, S(O)$_2NR^{30}R^{30}$, and C(O)$NR^{30}R^{30}$. In one aspect, $R^7$ is hydrogen.

In one aspect, the present application relates to a compound selected from Table 1.

TABLE 1

| Compound No. | Structure | MW | Positive MS peak | Negative MS peak |
|---|---|---|---|---|
| 100 | 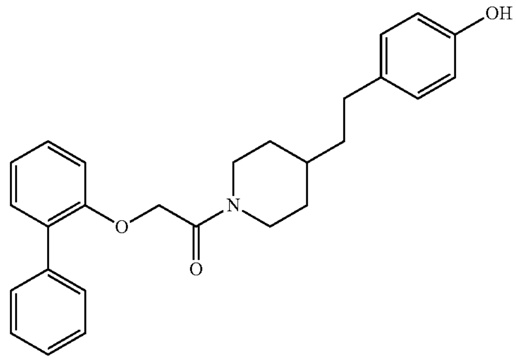 [SMILES: O=C(COc1ccccc1-c1ccccc1)N1CCC(CCc2ccc(O)cc2)CC1] | 415.5 | | 416 |
| 101 | 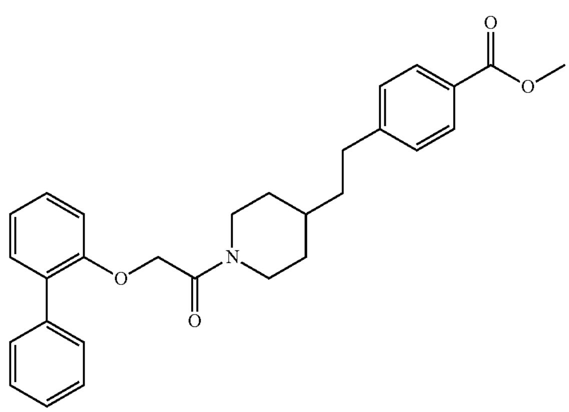 [SMILES: COC(=O)c1ccc(CCC2CCN(C(=O)COc3ccccc3-c3ccccc3)CC2)cc1] | 457.6 | | 458 |
| 102 | 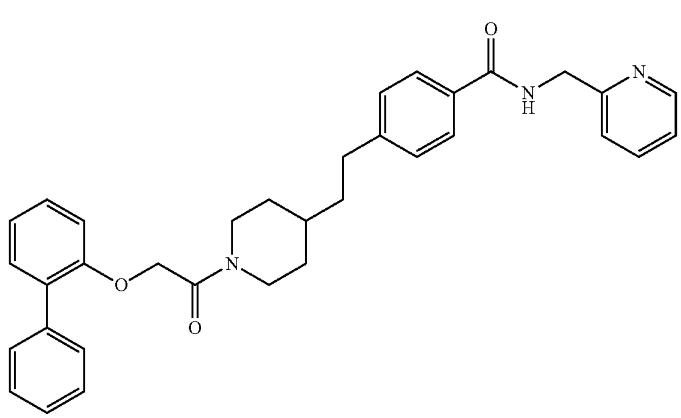 [SMILES: O=C(NCc1ccccn1)c1ccc(CCC2CCN(C(=O)COc3ccccc3-c3ccccc3)CC2)cc1] | 533.7 | | 534 |

TABLE 1-continued

| Compound No. | Structure | MW | Positive MS peak | Negative MS peak |
|---|---|---|---|---|
| 103 | 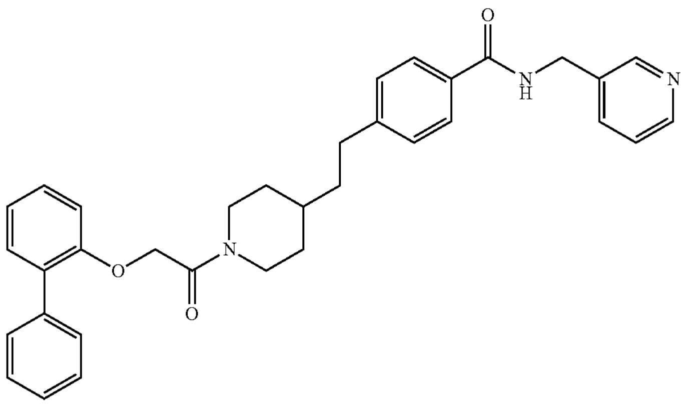 [SMILES: O=C(NCc1cccnc1)c1ccc(CCC2CCN(C(=O)COc3ccccc3-c3ccccc3)CC2)cc1] | 533.7 | 534 | |
| 104 | 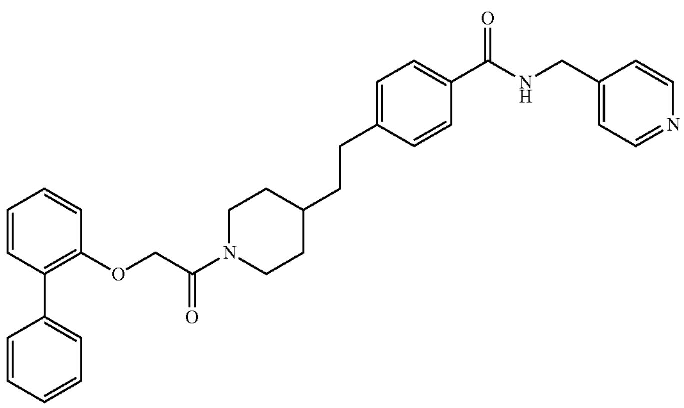 [SMILES: O=C(NCc1ccncc1)c1ccc(CCC2CCN(C(=O)COc3ccccc3-c3ccccc3)CC2)cc1] | 533.7 | 534 | |
| 105 | 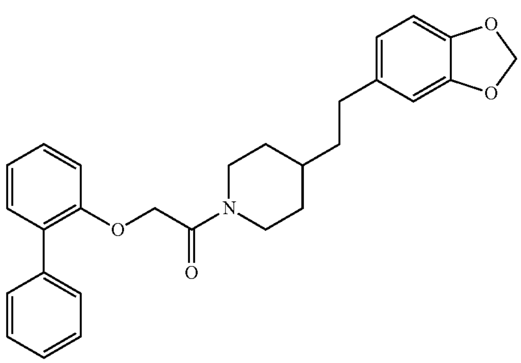 | 443.5 | 444 | |
| 106 | 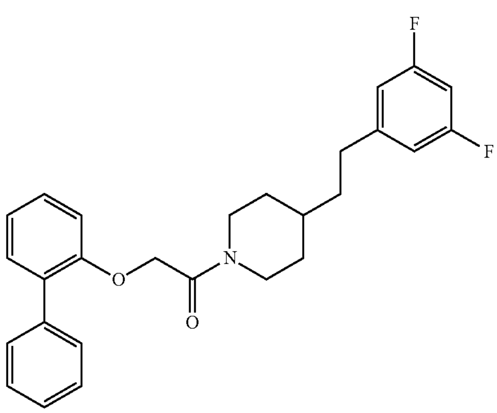 | 435.5 | 436 | |

TABLE 1-continued

| Compound No. | Structure | MW | Positive MS peak | Negative MS peak |
|---|---|---|---|---|
| 107 | 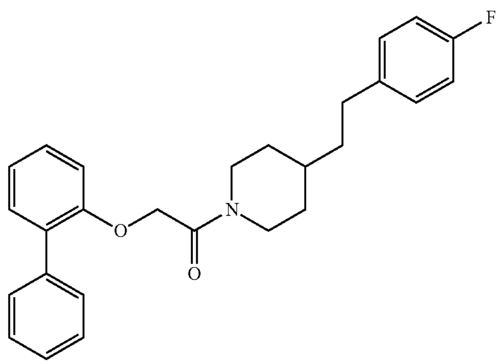 [SMILES: O=C(COc1ccccc1-c1ccccc1)N1CCC(CCc2ccc(F)cc2)CC1] | 417.5 | 418 | |
| 108 | 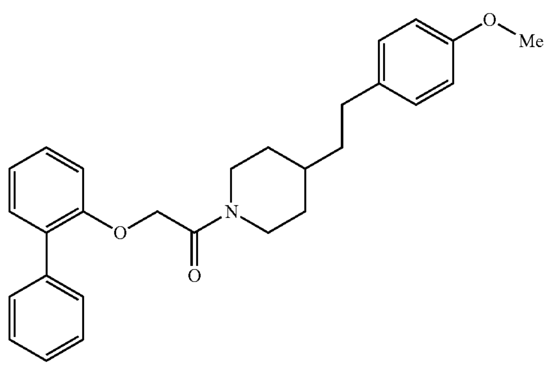 [SMILES: COc1ccc(CCC2CCN(C(=O)COc3ccccc3-c3ccccc3)CC2)cc1] | 429.6 | 430 | |
| 109 | 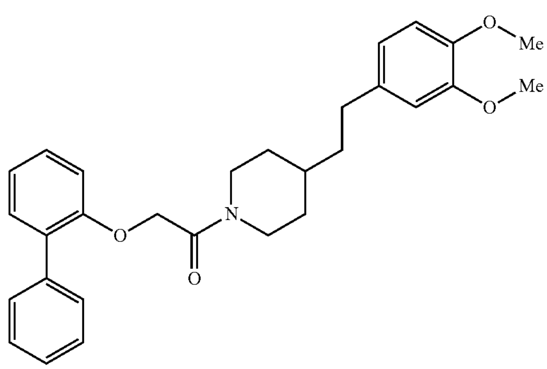 [SMILES: COc1ccc(CCC2CCN(C(=O)COc3ccccc3-c3ccccc3)CC2)cc1OC] | 459.6 | 460 | |
| 110 | 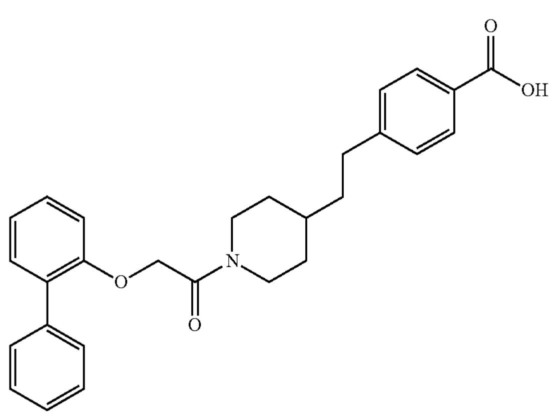 [SMILES: O=C(O)c1ccc(CCC2CCN(C(=O)COc3ccccc3-c3ccccc3)CC2)cc1] | 443.5 | 444 | |

TABLE 1-continued

| Compound No. | Structure | MW | Positive MS peak | Negative MS peak |
|---|---|---|---|---|
| 111 | 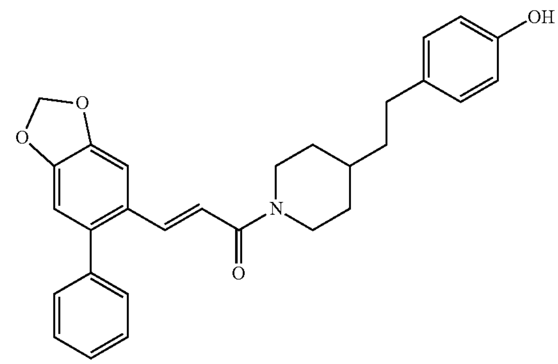 [SMILES: O=C(/C=C/c1cc2c(cc1-c1ccccc1)OCO2)N1CCC(CCc2ccc(O)cc2)CC1] | 455.5 | 456 | |
| 112 | 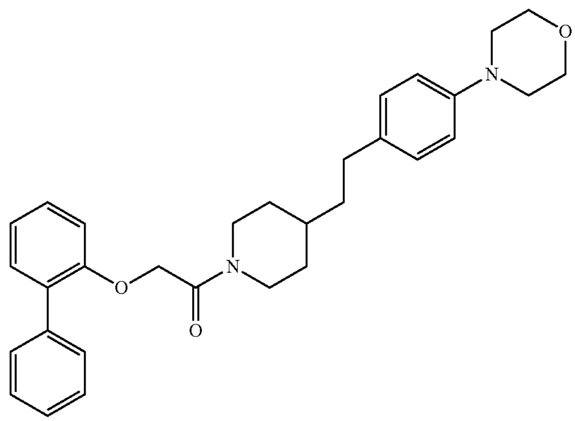 [SMILES: O=C(COc1ccccc1-c1ccccc1)N1CCC(CCc2ccc(N3CCOCC3)cc2)CC1] | 484.6 | 485 | |
| 113 | 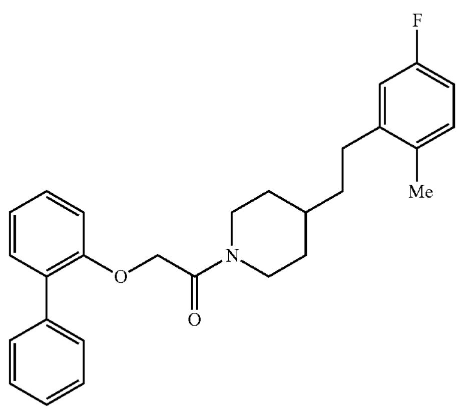 | 431.5 | 432 | |
| 114 | 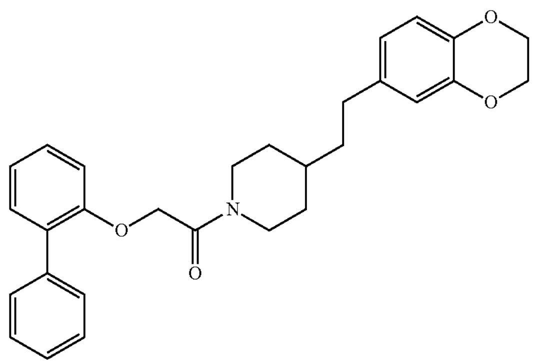 [SMILES: O=C(COc1ccccc1-c1ccccc1)N1CCC(CCc2ccc3c(c2)OCCO3)CC1] | 457.6 | 458 | |

TABLE 1-continued
| Compound No. | Structure | MW | Positive MS peak | Negative MS peak |
|---|---|---|---|---|
| 115 | 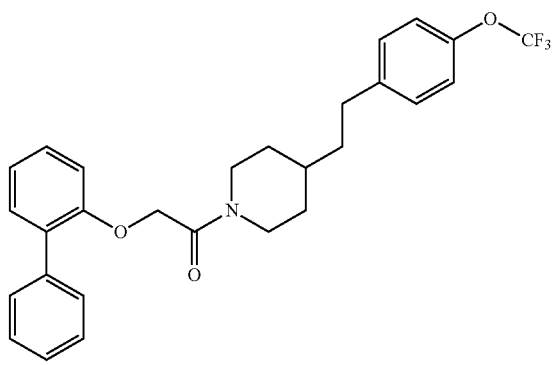 [SMILES: O=C(COc1ccccc1-c1ccccc1)N1CCC(CCc2ccc(OC(F)(F)F)cc2)CC1] | 483.5 | 484 | |
| 116 | 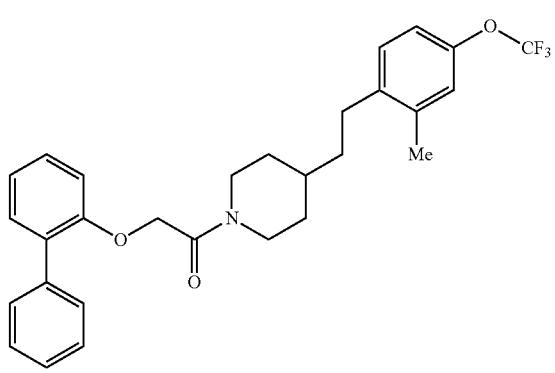 [SMILES: Cc1cc(OC(F)(F)F)ccc1CCC1CCN(C(=O)COc2ccccc2-c2ccccc2)CC1] | 497.6 | 498 | |
| 117 | 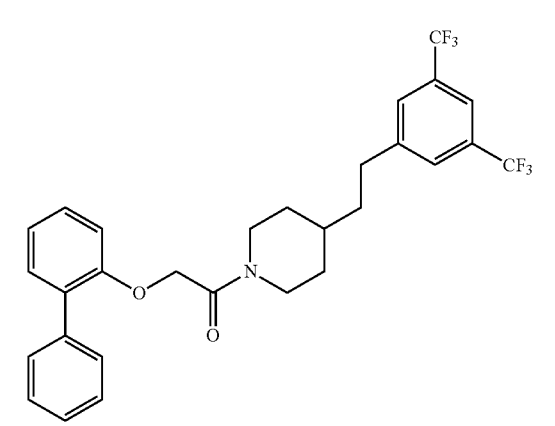 [SMILES: O=C(COc1ccccc1-c1ccccc1)N1CCC(CCc2cc(C(F)(F)F)cc(C(F)(F)F)c2)CC1] | 535.5 | 536 | |
| 118 | 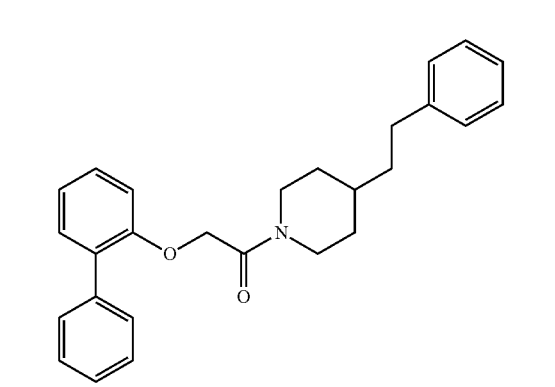 [SMILES: O=C(COc1ccccc1-c1ccccc1)N1CCC(CCc2ccccc2)CC1] | 399.5 | 400 | |

TABLE 1-continued

| Compound No. | Structure | MW | Positive MS peak | Negative MS peak |
|---|---|---|---|---|
| 119 | 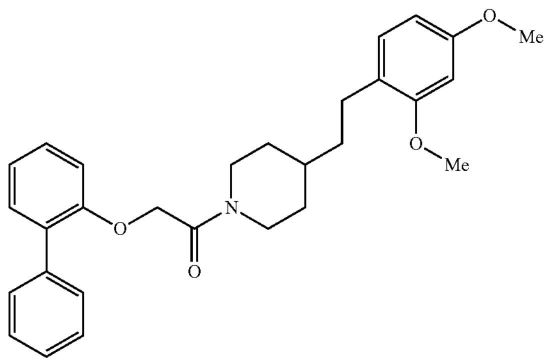 [SMILES: COc1ccc(CCC2CCN(C(=O)COc3ccccc3-c3ccccc3)CC2)c(OC)c1] | 459.6 | 460 | |
| 120 | 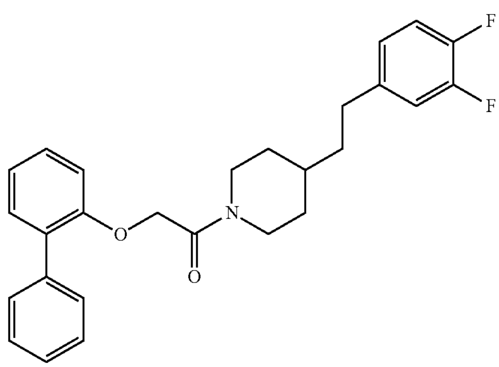 [SMILES: O=C(COc1ccccc1-c1ccccc1)N1CCC(CCc2ccc(F)c(F)c2)CC1] | 435.5 | 436 | |
| 121 | 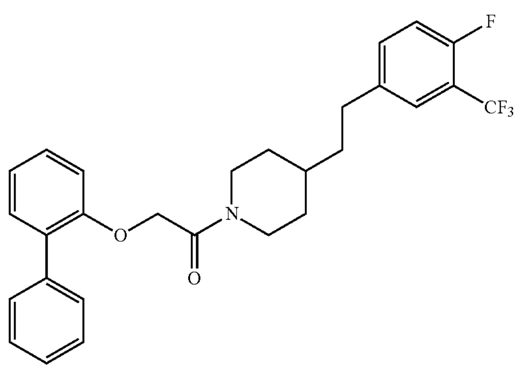 [SMILES: O=C(COc1ccccc1-c1ccccc1)N1CCC(CCc2ccc(F)c(C(F)(F)F)c2)CC1] | 485.5 | 486 | |
| 122 | 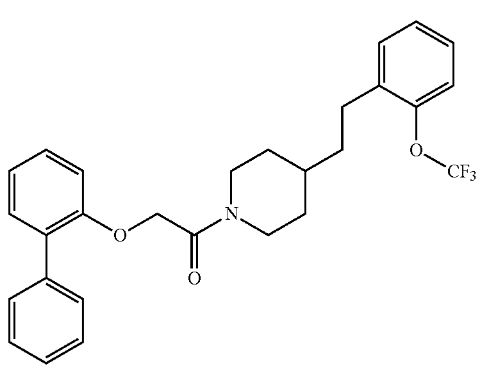 [SMILES: O=C(COc1ccccc1-c1ccccc1)N1CCC(CCc2ccccc2OC(F)(F)F)CC1] | 483.5 | 484 | |

TABLE 1-continued

| Compound No. | Structure | MW | Positive MS peak | Negative MS peak |
|---|---|---|---|---|
| 123 | 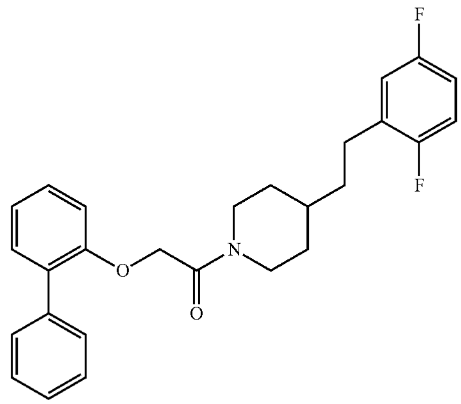 [SMILES: O=C(COc1ccccc1-c1ccccc1)N1CCC(CCc2cc(F)ccc2F)CC1] | 435.5 | 436 | |
| 124 | 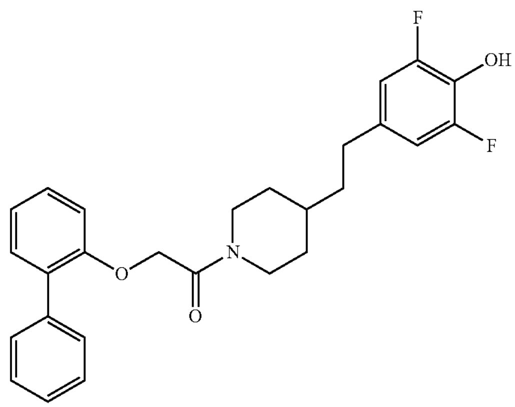 [SMILES: O=C(COc1ccccc1-c1ccccc1)N1CCC(CCc2cc(F)c(O)c(F)c2)CC1] | 451.5 | 452 | |
| 125 | 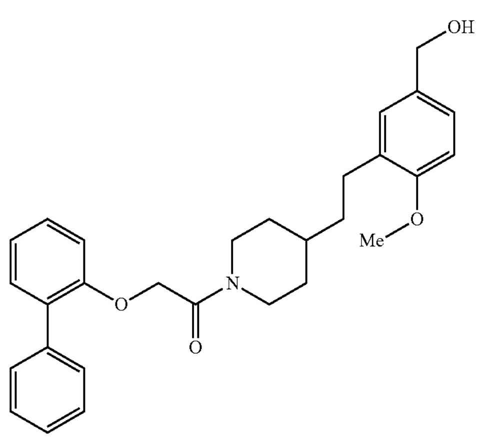 [SMILES: COc1ccc(CO)cc1CCC1CCN(C(=O)COc2ccccc2-c2ccccc2)CC1] | 459.6 | 460 | |

TABLE 1-continued

| Compound No. | Structure | MW | Positive MS peak | Negative MS peak |
|---|---|---|---|---|
| 126 | 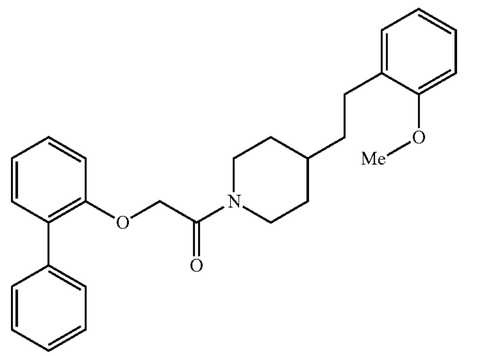 [SMILES: COc1ccccc1CCC1CCN(C(=O)COc2ccccc2-c2ccccc2)CC1] | 429.6 | 430 | |
| 127 | 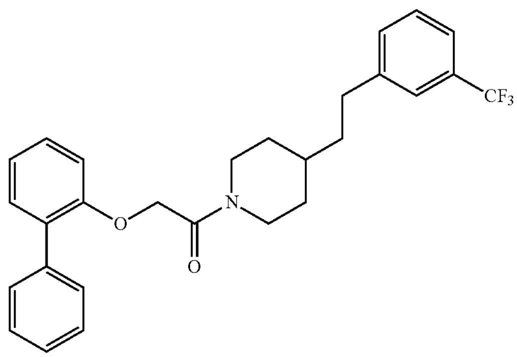 [SMILES: O=C(COc1ccccc1-c1ccccc1)N1CCC(CCc2cccc(C(F)(F)F)c2)CC1] | 467.5 | 468 | |
| 128 | 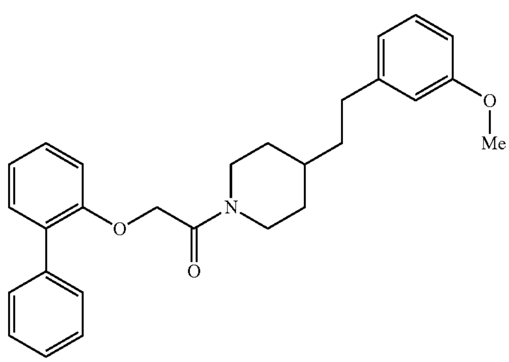 [SMILES: COc1cccc(CCC2CCN(C(=O)COc3ccccc3-c3ccccc3)CC2)c1] | 429.6 | 430 | |
| 129 | 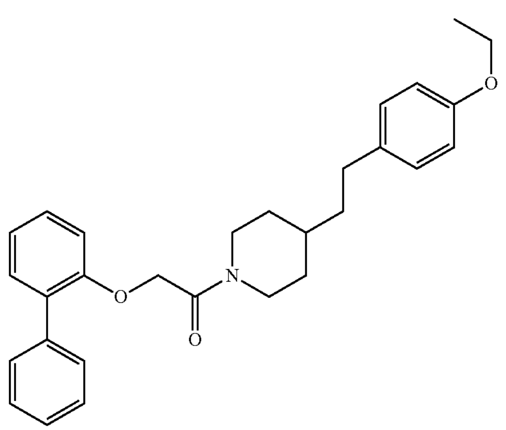 [SMILES: CCOc1ccc(CCC2CCN(C(=O)COc3ccccc3-c3ccccc3)CC2)cc1] | 443.6 | 444 | |

TABLE 1-continued

| Compound No. | Structure | MW | Positive MS peak | Negative MS peak |
|---|---|---|---|---|
| 130 | 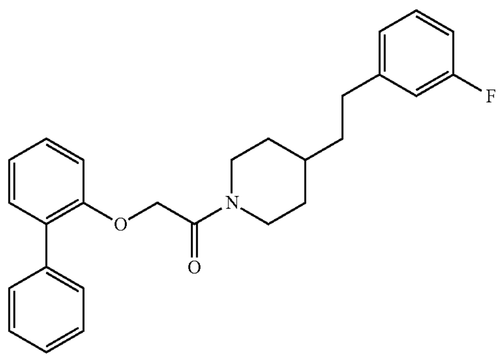 [SMILES: O=C(COc1ccccc1-c1ccccc1)N1CCC(CCc2cccc(F)c2)CC1] | 417.5 | 418 | |
| 131 | 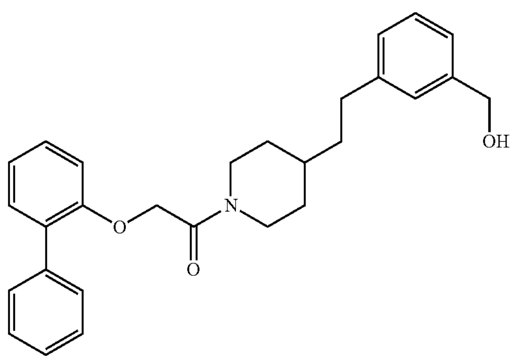 [SMILES: O=C(COc1ccccc1-c1ccccc1)N1CCC(CCc2cccc(CO)c2)CC1] | 429.6 | 430 | |
| 132 | 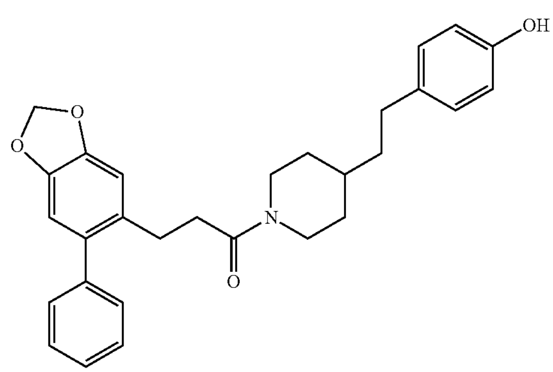 [SMILES: O=C(CCc1cc2c(cc1-c1ccccc1)OCO2)N1CCC(CCc2ccc(O)cc2)CC1] | 457.6 | 458 | |
| 133 | 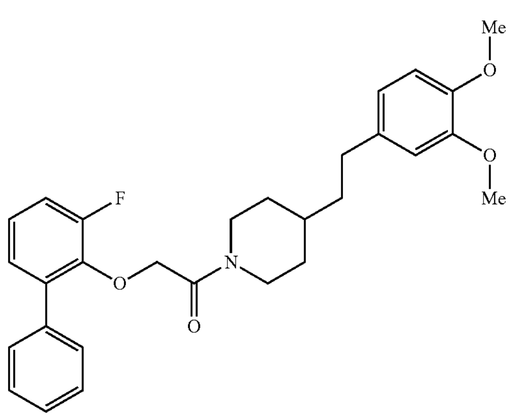 [SMILES: COc1ccc(CCC2CCN(C(=O)COc3c(F)cccc3-c3ccccc3)CC2)cc1OC] | 477.5 | 478 | |

TABLE 1-continued

| Compound No. | Structure | MW | Positive MS peak | Negative MS peak |
|---|---|---|---|---|
| 134 | 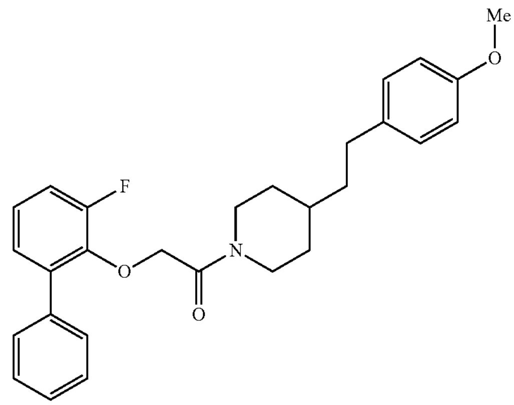 [SMILES: COc1ccc(CCC2CCN(C(=O)COc3c(F)cccc3-c3ccccc3)CC2)cc1] | 447.5 | 448 | |
| 135 | 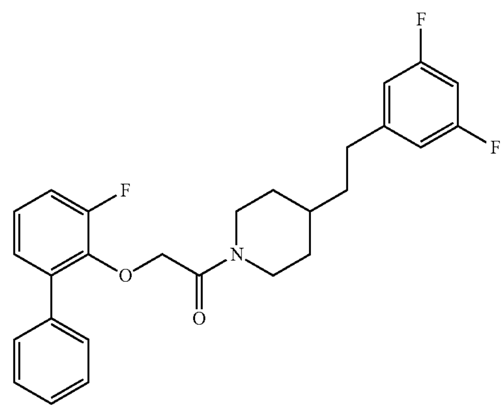 [SMILES: O=C(COc1c(F)cccc1-c1ccccc1)N1CCC(CCc2cc(F)cc(F)c2)CC1] | 453.5 | 454 | |
| 136 | 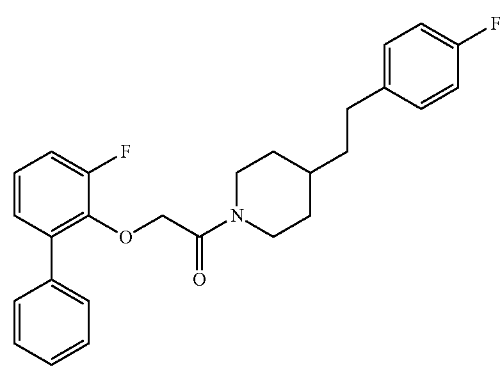 [SMILES: O=C(COc1c(F)cccc1-c1ccccc1)N1CCC(CCc2ccc(F)cc2)CC1] | 435.5 | 436 | |
| 137 | 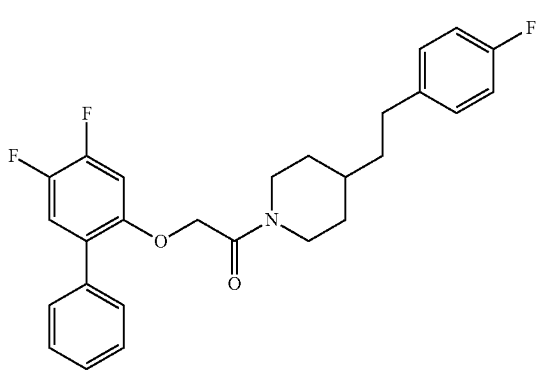 [SMILES: O=C(COc1cc(F)c(F)cc1-c1ccccc1)N1CCC(CCc2ccc(F)cc2)CC1] | 453.5 | 454 | |

TABLE 1-continued

| Compound No. | Structure | MW | Positive MS peak | Negative MS peak |
| --- | --- | --- | --- | --- |
| 138 | 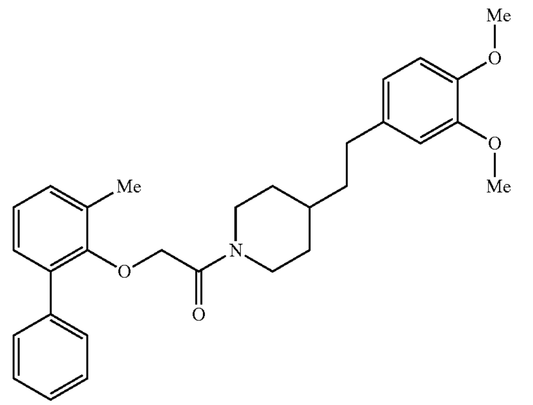 | 473.6 | 474 | |
| 139 | 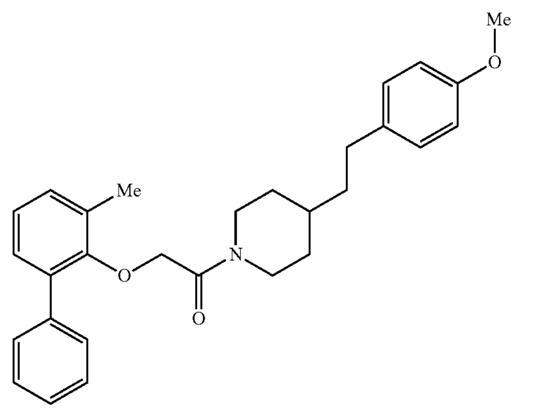 | 443.6 | 444 | |
| 140 | 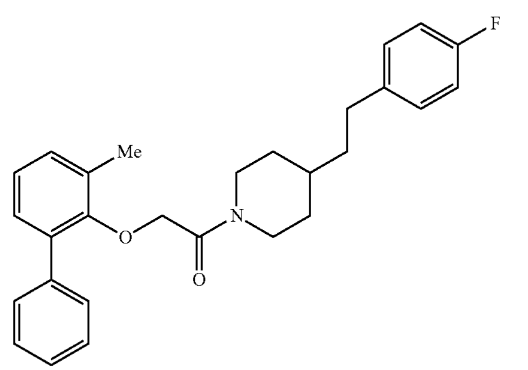 [SMILES: Cc1cccc(-c2ccccc2)c1OCC(=O)N1CCC(CCc2ccc(F)cc2)CC1] | 431.5 | 432 | |
| 141 | 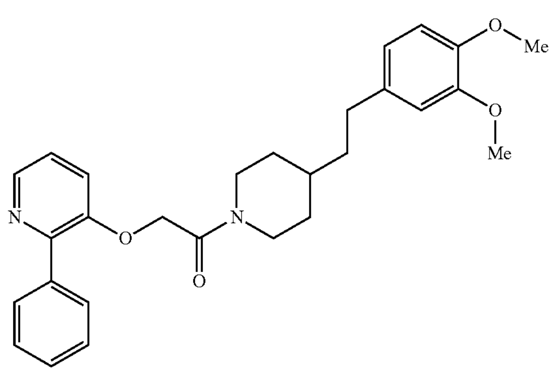 [SMILES: COc1ccc(CCC2CCN(C(=O)COc3cccnc3-c3ccccc3)CC2)cc1OC] | 460.6 | 461 | |

TABLE 1-continued

| Compound No. | Structure | MW | Positive MS peak | Negative MS peak |
| --- | --- | --- | --- | --- |
| 142 | 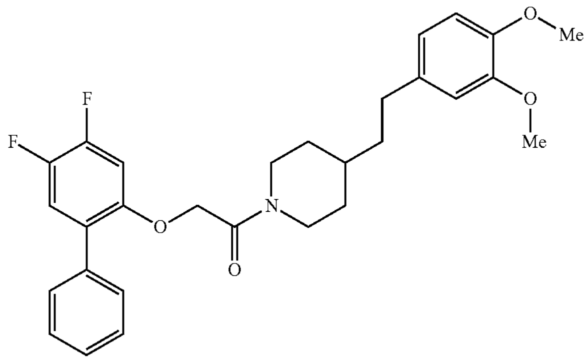 [SMILES: COc1ccc(CCC2CCN(C(=O)COc3cc(F)c(F)cc3-c3ccccc3)CC2)cc1OC] | 495.6 | 496 | |
| 143 | 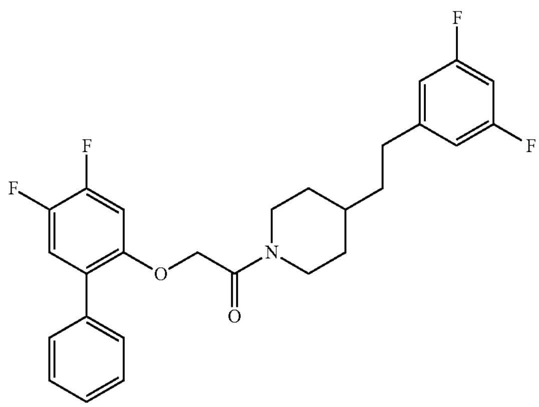 [SMILES: O=C(COc1cc(F)c(F)cc1-c1ccccc1)N1CCC(CCc2cc(F)cc(F)c2)CC1] | 471.5 | 472 | |
| 144 | 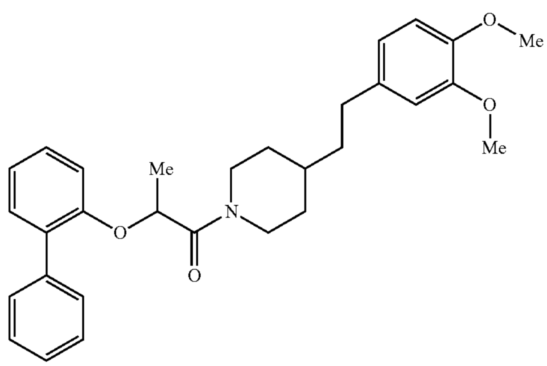 [SMILES: COc1ccc(CCC2CCN(C(=O)C(C)Oc3ccccc3-c3ccccc3)CC2)cc1OC] | 473.6 | 474 | |
| 145 | 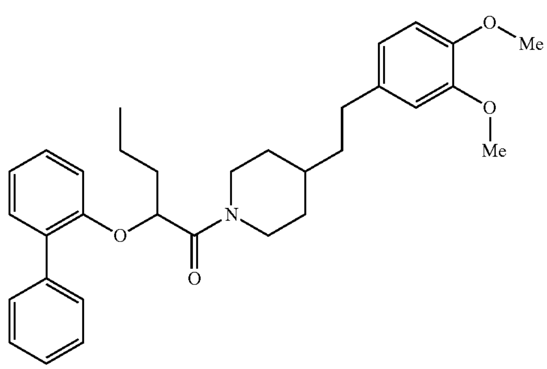 [SMILES: CCCC(Oc1ccccc1-c1ccccc1)C(=O)N1CCC(CCc2ccc(OC)c(OC)c2)CC1] | 501.6 | 502 | |

TABLE 1-continued

| Compound No. | Structure | MW | Positive MS peak | Negative MS peak |
|---|---|---|---|---|
| 146 | 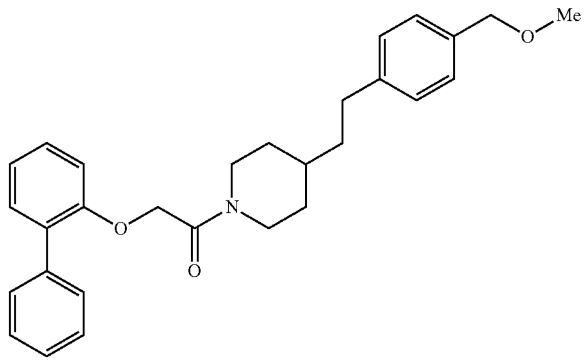 [SMILES: COCc1ccc(CCC2CCN(C(=O)COc3ccccc3-c3ccccc3)CC2)cc1] | 443.6 | 444 | |
| 147 | 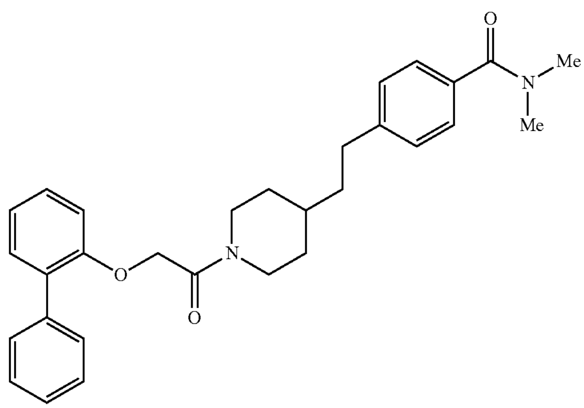 [SMILES: CN(C)C(=O)c1ccc(CCC2CCN(C(=O)COc3ccccc3-c3ccccc3)CC2)cc1] | 470.6 | 471 | |
| 148 | 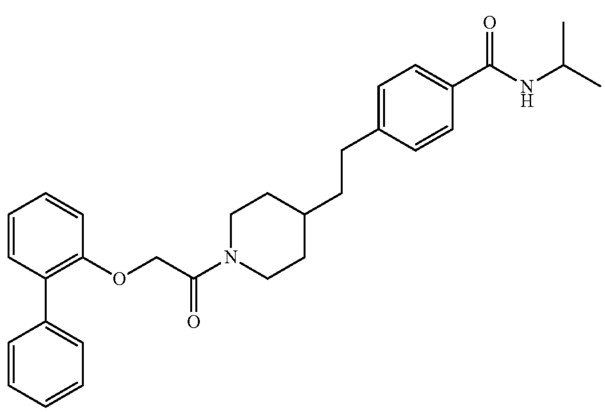 [SMILES: CC(C)NC(=O)c1ccc(CCC2CCN(C(=O)COc3ccccc3-c3ccccc3)CC2)cc1] | 484.6 | 485 | |
| 149 | 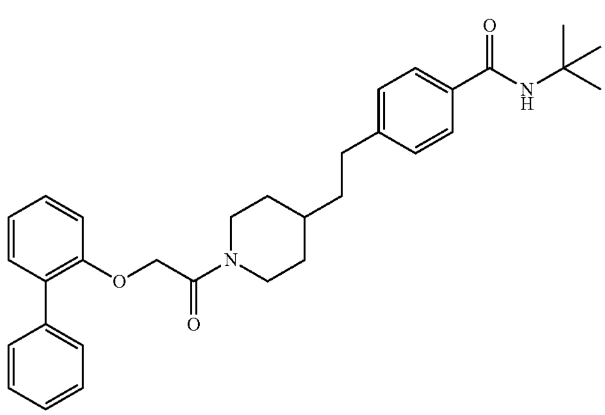 [SMILES: CC(C)(C)NC(=O)c1ccc(CCC2CCN(C(=O)COc3ccccc3-c3ccccc3)CC2)cc1] | 498.6 | 499 | |

TABLE 1-continued

| Compound No. | Structure | MW | Positive MS peak | Negative MS peak |
|---|---|---|---|---|
| 150 | 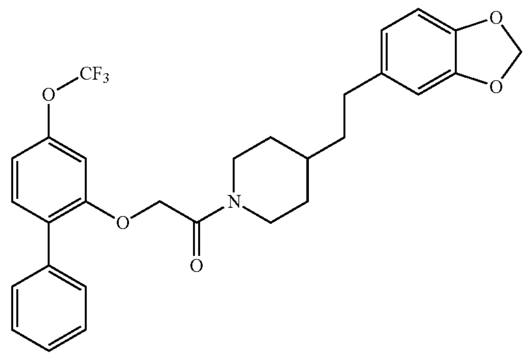 [SMILES: O=C(COc1cc(OC(F)(F)F)ccc1-c1ccccc1)N1CCC(CCc2ccc3c(c2)OCO3)CC1] | 527.5 | 528 | |
| 151 | 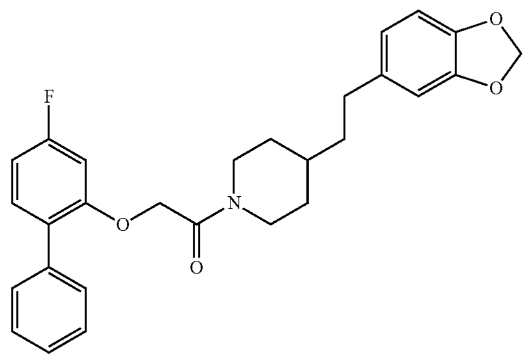 [SMILES: O=C(COc1cc(F)ccc1-c1ccccc1)N1CCC(CCc2ccc3c(c2)OCO3)CC1] | 461.5 | 462 | |
| 152 | 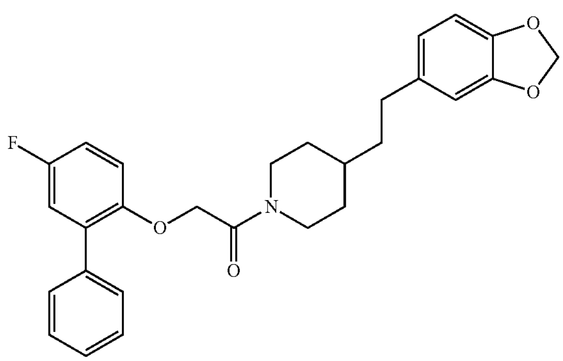 [SMILES: O=C(COc1ccc(F)cc1-c1ccccc1)N1CCC(CCc2ccc3c(c2)OCO3)CC1] | 461.5 | 462 | |
| 153 | 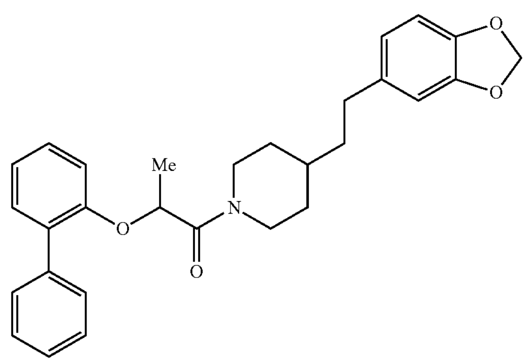 [SMILES: CC(Oc1ccccc1-c1ccccc1)C(=O)N1CCC(CCc2ccc3c(c2)OCO3)CC1] | 457.6 | 458 | |

TABLE 1-continued

| Compound No. | Structure | MW | Positive MS peak | Negative MS peak |
|---|---|---|---|---|
| 154 | 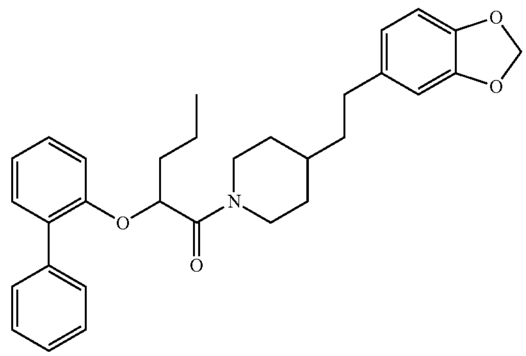 [SMILES: CCCC(Oc1ccccc1-c1ccccc1)C(=O)N1CCC(CCc2ccc3c(c2)OCO3)CC1] | 485.6 | 486 | |
| 155 | 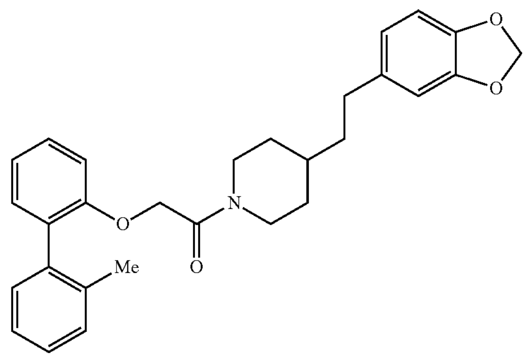 | 457.6 | 458 | |
| 156 | 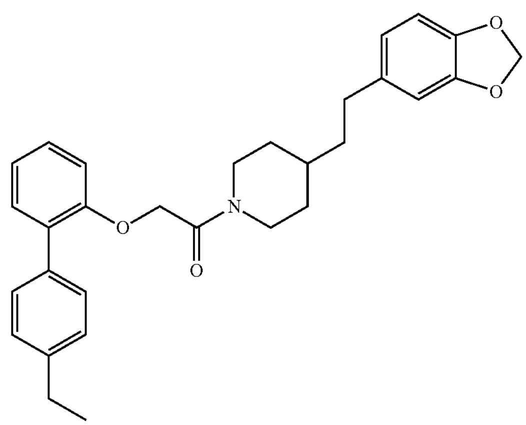 [SMILES: CCc1ccc(-c2ccccc2OCC(=O)N2CCC(CCc3ccc4c(c3)OCO4)CC2)cc1] | 471.6 | 472 | |
| 157 | 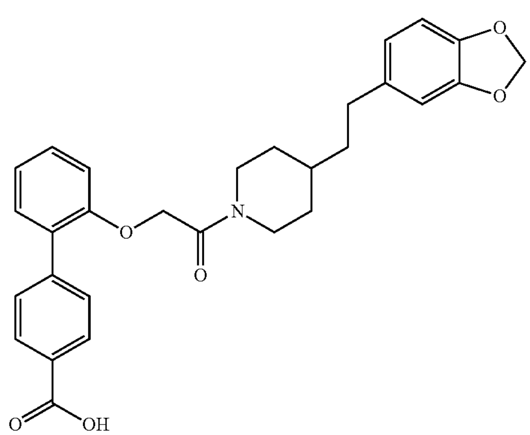 [SMILES: O=C(O)c1ccc(-c2ccccc2OCC(=O)N2CCC(CCc3ccc4c(c3)OCO4)CC2)cc1] | 487.5 | 488 | |

TABLE 1-continued

| Compound No. | Structure | MW | Positive MS peak | Negative MS peak |
|---|---|---|---|---|
| 158 | 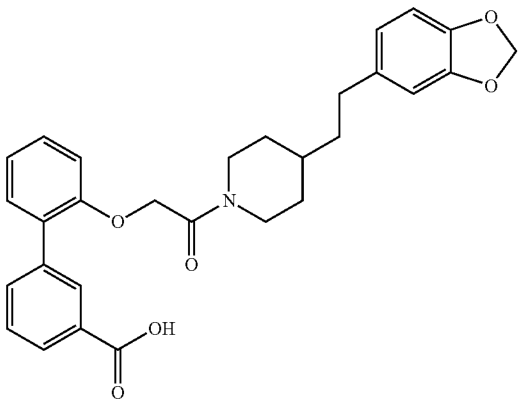 [SMILES: O=C(O)c1cccc(-c2ccccc2OCC(=O)N2CCC(CCc3ccc4c(c3)OCO4)CC2)c1] | 487.5 | 488 | |
| 159 | 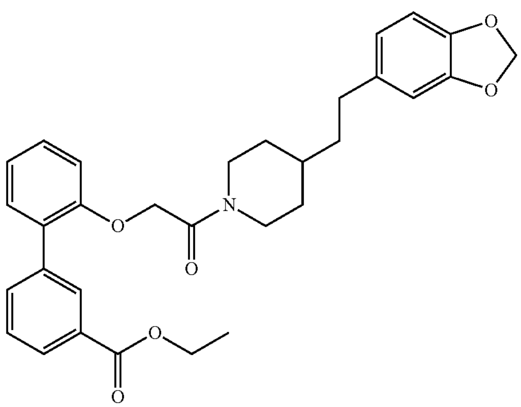 [SMILES: CCOC(=O)c1cccc(-c2ccccc2OCC(=O)N2CCC(CCc3ccc4c(c3)OCO4)CC2)c1] | 515.6 | 516 | |
| 160 | 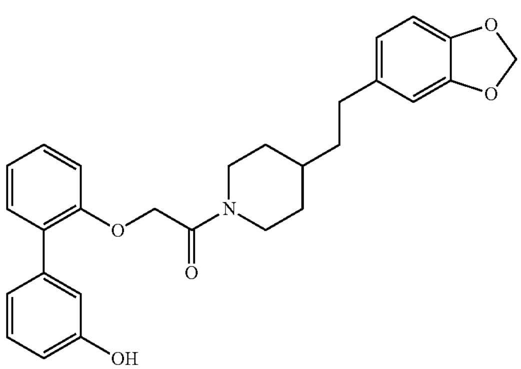 | 458.5 | 460 | |

TABLE 1-continued

| Compound No. | Structure | MW | Positive MS peak | Negative MS peak |
|---|---|---|---|---|
| 161 | 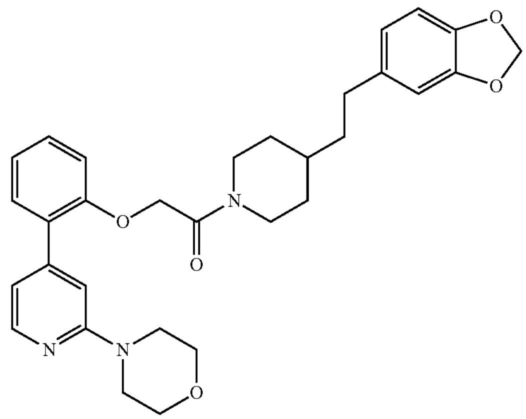 [SMILES: O=C(COc1ccccc1-c1ccnc(N2CCOCC2)c1)N1CCC(CCc2ccc3c(c2)OCO3)CC1] | 529.6 | 530 | |
| 162 | 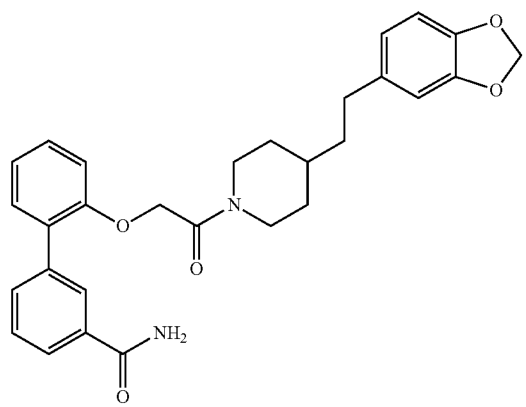 | 486.6 | 487 | |
| 163 | 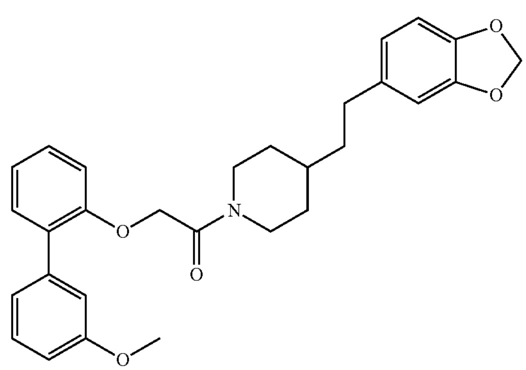 [SMILES: COc1cccc(-c2ccccc2OCC(=O)N2CCC(CCc3ccc4c(c3)OCO4)CC2)c1] | 473.6 | 474 | |

TABLE 1-continued
| Compound No. | Structure | MW | Positive MS peak | Negative MS peak |
|---|---|---|---|---|
| 164 | 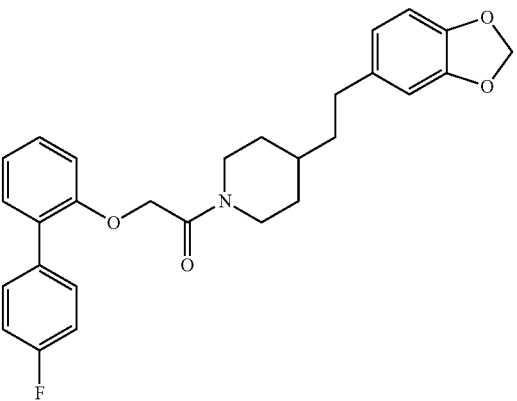 [SMILES: O=C(COc1ccccc1-c1ccc(F)cc1)N1CCC(CCc2ccc3c(c2)OCO3)CC1] | 461.5 | 462 | |
| 165 | 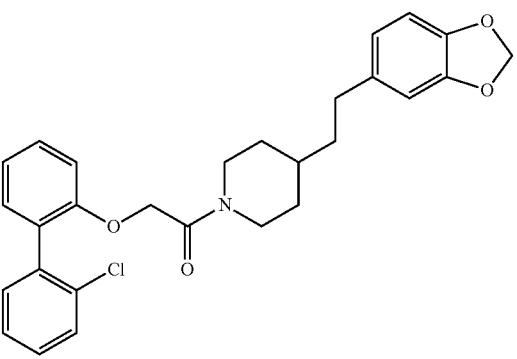 | 478.0 | 478 | |
| 166 | 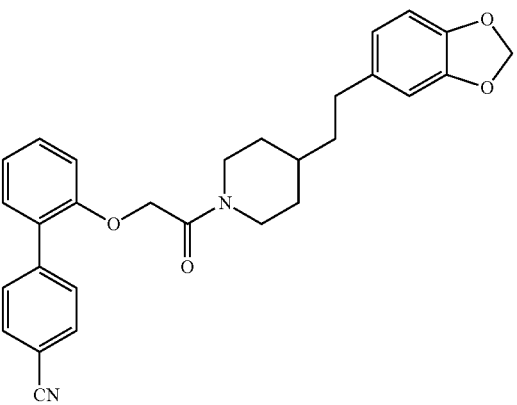 [SMILES: N#Cc1ccc(-c2ccccc2OCC(=O)N2CCC(CCc3ccc4c(c3)OCO4)CC2)cc1] | 468.5 | 469 | |
| 167 | 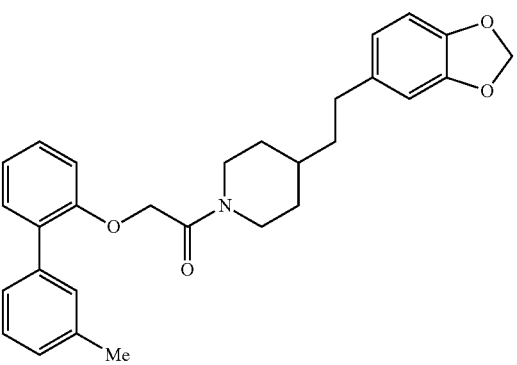 [SMILES: Cc1cccc(-c2ccccc2OCC(=O)N2CCC(CCc3ccc4c(c3)OCO4)CC2)c1] | 457.6 | 458 | |

TABLE 1-continued

| Compound No. | Structure | MW | Positive MS peak | Negative MS peak |
|---|---|---|---|---|
| 168 | 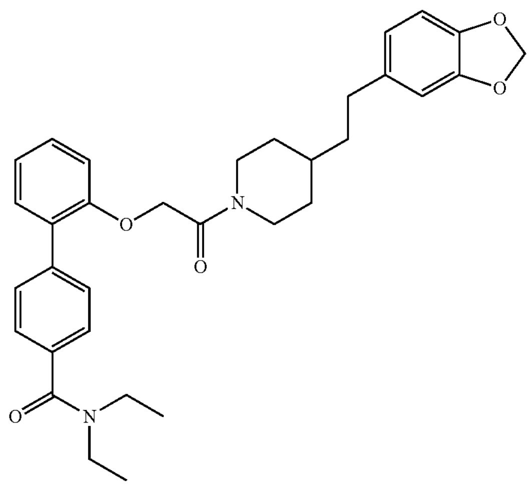 [SMILES: CCN(CC)C(=O)c1ccc(-c2ccccc2OCC(=O)N2CCC(CCc3ccc4c(c3)OCO4)CC2)cc1] | 542.7 | 543 | |
| 169 | 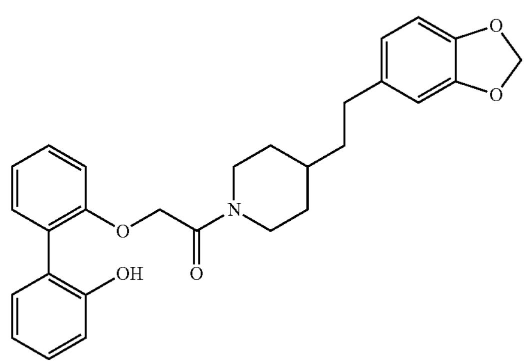 | 459.5 | 460 | 458 |
| 170 | 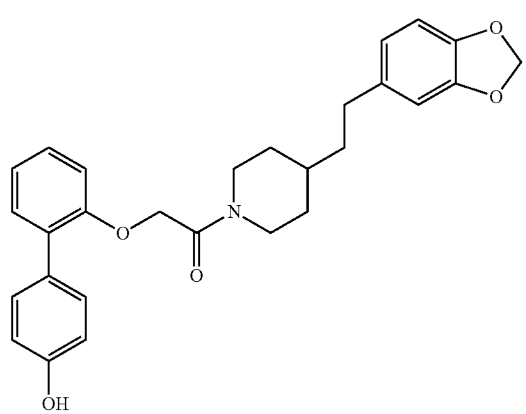 | 459.5 | 460 | 458 |

TABLE 1-continued

| Compound No. | Structure | MW | Positive MS peak | Negative MS peak |
|---|---|---|---|---|
| 171 | 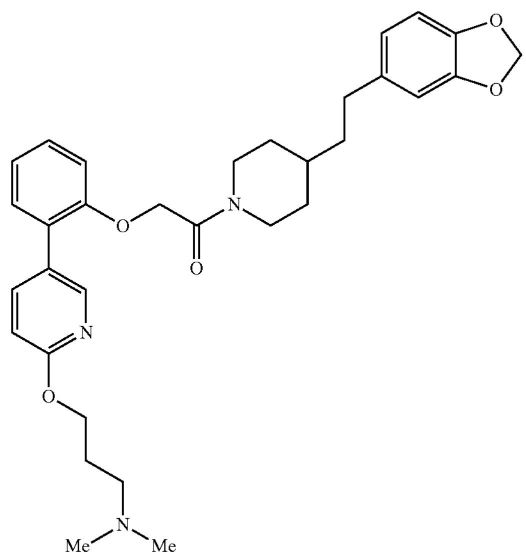 [SMILES: CN(C)CCCOc1ccc(-c2ccccc2OCC(=O)N2CCC(CCc3ccc4c(c3)OCO4)CC2)cn1] | 545.7 | 546 | |
| 172 | 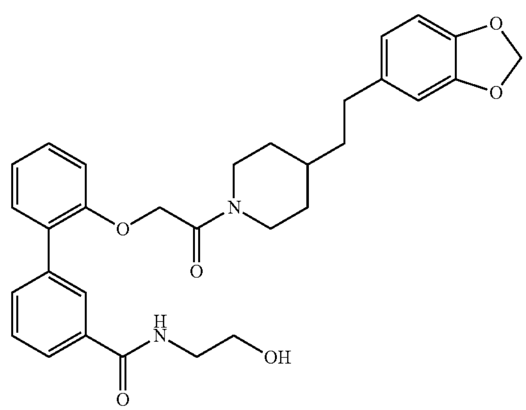 [SMILES: O=C(NCCO)c1cccc(-c2ccccc2OCC(=O)N2CCC(CCc3ccc4c(c3)OCO4)CC2)c1] | 530.6 | 531 | 529 |
| 173 | 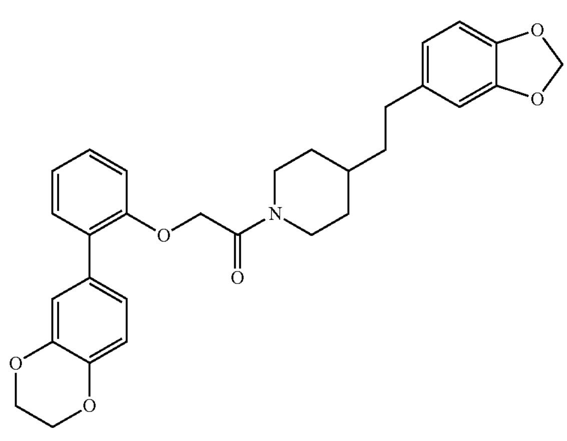 [SMILES: O=C(COc1ccccc1-c1ccc2c(c1)OCCO2)N1CCC(CCc2ccc3c(c2)OCO3)CC1] | 501.6 | 502 | |

TABLE 1-continued

| Compound No. | Structure | MW | Positive MS peak | Negative MS peak |
|---|---|---|---|---|
| 174 | 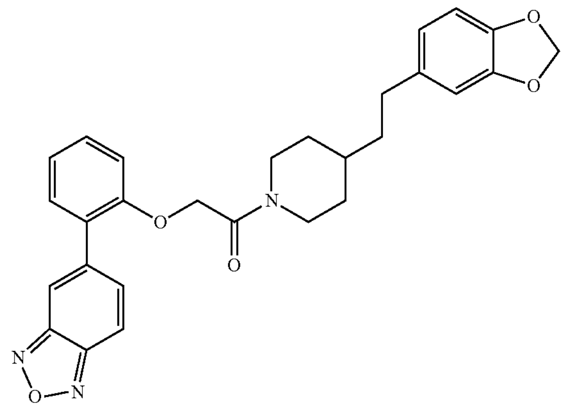 [SMILES: O=C(COc1ccccc1-c1ccc2nonc2c1)N1CCC(CCc2ccc3c(c2)OCO3)CC1] | 485.5 | 486 | |
| 175 | 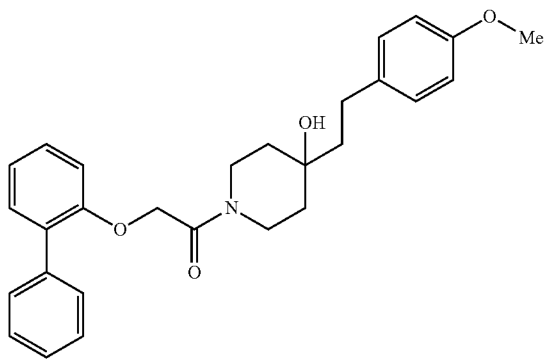 [SMILES: COc1ccc(CCC2(O)CCN(C(=O)COc3ccccc3-c3ccccc3)CC2)cc1] | 445.6 | 446 | |
| 176 | 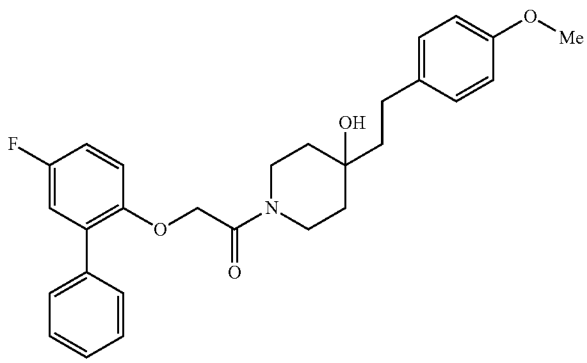 [SMILES: COc1ccc(CCC2(O)CCN(C(=O)COc3ccc(F)cc3-c3ccccc3)CC2)cc1] | 463.5 | 464 | |
| 177 | 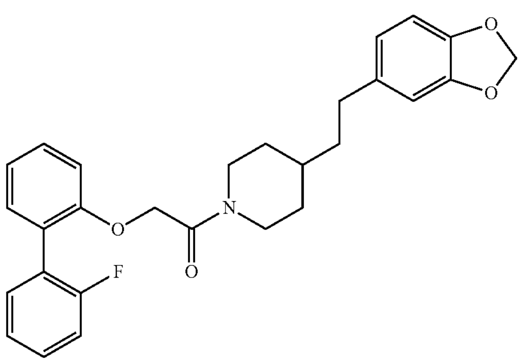 [SMILES: O=C(COc1ccccc1-c1ccccc1F)N1CCC(CCc2ccc3c(c2)OCO3)CC1] | 461.5 | 462 | |

TABLE 1-continued

| Compound No. | Structure | MW | Positive MS peak | Negative MS peak |
| --- | --- | --- | --- | --- |
| 178 | 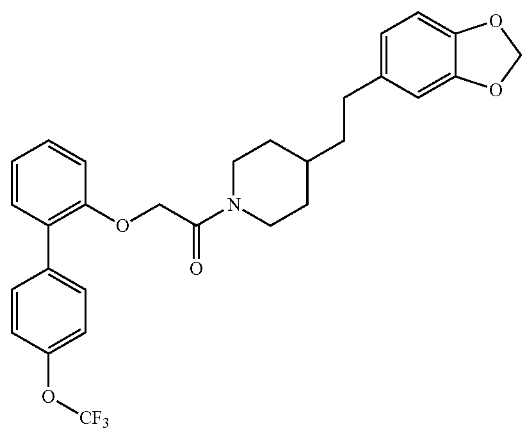 [SMILES: O=C(COc1ccccc1-c1ccc(OC(F)(F)F)cc1)N1CCC(CCc2ccc3c(c2)OCO3)CC1] | 527.5 | 528 | |
| 179 | 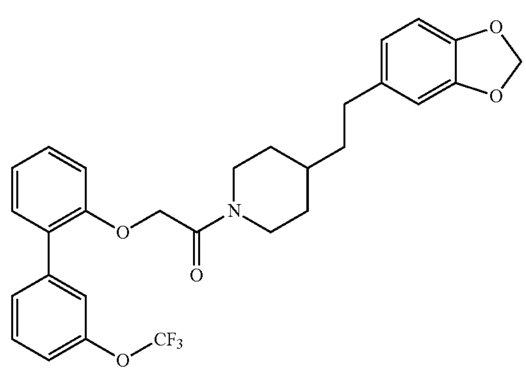 [SMILES: O=C(COc1ccccc1-c1cccc(OC(F)(F)F)c1)N1CCC(CCc2ccc3c(c2)OCO3)CC1] | 537.5 | 528 | |
| 180 | 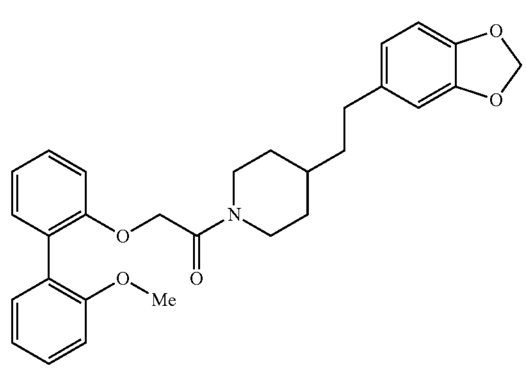 [SMILES: COc1ccccc1-c1ccccc1OCC(=O)N1CCC(CCc2ccc3c(c2)OCO3)CC1] | 473.6 | 474 | |

TABLE 1-continued

| Compound No. | Structure | MW | Positive MS peak | Negative MS peak |
|---|---|---|---|---|
| 181 | 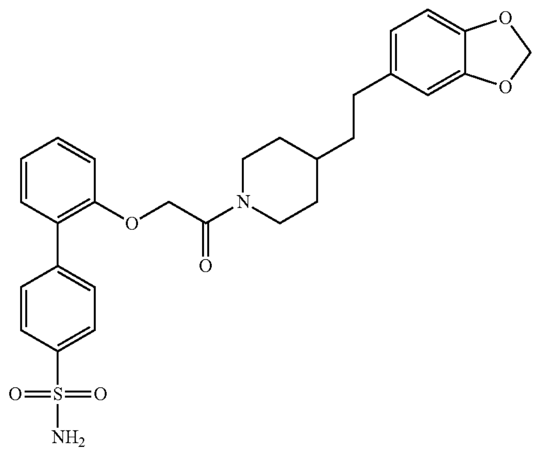 [SMILES: NS(=O)(=O)c1ccc(-c2ccccc2OCC(=O)N2CCC(CCc3ccc4c(c3)OCO4)CC2)cc1] | 522.6 | 523 | 521 |
| 182 | 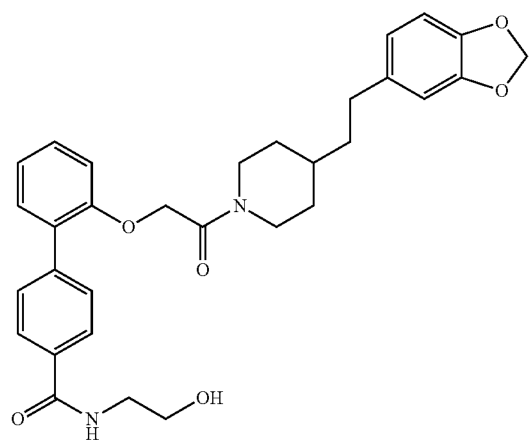 [SMILES: O=C(NCCO)c1ccc(-c2ccccc2OCC(=O)N2CCC(CCc3ccc4c(c3)OCO4)CC2)cc1] | 530.6 | 531 | 529 |
| 183 | 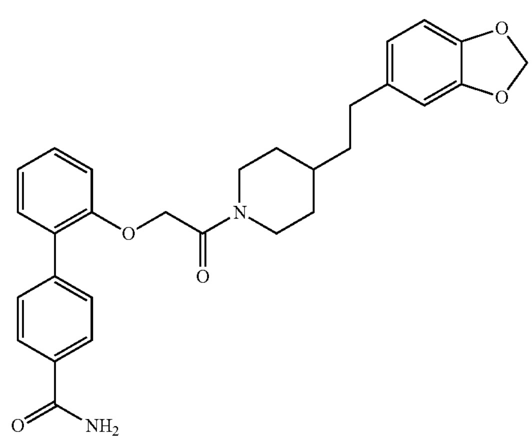 [SMILES: NC(=O)c1ccc(-c2ccccc2OCC(=O)N2CCC(CCc3ccc4c(c3)OCO4)CC2)cc1] | 486.6 | 487 | |

TABLE 1-continued

| Compound No. | Structure | MW | Positive MS peak | Negative MS peak |
|---|---|---|---|---|
| 184 | 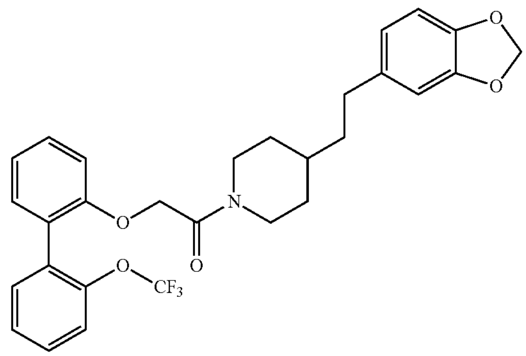 [SMILES: O=C(COc1ccccc1-c1ccccc1OC(F)(F)F)N1CCC(CCc2ccc3c(c2)OCO3)CC1] | 527.5 | 528 | |
| 185 | 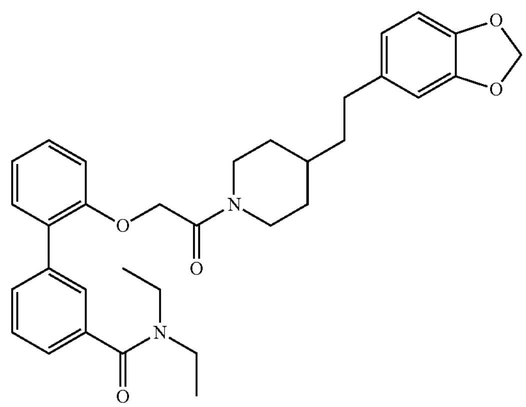 [SMILES: CCN(CC)C(=O)c1cccc(-c2ccccc2OCC(=O)N2CCC(CCc3ccc4c(c3)OCO4)CC2)c1] | 542.7 | 543 | |
| 186 | 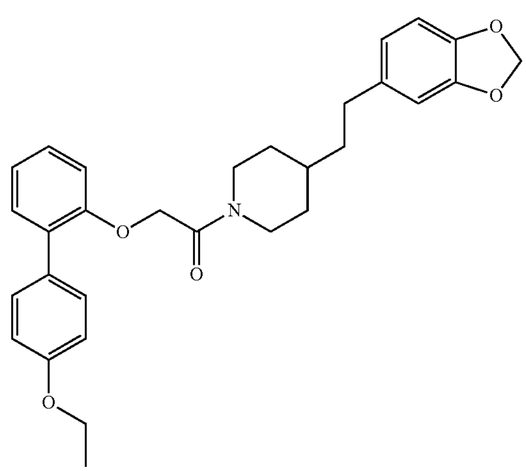 [SMILES: CCOc1ccc(-c2ccccc2OCC(=O)N2CCC(CCc3ccc4c(c3)OCO4)CC2)cc1] | 487.6 | 488 | |

TABLE 1-continued

| Compound No. | Structure | MW | Positive MS peak | Negative MS peak |
|---|---|---|---|---|
| 187 | 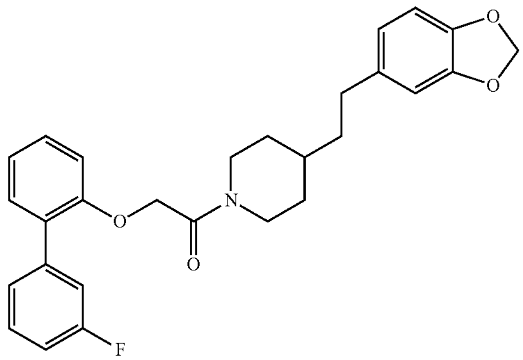 [SMILES: O=C(COc1ccccc1-c1cccc(F)c1)N1CCC(CCc2ccc3c(c2)OCO3)CC1] | 461.5 | 462 | |
| 188 | 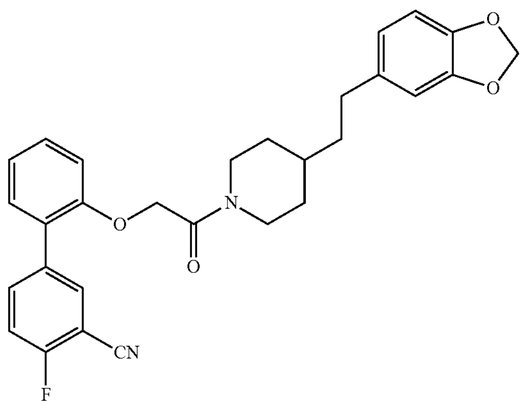 [SMILES: N#Cc1cc(-c2ccccc2OCC(=O)N2CCC(CCc3ccc4c(c3)OCO4)CC2)ccc1F] | 486.5 | 487 | |
| 189 | 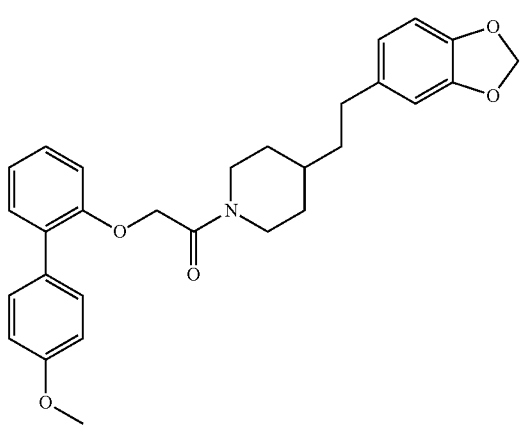 [SMILES: COc1ccc(-c2ccccc2OCC(=O)N2CCC(CCc3ccc4c(c3)OCO4)CC2)cc1] | 473.6 | 474 | |

TABLE 1-continued

| Compound No. | Structure | MW | Positive MS peak | Negative MS peak |
|---|---|---|---|---|
| 190 | 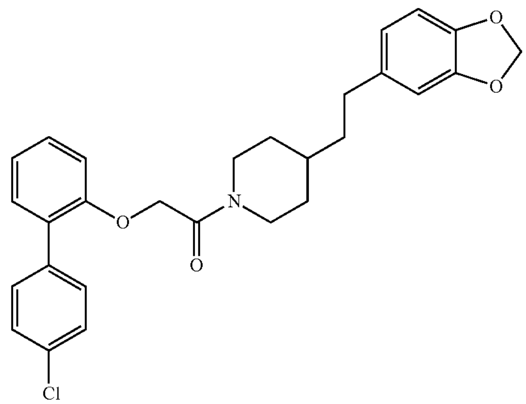 [SMILES: O=C(COc1ccccc1-c1ccc(Cl)cc1)N1CCC(CCc2ccc3c(c2)OCO3)CC1] | 478.0 | 478 | |
| 191 | 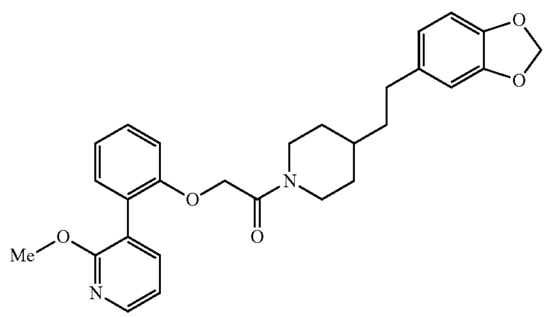 [SMILES: COc1ncccc1-c1ccccc1OCC(=O)N1CCC(CCc2ccc3c(c2)OCO3)CC1] | 474.6 | 475 | |
| 192 | 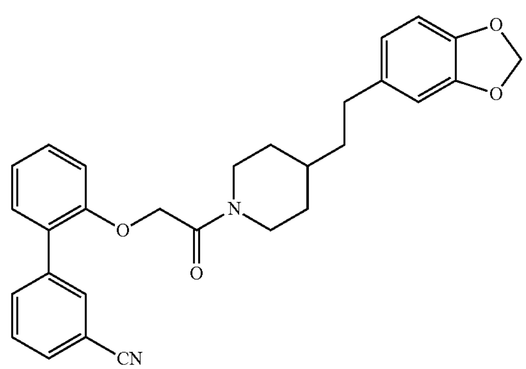 [SMILES: N#Cc1cccc(-c2ccccc2OCC(=O)N2CCC(CCc3ccc4c(c3)OCO4)CC2)c1] | 468.5 | 469 | |
| 193 | 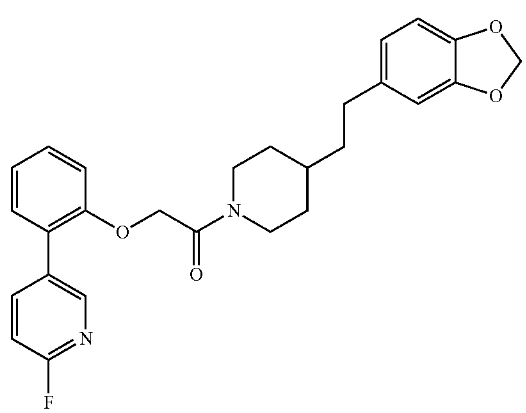 [SMILES: O=C(COc1ccccc1-c1ccc(F)nc1)N1CCC(CCc2ccc3c(c2)OCO3)CC1] | 462.5 | 463 | |

TABLE 1-continued

| Compound No. | Structure | MW | Positive MS peak | Negative MS peak |
|---|---|---|---|---|
| 194 | 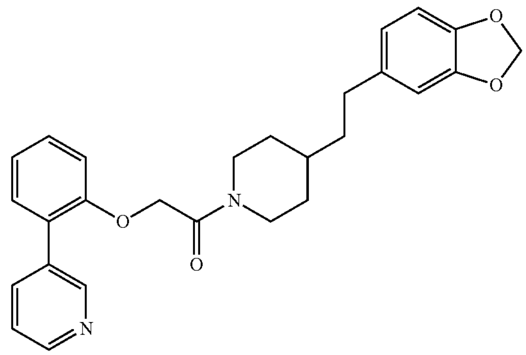 [SMILES: O=C(COc1ccccc1-c1cccnc1)N1CCC(CCc2ccc3c(c2)OCO3)CC1] | 444.5 | 445 | |
| 195 | 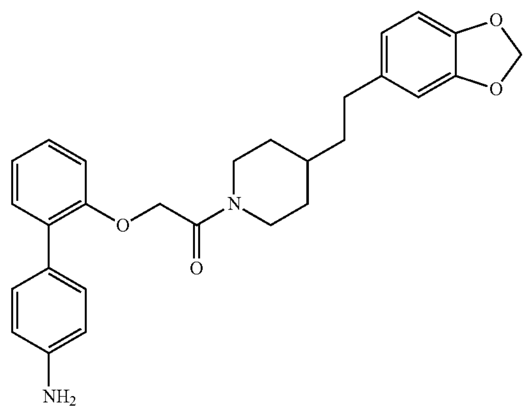 [SMILES: Nc1ccc(-c2ccccc2OCC(=O)N2CCC(CCc3ccc4c(c3)OCO4)CC2)cc1] | 458.6 | 459 | |
| 196 | 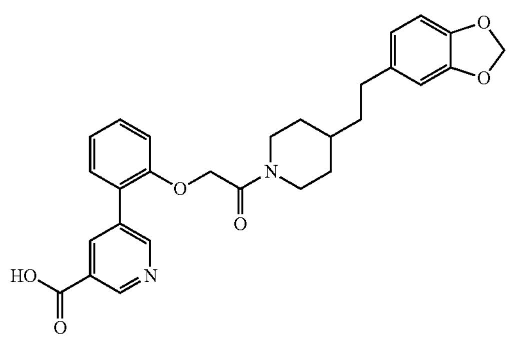 [SMILES: O=C(O)c1cncc(-c2ccccc2OCC(=O)N2CCC(CCc3ccc4c(c3)OCO4)CC2)c1] | 488.5 | 489 | 487 |
| 197 | 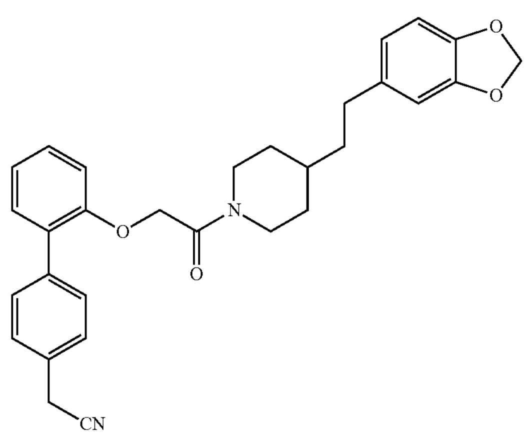 [SMILES: N#CCc1ccc(-c2ccccc2OCC(=O)N2CCC(CCc3ccc4c(c3)OCO4)CC2)cc1] | 482.6 | 483 | |

TABLE 1-continued
| Compound No. | Structure | MW | Positive MS peak | Negative MS peak |
|---|---|---|---|---|
| 198 | 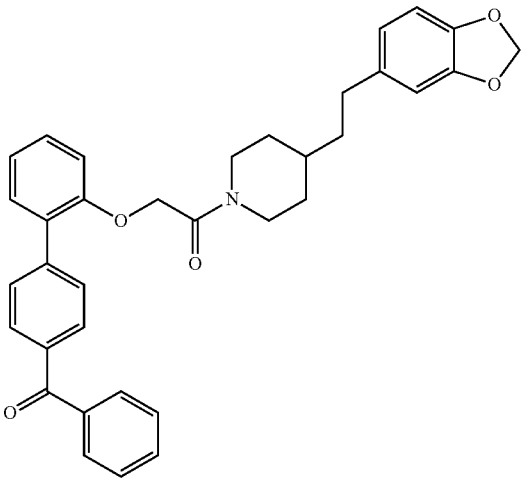 [SMILES: O=C(c1ccccc1)c1ccc(-c2ccccc2OCC(=O)N2CCC(CCc3ccc4c(c3)OCO4)CC2)cc1] | 547.6 | 548 | |
| 199 | 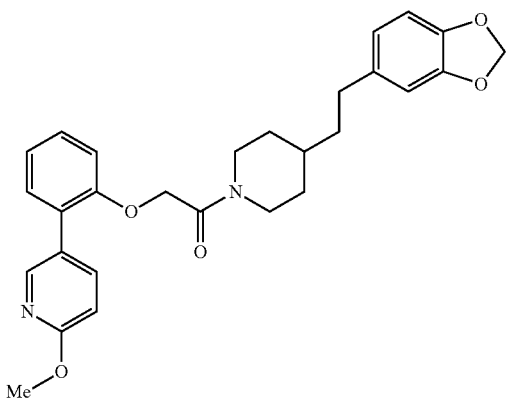 [SMILES: COc1ccc(-c2ccccc2OCC(=O)N2CCC(CCc3ccc4c(c3)OCO4)CC2)cn1] | 474.6 | 475 | |
| 200 | 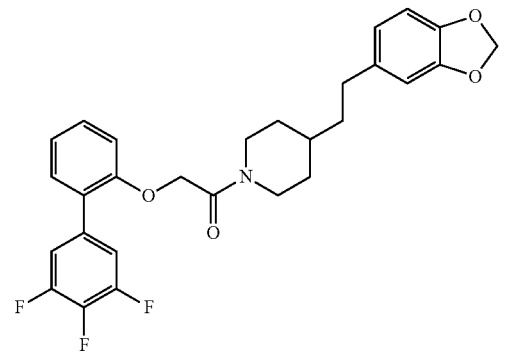 [SMILES: O=C(COc1ccccc1-c1cc(F)c(F)c(F)c1)N1CCC(CCc2ccc3c(c2)OCO3)CC1] | 497.5 | 498 | |

TABLE 1-continued

| Compound No. | Structure | MW | Positive MS peak | Negative MS peak |
|---|---|---|---|---|
| 201 | 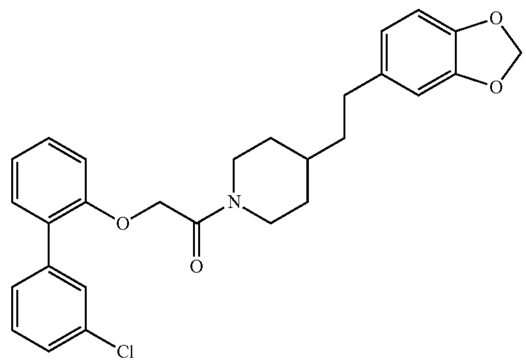 [SMILES: O=C(COc1ccccc1-c1cccc(Cl)c1)N1CCC(CCc2ccc3c(c2)OCO3)CC1] | 478.0 | 478 | |
| 202 | 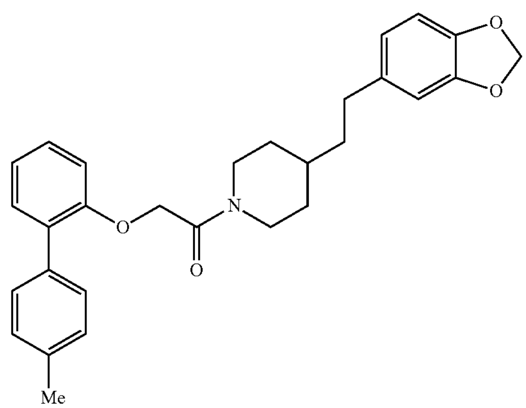 | 457.6 | 458 | |
| 203 | 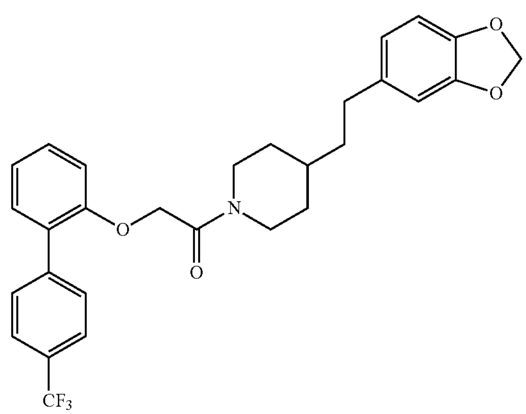 [SMILES: O=C(COc1ccccc1-c1ccc(C(F)(F)F)cc1)N1CCC(CCc2ccc3c(c2)OCO3)CC1] | 511.5 | 512 | |
| 204 | 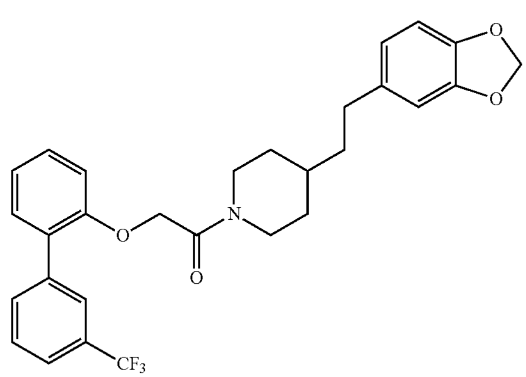 [SMILES: O=C(COc1ccccc1-c1cccc(C(F)(F)F)c1)N1CCC(CCc2ccc3c(c2)OCO3)CC1] | 511.5 | 512 | |

TABLE 1-continued

| Compound No. | Structure | MW | Positive MS peak | Negative MS peak |
|---|---|---|---|---|
| 205 | 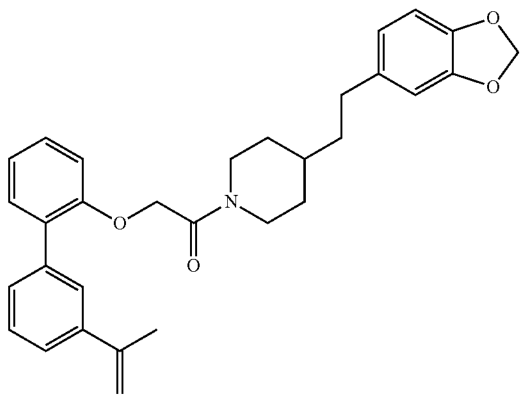 [SMILES: C=C(C)c1cccc(-c2ccccc2OCC(=O)N2CCC(CCc3ccc4c(c3)OCO4)CC2)c1] | 483.6 | 484 | |
| 206 | 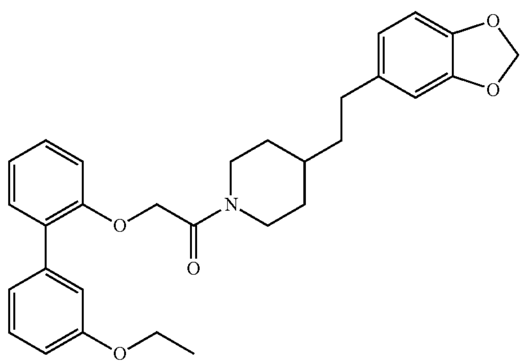 [SMILES: CCOc1cccc(-c2ccccc2OCC(=O)N2CCC(CCc3ccc4c(c3)OCO4)CC2)c1] | 487.6 | 488 | |
| 207 | 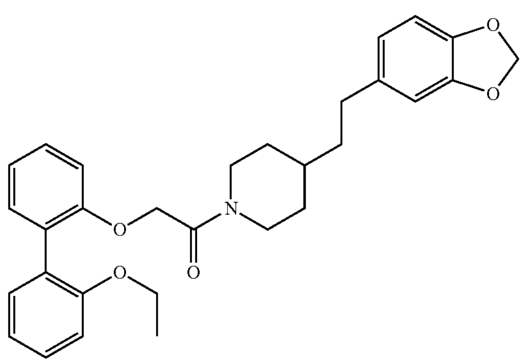 [SMILES: CCOc1ccccc1-c1ccccc1OCC(=O)N1CCC(CCc2ccc3c(c2)OCO3)CC1] | 487.6 | 488 | |
| 208 | 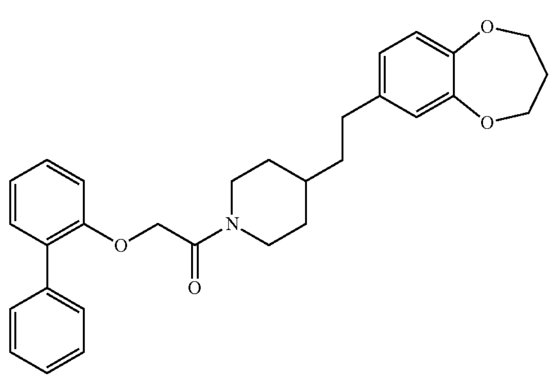 [SMILES: O=C(COc1ccccc1-c1ccccc1)N1CCC(CCc2ccc3c(c2)OCCCO3)CC1] | 471.6 | 472 | |

TABLE 1-continued
| Compound No. | Structure | MW | Positive MS peak | Negative MS peak |
|---|---|---|---|---|
| 209 | 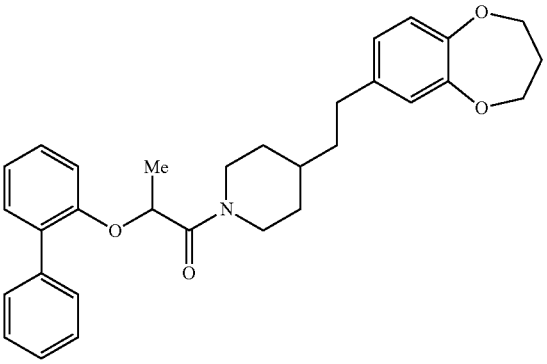 [SMILES: CC(Oc1ccccc1-c1ccccc1)C(=O)N1CCC(CCc2ccc3c(c2)OCCCO3)CC1] | 485.6 | 486 | |
| 210 | 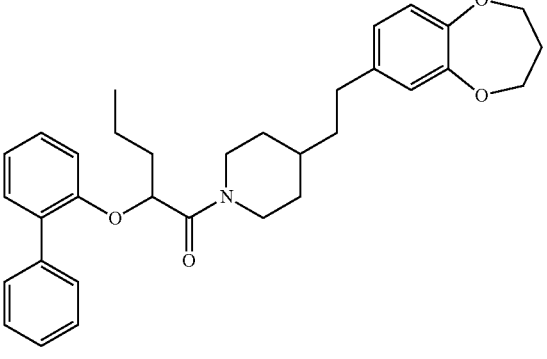 | 513.7 | 514 | |
| 211 | 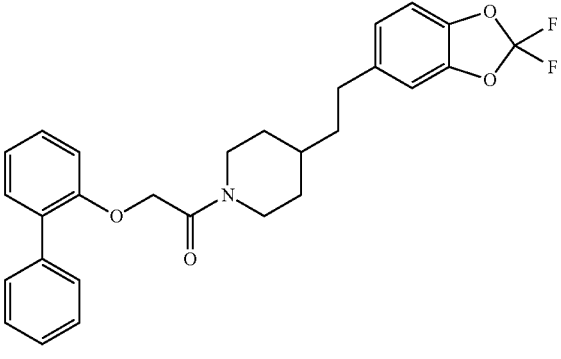 [SMILES: O=C(COc1ccccc1-c1ccccc1)N1CCC(CCc2ccc3c(c2)OC(F)(F)O3)CC1] | 479.5 | 480 | |
| 213 | 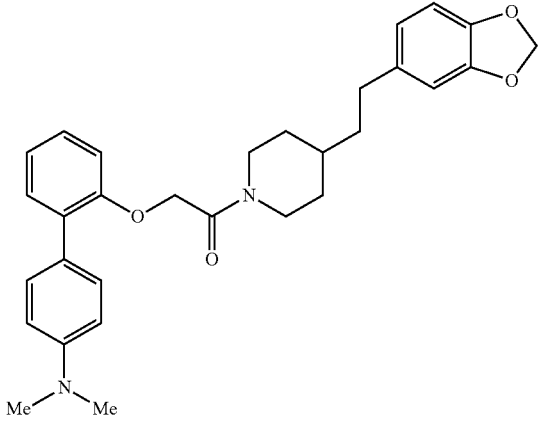 [SMILES: CN(C)c1ccc(-c2ccccc2OCC(=O)N2CCC(CCc3ccc4c(c3)OCO4)CC2)cc1] | 486.6 | 487 | |

TABLE 1-continued

| Compound No. | Structure | MW | Positive MS peak | Negative MS peak |
|---|---|---|---|---|
| 216 | 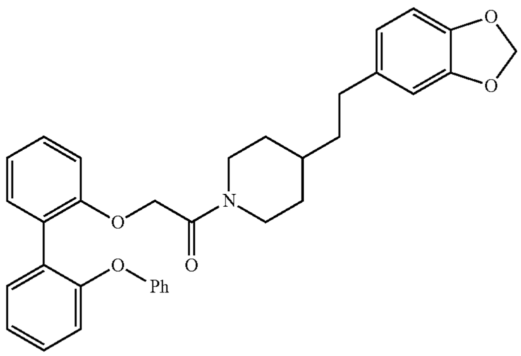 [SMILES: O=C(COc1ccccc1-c1ccccc1Oc1ccccc1)N1CCC(CCc2ccc3c(c2)OCO3)CC1] | 535.6 | 536 | |
| 217 | 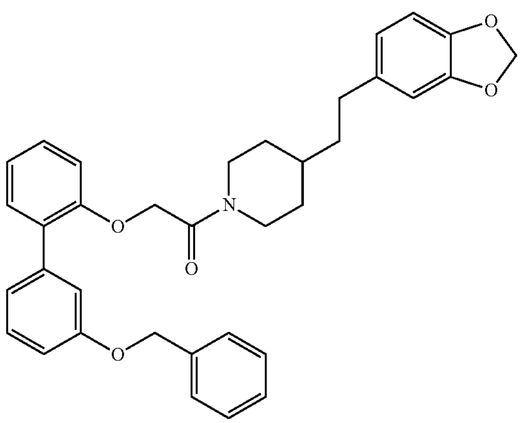 [SMILES: O=C(COc1ccccc1-c1cccc(OCc2ccccc2)c1)N1CCC(CCc2ccc3c(c2)OCO3)CC1] | 548.7 | 550 | |
| 218 | 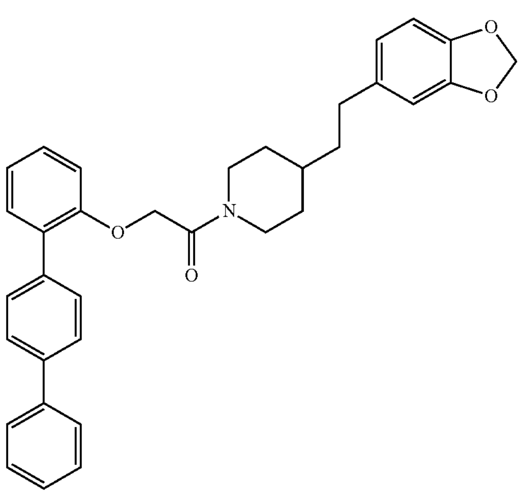 [SMILES: O=C(COc1ccccc1-c1ccc(-c2ccccc2)cc1)N1CCC(CCc2ccc3c(c2)OCO3)CC1] | 519.6 | 520 | |

TABLE 1-continued

| Compound No. | Structure | MW | Positive MS peak | Negative MS peak |
| --- | --- | --- | --- | --- |
| 219 | 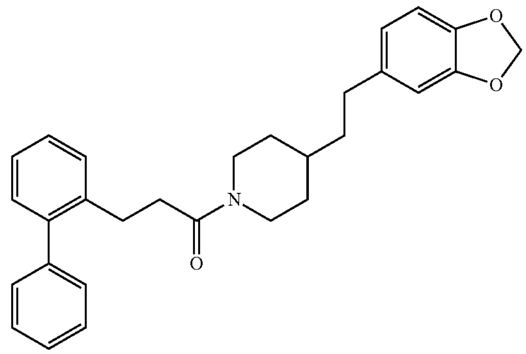 [SMILES: O=C(CCc1ccccc1-c1ccccc1)N1CCC(CCc2ccc3c(c2)OCO3)CC1] | 441.6 | 442 | |
| 220 | 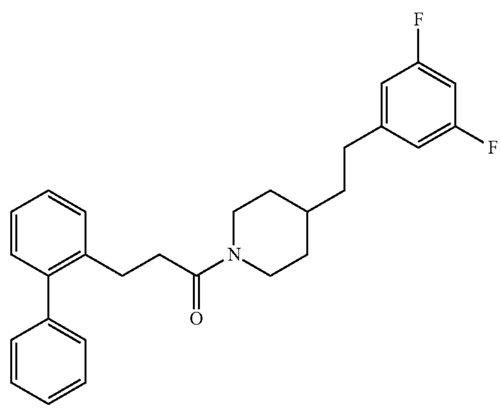 | 433.6 | 434 | |
| 221 | 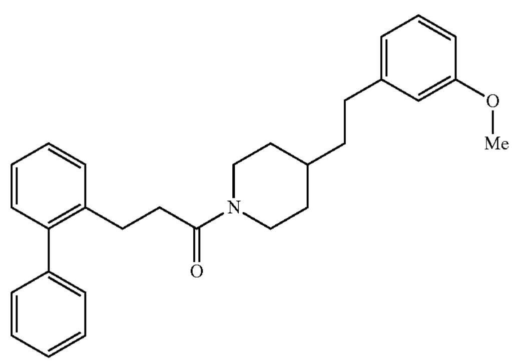 [SMILES: COc1cccc(CCC2CCN(C(=O)CCc3ccccc3-c3ccccc3)CC2)c1] | 427.6 | 428 | |
| 222 | 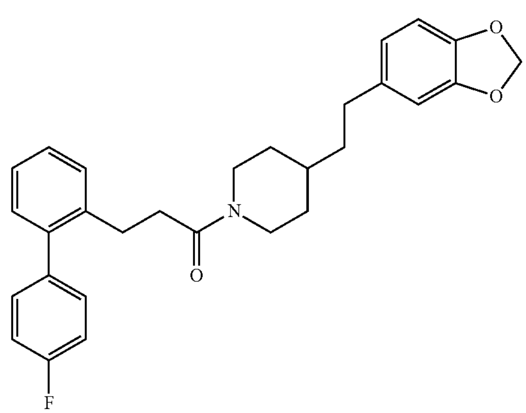 [SMILES: O=C(CCc1ccccc1-c1ccc(F)cc1)N1CCC(CCc2ccc3c(c2)OCO3)CC1] | 459.6 | 460 | |

TABLE 1-continued
| Compound No. | Structure | MW | Positive MS peak | Negative MS peak |
|---|---|---|---|---|
| 223 | 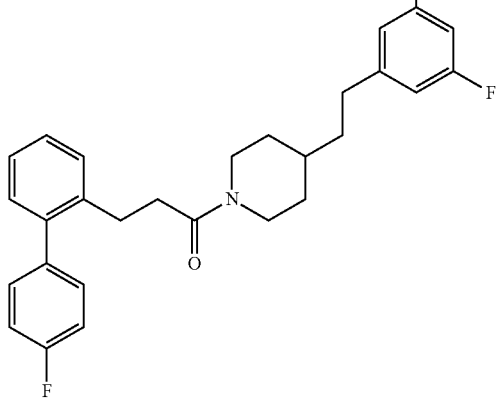 | 451.5 | 452 | |
| 224 | 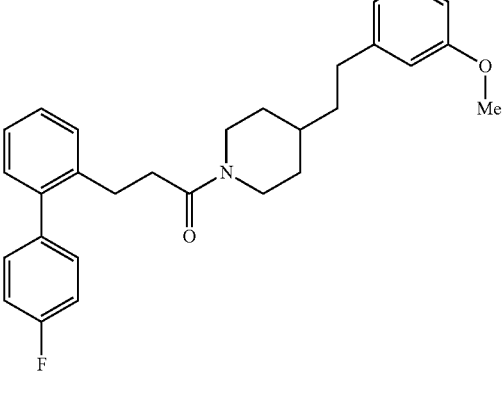 | 445.6 | 446 | |
| 225 | 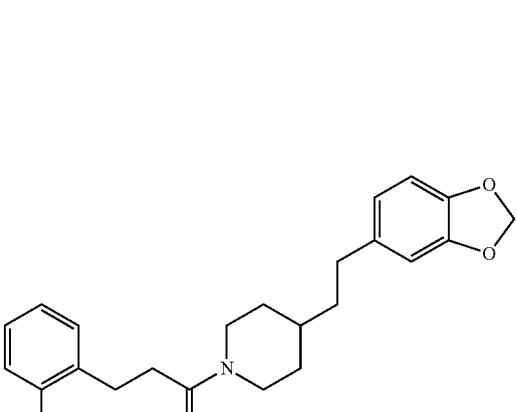 | 466.6 | 467 | |

TABLE 1-continued

| Compound No. | Structure | MW | Positive MS peak | Negative MS peak |
|---|---|---|---|---|
| 226 | 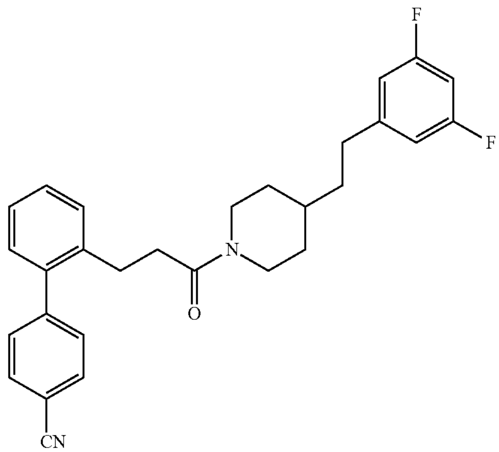 [SMILES: N#Cc1ccc(-c2ccccc2CCC(=O)N2CCC(CCc3cc(F)cc(F)c3)CC2)cc1] | 458.5 | 459 | |
| 227 | 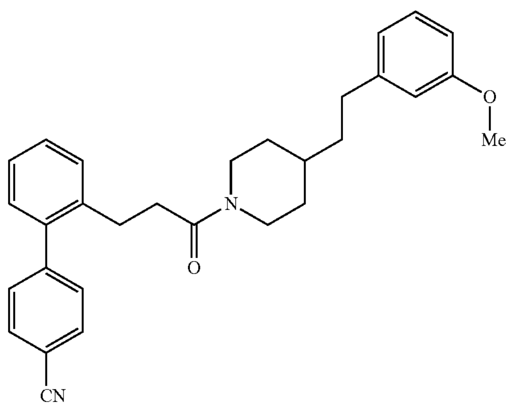 [SMILES: COc1cccc(CCC2CCN(C(=O)CCc3ccccc3-c3ccc(C#N)cc3)CC2)c1] | 452.6 | 453 | |
| 228 | 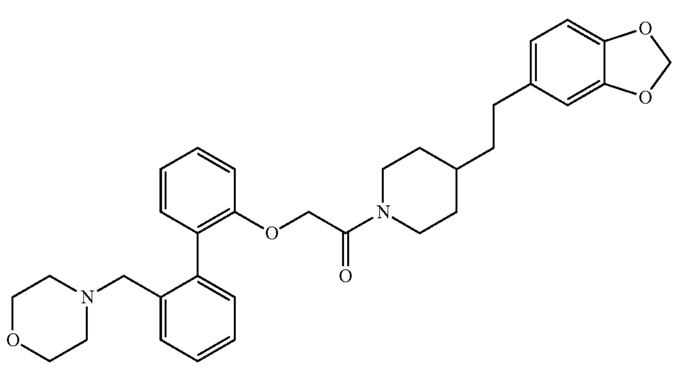 [SMILES: O=C(COc1ccccc1-c1ccccc1CN1CCOCC1)N1CCC(CCc2ccc3c(c2)OCO3)CC1] | 542.6 | 543 | |

TABLE 1-continued

| Compound No. | Structure | MW | Positive MS peak | Negative MS peak |
|---|---|---|---|---|
| 229 | 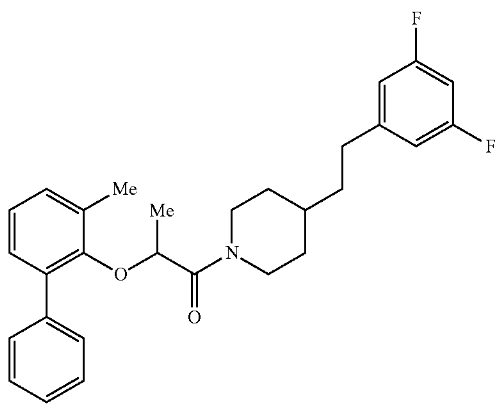 [SMILES: Cc1cccc(-c2ccccc2)c1OC(C)C(=O)N1CCC(CCc2cc(F)cc(F)c2)CC1] | 463.6 | 464 | |
| 230 | 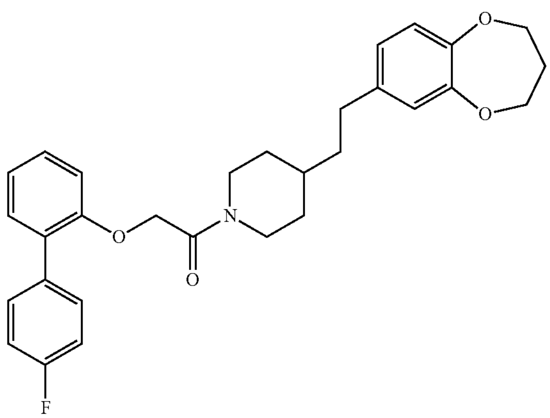 | 489.6 | 490 | |
| 231 | 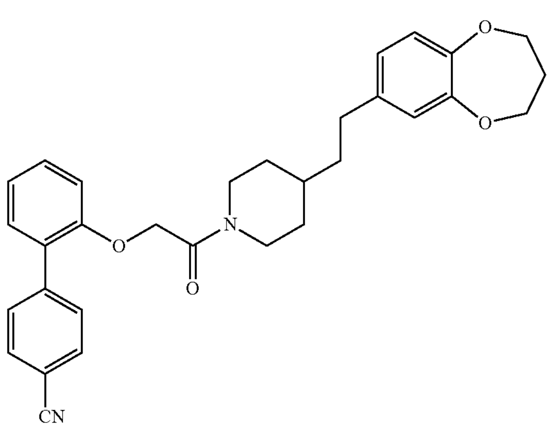 [SMILES: N#Cc1ccc(-c2ccccc2OCC(=O)N2CCC(CCc3ccc4c(c3)OCCCO4)CC2)cc1] | 496.6 | 497 | |

TABLE 1-continued
| Compound No. | Structure | MW | Positive MS peak | Negative MS peak |
|---|---|---|---|---|
| 232 | 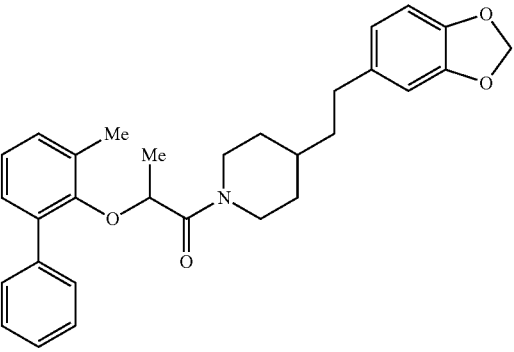 [SMILES: Cc1cccc(-c2ccccc2)c1OC(C)C(=O)N1CCC(CCc2ccc3c(c2)OCO3)CC1] | 515.6 | 516 | |
| 233 | 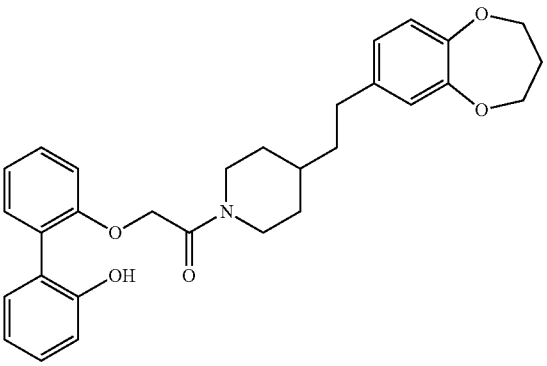 [SMILES: O=C(COc1ccccc1-c1ccccc1O)N1CCC(CCc2ccc3c(c2)OCCCO3)CC1] | 487.6 | 488 | 486 |
| 234 | 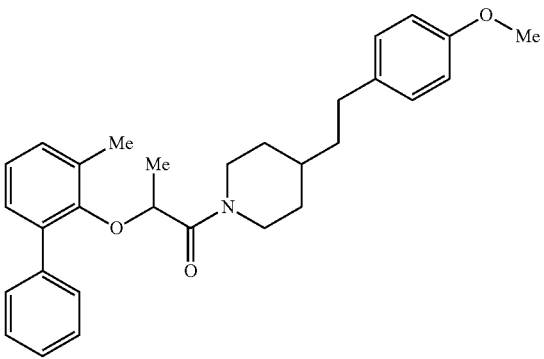 [SMILES: COc1ccc(CCC2CCN(C(=O)C(C)Oc3c(C)cccc3-c3ccccc3)CC2)cc1] | 457.6 | 458 | |
| 235 | 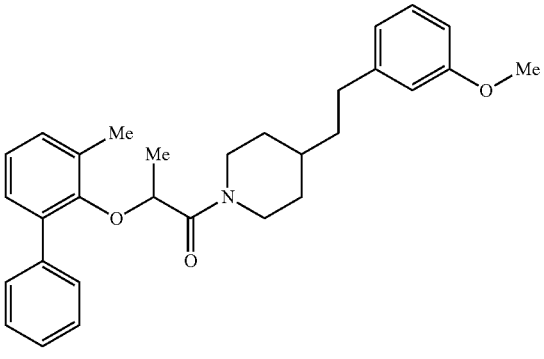 [SMILES: COc1cccc(CCC2CCN(C(=O)C(C)Oc3c(C)cccc3-c3ccccc3)CC2)c1] | 457.6 | 458 | |

TABLE 1-continued

| Compound No. | Structure | MW | Positive MS peak | Negative MS peak |
|---|---|---|---|---|
| 236 | 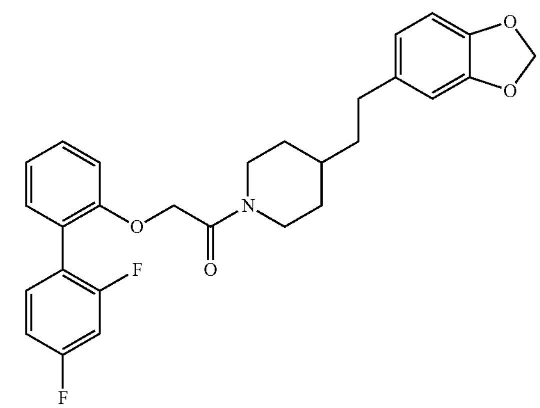 [SMILES: O=C(COc1ccccc1-c1ccc(F)cc1F)N1CCC(CCc2ccc3c(c2)OCO3)CC1] | 479.5 | 480 | |
| 237 | 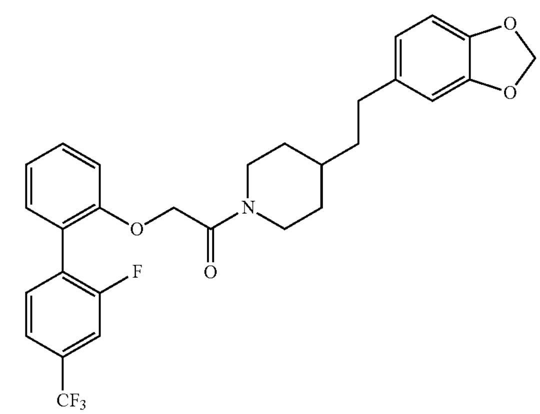 [SMILES: O=C(COc1ccccc1-c1ccc(C(F)(F)F)cc1F)N1CCC(CCc2ccc3c(c2)OCO3)CC1] | 529.5 | 530 | |
| 238 | 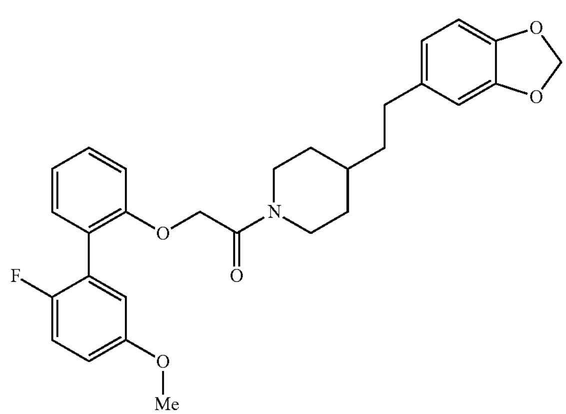 [SMILES: COc1ccc(F)c(-c2ccccc2OCC(=O)N2CCC(CCc3ccc4c(c3)OCO4)CC2)c1] | 491.6 | 492 | |

TABLE 1-continued

| Compound No. | Structure | MW | Positive MS peak | Negative MS peak |
|---|---|---|---|---|
| 239 | 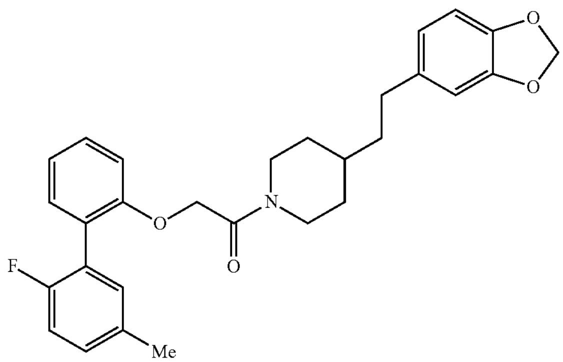 [SMILES: Cc1ccc(F)c(-c2ccccc2OCC(=O)N2CCC(CCc3ccc4c(c3)OCO4)CC2)c1] | 475.6 | 476 | |
| 240 | 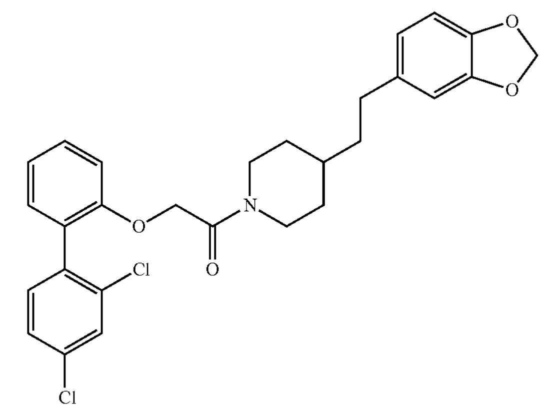 [SMILES: O=C(COc1ccccc1-c1ccc(Cl)cc1Cl)N1CCC(CCc2ccc3c(c2)OCO3)CC1] | 512.4 | 512/514 | |
| 241 | 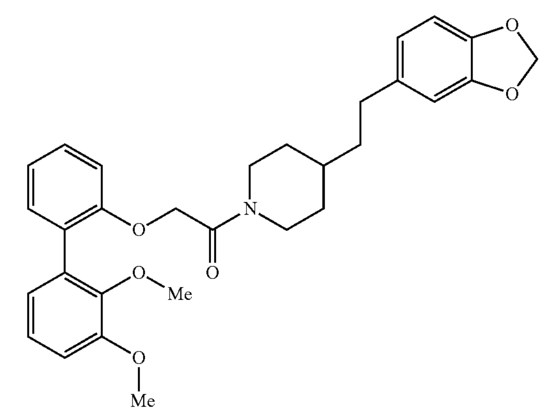 [SMILES: COc1cccc(-c2ccccc2OCC(=O)N2CCC(CCc3ccc4c(c3)OCO4)CC2)c1OC] | 503.6 | 504 | |
| 242 | 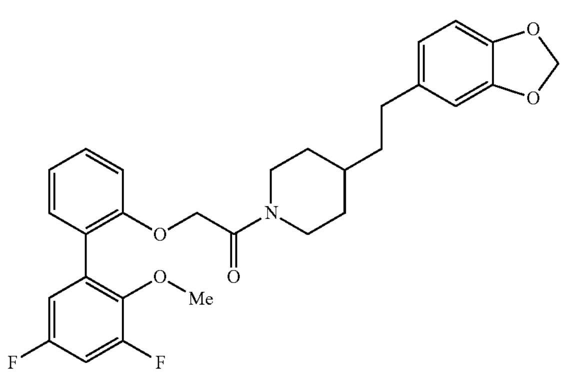 [SMILES: COc1c(F)cc(F)cc1-c1ccccc1OCC(=O)N1CCC(CCc2ccc3c(c2)OCO3)CC1] | 509.5 | 510 | |

TABLE 1-continued

| Compound No. | Structure | MW | Positive MS peak | Negative MS peak |
|---|---|---|---|---|
| 243 | 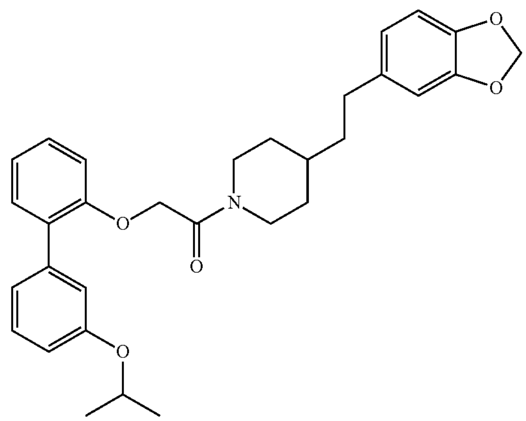 [SMILES: CC(C)Oc1cccc(-c2ccccc2OCC(=O)N2CCC(CCc3ccc4c(c3)OCO4)CC2)c1] | 501.6 | 502 | |
| 244 | 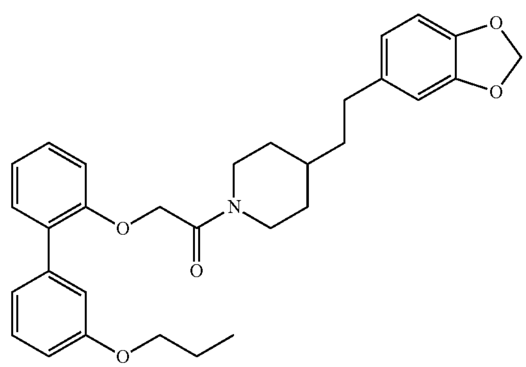 [SMILES: CCCOc1cccc(-c2ccccc2OCC(=O)N2CCC(CCc3ccc4c(c3)OCO4)CC2)c1] | 501.6 | 502 | |
| 245 | 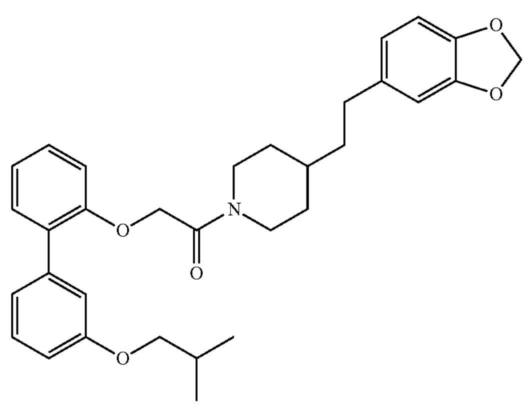 [SMILES: CC(C)COc1cccc(-c2ccccc2OCC(=O)N2CCC(CCc3ccc4c(c3)OCO4)CC2)c1] | 515.6 | 516 | |
| 246 | 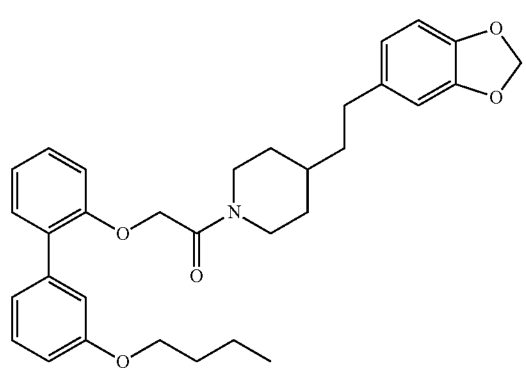 [SMILES: CCCCOc1cccc(-c2ccccc2OCC(=O)N2CCC(CCc3ccc4c(c3)OCO4)CC2)c1] | 515.6 | 516 | |

TABLE 1-continued
| Compound No. | Structure | MW | Positive MS peak | Negative MS peak |
|---|---|---|---|---|
| 247 | 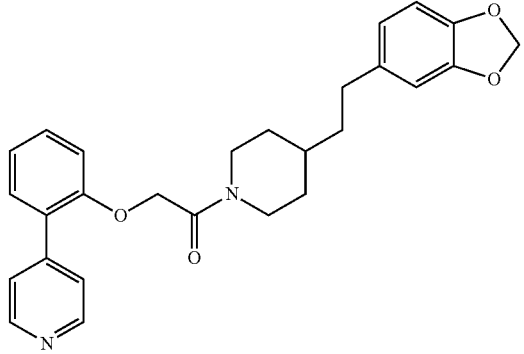 [SMILES: O=C(COc1ccccc1-c1ccncc1)N1CCC(CCc2ccc3c(c2)OCO3)CC1] | 444.5 | 445 | |
| 248 | 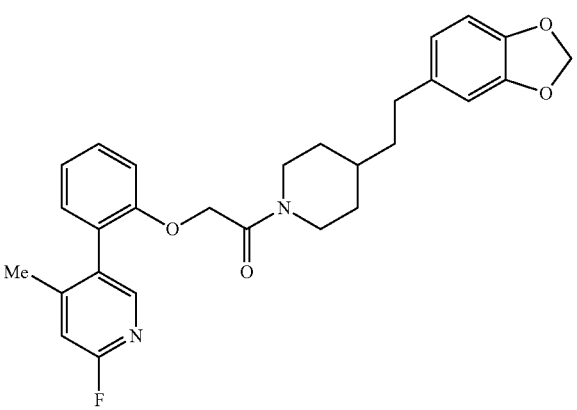 [SMILES: Cc1cc(F)ncc1-c1ccccc1OCC(=O)N1CCC(CCc2ccc3c(c2)OCO3)CC1] | 476.5 | 477 | |
| 249 | 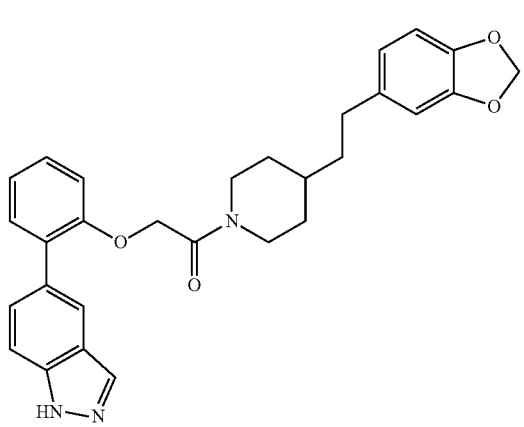 [SMILES: O=C(COc1ccccc1-c1ccc2[nH]ncc2c1)N1CCC(CCc2ccc3c(c2)OCO3)CC1] | 483.6 | 484 | 482 |

TABLE 1-continued

| Compound No. | Structure | MW | Positive MS peak | Negative MS peak |
|---|---|---|---|---|
| 250 | 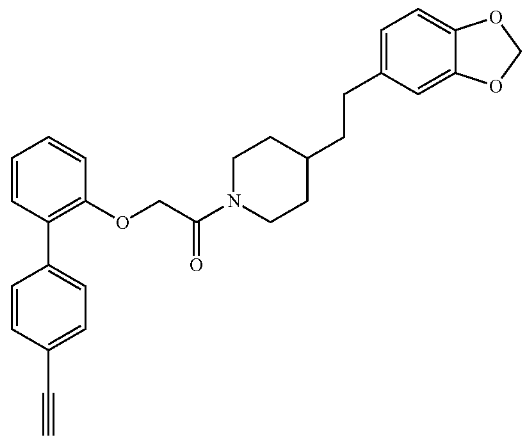 [SMILES: C#Cc1ccc(-c2ccccc2OCC(=O)N2CCC(CCc3ccc4c(c3)OCO4)CC2)cc1] | 467.6 | 468 | |
| 251 | 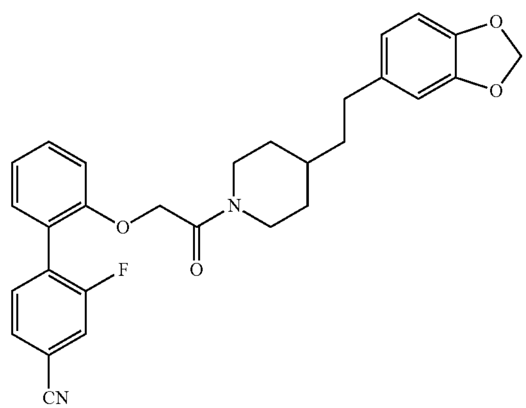 [SMILES: N#Cc1ccc(-c2ccccc2OCC(=O)N2CCC(CCc3ccc4c(c3)OCO4)CC2)c(F)c1] | 486.5 | 487 | |
| 252 | 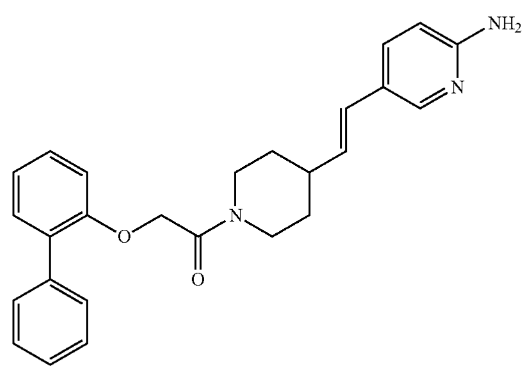 [SMILES: Nc1ccc(/C=C/C2CCN(C(=O)COc3ccccc3-c3ccccc3)CC2)cn1] | 413.5 | 414 | |
| 253 | 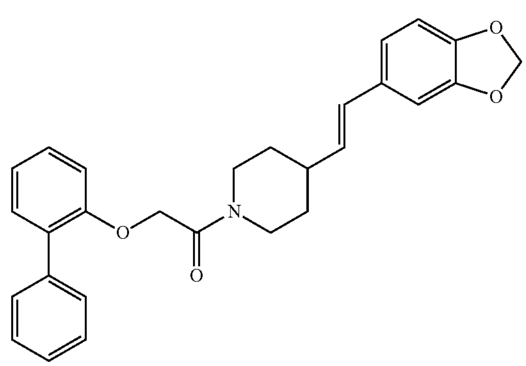 [SMILES: O=C(COc1ccccc1-c1ccccc1)N1CCC(/C=C/c2ccc3c(c2)OCO3)CC1] | 441.5 | 442 | |

TABLE 1-continued
| Compound No. | Structure | MW | Positive MS peak | Negative MS peak |
|---|---|---|---|---|
| 254 | 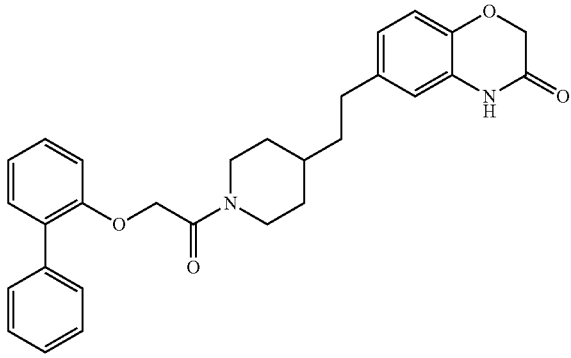 [SMILES: O=C1COc2ccc(CCC3CCN(C(=O)COc4ccccc4-c4ccccc4)CC3)cc2N1] | 470.6 | 471 | 469 |
| 255 | 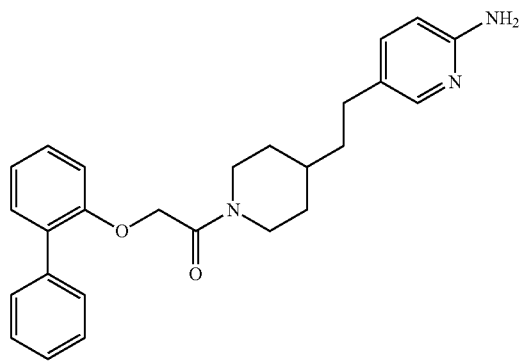 [SMILES: Nc1ccc(CCC2CCN(C(=O)COc3ccccc3-c3ccccc3)CC2)cn1] | 415.5 | 416 | |
| 256 | 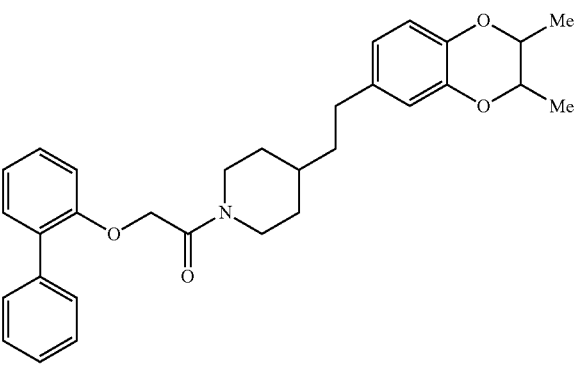 [SMILES: CC1Oc2ccc(CCC3CCN(C(=O)COc4ccccc4-c4ccccc4)CC3)cc2OC1C] | 485.6 | 486 | |
| 257 | 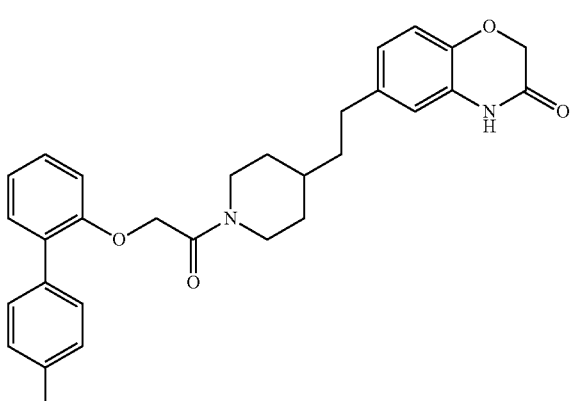 | 495.6 | 496 | 494 |

TABLE 1-continued

| Compound No. | Structure | MW | Positive MS peak | Negative MS peak |
|---|---|---|---|---|
| 258 | 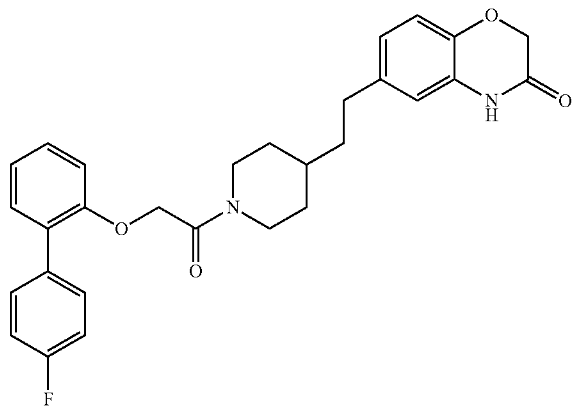 [SMILES: O=C1COc2ccc(CCC3CCN(C(=O)COc4ccccc4-c4ccc(F)cc4)CC3)cc2N1] | 488.6 | 489 | 487 |
| 259 | 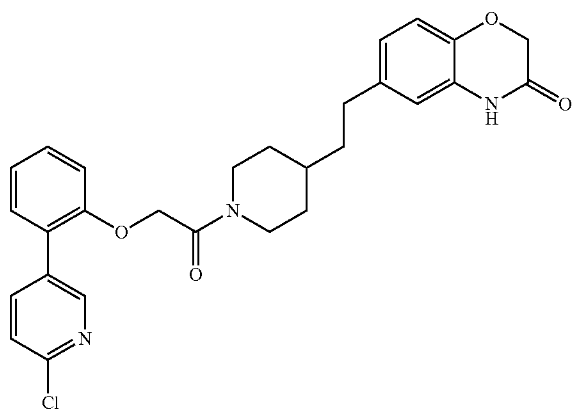 [SMILES: O=C1COc2ccc(CCC3CCN(C(=O)COc4ccccc4-c4ccc(Cl)nc4)CC3)cc2N1] | 506.0 | 506 | 504 |
| 260 | 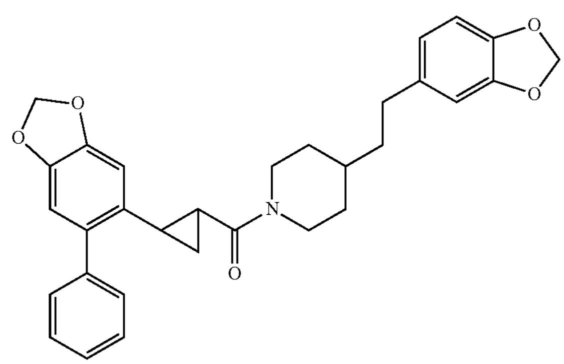 [SMILES: O=C(C1CC1c1cc2c(cc1-c1ccccc1)OCO2)N1CCC(CCc2ccc3c(c2)OCO3)CC1] | 497.6 | 498 | |
| 261 | 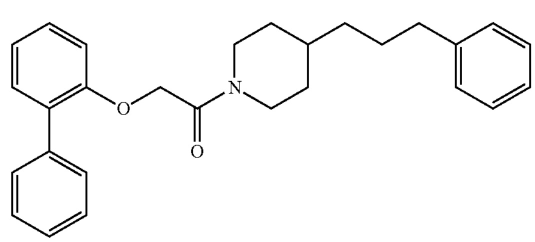 [SMILES: O=C(COc1ccccc1-c1ccccc1)N1CCC(CCCc2ccccc2)CC1] | 413.6 | 414 | |

TABLE 1-continued

| Compound No. | Structure | MW | Positive MS peak | Negative MS peak |
|---|---|---|---|---|
| 262 | 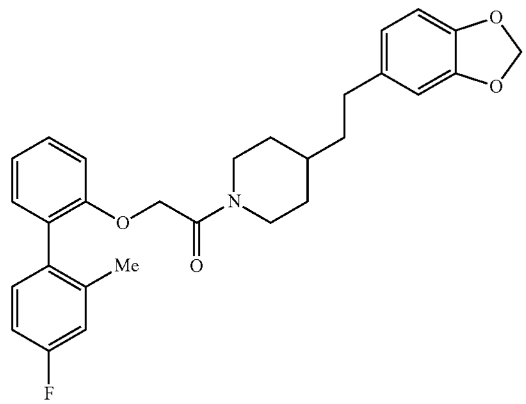 [SMILES: Cc1cc(F)ccc1-c1ccccc1OCC(=O)N1CCC(CCc2ccc3c(c2)OCO3)CC1] | 475.6 | 476 | |
| 263 | 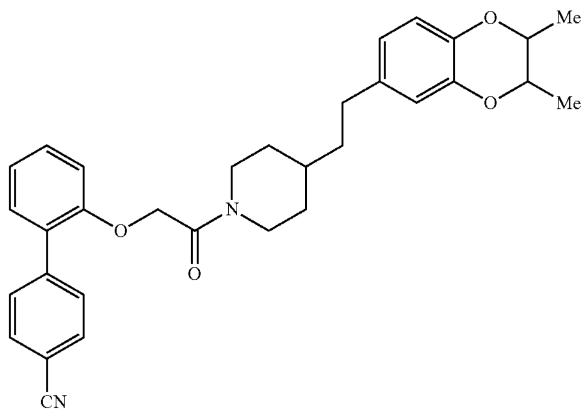 | 510.6 | 511 | |
| 264 | 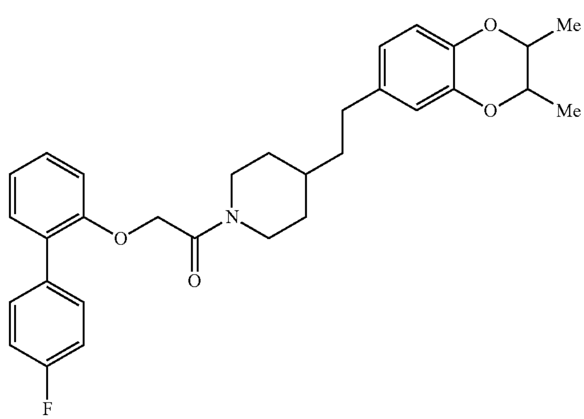 | 503.6 | 504 | |

TABLE 1-continued

| Compound No. | Structure | MW | Positive MS peak | Negative MS peak |
|---|---|---|---|---|
| 265 | 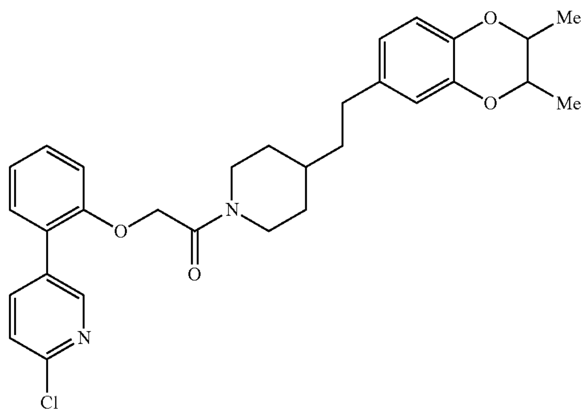 | 521.1 | 521 | |
| 266 | 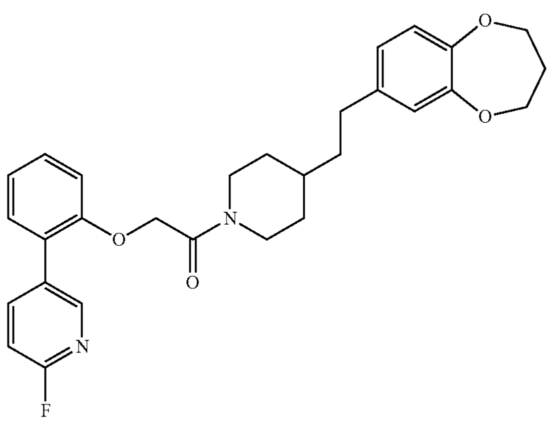 | 490.6 | 491 | |
| 267 | 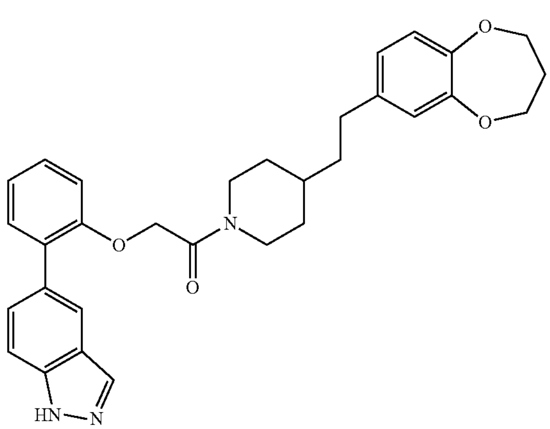 [SMILES: O=C(COc1ccccc1-c1ccc2[nH]ncc2c1)N1CCC(CCc2ccc3c(c2)OCCCO3)CC1] | 511.6 | 512 | |

TABLE 1-continued
| Compound No. | Structure | MW | Positive MS peak | Negative MS peak |
|---|---|---|---|---|
| 268 | 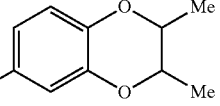 | 525.6 | 526 | 524 |
| 269 | 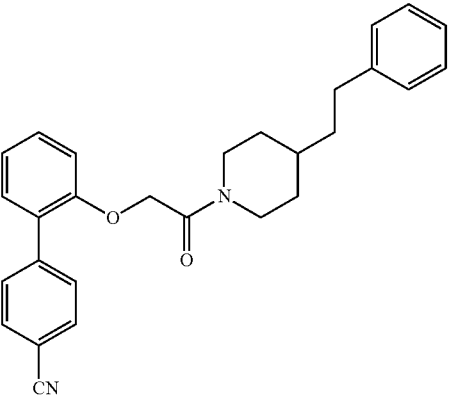 [SMILES: N#Cc1ccc(-c2ccccc2OCC(=O)N2CCC(CCc3ccccc3)CC2)cc1] | 424.5 | 425 | |
| 270 | 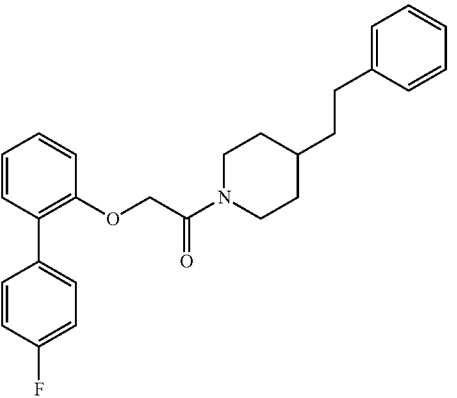 [SMILES: O=C(COc1ccccc1-c1ccc(F)cc1)N1CCC(CCc2ccccc2)CC1] | 417.5 | 418 | |

TABLE 1-continued

| Compound No. | Structure | MW | Positive MS peak | Negative MS peak |
|---|---|---|---|---|
| 271 | 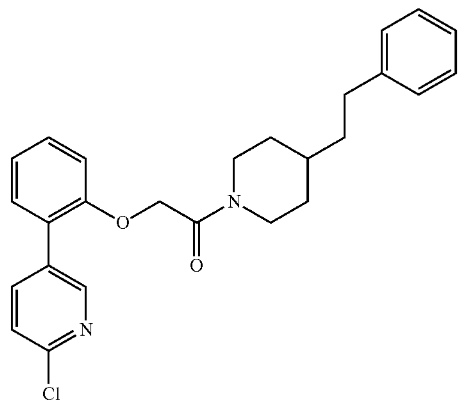 [SMILES: O=C(COc1ccccc1-c1ccc(Cl)nc1)N1CCC(CCc2ccccc2)CC1] | 435.0 | 435 | |
| 272 | 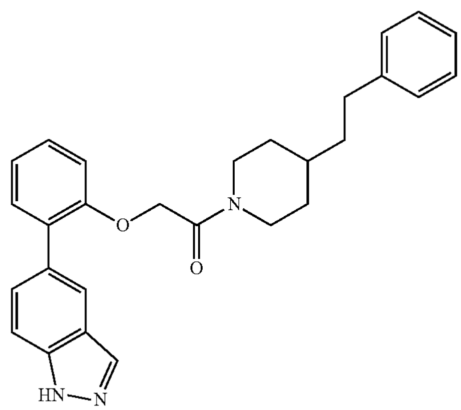 [SMILES: O=C(COc1ccccc1-c1ccc2[nH]ncc2c1)N1CCC(CCc2ccccc2)CC1] | 439.6 | 440 | 438 |
| 273 | 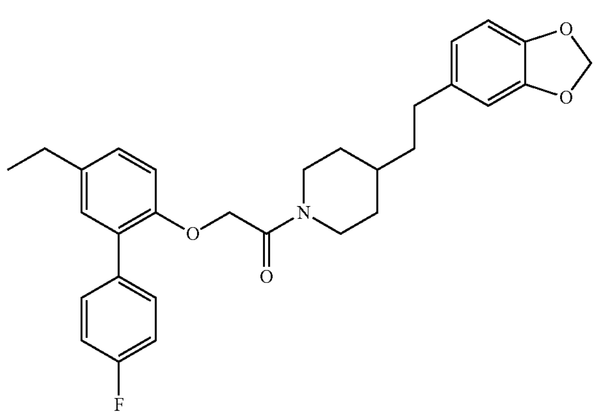 [SMILES: CCc1ccc(OCC(=O)N2CCC(CCc3ccc4c(c3)OCO4)CC2)c(-c2ccc(F)cc2)c1] | 489.6 | 490 | |

TABLE 1-continued

| Compound No. | Structure | MW | Positive MS peak | Negative MS peak |
|---|---|---|---|---|
| 274 | 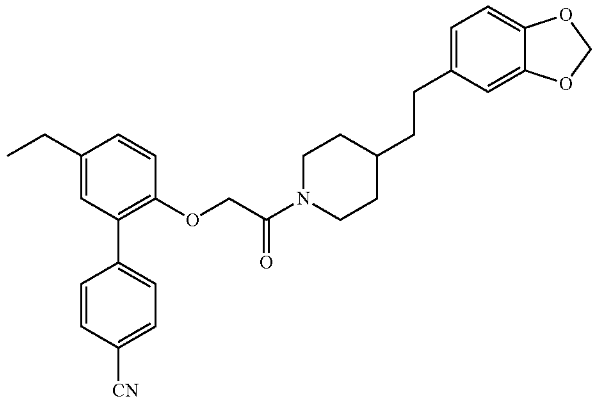 [SMILES: CCc1ccc(OCC(=O)N2CCC(CCc3ccc4c(c3)OCO4)CC2)c(-c2ccc(C#N)cc2)c1] | 496.6 | 497 | |
| 275 | 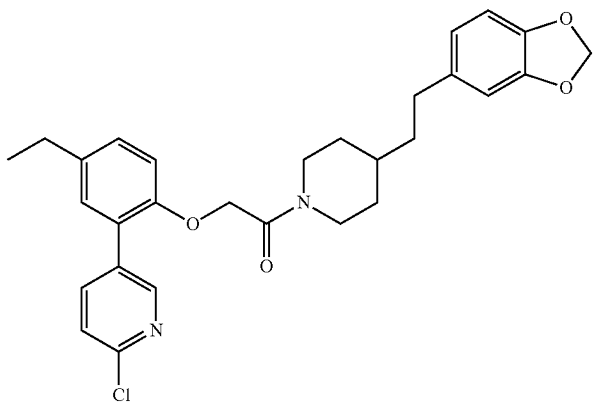 [SMILES: CCc1ccc(OCC(=O)N2CCC(CCc3ccc4c(c3)OCO4)CC2)c(-c2ccc(Cl)nc2)c1] | 507.0 | 507 | |
| 276 | 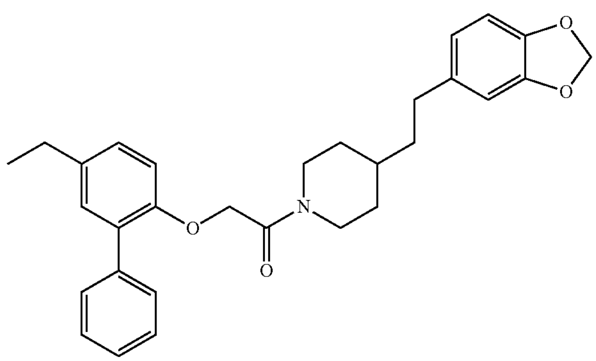 [SMILES: CCc1ccc(OCC(=O)N2CCC(CCc3ccc4c(c3)OCO4)CC2)c(-c2ccccc2)c1] | 471.6 | 472 | |
| 277 | 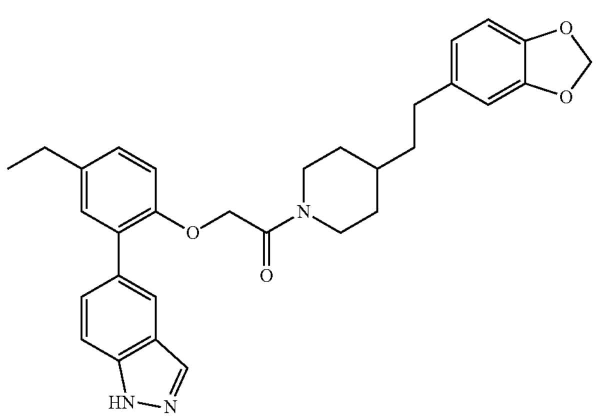 [SMILES: CCc1ccc(OCC(=O)N2CCC(CCc3ccc4c(c3)OCO4)CC2)c(-c2ccc3[nH]ncc3c2)c1] | 511.6 | | 510 |

TABLE 1-continued

| Compound No. | Structure | MW | Positive MS peak | Negative MS peak |
|---|---|---|---|---|
| 278 | 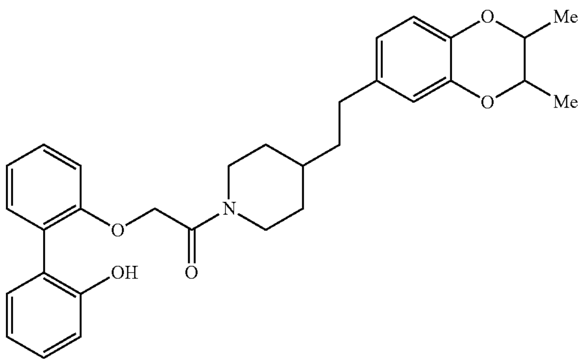 [SMILES: CC1Oc2ccc(CCC3CCN(C(=O)COc4ccccc4-c4ccccc4O)CC3)cc2OC1C] | 501.6 | | 500 |
| 279 | 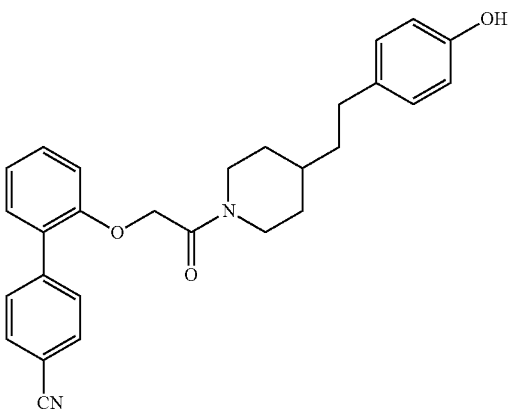 [SMILES: N#Cc1ccc(-c2ccccc2OCC(=O)N2CCC(CCc3ccc(O)cc3)CC2)cc1] | 440.5 | | 439 |
| 280 | 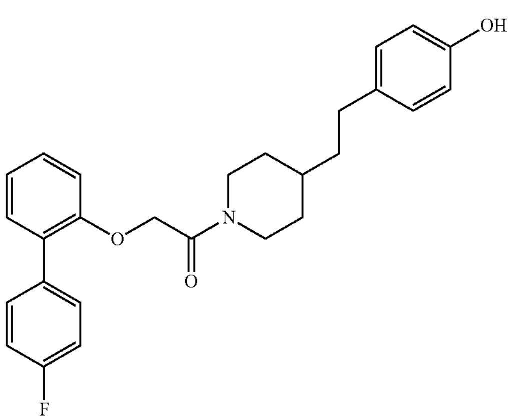 [SMILES: O=C(COc1ccccc1-c1ccc(F)cc1)N1CCC(CCc2ccc(O)cc2)CC1] | 433.5 | 434 | 432 |

TABLE 1-continued

| Compound No. | Structure | MW | Positive MS peak | Negative MS peak |
|---|---|---|---|---|
| 281 | 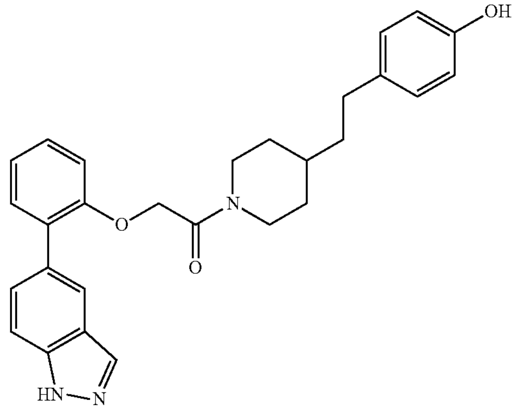 [SMILES: O=C(COc1ccccc1-c1ccc2[nH]ncc2c1)N1CCC(CCc2ccc(O)cc2)CC1] | 455.6 | 456 | 454 |
| 282 | 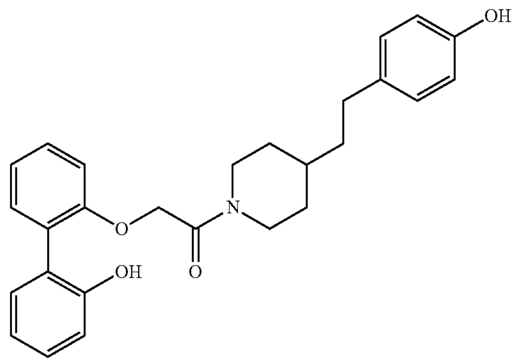 [SMILES: O=C(COc1ccccc1-c1ccccc1O)N1CCC(CCc2ccc(O)cc2)CC1] | 431.5 | 432 | 430 |
| 283 | 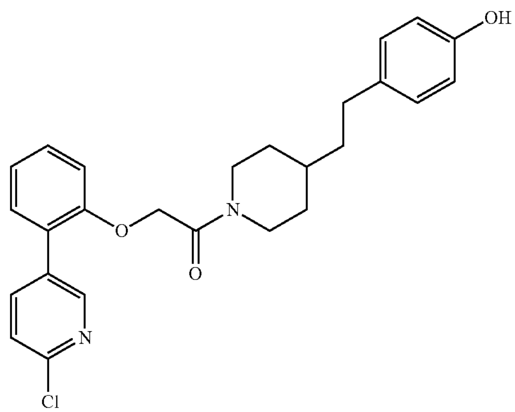 [SMILES: O=C(COc1ccccc1-c1ccc(Cl)nc1)N1CCC(CCc2ccc(O)cc2)CC1] | 451.0 | 450 | 449 |
| 284 | 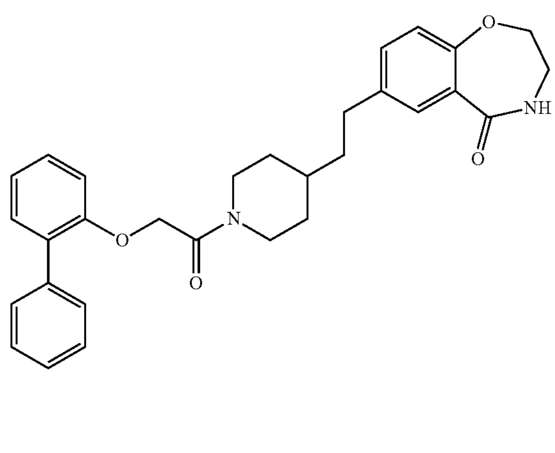 [SMILES: O=C1NCCOc2ccc(CCC3CCN(C(=O)COc4ccccc4-c4ccccc4)CC3)cc21] | 484.6 | 485 | |

TABLE 1-continued

| Compound No. | Structure | MW | Positive MS peak | Negative MS peak |
|---|---|---|---|---|
| 285 | 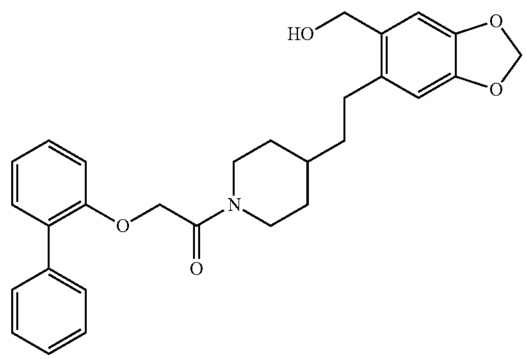 [SMILES: O=C(COc1ccccc1-c1ccccc1)N1CCC(CCc2cc3c(cc2CO)OCO3)CC1] | 473.6 | 474 | |
| 286 | 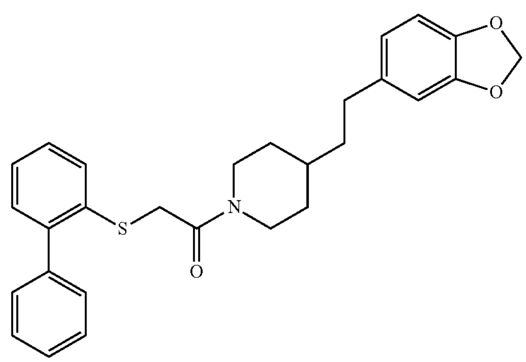 | 459.6 | 460 | |
| 287 | 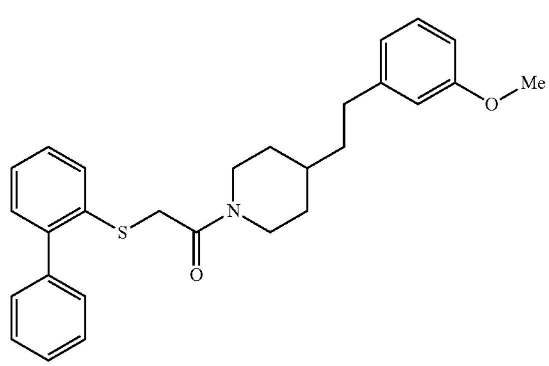 [SMILES: COc1cccc(CCC2CCN(C(=O)CSc3ccccc3-c3ccccc3)CC2)c1] | 445.6 | 446 | |
| 288 | 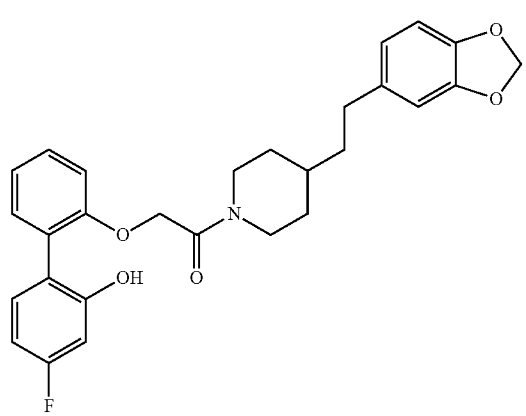 [SMILES: O=C(COc1ccccc1-c1ccc(F)cc1O)N1CCC(CCc2ccc3c(c2)OCO3)CC1] | 477.5 | | 476 |

TABLE 1-continued

| Compound No. | Structure | MW | Positive MS peak | Negative MS peak |
|---|---|---|---|---|
| 289 | 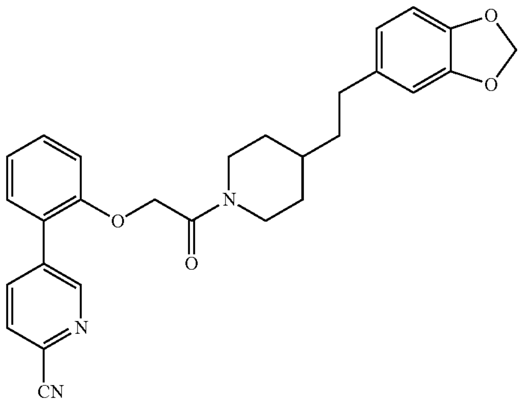 [SMILES: N#Cc1ccc(-c2ccccc2OCC(=O)N2CCC(CCc3ccc4c(c3)OCO4)CC2)cn1] | 469.5 | 470 | |
| 290 | 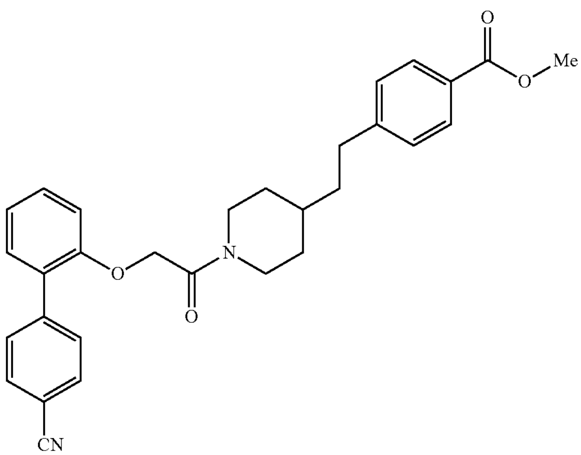 [SMILES: COC(=O)c1ccc(CCC2CCN(C(=O)COc3ccccc3-c3ccc(C#N)cc3)CC2)cc1] | 482.6 | 483 | |
| 291 | 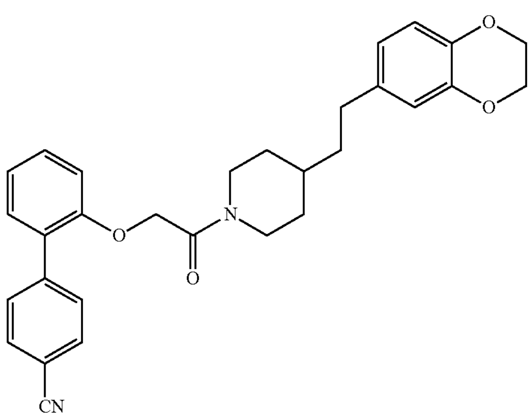 | 482.6 | 483 | |

TABLE 1-continued

| Compound No. | Structure | MW | Positive MS peak | Negative MS peak |
|---|---|---|---|---|
| 292 | 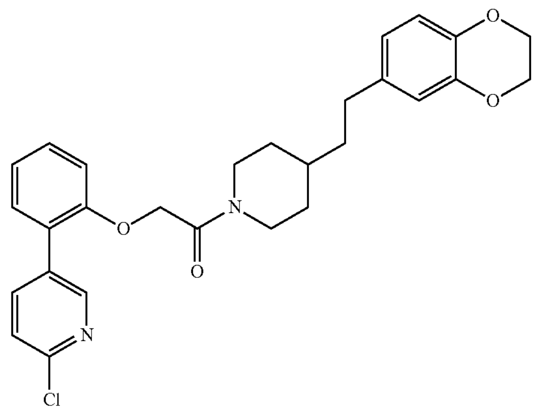 | 493.0 | 493 | |
| 293 | 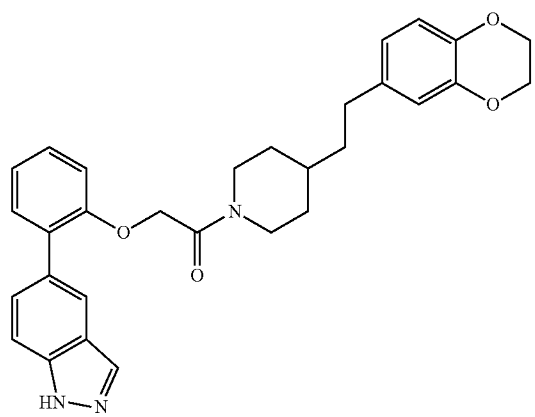 [SMILES: O=C(COc1ccccc1-c1ccc2[nH]ncc2c1)N1CCC(CCc2ccc3c(c2)OCCO3)CC1] | 497.6 | 498 | 496 |
| 294 | 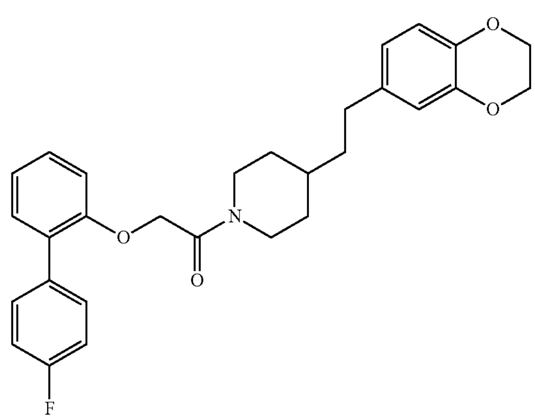 | 475.6 | 476 | |

TABLE 1-continued

| Compound No. | Structure | MW | Positive MS peak | Negative MS peak |
|---|---|---|---|---|
| 295 | 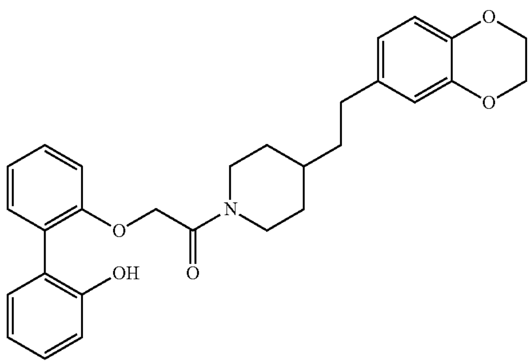 [SMILES: O=C(COc1ccccc1-c1ccccc1O)N1CCC(CCc2ccc3c(c2)OCCO3)CC1] | 473.6 | 474 | |
| 296 | 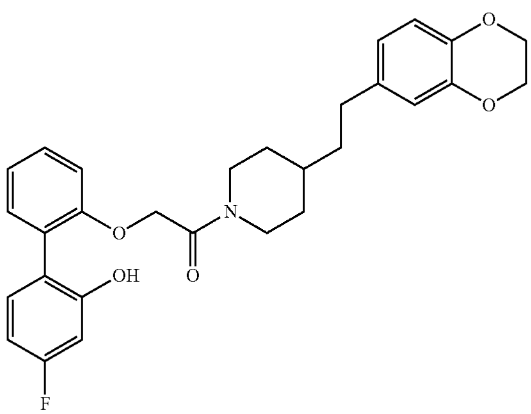 [SMILES: O=C(COc1ccccc1-c1ccc(F)cc1O)N1CCC(CCc2ccc3c(c2)OCCO3)CC1] | 491.6 | 492 | 490 |
| 297 | 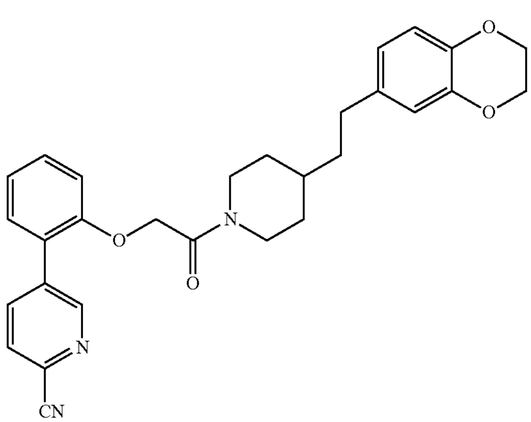 | 483.6 | 484 | |

TABLE 1-continued

| Compound No. | Structure | MW | Positive MS peak | Negative MS peak |
|---|---|---|---|---|
| 298 | 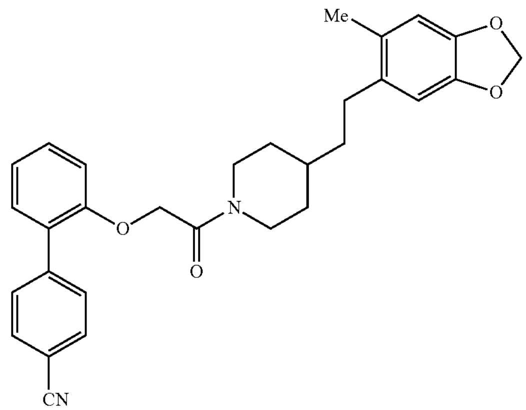 [SMILES: Cc1cc2c(cc1CCC1CCN(C(=O)COc3ccccc3-c3ccc(C#N)cc3)CC1)OCO2] | 482.6 | 483 | |
| 299 | 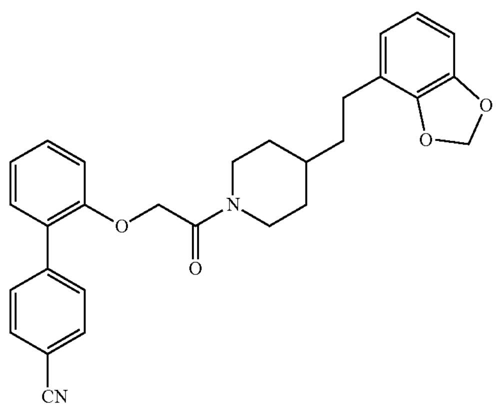 [SMILES: N#Cc1ccc(-c2ccccc2OCC(=O)N2CCC(CCc3cccc4c3OCO4)CC2)cc1] | 468.5 | 469 | |
| 300 | 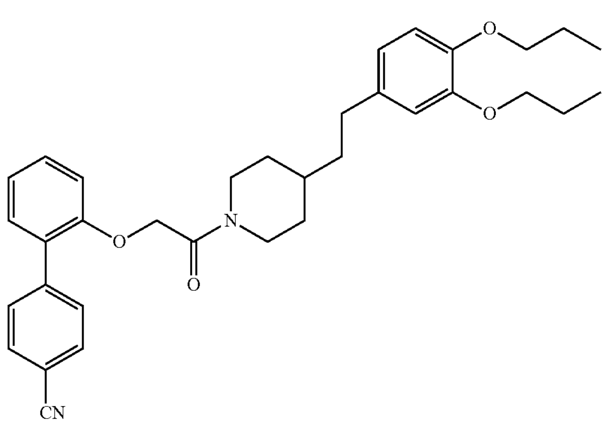 [SMILES: CCCOc1ccc(CCC2CCN(C(=O)COc3ccccc3-c3ccc(C#N)cc3)CC2)cc1OCCC] | 540.7 | 541 | |

TABLE 1-continued

| Compound No. | Structure | MW | Positive MS peak | Negative MS peak |
|---|---|---|---|---|
| 301 | 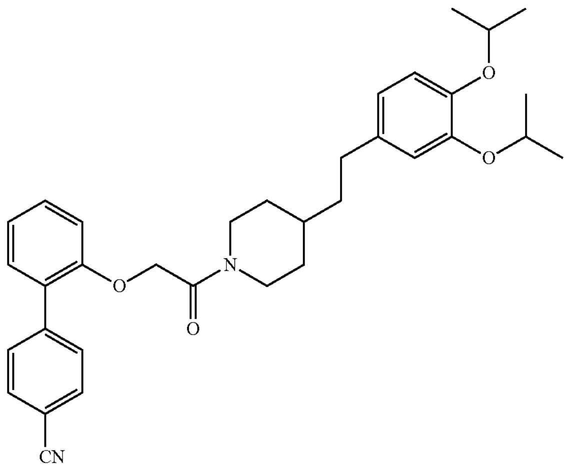 [SMILES: CC(C)Oc1ccc(CCC2CCN(C(=O)COc3ccccc3-c3ccc(C#N)cc3)CC2)cc1OC(C)C] | 540.7 | 541 | |
| 302 | 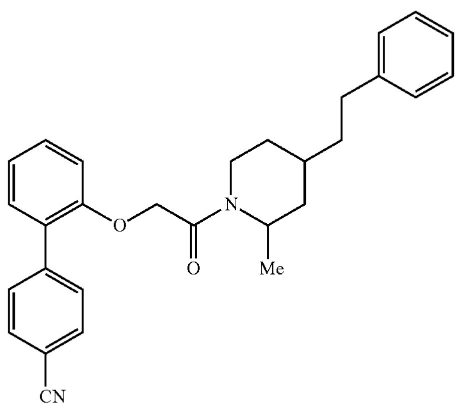 [SMILES: CC1CC(CCc2ccccc2)CCN1C(=O)COc1ccccc1-c1ccc(C#N)cc1] | 438.6 | 439 | |
| 303 | 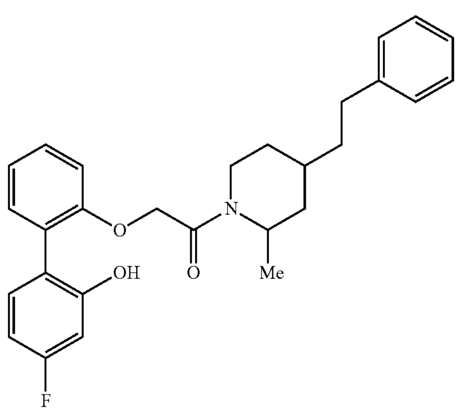 [SMILES: CC1CC(CCc2ccccc2)CCN1C(=O)COc1ccccc1-c1ccc(F)cc1O] | 447.5 | 448 | 446 |

TABLE 1-continued

| Compound No. | Structure | MW | Positive MS peak | Negative MS peak |
|---|---|---|---|---|
| 304 | 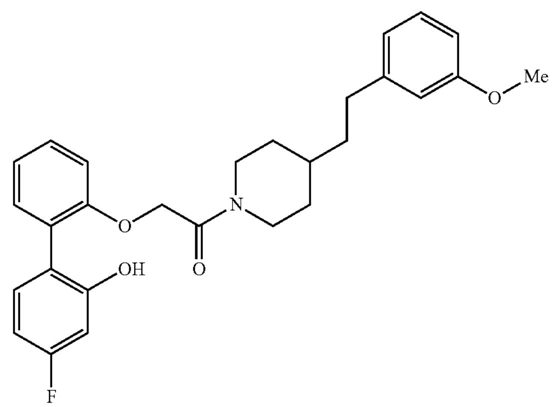 [SMILES: COc1cccc(CCC2CCN(C(=O)COc3ccccc3-c3ccc(F)cc3O)CC2)c1] | 463.5 | 464 | 462 |
| 305 | 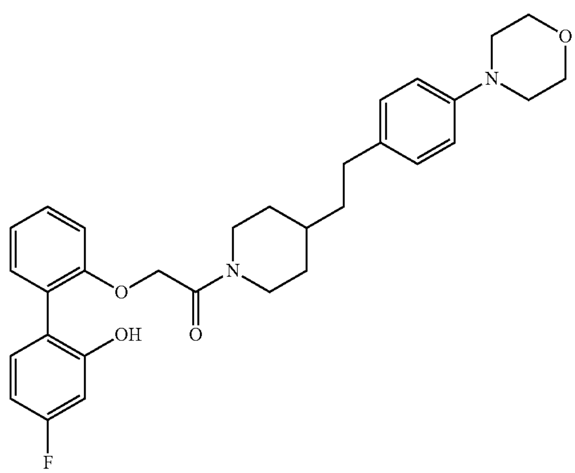 [SMILES: O=C(COc1ccccc1-c1ccc(F)cc1O)N1CCC(CCc2ccc(N3CCOCC3)cc2)CC1] | 518.6 | 519 | 517 |
| 306 | 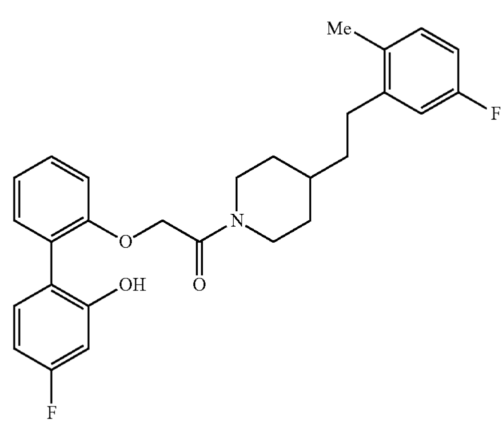 [SMILES: Cc1ccc(F)cc1CCC1CCN(C(=O)COc2ccccc2-c2ccc(F)cc2O)CC1] | 465.5 | 466 | 464 |

TABLE 1-continued
| Compound No. | Structure | MW | Positive MS peak | Negative MS peak |
|---|---|---|---|---|
| 307 | 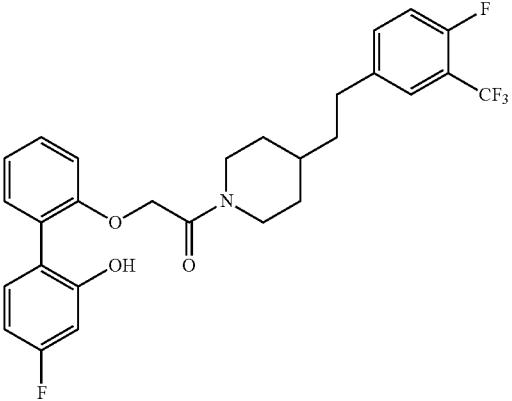 [SMILES: O=C(COc1ccccc1-c1ccc(F)cc1O)N1CCC(CCc2ccc(F)c(C(F)(F)F)c2)CC1] | 519.5 | 519 | 517 |
| 308 | 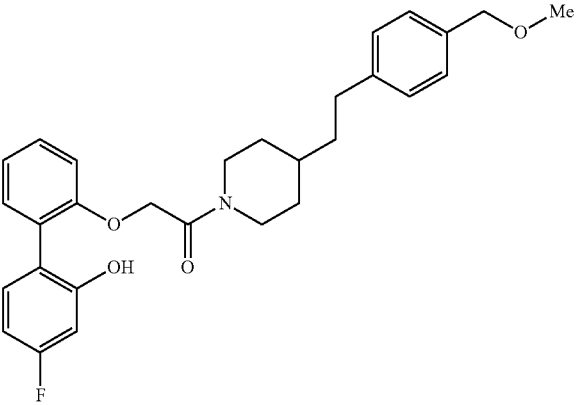 [SMILES: COCc1ccc(CCC2CCN(C(=O)COc3ccccc3-c3ccc(F)cc3O)CC2)cc1] | 477.6 | 478 | 476 |
| 309 | 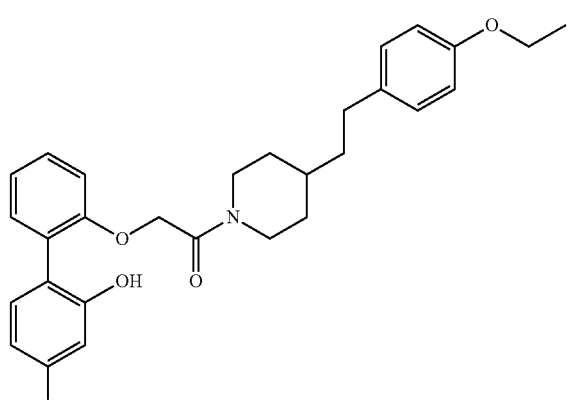 | 477.6 | 478 | 476 |

TABLE 1-continued
| Compound No. | Structure | MW | Positive MS peak | Negative MS peak |
|---|---|---|---|---|
| 310 | 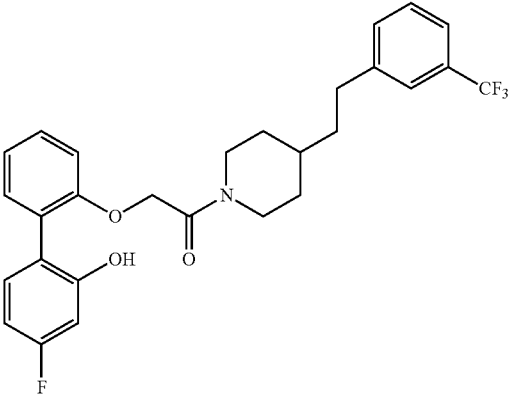 [SMILES: O=C(COc1ccccc1-c1ccc(F)cc1O)N1CCC(CCc2cccc(C(F)(F)F)c2)CC1] | 501.5 | 502 | 500 |
| 311 | 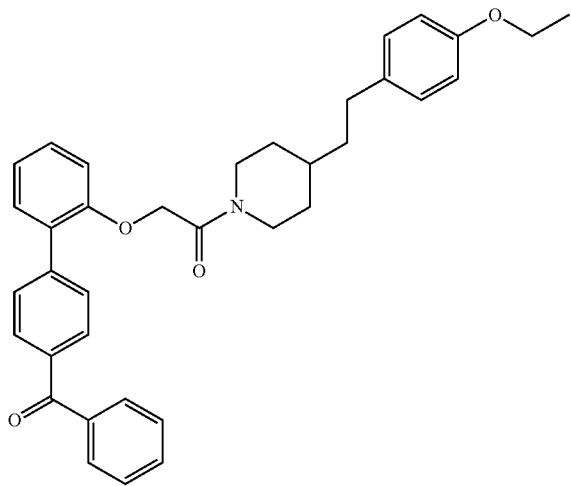 [SMILES: CCOc1ccc(CCC2CCN(C(=O)COc3ccccc3-c3ccc(C(=O)c4ccccc4)cc3)CC2)cc1] | 547.7 | 548 | |
| 312 | 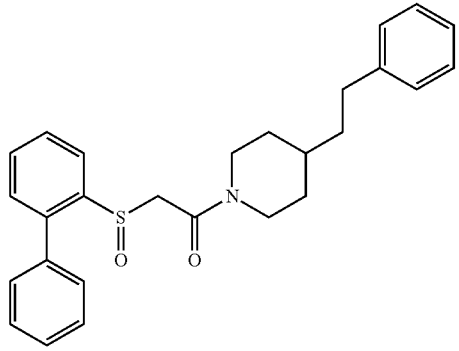 [SMILES: O=C(CS(=O)c1ccccc1-c1ccccc1)N1CCC(CCc2ccccc2)CC1] | 431.6 | 432 | |

TABLE 1-continued

| Compound No. | Structure | MW | Positive MS peak | Negative MS peak |
|---|---|---|---|---|
| 313 | 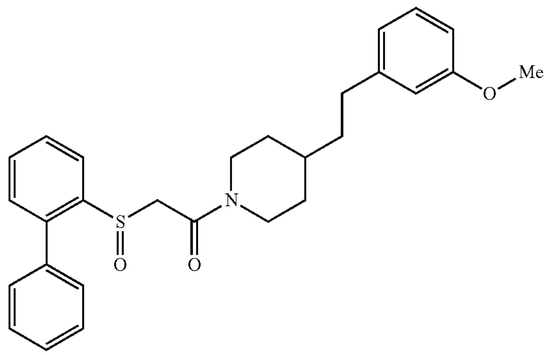 [SMILES: COc1cccc(CCC2CCN(C(=O)CS(=O)c3ccccc3-c3ccccc3)CC2)c1] | 461.6 | 462 | |
| 314 | 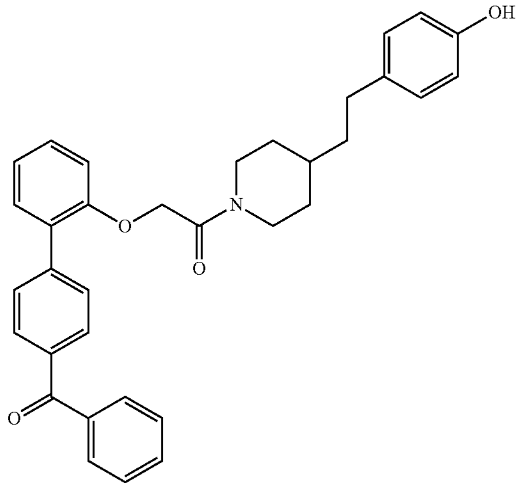 [SMILES: O=C(c1ccccc1)c1ccc(-c2ccccc2OCC(=O)N2CCC(CCc3ccc(O)cc3)CC2)cc1] | 519.6 | 520 | |
| 315 | 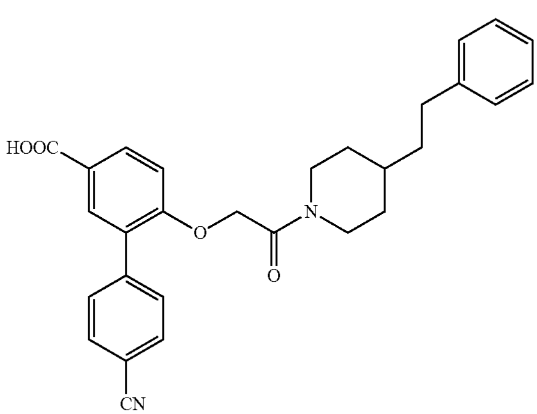 [SMILES: N#Cc1ccc(-c2cc(C(=O)O)ccc2OCC(=O)N2CCC(CCc3ccccc3)CC2)cc1] | 468.5 | | 467 |

TABLE 1-continued

| Compound No. | Structure | MW | Positive MS peak | Negative MS peak |
|---|---|---|---|---|
| 316 | 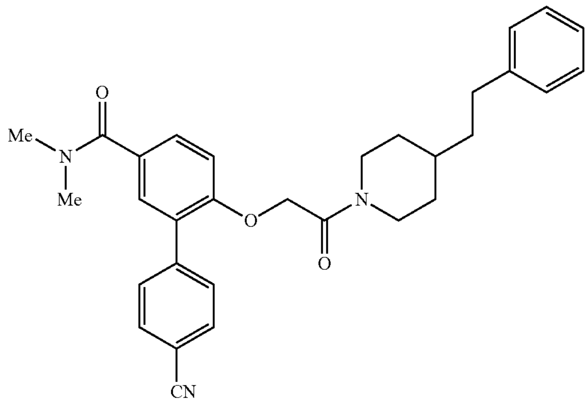 [SMILES: CN(C)C(=O)c1ccc(OCC(=O)N2CCC(CCc3ccccc3)CC2)c(-c2ccc(C#N)cc2)c1] | 495.6 | 496 | |
| 317 | 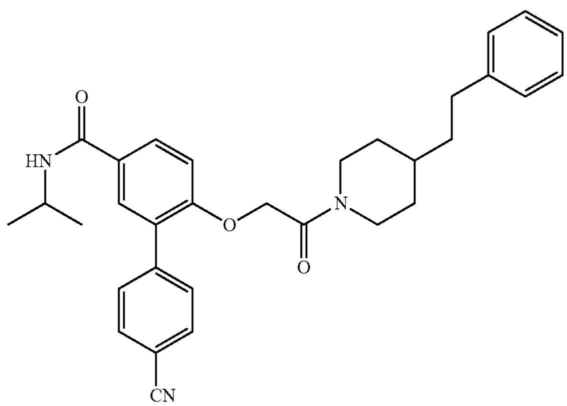 [SMILES: CC(C)NC(=O)c1ccc(OCC(=O)N2CCC(CCc3ccccc3)CC2)c(-c2ccc(C#N)cc2)c1] | 509.6 | 510 | |
| 318 | 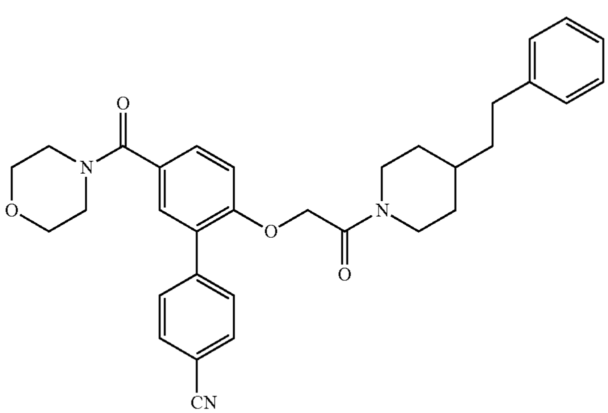 [SMILES: N#Cc1ccc(-c2cc(C(=O)N3CCOCC3)ccc2OCC(=O)N2CCC(CCc3ccccc3)CC2)cc1] | 537.7 | 538 | |

TABLE 1-continued

| Compound No. | Structure | MW | Positive MS peak | Negative MS peak |
|---|---|---|---|---|
| 319 | 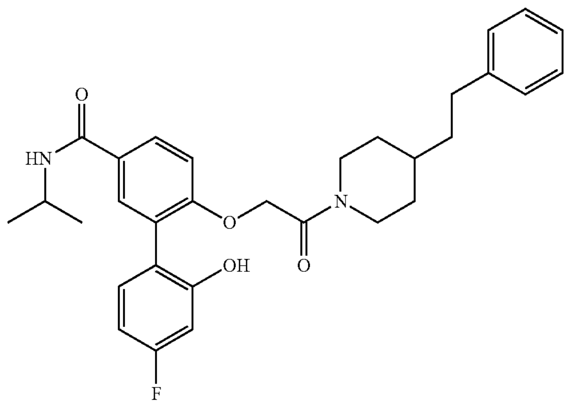 [SMILES: CC(C)NC(=O)c1ccc(OCC(=O)N2CCC(CCc3ccccc3)CC2)c(-c2ccc(F)cc2O)c1] | 518.6 | 519 | 517 |
| 320 | 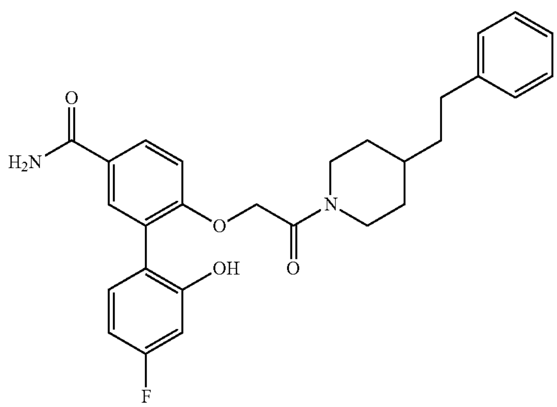 [SMILES: NC(=O)c1ccc(OCC(=O)N2CCC(CCc3ccccc3)CC2)c(-c2ccc(F)cc2O)c1] | 476.5 | 477 | 475 |
| 321 | 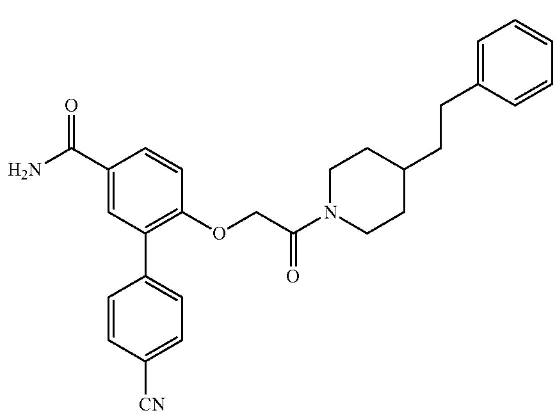 [SMILES: N#Cc1ccc(-c2cc(C(N)=O)ccc2OCC(=O)N2CCC(CCc3ccccc3)CC2)cc1] | 467.6 | 468 | |

TABLE 1-continued
| Compound No. | Structure | MW | Positive MS peak | Negative MS peak |
|---|---|---|---|---|
| 322 | 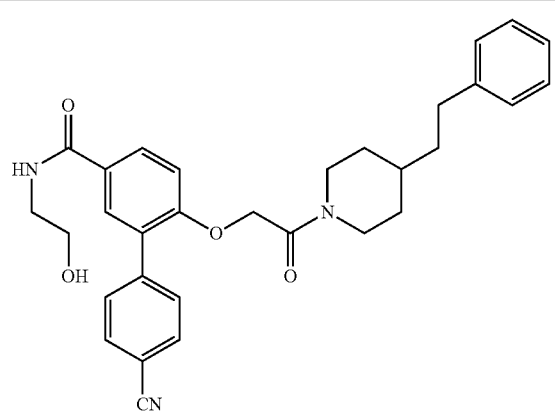 [SMILES: N#Cc1ccc(-c2cc(C(=O)NCCO)ccc2OCC(=O)N2CCC(CCc3ccccc3)CC2)cc1] | 511.6 | 512 | |
| 323 | 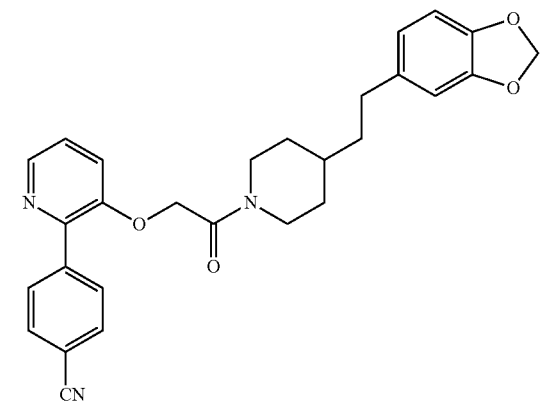 [SMILES: N#Cc1ccc(-c2ncccc2OCC(=O)N2CCC(CCc3ccc4c(c3)OCO4)CC2)cc1] | 469.5 | 470 | |
| 324 | 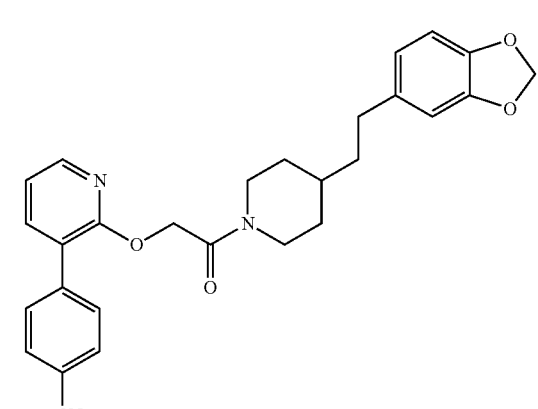 | 469.5 | 470 | |

TABLE 1-continued

| Compound No. | Structure | MW | Positive MS peak | Negative MS peak |
|---|---|---|---|---|
| 325 | 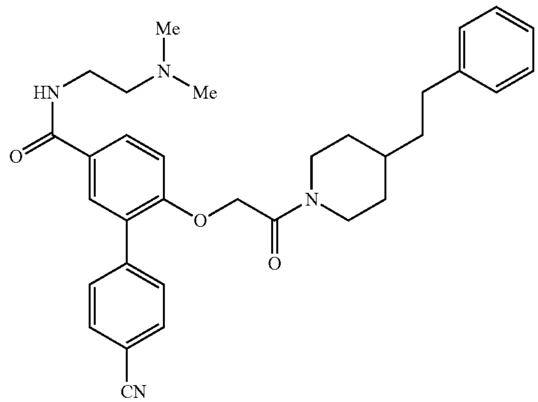 [SMILES: CN(C)CCNC(=O)c1ccc(OCC(=O)N2CCC(CCc3ccccc3)CC2)c(-c2ccc(C#N)cc2)c1] | 538.7 | 539 | |
| 326 | 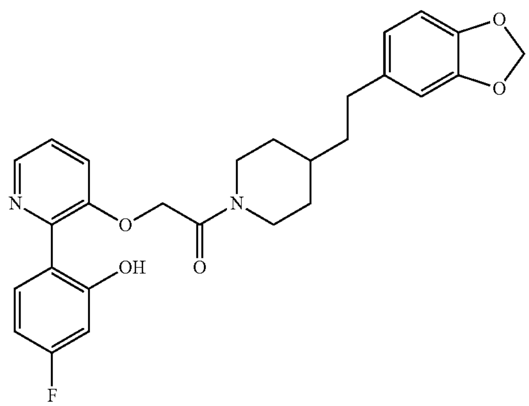 [SMILES: O=C(COc1cccnc1-c1ccc(F)cc1O)N1CCC(CCc2ccc3c(c2)OCO3)CC1] | 478.5 | 479 | 477 |
| 327 | 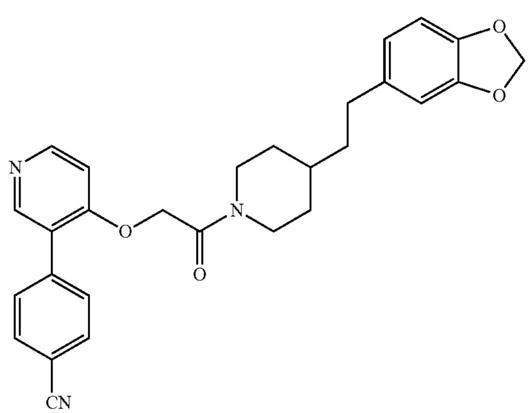 [SMILES: N#Cc1ccc(-c2cnccc2OCC(=O)N2CCC(CCc3ccc4c(c3)OCO4)CC2)cc1] | 469.5 | 470 | 468 |

TABLE 1-continued
| Compound No. | Structure | MW | Positive MS peak | Negative MS peak |
|---|---|---|---|---|
| 328 | 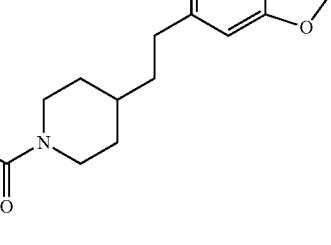 | 484.6 | 485 | 483 |
| 329 | 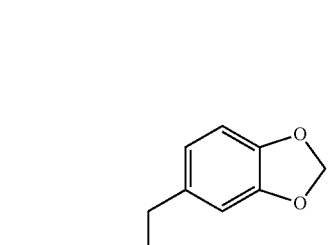 | 478.5 | | 477 |
| 330 | 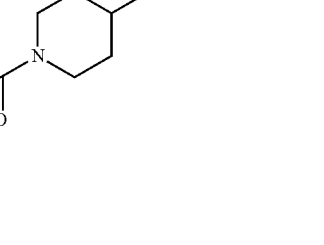 | 434.5 | 435 | 433 |

TABLE 1-continued

| Compound No. | Structure | MW | Positive MS peak | Negative MS peak |
|---|---|---|---|---|
| 331 | 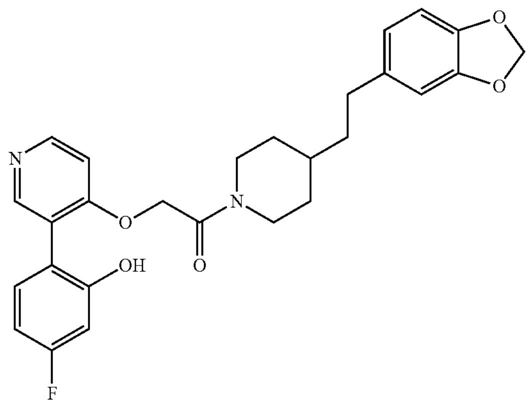 [SMILES: O=C(COc1ccncc1-c1ccc(F)cc1O)N1CCC(CCc2ccc3c(c2)OCO3)CC1] | 478.5 | 479 | 477 |
| 332 | 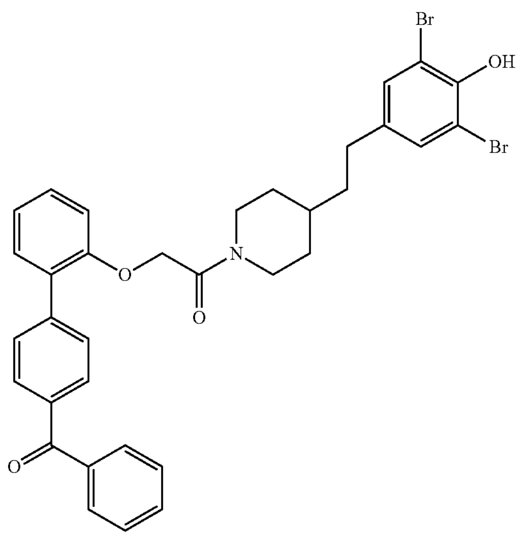 [SMILES: O=C(c1ccccc1)c1ccc(-c2ccccc2OCC(=O)N2CCC(CCc3cc(Br)c(O)c(Br)c3)CC2)cc1] | 675.1 | | 674/676/678 |
| 333 | 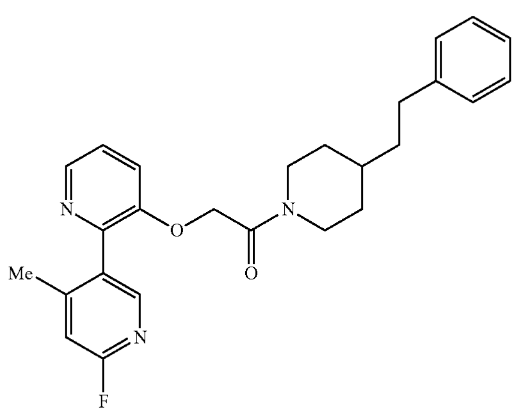 [SMILES: Cc1cc(F)ncc1-c1ncccc1OCC(=O)N1CCC(CCc2ccccc2)CC1] | 433.5 | 434 | |

TABLE 1-continued

| Compound No. | Structure | MW | Positive MS peak | Negative MS peak |
|---|---|---|---|---|
| 334 | 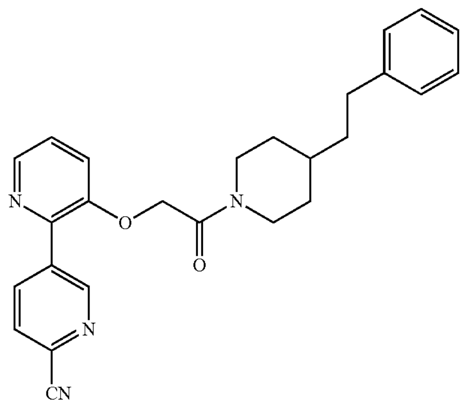 [SMILES: N#Cc1ccc(-c2ncccc2OCC(=O)N2CCC(CCc3ccccc3)CC2)cn1] | 426.5 | 427 | |
| 335 | 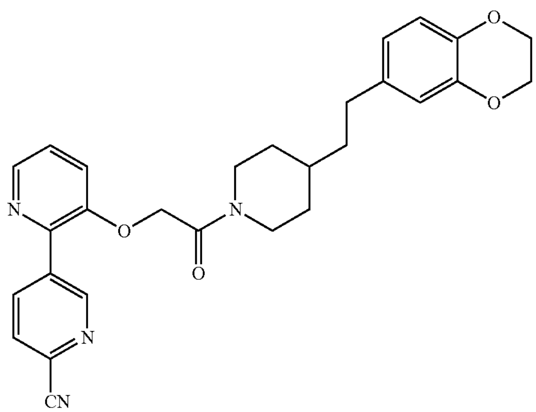 [SMILES: N#Cc1ccc(-c2ncccc2OCC(=O)N2CCC(CCc3ccc4c(c3)OCCO4)CC2)cn1] | 484.6 | 485 | |
| 336 | 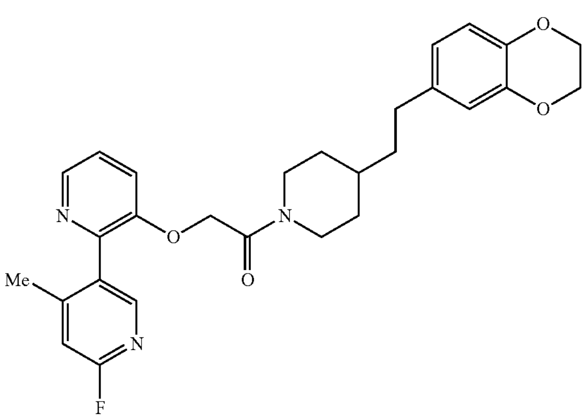 [SMILES: O=C(COc1cccnc1-c1ccc(F)cc1O)N1CCC(CCc2ccc3c(c2)OCCO3)CC1] | 491.6 | 492 | |

TABLE 1-continued
| Compound No. | Structure | MW | Positive MS peak | Negative MS peak |
|---|---|---|---|---|
| 337 | 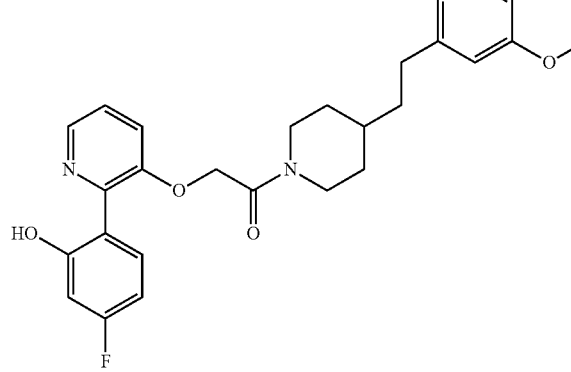 | 492.5 | 493 | 491 |
| 338 | 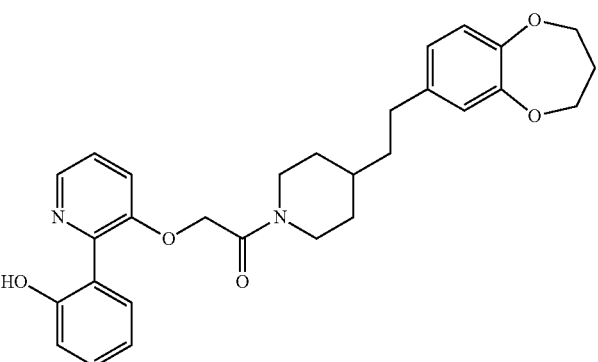 | 506.6 | 507 | 505 |
| 339 | 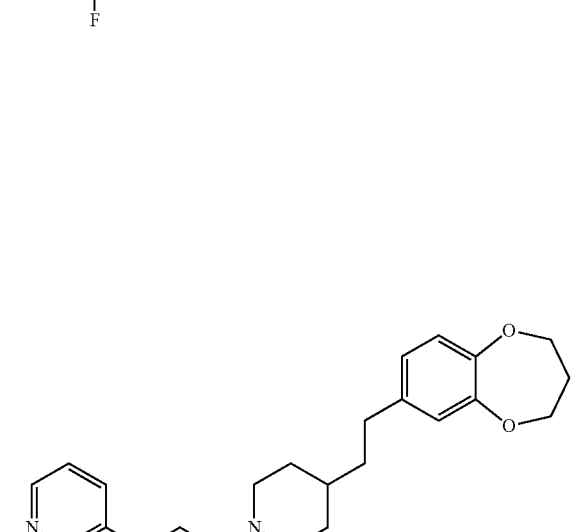 | 491.6 | 492 | |

TABLE 1-continued

| Compound No. | Structure | MW | Positive MS peak | Negative MS peak |
|---|---|---|---|---|
| 340 | 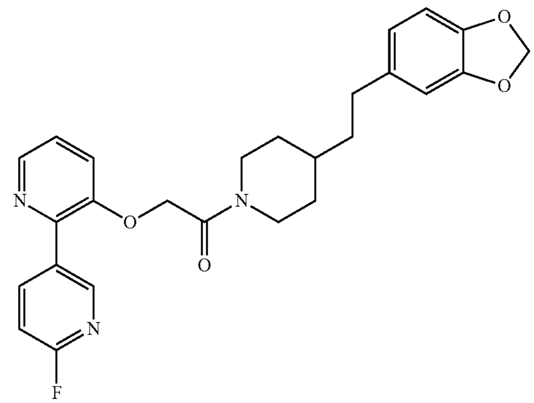 [SMILES: O=C(COc1cccnc1-c1ccc(F)nc1)N1CCC(CCc2ccc3c(c2)OCO3)CC1] | 463.5 | 464 | |
| 341 | 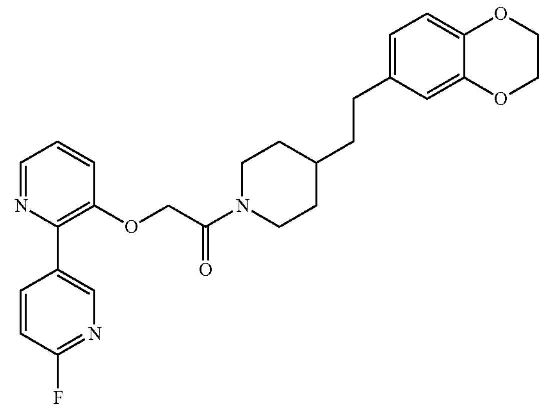 [SMILES: O=C(COc1cccnc1-c1ccc(F)nc1)N1CCC(CCc2ccc3c(c2)OCCO3)CC1] | 477.5 | 478 | |
| 342 | 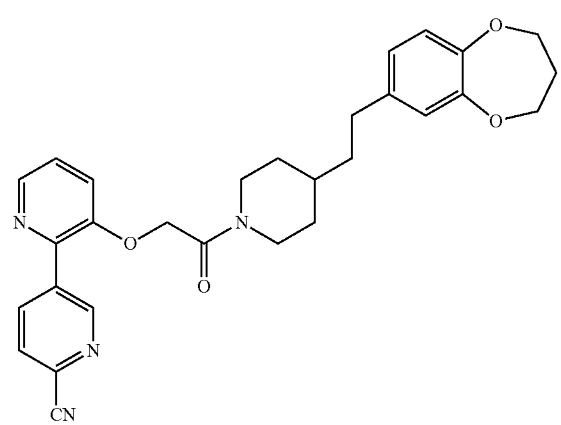 [SMILES: N#Cc1ccc(-c2ncccc2OCC(=O)N2CCC(CCc3ccc4c(c3)OCCCO4)CC2)cn1] | 498.6 | 499 | |

TABLE 1-continued

| Compound No. | Structure | MW | Positive MS peak | Negative MS peak |
|---|---|---|---|---|
| 343 | 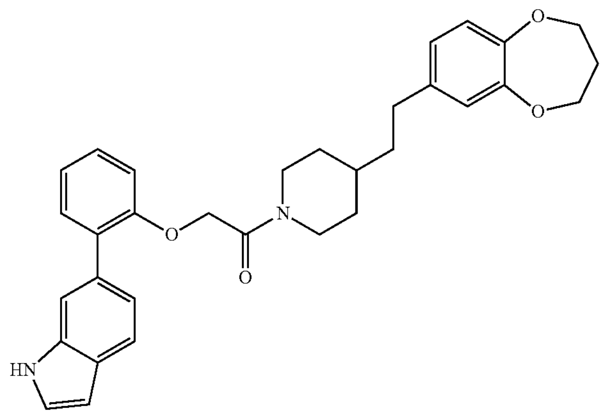 [SMILES: O=C(COc1ccccc1-c1ccc2cc[nH]c2c1)N1CCC(CCc2ccc3c(c2)OCCCO3)CC1] | 511.5 | 511 | |
| 344 | 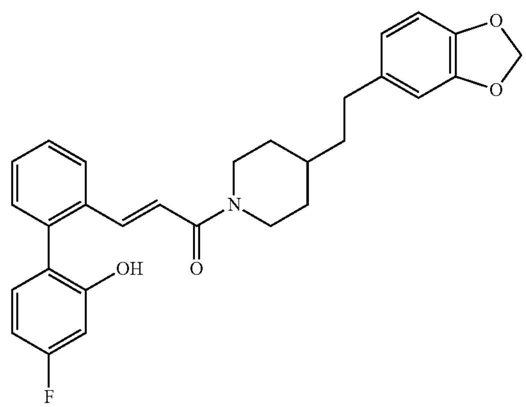 [SMILES: O=C(/C=C/c1ccccc1-c1ccc(F)cc1O)N1CCC(CCc2ccc3c(c2)OCO3)CC1] | 473.5 | 474 | |
| 345 | 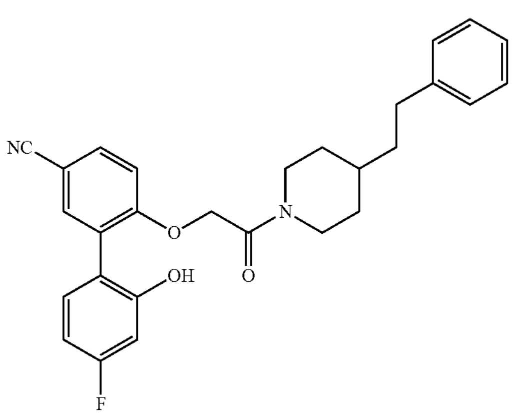 [SMILES: N#Cc1ccc(OCC(=O)N2CCC(CCc3ccccc3)CC2)c(-c2ccc(F)cc2O)c1] | 458.5 | 459 | |

TABLE 1-continued
| Compound No. | Structure | MW | Positive MS peak | Negative MS peak |
|---|---|---|---|---|
| 346 | 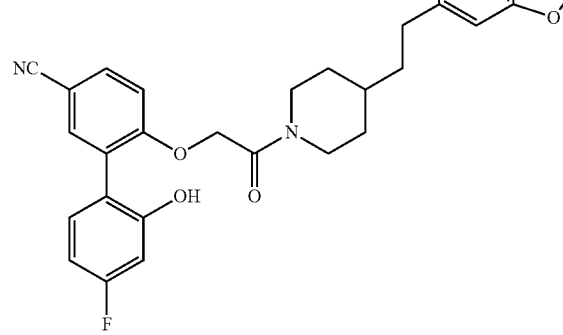 | 502.5 | 503 | |
| 347 | 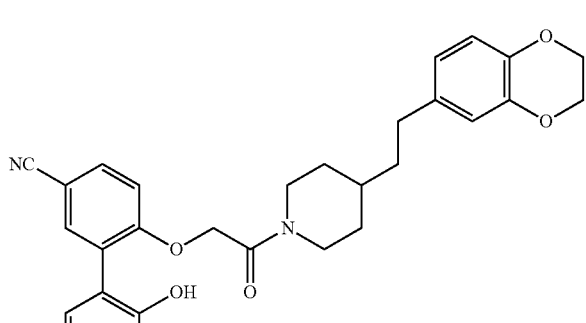 | 516.6 | 517 | |
| 348 | 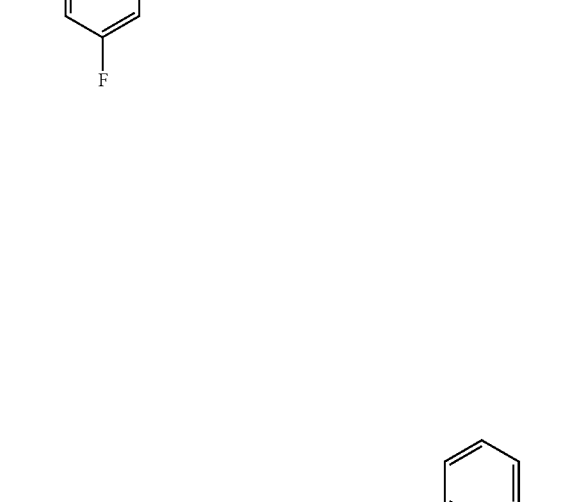 | 433.5 | 434 | |

TABLE 1-continued

| Compound No. | Structure | MW | Positive MS peak | Negative MS peak |
|---|---|---|---|---|
| 349 | 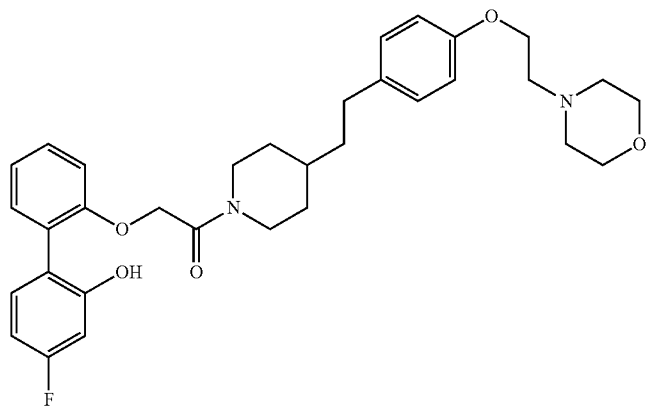 [SMILES: O=C(COc1ccccc1-c1ccc(F)cc1O)N1CCC(CCc2ccc(OCCN3CCOCC3)cc2)CC1] | 562.7 | 563 | |
| 350 | 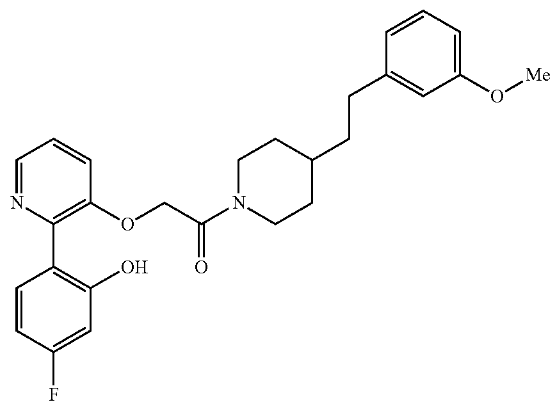 [SMILES: COc1cccc(CCC2CCN(C(=O)COc3cccnc3-c3ccc(F)cc3O)CC2)c1] | 464.5 | 465 | |
| 351 | 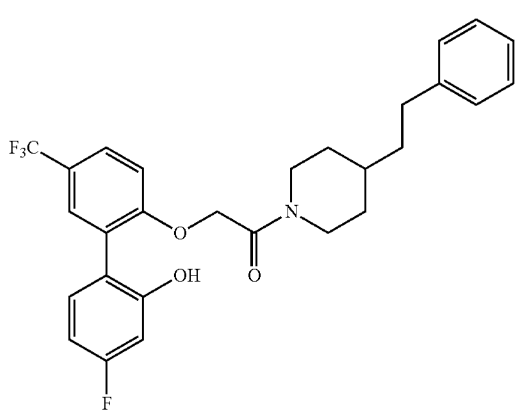 [SMILES: O=C(COc1ccc(C(F)(F)F)cc1-c1ccc(F)cc1O)N1CCC(CCc2ccccc2)CC1] | 501.5 | 502 | |

TABLE 1-continued
| Compound No. | Structure | MW | Positive MS peak | Negative MS peak |
|---|---|---|---|---|
| 352 | 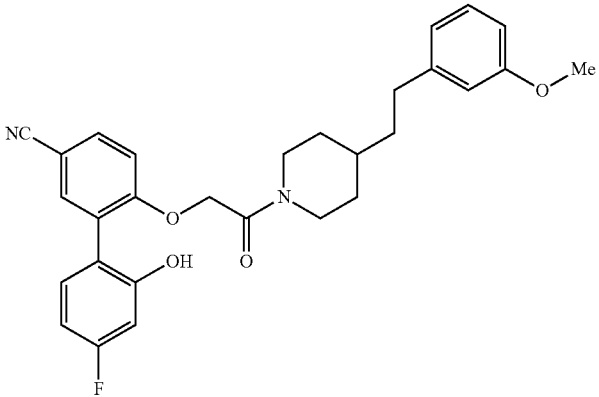 | 488.6 | 489 | |
| 353 | 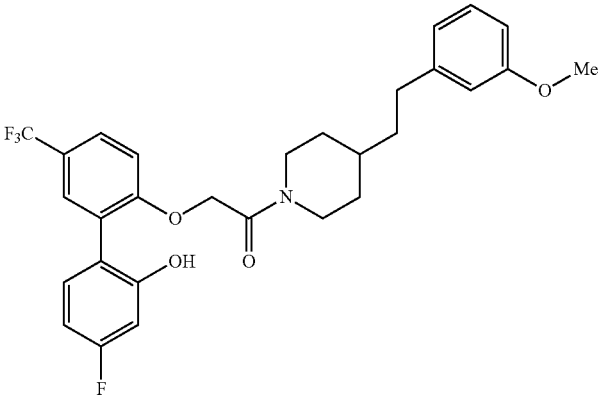 [SMILES: COc1cccc(CCC2CCN(C(=O)COc3ccc(C#N)cc3-c3ccc(F)cc3O)CC2)c1] | 531.5 | 532 | |
| 354 | 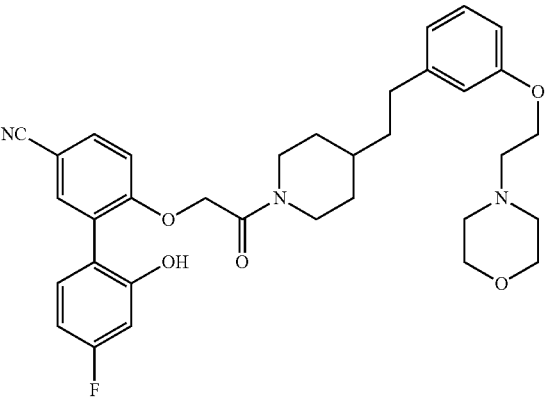 [SMILES: N#Cc1ccc(OCC(=O)N2CCC(CCc3cccc(OCCN4CCOCC4)c3)CC2)c(-c2ccc(F)cc2O)c1] | 587.7 | 588 | |

TABLE 1-continued

| Compound No. | Structure | MW | Positive MS peak | Negative MS peak |
|---|---|---|---|---|
| 355 | 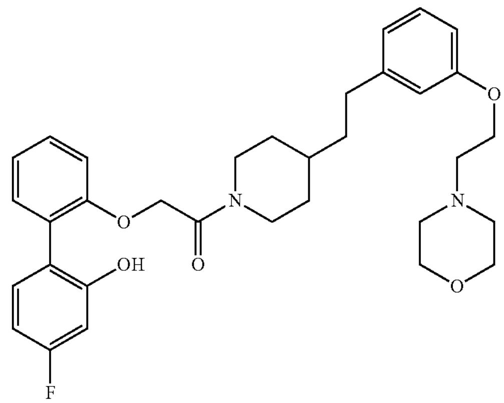 [SMILES: O=C(COc1ccccc1-c1ccc(F)cc1O)N1CCC(CCc2cccc(OCCN3CCOCC3)c2)CC1] | 562.7 | 563 | |
| 356 | 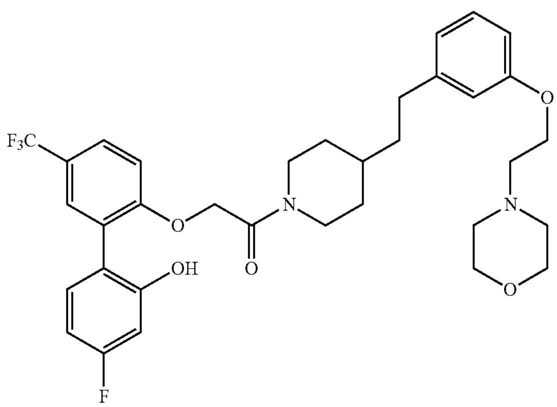 [SMILES: O=C(COc1ccc(C(F)(F)F)cc1-c1ccc(F)cc1O)N1CCC(CCc2cccc(OCCN3CCOCC3)c2)CC1] | 630.7 | 631 | |
| 357 | 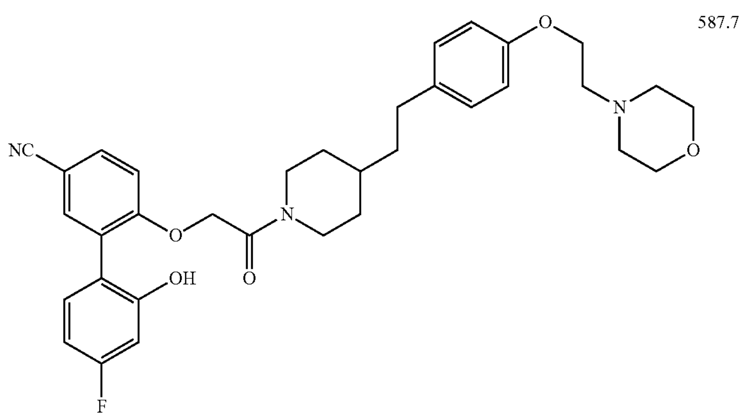 | 587.7 | 588 | |

TABLE 1-continued
| Compound No. | Structure | MW | Positive MS peak | Negative MS peak |
|---|---|---|---|---|
| 358 | 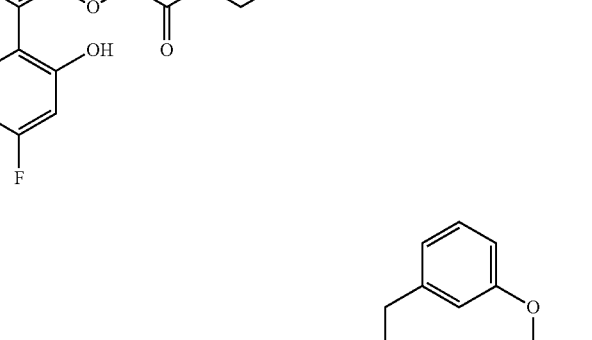 | 563.7 | 564 | |
| 359 | 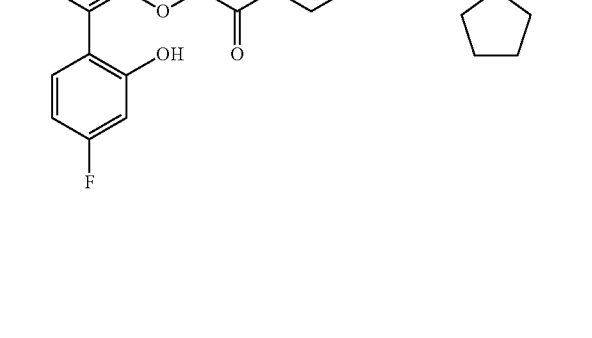 | 546.7 | 547 | |
| 360 | 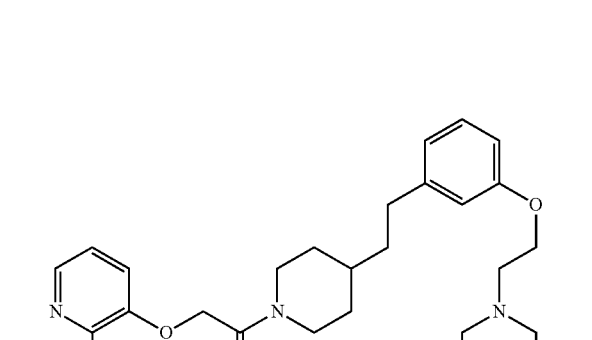 | 561.7 | 562 | |

TABLE 1-continued

| Compound No. | Structure | MW | Positive MS peak | Negative MS peak |
|---|---|---|---|---|
| 361 | 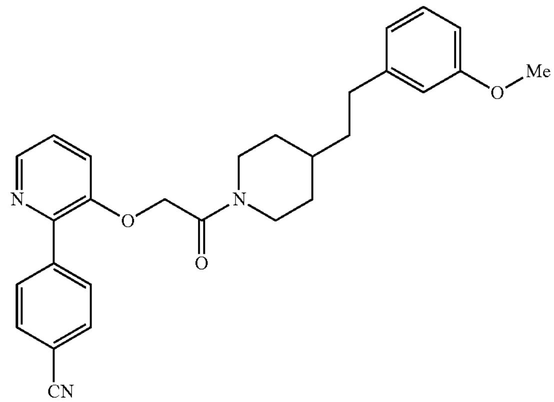 [SMILES: COc1cccc(CCC2CCN(C(=O)COc3cccnc3-c3ccc(C#N)cc3)CC2)c1] | 455.6 | 456 | |
| 362 | 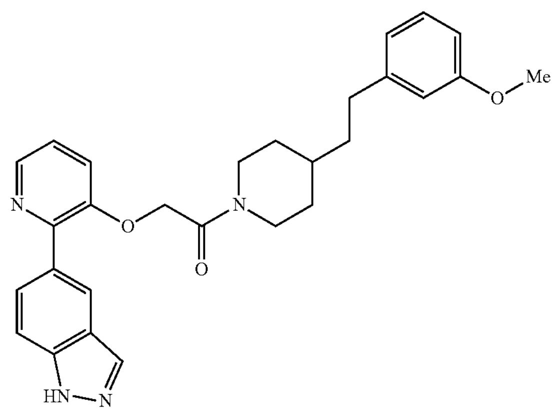 [SMILES: COc1cccc(CCC2CCN(C(=O)COc3cccnc3-c3ccc4[nH]ncc4c3)CC2)c1] | 470.6 | 471 | 469 |
| 363 | 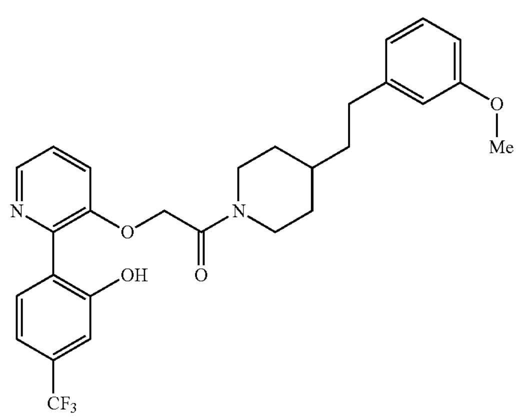 [SMILES: COc1cccc(CCC2CCN(C(=O)COc3cccnc3-c3ccc(C(F)(F)F)cc3O)CC2)c1] | 514.5 | 515 | 513 |

TABLE 1-continued

| Compound No. | Structure | MW | Positive MS peak | Negative MS peak |
|---|---|---|---|---|
| 364 | 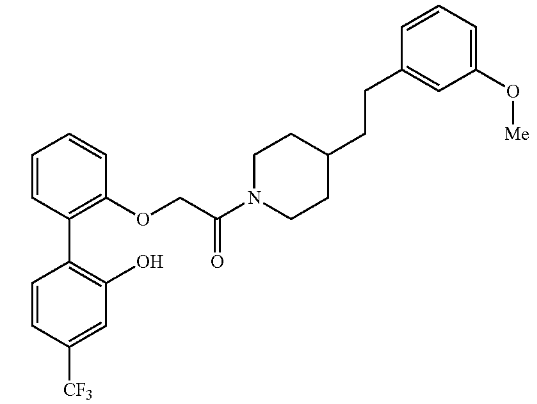 [SMILES: COc1cccc(CCC2CCN(C(=O)COc3ccccc3-c3ccc(C(F)(F)F)cc3O)CC2)c1] | 513.6 | 514 | 512 |
| 365 | 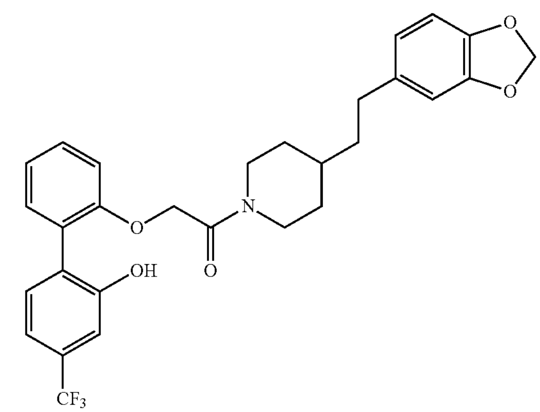 [SMILES: O=C(COc1ccccc1-c1ccc(C(F)(F)F)cc1O)N1CCC(CCc2ccc3c(c2)OCO3)CC1] | 527.5 | 528 | 526 |
| 366 | 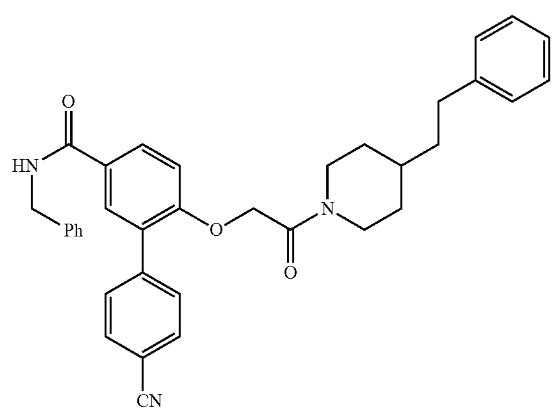 [SMILES: N#Cc1ccc(-c2cc(C(=O)NCc3ccccc3)ccc2OCC(=O)N2CCC(CCc3ccccc3)CC2)cc1] | 557.7 | 469 | 467 |

TABLE 1-continued
| Compound No. | Structure | MW | Positive MS peak | Negative MS peak |
|---|---|---|---|---|
| 367 | 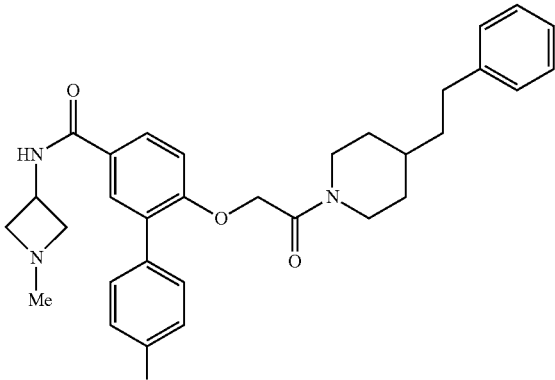 | 536.7 | 537 | |
| 368 | 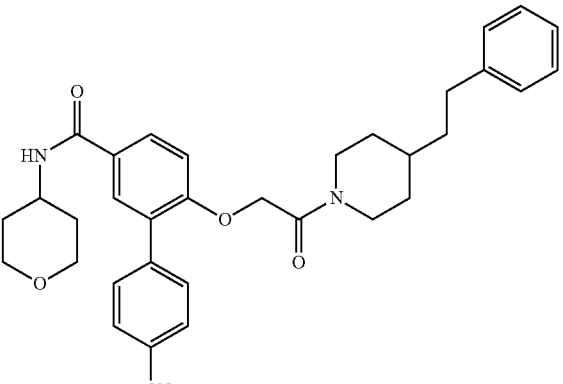 | 551.7 | 552 | 550 |
| 369 | 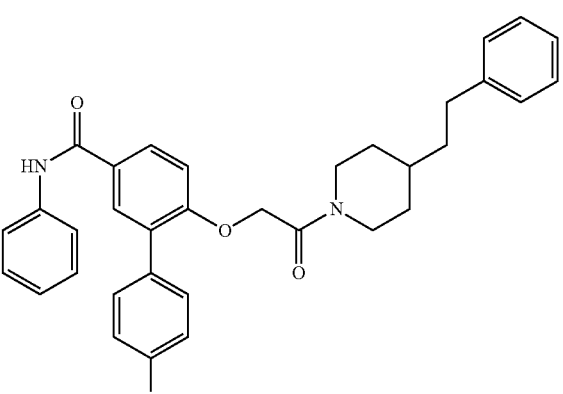 | 543.7 | 544 | 542 |

TABLE 1-continued
| Compound No. | Structure | MW | Positive MS peak | Negative MS peak |
|---|---|---|---|---|
| 370 | 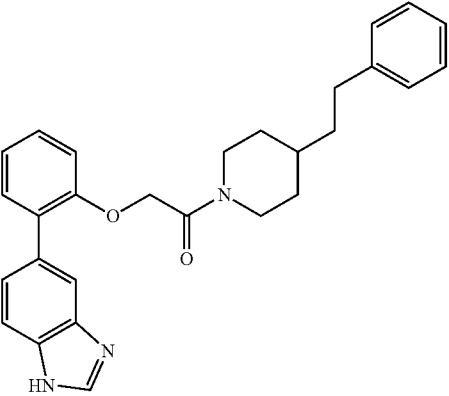 [SMILES: O=C(COc1ccccc1-c1ccc2[nH]cnc2c1)N1CCC(CCc2ccccc2)CC1] | 439.6 | 440 | 438 |
| 371 | 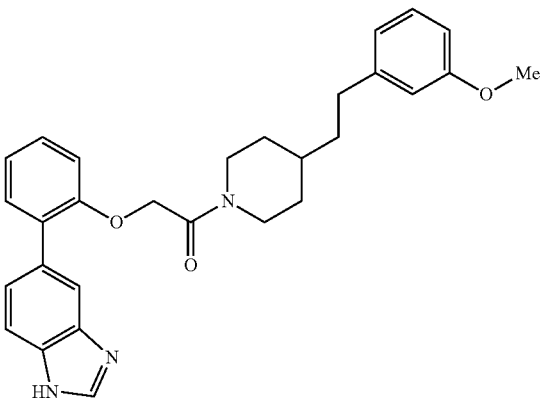 [SMILES: COc1cccc(CCC2CCN(C(=O)COc3ccccc3-c3ccc4[nH]cnc4c3)CC2)c1] | 469.6 | 470 | 468 |
| 372 | 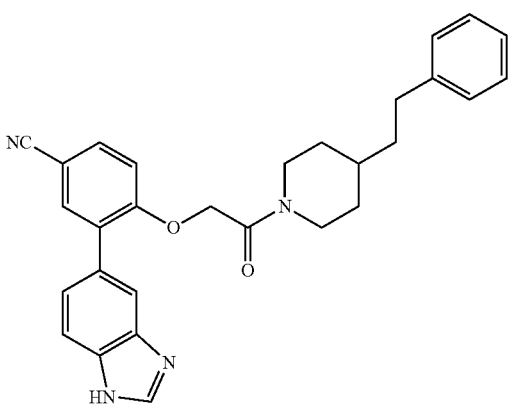 [SMILES: N#Cc1ccc(OCC(=O)N2CCC(CCc3ccccc3)CC2)c(-c2ccc3[nH]cnc3c2)c1] | 464.6 | 465 | 463 |

TABLE 1-continued
| Compound No. | Structure | MW | Positive MS peak | Negative MS peak |
|---|---|---|---|---|
| 373 | 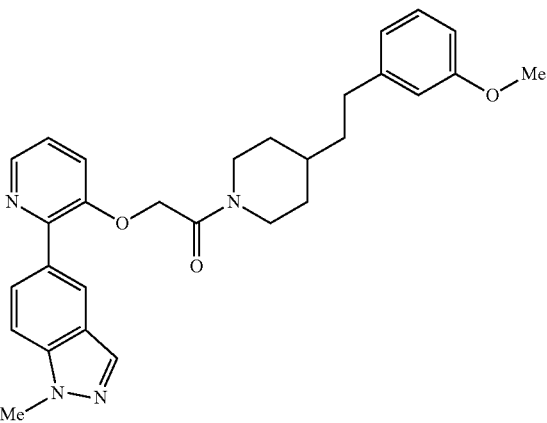 [SMILES: COc1cccc(CCC2CCN(C(=O)COc3cccnc3-c3ccc4c(cnn4C)c3)CC2)c1] | 484.6 | 485 | |
| 374 | 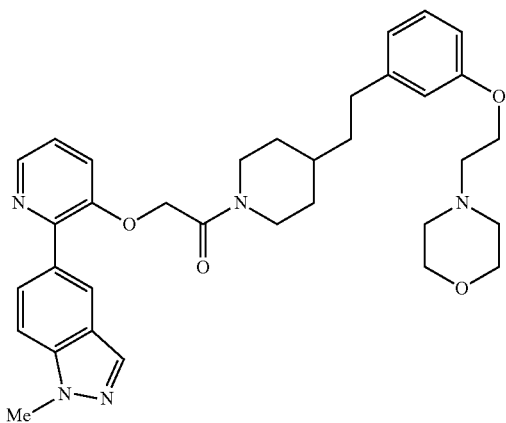 [SMILES: Cn1ncc2cc(-c3ncccc3OCC(=O)N3CCC(CCc4cccc(OCCN5CCOCC5)c4)CC3)ccc21] | 583.7 | 584 | |
| 375 | 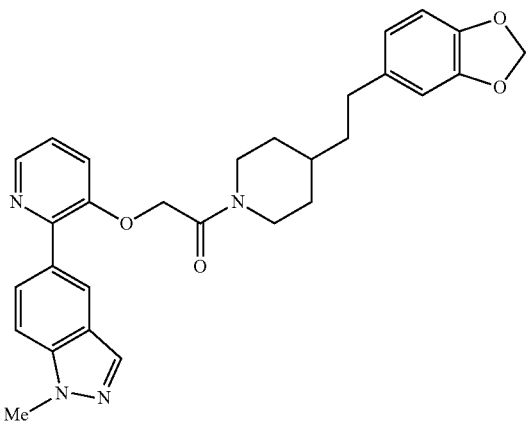 [SMILES: Cn1ncc2cc(-c3ncccc3OCC(=O)N3CCC(CCc4ccc5c(c4)OCO5)CC3)ccc21] | 498.6 | 499 | |

TABLE 1-continued

| Compound No. | Structure | MW | Positive MS peak | Negative MS peak |
|---|---|---|---|---|
| 376 | 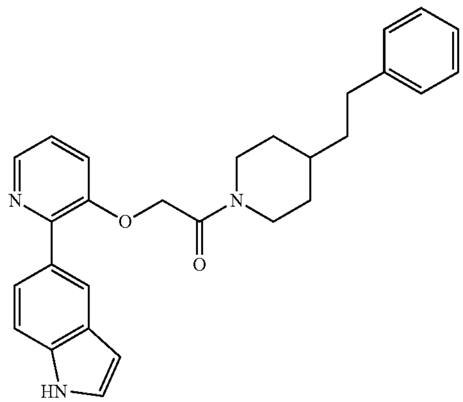 [SMILES: O=C(COc1cccnc1-c1ccc2[nH]ccc2c1)N1CCC(CCc2ccccc2)CC1] | 439.6 | 440 | 438 |
| 377 | 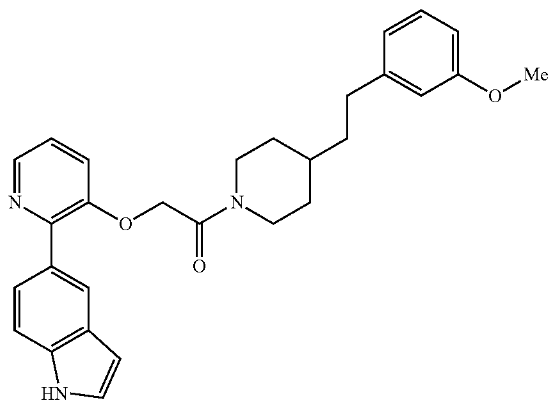 [SMILES: COc1cccc(CCC2CCN(C(=O)COc3cccnc3-c3ccc4[nH]ccc4c3)CC2)c1] | 469.6 | 470 | 468 |
| 378 | 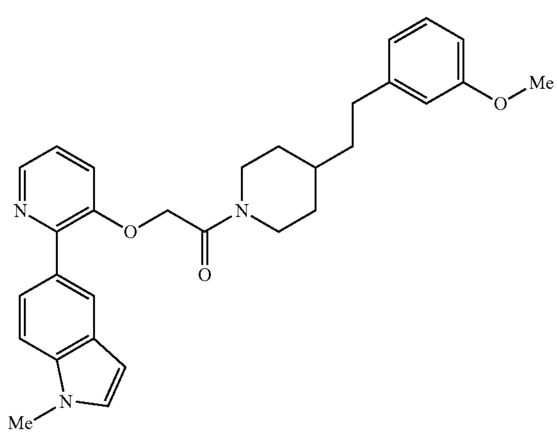 [SMILES: COc1cccc(CCC2CCN(C(=O)COc3cccnc3-c3ccc4c(ccn4C)c3)CC2)c1] | 483.6 | 484 | |

TABLE 1-continued
| Compound No. | Structure | MW | Positive MS peak | Negative MS peak |
|---|---|---|---|---|
| 379 | 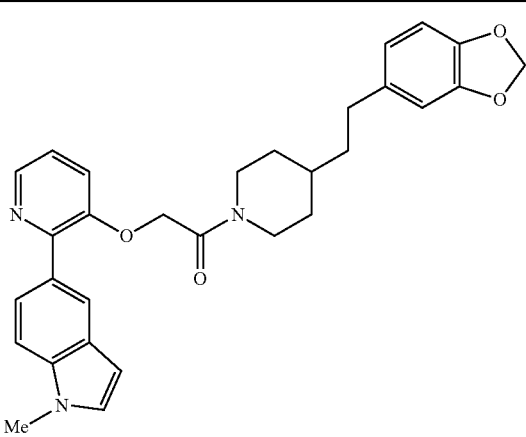 | 497.6 | 498 | |
| 380 | 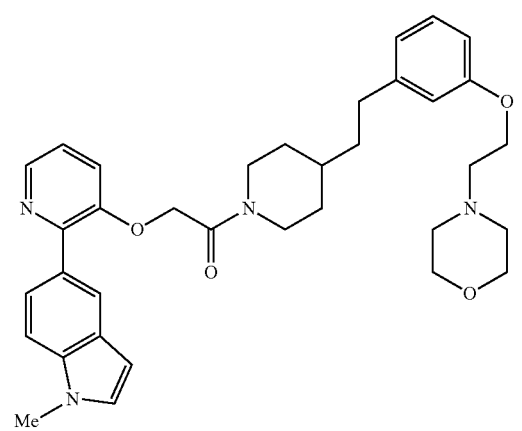 [SMILES: Cn1ccc2cc(-c3ncccc3OCC(=O)N3CCC(CCc4cccc(OCCN5CCOCC5)c4)CC3)ccc21] | 582.7 | 583 | |
| 381 | 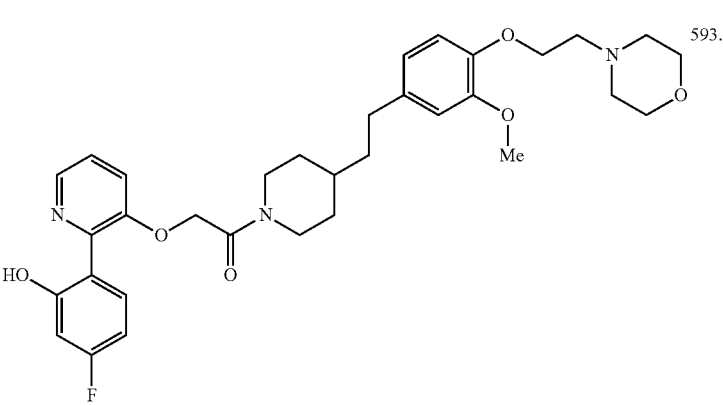 | 593.7 | 594 | |

TABLE 1-continued
| Compound No. | Structure | MW | Positive MS peak | Negative MS peak |
|---|---|---|---|---|
| 382 | 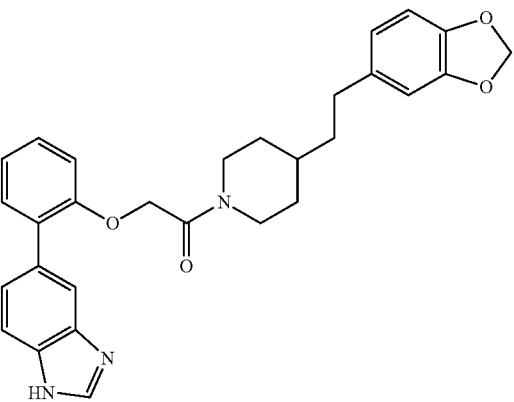 [SMILES: O=C(COc1ccccc1-c1ccc2[nH]cnc2c1)N1CCC(CCc2ccc3c(c2)OCO3)CC1] | 483.6 | 484 | 482 |
| 383 | 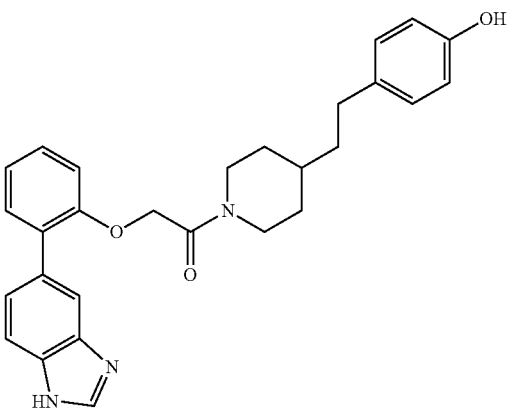 [SMILES: O=C(COc1ccccc1-c1ccc2[nH]cnc2c1)N1CCC(CCc2ccc(O)cc2)CC1] | 455.6 | 456 | 454 |
| 384 | 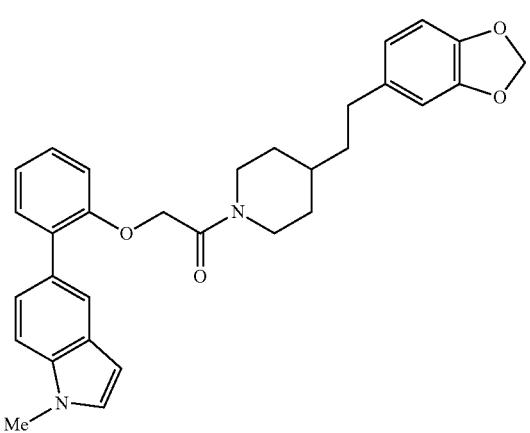 | 496.6 | 497 | |

TABLE 1-continued

| Compound No. | Structure | MW | Positive MS peak | Negative MS peak |
|---|---|---|---|---|
| 385 | 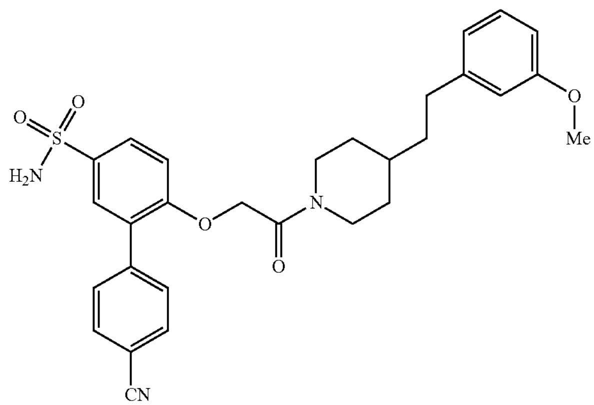 [SMILES: COc1cccc(CCC2CCN(C(=O)COc3ccc(S(N)(=O)=O)cc3-c3ccc(C#N)cc3)CC2)c1] | 533.6 | 534 | 532 |
| 386 | 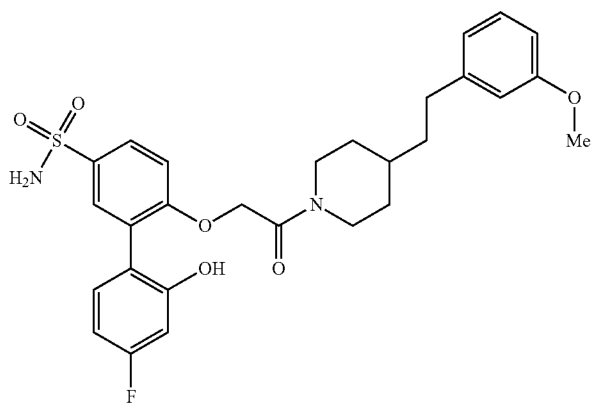 [SMILES: COc1cccc(CCC2CCN(C(=O)COc3ccc(S(N)(=O)=O)cc3-c3ccc(F)cc3O)CC2)c1] | 542.6 | 543 | 541 |
| 387 | 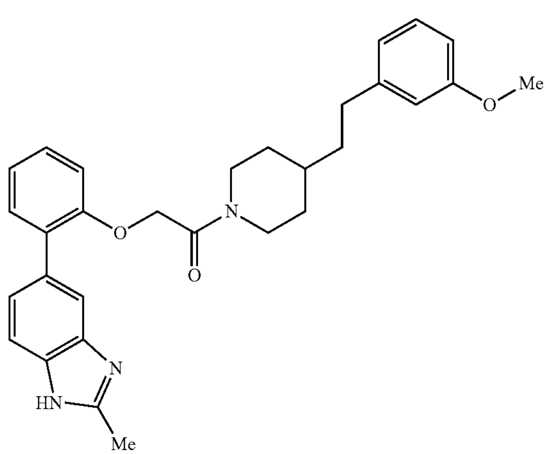 [SMILES: COc1cccc(CCC2CCN(C(=O)COc3ccccc3-c3ccc4[nH]c(C)nc4c3)CC2)c1] | 483.6 | 484 | 482 |

TABLE 1-continued
| Compound No. | Structure | MW | Positive MS peak | Negative MS peak |
|---|---|---|---|---|
| 388 | 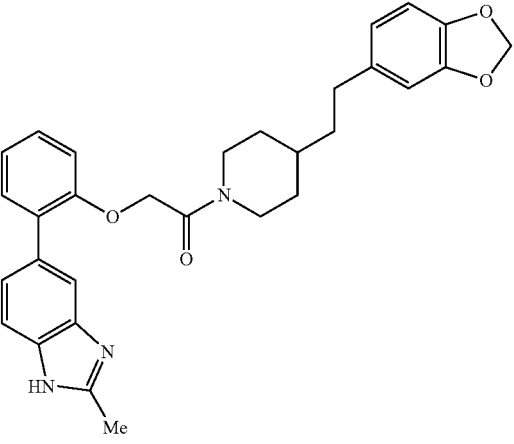 [SMILES: Cc1nc2cc(-c3ccccc3OCC(=O)N3CCC(CCc4ccc5c(c4)OCO5)CC3)ccc2[nH]1] | 497.6 | 498 | 496 |
| 389 | 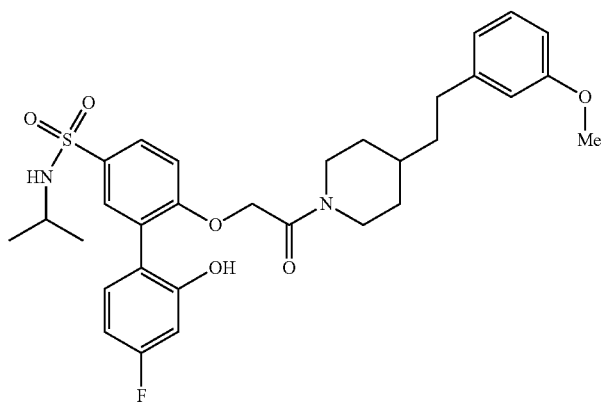 [SMILES: COc1cccc(CCC2CCN(C(=O)COc3ccc(S(=O)(=O)NC(C)C)cc3-c3ccc(F)cc3O)CC2)c1] | 584.7 | 585 | 583 |
| 390 | 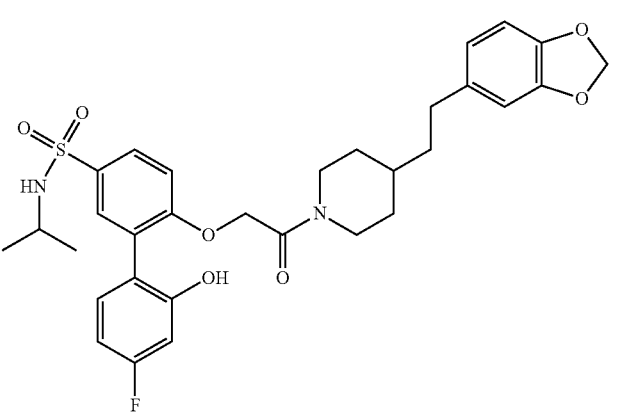 [SMILES: CC(C)NS(=O)(=O)c1ccc(OCC(=O)N2CCC(CCc3ccc4c(c3)OCO4)CC2)c(-c2ccc(F)cc2O)c1] | 598.7 | 599 | 597 |

TABLE 1-continued
| Compound No. | Structure | MW | Positive MS peak | Negative MS peak |
| --- | --- | --- | --- | --- |
| 391 | 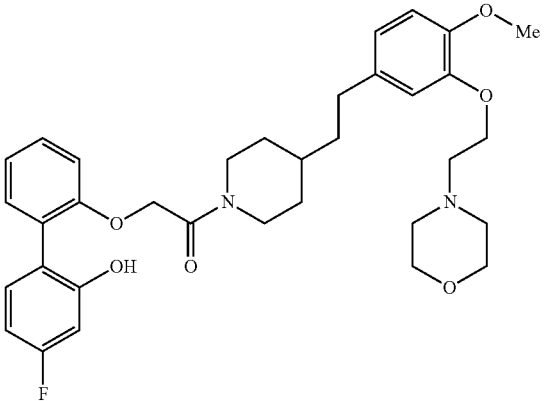 [SMILES: COc1ccc(CCC2CCN(C(=O)COc3ccccc3-c3ccc(F)cc3O)CC2)cc1OCCN1CCOCC1] | 592.7 | 593 | 591 |
| 392 | 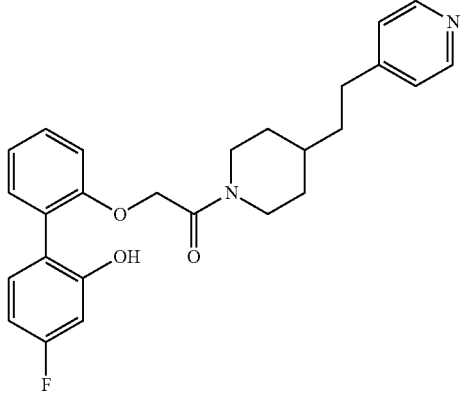 | 434.5 | 435 | 433 |
| 393 | 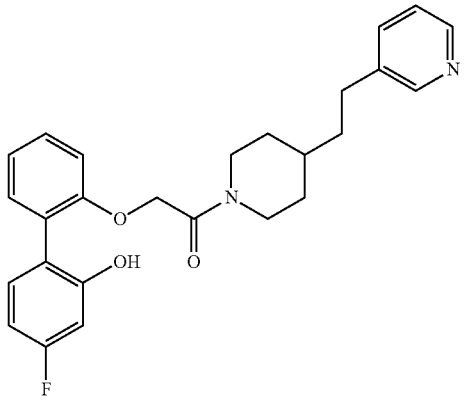 | 434.5 | 435 | 433 |

TABLE 1-continued

| Compound No. | Structure | MW | Positive MS peak | Negative MS peak |
|---|---|---|---|---|
| 396 | 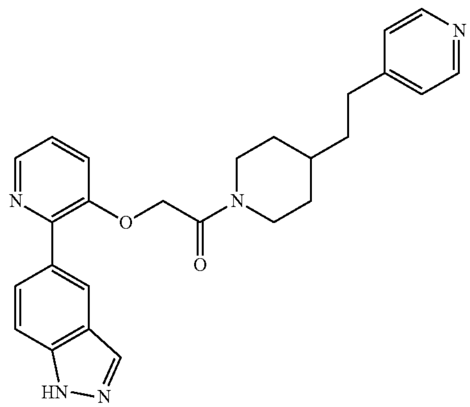 [SMILES: O=C(COc1cccnc1-c1ccc2[nH]ncc2c1)N1CCC(CCc2ccncc2)CC1] | 441.5 | 442 | |
| 397 | 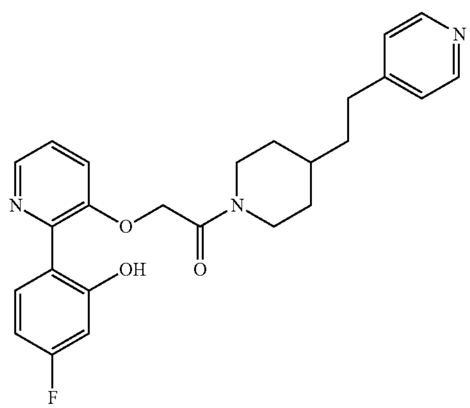 [SMILES: O=C(COc1cccnc1-c1ccc(F)cc1O)N1CCC(CCc2ccncc2)CC1] | 435.5 | 436 | 434 |
| 398 | 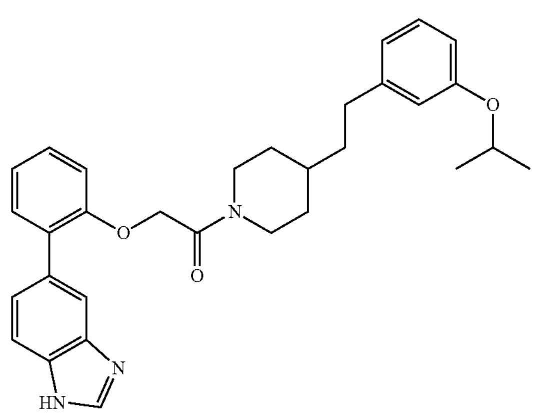 [SMILES: CC(C)Oc1cccc(CCC2CCN(C(=O)COc3ccccc3-c3ccc4[nH]cnc4c3)CC2)c1] | 497.6 | 498 | 496 |

TABLE 1-continued

| Compound No. | Structure | MW | Positive MS peak | Negative MS peak |
|---|---|---|---|---|
| 399 | 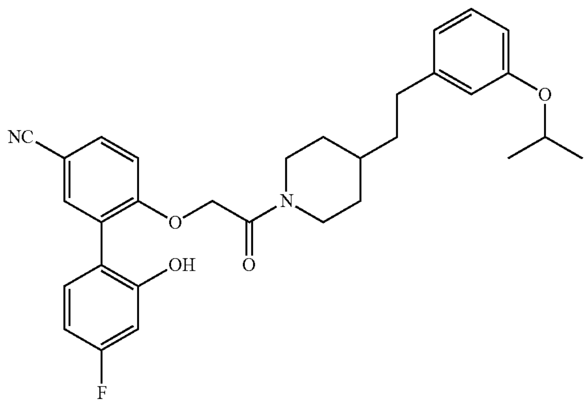 [SMILES: CC(C)Oc1cccc(CCC2CCN(C(=O)COc3ccc(C#N)cc3-c3ccc(F)cc3O)CC2)c1] | 516.6 | 517 | 515 |
| 400 | 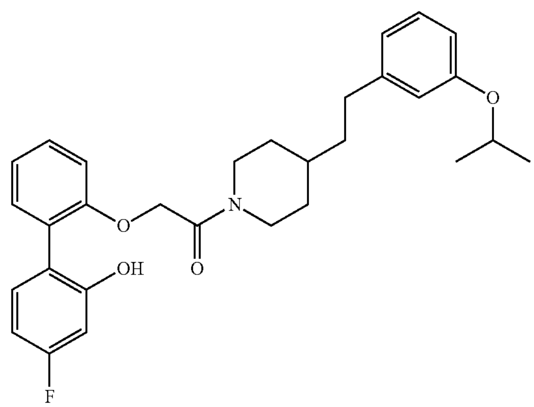 [SMILES: CC(C)Oc1cccc(CCC2CCN(C(=O)COc3ccccc3-c3ccc(F)cc3O)CC2)c1] | 491.6 | 492 | 490 |
| 401 | 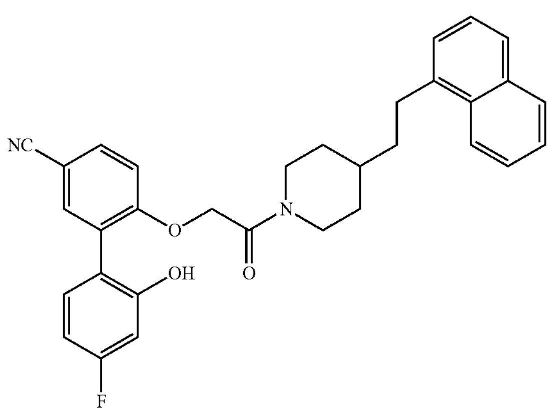 [SMILES: N#Cc1ccc(OCC(=O)N2CCC(CCc3cccc4ccccc34)CC2)c(-c2ccc(F)cc2O)c1] | 508.6 | 509 | 507 |

TABLE 1-continued
| Compound No. | Structure | MW | Positive MS peak | Negative MS peak |
| --- | --- | --- | --- | --- |
| 402 | 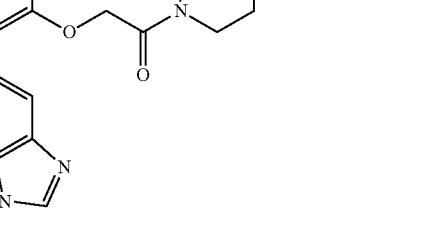 | 489.6 | 490 | 488 |
| 403 | 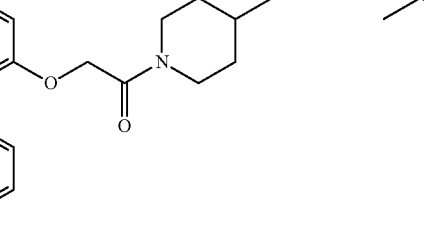 | 482.6 | 483 | |
| 404 | 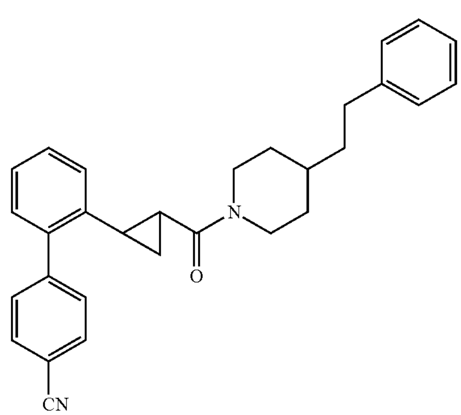 [SMILES: N#Cc1ccc(-c2ccccc2C2CC2C(=O)N2CCC(CCc3ccccc3)CC2)cc1] | 434.6 | 435 | |

TABLE 1-continued

| Compound No. | Structure | MW | Positive MS peak | Negative MS peak |
|---|---|---|---|---|
| 405 | 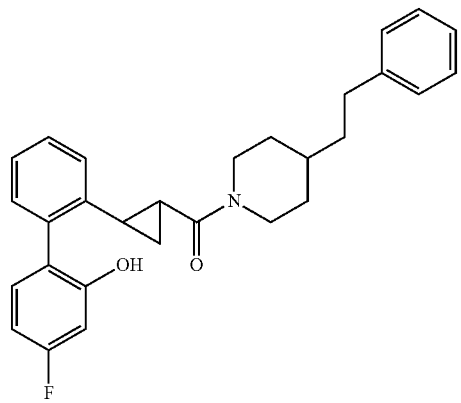 [SMILES: O=C(C1CC1c1ccccc1-c1ccc(F)cc1O)N1CCC(CCc2ccccc2)CC1] | 443.6 | 444 | 442 |
| 406 | 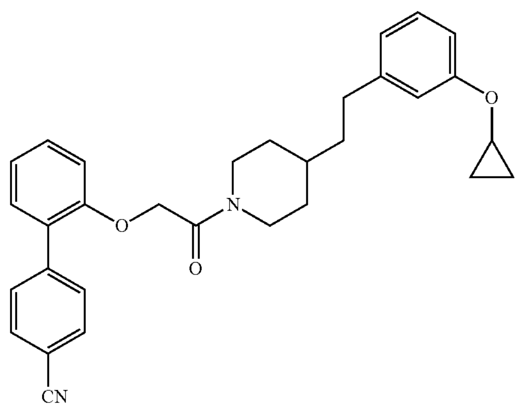 [SMILES: N#Cc1ccc(-c2ccccc2OCC(=O)N2CCC(CCc3cccc(OC4CC4)c3)CC2)cc1] | 480.6 | 481 | |
| 407 | 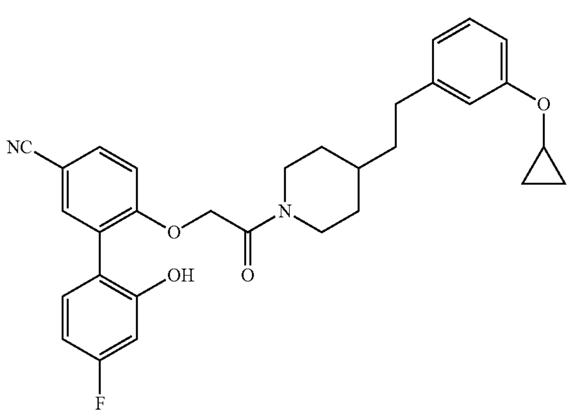 [SMILES: N#Cc1ccc(OCC(=O)N2CCC(CCc3cccc(OC4CC4)c3)CC2)c(-c2ccc(F)cc2O)c1] | 514.6 | 515 | 513 |

TABLE 1-continued
| Compound No. | Structure | MW | Positive MS peak | Negative MS peak |
|---|---|---|---|---|
| 408 | 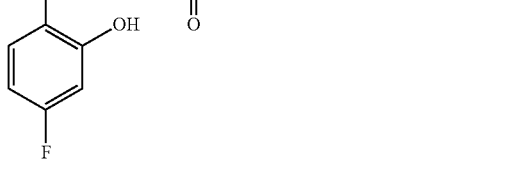 | 492.6 | 493 | 491 |
| 409 | 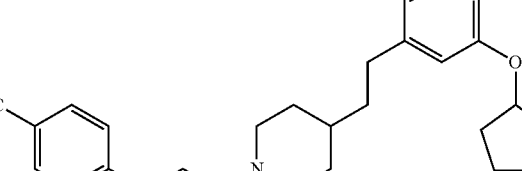 | 542.6 | 543 | 541 |
| 410 | 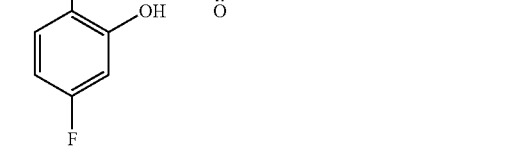 | 518.6 | 519 | 517 |

TABLE 1-continued

| Compound No. | Structure | MW | Positive MS peak | Negative MS peak |
|---|---|---|---|---|
| 411 | 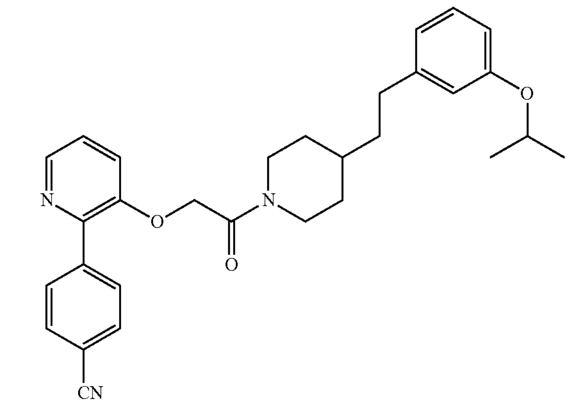 [SMILES: CC(C)Oc1cccc(CCC2CCN(C(=O)COc3cccnc3-c3ccc(C#N)cc3)CC2)c1] | 483.6 | 484 | |
| 412 | 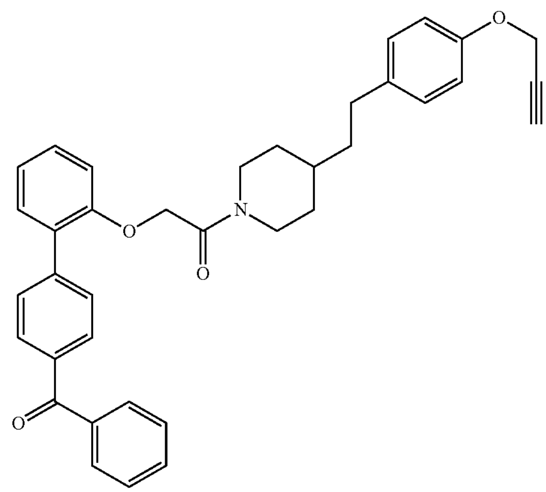 [SMILES: C#CCOc1ccc(CCC2CCN(C(=O)COc3ccccc3-c3ccc(C(=O)c4ccccc4)cc3)CC2)cc1] | 557.68 | 558 | |
| 413 | 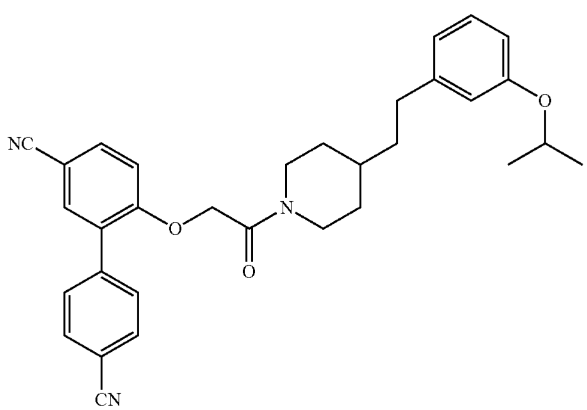 [SMILES: CC(C)Oc1cccc(CCC2CCN(C(=O)COc3ccc(C#N)cc3-c3ccc(C#N)cc3)CC2)c1] | 507.6 | 508 | |

TABLE 1-continued
| Compound No. | Structure | MW | Positive MS peak | Negative MS peak |
|---|---|---|---|---|
| 414 | 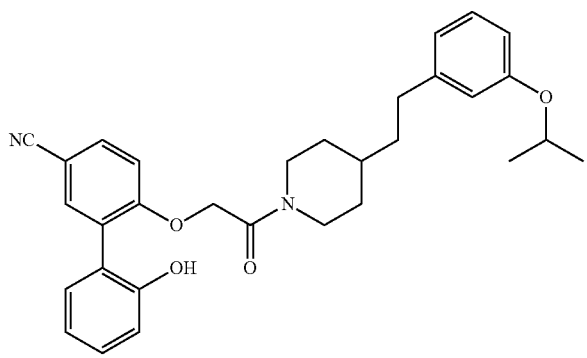 [SMILES: CC(C)Oc1cccc(CCC2CCN(C(=O)COc3ccc(C#N)cc3-c3ccccc3O)CC2)c1] | 498.6 | 499 | 497 |
| 415 | 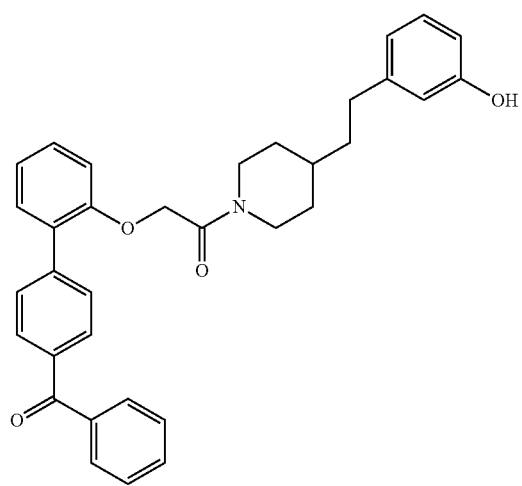 [SMILES: O=C(c1ccccc1)c1ccc(-c2ccccc2OCC(=O)N2CCC(CCc3cccc(O)c3)CC2)cc1] | 551.72 | | |
| 416 | 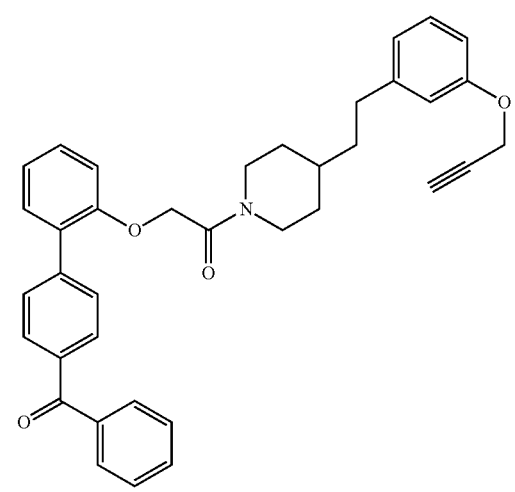 [SMILES: C#CCOc1cccc(CCC2CCN(C(=O)COc3ccccc3-c3ccc(C(=O)c4ccccc4)cc3)CC2)c1] | 573.72 | | |

TABLE 1-continued
| Compound No. | Structure | MW | Positive MS peak | Negative MS peak |
|---|---|---|---|---|
| 417 | 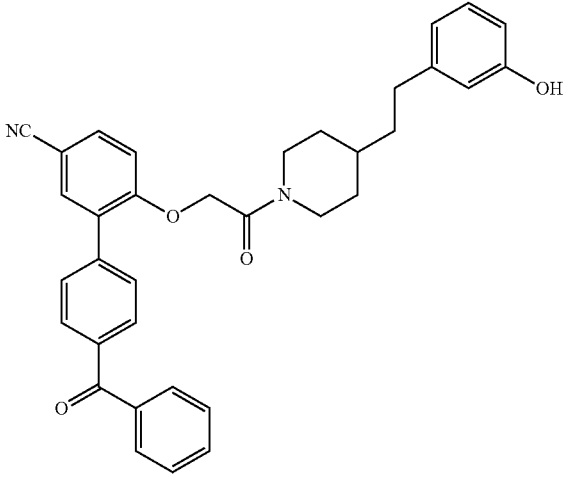 [SMILES: N#Cc1ccc(OCC(=O)N2CCC(CCc3cccc(O)c3)CC2)c(-c2ccc(C(=O)c3ccccc3)cc2)c1] | 560.68 | | |
| 418 | 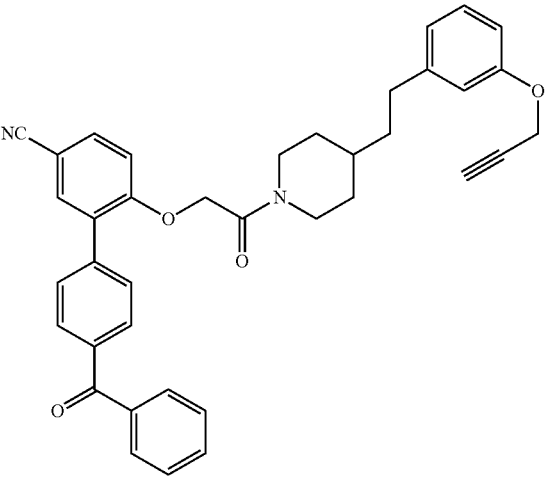 [SMILES: C#CCOc1cccc(CCC2CCN(C(=O)COc3ccc(C#N)cc3-c3ccc(C(=O)c4ccccc4)cc3)CC2)c1] | 598.73 | | |
| 419 | 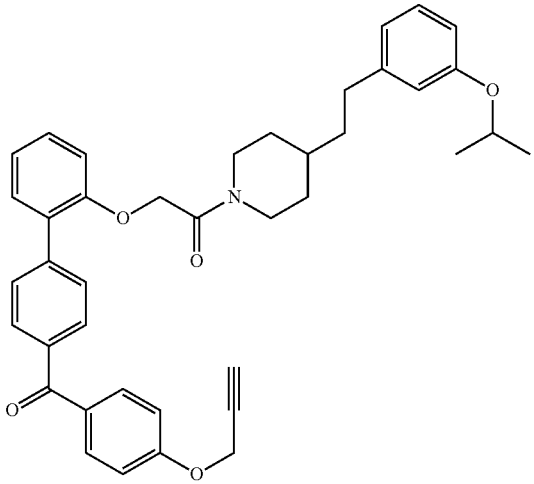 [SMILES: C#CCOc1ccc(C(=O)c2ccc(-c3ccccc3OCC(=O)N3CCC(CCc4cccc(OC(C)C)c4)CC3)cc2)cc1] | 615.8 | 616 | |

TABLE 1-continued

| Compound No. | Structure | MW | Positive MS peak | Negative MS peak |
| --- | --- | --- | --- | --- |
| 420 | 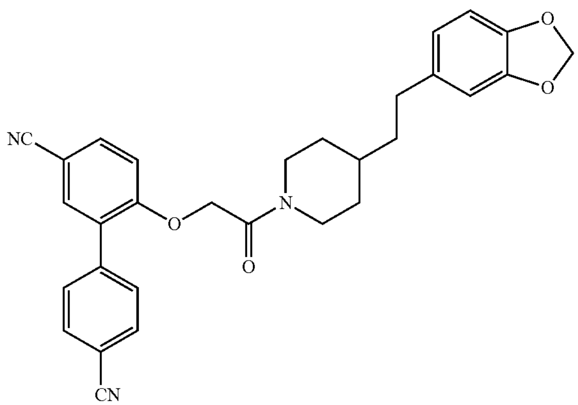 [SMILES: N#Cc1ccc(-c2cc(C#N)ccc2OCC(=O)N2CCC(CCc3ccc4c(c3)OCO4)CC2)cc1] | 493.6 | 494 | |
| 421 | 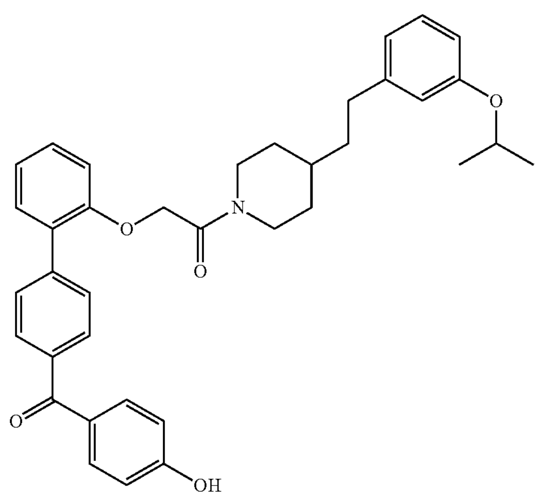 [SMILES: CC(C)Oc1cccc(CCC2CCN(C(=O)COc3ccccc3-c3ccc(C(=O)c4ccc(O)cc4)cc3)CC2)c1] | 593.75 | | |
| 422 | 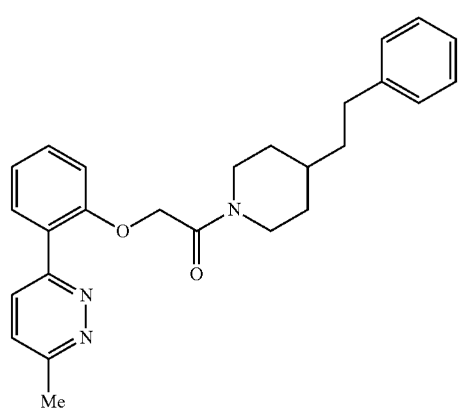 [SMILES: Cc1ccc(-c2ccccc2OCC(=O)N2CCC(CCc3ccccc3)CC2)nn1] | 415.5 | 416 | |

TABLE 1-continued

| Compound No. | Structure | MW | Positive MS peak | Negative MS peak |
|---|---|---|---|---|
| 423 | 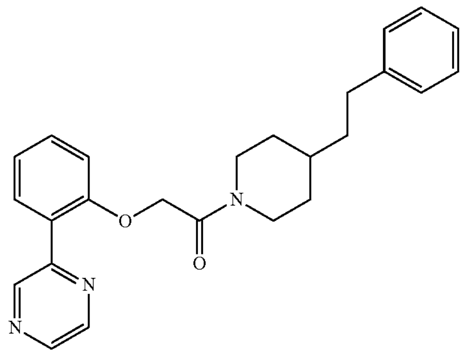 [SMILES: O=C(COc1ccccc1-c1cnccn1)N1CCC(CCc2ccccc2)CC1] | 401.5 | 402 | |
| 424 | 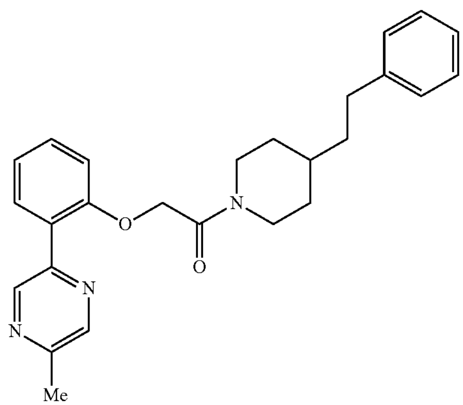 [SMILES: Cc1cnc(-c2ccccc2OCC(=O)N2CCC(CCc3ccccc3)CC2)cn1] | 415.5 | 416 | |
| 425 | 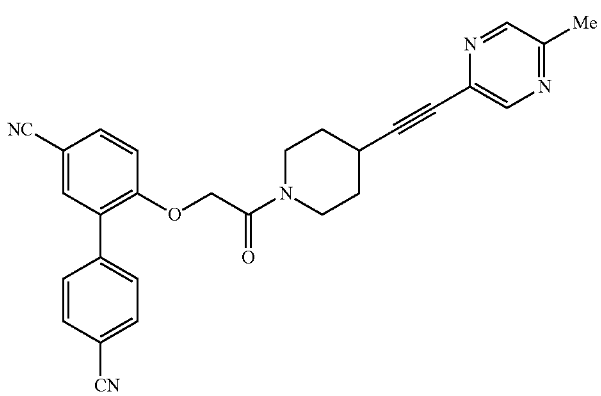 [SMILES: Cc1cnc(C#CC2CCN(C(=O)COc3ccc(C#N)cc3-c3ccc(C#N)cc3)CC2)cn1] | 461.5 | 462 | |
| 426 | 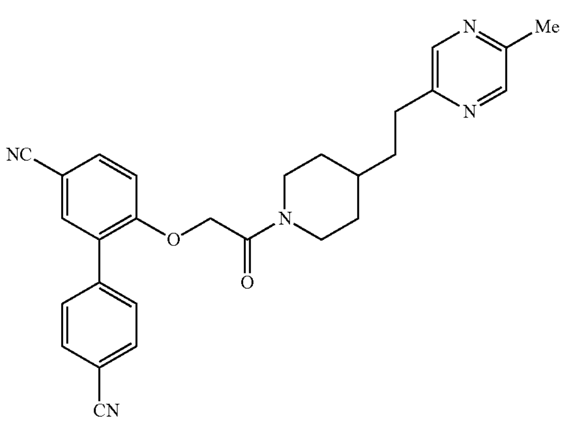 [SMILES: Cc1cnc(CCC2CCN(C(=O)COc3ccc(C#N)cc3-c3ccc(C#N)cc3)CC2)cn1] | 465.6 | 466 | |

TABLE 1-continued

| Compound No. | Structure | MW | Positive MS peak | Negative MS peak |
| --- | --- | --- | --- | --- |
| 427 | 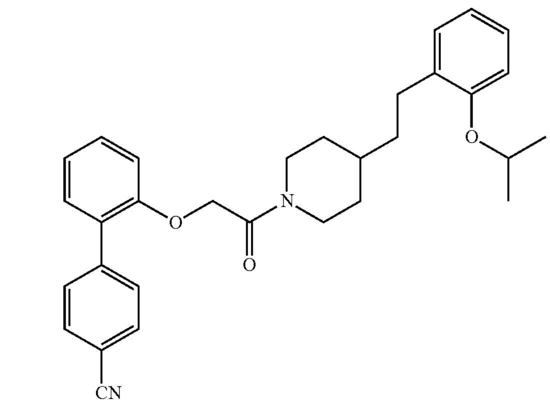 [SMILES: CC(C)Oc1ccccc1CCC1CCN(C(=O)COc2ccccc2-c2ccc(C#N)cc2)CC1] | 482.6 | | 483 |
| 428 | 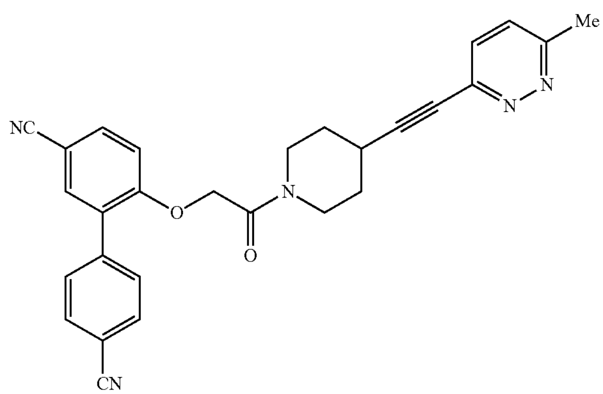 [SMILES: Cc1ccc(C#CC2CCN(C(=O)COc3ccc(C#N)cc3-c3ccc(C#N)cc3)CC2)nn1] | 461.5 | | 462 |
| 429 | 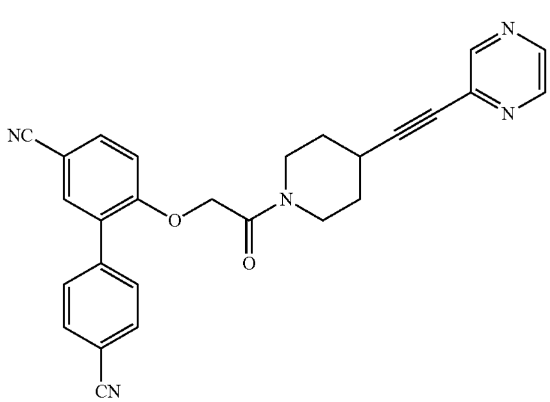 [SMILES: N#Cc1ccc(-c2cc(C#N)ccc2OCC(=O)N2CCC(C#Cc3cnccn3)CC2)cc1] | 447.5 | | 448 |

TABLE 1-continued

| Compound No. | Structure | MW | Positive MS peak | Negative MS peak |
|---|---|---|---|---|
| 430 | 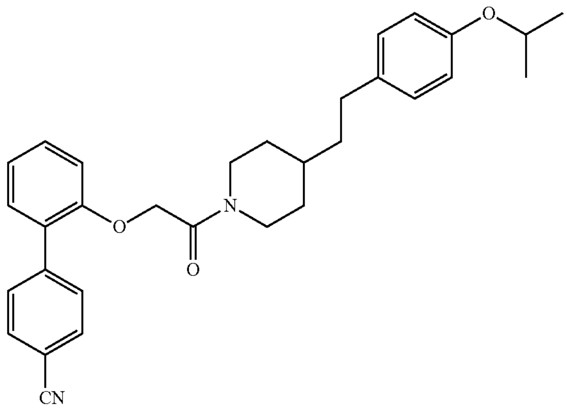 [SMILES: CC(C)Oc1ccc(CCC2CCN(C(=O)COc3ccccc3-c3ccc(C#N)cc3)CC2)cc1] | 482.6 | 483 | |
| 431 | 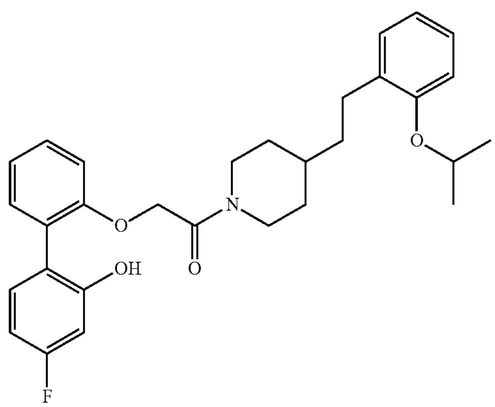 [SMILES: CC(C)Oc1ccccc1CCC1CCN(C(=O)COc2ccccc2-c2ccc(F)cc2O)CC1] | 491.6 | 492 | 490 |
| 432 | 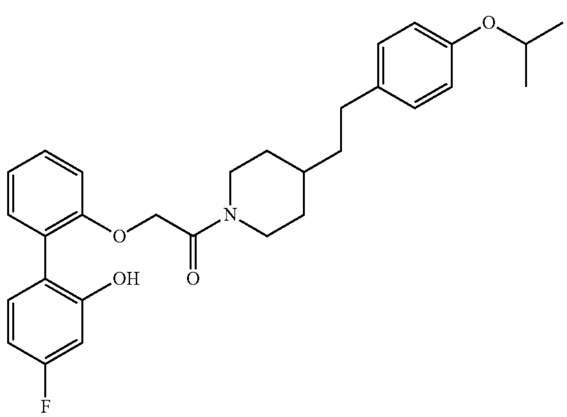 [SMILES: CC(C)Oc1ccc(CCC2CCN(C(=O)COc3ccccc3-c3ccc(F)cc3O)CC2)cc1] | 491.6 | 492 | 490 |

TABLE 1-continued

| Compound No. | Structure | MW | Positive MS peak | Negative MS peak |
|---|---|---|---|---|
| 433 | 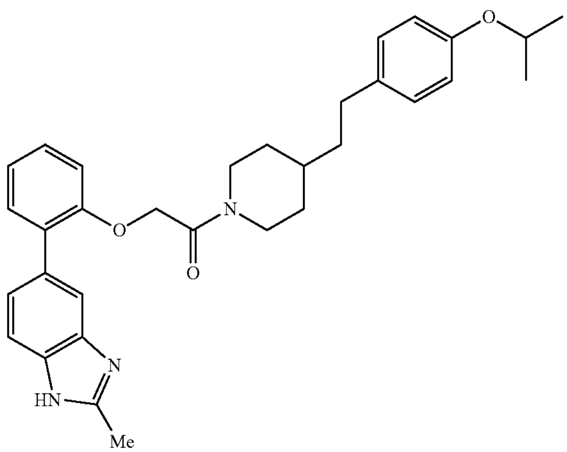 [SMILES: Cc1nc2cc(-c3ccccc3OCC(=O)N3CCC(CCc4ccc(OC(C)C)cc4)CC3)ccc2[nH]1] | 511.7 | 512 | 510 |
| 434 | 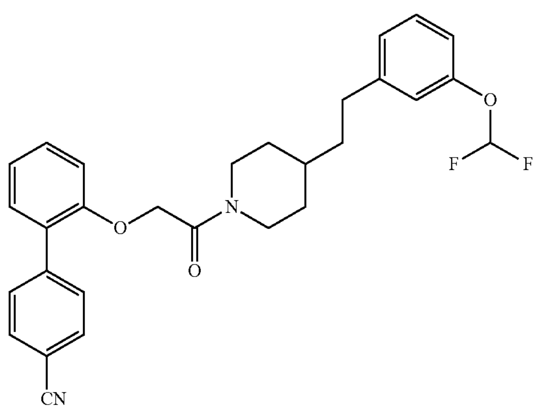 [SMILES: N#Cc1ccc(-c2ccccc2OCC(=O)N2CCC(CCc3cccc(OC(F)F)c3)CC2)cc1] | 490.5 | 491 | |
| 435 | 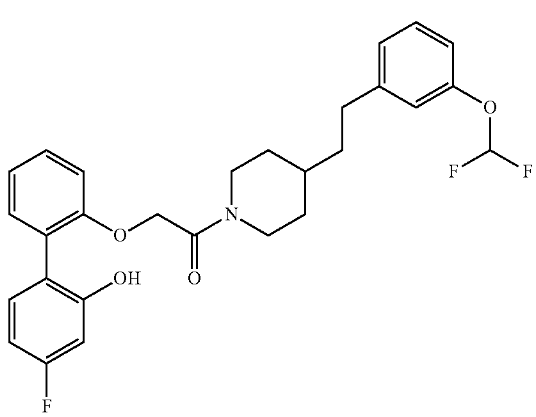 [SMILES: O=C(COc1ccccc1-c1ccc(F)cc1O)N1CCC(CCc2cccc(OC(F)F)c2)CC1] | 499.5 | 500 | 498 |

TABLE 1-continued

| Compound No. | Structure | MW | Positive MS peak | Negative MS peak |
|---|---|---|---|---|
| 436 | 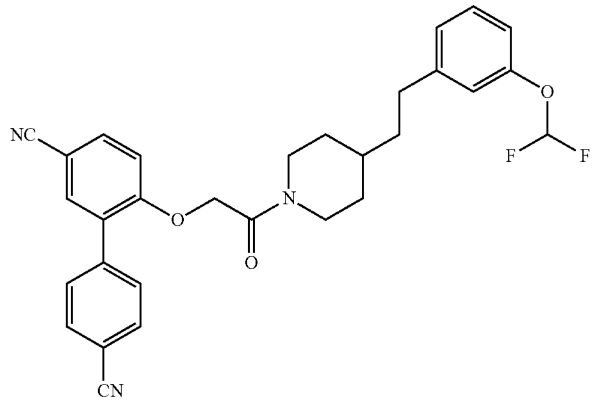 [SMILES: N#Cc1ccc(-c2cc(C#N)ccc2OCC(=O)N2CCC(CCc3cccc(OC(F)F)c3)CC2)cc1] | 515.6 | 516 | |
| 437 | 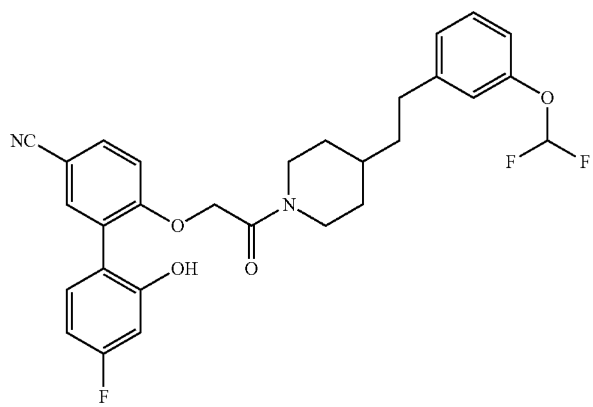 [SMILES: N#Cc1ccc(OCC(=O)N2CCC(CCc3cccc(OC(F)F)c3)CC2)c(-c2ccc(F)cc2O)c1] | 524.5 | 525 | 523 |
| 438 | 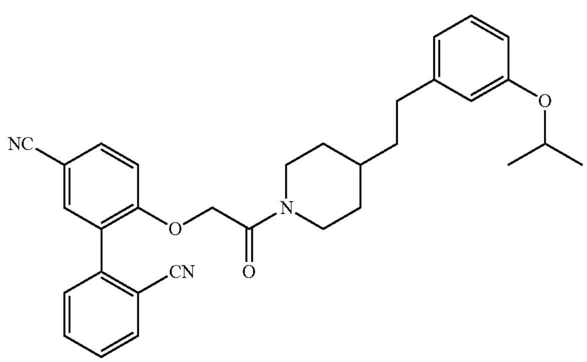 [SMILES: CC(C)Oc1cccc(CCC2CCN(C(=O)COc3ccc(C#N)cc3-c3ccccc3C#N)CC2)c1] | 482.6 | 483 | |
| 439 | 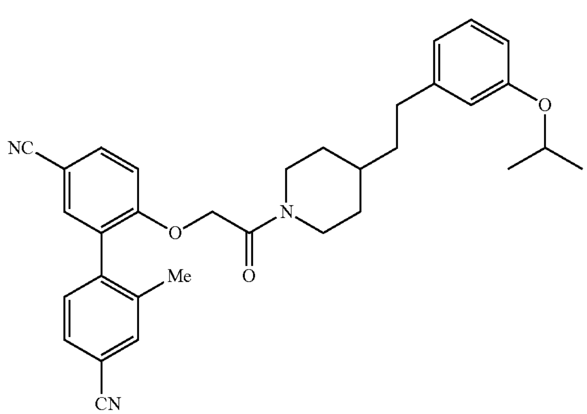 [SMILES: Cc1cc(C#N)ccc1-c1cc(C#N)ccc1OCC(=O)N1CCC(CCc2cccc(OC(C)C)c2)CC1] | 496.6 | 497 | |

TABLE 1-continued

| Compound No. | Structure | MW | Positive MS peak | Negative MS peak |
|---|---|---|---|---|
| 440 | 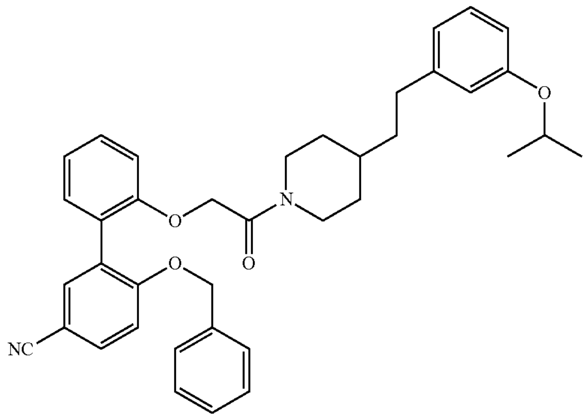 [SMILES: CC(C)Oc1cccc(CCC2CCN(C(=O)COc3ccccc3-c3cc(C#N)ccc3OCc3ccccc3)CC2)c1] | 588.7 | 589 | |
| 441 | 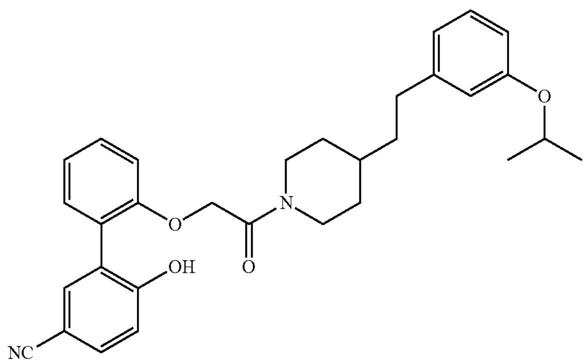 [SMILES: CC(C)Oc1cccc(CCC2CCN(C(=O)COc3ccccc3-c3cc(C#N)ccc3O)CC2)c1] | 498.6 | 499 | 497 |
| 442 | 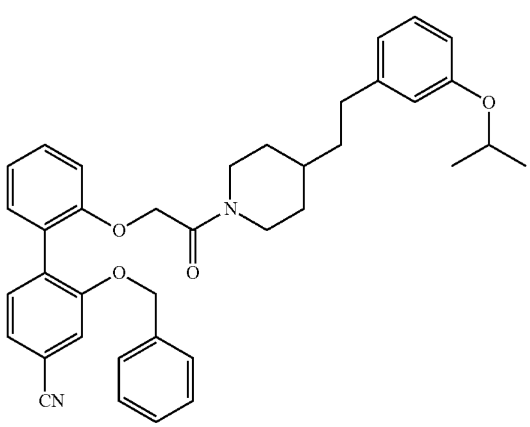 [SMILES: CC(C)Oc1cccc(CCC2CCN(C(=O)COc3ccccc3-c3ccc(C#N)cc3OCc3ccccc3)CC2)c1] | 588.7 | 589 | |

TABLE 1-continued

| Compound No. | Structure | MW | Positive MS peak | Negative MS peak |
|---|---|---|---|---|
| 443 | 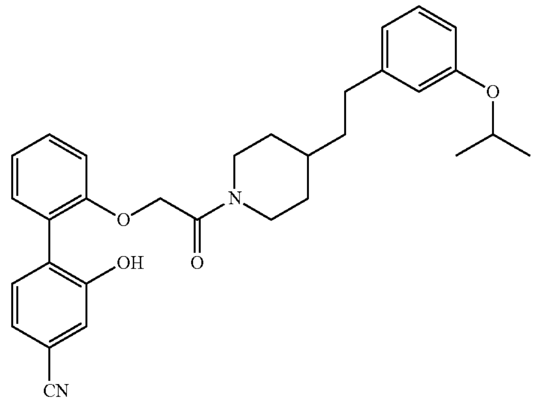 [SMILES: CC(C)Oc1cccc(CCC2CCN(C(=O)COc3ccccc3-c3ccc(C#N)cc3O)CC2)c1] | 498.6 | 499 | 497 |
| 444 | 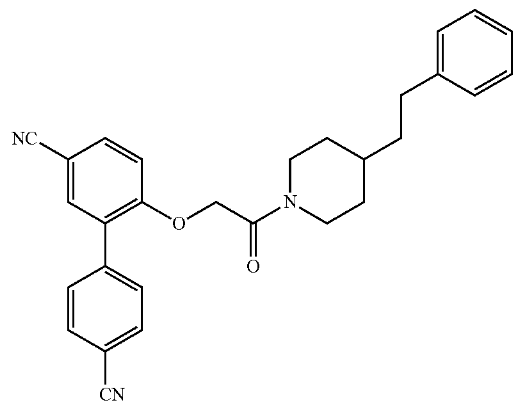 [SMILES: N#Cc1ccc(-c2cc(C#N)ccc2OCC(=O)N2CCC(CCc3ccccc3)CC2)cc1] | 444.5 | 445 | |

2. Pharmaceutical Compositions and Administrations

In one aspect, the present application relates to a pharmaceutical composition comprising a compound of the application, or a pharmaceutically acceptable salt, solvate, or prodrug thereof, and a pharmaceutically acceptable excipient.

The compound or composition of the application are administered orally, nasally, transdermally, pulmonary, inhalationally, buccally, sublingually, intraperitoneally, subcutaneously, intramuscularly, intravenously, rectally, intrapleurally, intrathecally and parenterally. In one aspect, the compound is administered orally. One skilled in the art will recognize the advantages of certain routes of administration.

The dosage regimen utilizing the compounds or compositions is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the application can be found in *Remington: the Science and Practice of Pharmacy*, 19th edition, Mack Publishing Co., Easton, Pa. (1995). In an embodiment, the compounds described herein, and the pharmaceutically acceptable salts, solvates, and prodrugs thereof, are used in pharmaceutical preparations in combination with a pharmaceutically acceptable excipient, carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

In one aspect, the compound or composition is prepared for oral administration, wherein the compounds of the application, or pharmaceutically acceptable salts, solvates, or prodrugs thereof are combined with a suitable solid or liquid carrier or diluent to form capsules, tablets, pills, powders, syrups, solutions, suspensions and the like.

The tablets, pills, capsules, and the like contain from about 1 to about 99 weight percent of the active ingredient and a binder such as gum tragacanth, acacias, corn starch or gelatin; excipients such as dicalcium phosphate; a disintegrating agent such as corn starch, potato starch or alginic acid; a lubricant such as magnesium stearate; and/or a sweetening agent such as sucrose, lactose, saccharin, xylitol, and the like. When a dosage unit form is a capsule, it often contains, in addition to materials of the above type, a liquid carrier such as a fatty oil.

In one aspect, various other materials are present as coatings or to modify the physical form of the dosage unit.

For instance, in some embodiments, tablets are coated with shellac, sugar or both. In some embodiments, a syrup or elixir contains, in addition to the active ingredient, sucrose as a sweetening agent, methyl and propylparabens as preservatives, a dye and a flavoring such as cherry or orange flavor, and the like.

In one aspect, relating to parenteral administration, the compound of the application, or a pharmaceutically acceptable salt, solvate, or prodrug thereof, may be combined with sterile aqueous or organic media to form injectable solutions or suspensions. In one embodiment, injectable compositions are aqueous isotonic solutions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%; in another aspect, the compositions contain about 1 to 50%, of the active ingredient.

For example, injectable solutions are produced using solvents such as sesame or peanut oil or aqueous propylene glycol, as well as aqueous solutions of water-soluble pharmaceutically-acceptable salts of the compounds. In some embodiments, dispersions are prepared in glycerol, liquid polyethylene glycols and mixtures thereof in oils. Under ordinary conditions of storage and use, these preparations contain a preservative to prevent the growth of microorganisms. The terms "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

For rectal administration, suitable pharmaceutical compositions are, for example, topical preparations, suppositories or enemas. Suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, in another embodiment, compositions contain about 1 to 50%, of the active ingredient.

In one aspect, the compounds of the application are formulated to deliver the active agent by pulmonary administration, e.g., administration of an aerosol formulation containing the active agent from, for example, a manual pump spray, nebulizer or pressurized metered-dose inhaler. In one aspect, suitable formulations of this type also include other agents, such as antistatic agents, to maintain the compounds of the application as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a headspace representing greater than about 15% of the total volume of the canister. Often, the polymer intended for pulmonary administration is dissolved, suspended or emulsified in a mixture of a solvent, surfactant and propellant. The mixture is maintained under pressure in a canister that has been sealed with a metering valve.

For nasal administration, either a solid or a liquid carrier can be used. The solid carrier includes a coarse powder having particle size in the range of, for example, from about 20 to about 500 microns and such formulation is administered by rapid inhalation through the nasal passages. In one aspect where the liquid carrier is used, the formulation is administered as a nasal spray or drops and includes oil or aqueous solutions of the active ingredients.

Also contemplated are formulations that are rapidly dispersing dosage forms, also known as "flash dose" forms. In one aspect, the compounds of the application are formulated as compositions that release their active ingredients within a short period of time, e.g., typically less than about five minutes, in another embodiment, less than about ninety seconds, in another embodiment, less than about thirty seconds and in another embodiment, in less than about ten or fifteen seconds. Such formulations are suitable for administration to a subject via a variety of routes, for example by insertion into a body cavity or application to a moist body surface or open wound.

Typically, a "flash dosage" is a solid dosage form that is administered orally, which rapidly disperses in the mouth, and hence does not require great effort in swallowing and allows the compound to be rapidly ingested or absorbed through the oral mucosal membranes. In some embodiments, suitable rapidly dispersing dosage forms are also used in other applications, including the treatment of wounds and other bodily insults and diseased states in which release of the medicament by externally supplied moisture is not possible.

"Flash dose" forms are known in the art; see for example, effervescent dosage forms and quick release coatings of insoluble microparticles in U.S. Pat. Nos. 5,578,322 and 5,607,697; freeze dried foams and liquids in U.S. Pat. Nos. 4,642,903 and 5,631,023; melt spinning of dosage forms in U.S. Pat. Nos. 4,855,326, 5,380,473 and 5,518,730; solid, free-form fabrication in U.S. Pat. No. 6,471,992; saccharide-based carrier matrix and a liquid binder in U.S. Pat. Nos. 5,587,172, 5,616,344, 6,277,406, and 5,622,719; and other forms known to the art.

The compounds of the application are also formulated as "pulsed release" formulations, in which the compound is released from the pharmaceutical compositions in a series of releases (i.e., pulses). The compounds are also formulated as "sustained release" formulations in which the compound is continuously released from the pharmaceutical composition over a prolonged period.

Also contemplated are formulations, e.g., liquid formulations, including cyclic or acyclic encapsulating or solvating agents, e.g., cyclodextrins, polyethers, or polysaccharides (e.g., methylcellulose), or in another embodiment, polyanionic β-cyclodextrin derivatives with a sodium sulfonate salt group separate from the lipophilic cavity by an alkyl ether spacer group or polysaccharides. In one embodiment, the agent is methylcellulose. In another embodiment, the agent is a polyanionic β-cyclodextrin derivative with a sodium sulfonate salt separated from the lipophilic cavity by a butyl ether spacer group, e.g., CAPTISOL® (CyDex, Overland, Kans.). One skilled in the art can evaluate suitable agent/disclosed compound formulation ratios by preparing a solution of the agent in water, e.g., a 40% by weight solution; preparing serial dilutions, e.g. to make solutions of 20%, 10, 5%, 2.5%, 0% (control), and the like; adding an excess (compared to the amount that can be solubilized by the agent) of the disclosed compound; mixing under appropriate conditions, e.g., heating, agitation, sonication, and the like; centrifuging or filtering the resulting mixtures to obtain clear solutions; and analyzing the solutions for concentration of the disclosed compound.

3. Methods of Use

In one aspect, the present application relates to a method of preventing or treating an immune disorder, an inflammatory disorder, or an allergic disorder in a subject comprising administering to the subject an effective amount of a compound or composition of the application.

In one aspect, the immune disorder is selected from multiple sclerosis, myasthenia gravis, Guillain-Barre, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, psoriasis, dermatitis herpetiformis, pemphigus vulgaris, vitiligo, Crohn's disease, ulcerative colitis, primary biliary cirrhosis, autoimmune hepatitis, Type 1 diabetes mellitus, immune-mediated diabetes mellitus, Grave's disease, Hashimoto's thyroiditis, autoimmune oophoritis disorder of the adrenal gland, orchitis, autoimmune disorder of the adrenal gland, rheumatoid arthritis, systemic lupus erythematosus, scleroderma, polymyositis, dermatomyositis, ankylosing spondylitis, and Sjogren's syndrome.

In one aspect, the inflammatory disorder is selected from transplant rejection, skin graft rejection, arthritis, rheumatoid arthritis, osteoarthritis, bone diseases associated with increased bone resorption, inflammatory bowel disease, ileitis, ulcerative colitis, Barrett's syndrome, Crohn's disease, asthma, adult respiratory distress syndrome, chronic obstructive airway disease, corneal dystrophy, trachoma, onchocerciasis, uveitis, sympathetic ophthalmitis, endophthalmitis, gingivitis, periodontitis, tuberculosis, leprosy, uremic complications, glomerulonephritis, nephrosis, sclerodermatitis, psoriasis, eczema, chronic demyelinating diseases of the nervous system, multiple sclerosis, AIDS-related neurodegeneration, Alzheimer's disease, infectious meningitis, encephalomyelitis, Parkinson's disease, Huntington's disease, amyotrophic lateral sclerosis, viral encephalitis, autoimmune encephalitis, autoimmune disorders, immune-complex vasculitis, systemic lupus erythematosus (SLE), cardiomyopathy, ischemic heart disease, hypercholesterolemia, atherosclerosis, preeclampsia, chronic liver failure, brain trauma, spinal cord trauma, and cancer.

In one aspect, the allergic disorder is selected from allergic rhinitis, sinusitis, rhinosinusitis, chronic otitis media, recurrent otitis media, drug reactions, insect sting reactions, latex reactions, conjunctivitis, urticaria, anaphylaxis reactions, anaphylactoid reactions, atopic dermatitis, asthma, or food allergies.

In one aspect the present application relates to a method of modulating antigen receptor signaling comprising administering a compound or composition of the application. In another aspect, the method of modulating antigen receptor further comprises modulating subsequent biochemical pathways culminating in cellular activation. In another aspect, the method of modulating antigen receptor further comprises modulating subsequent biochemical pathways culminating in cellular activation and production of a responsive cytokine. In one aspect, the antigen receptor is a T cell receptor. In another aspect, the cytokine is selected from IL-2, IL-4, IL-5, IL-7, IL-10, IL-17, IL-21, IFNγ, and TNFα. In one aspect, the modulating occurs in vitro. In another aspect, the modulating occurs in vivo. In one aspect, the present application relates to a method of modulating antigen receptor (e.g., T cell receptor) signaling and subsequent biochemical pathways culminating in cellular activation and production of responsive cytokines, including but not limited to IL-2, IL-4, IL-5, IL-7, IL-10, IL-17, IL-21, IFNγ, and TNFα, with a compound or composition of the application.

In one aspect, the present application relates to a method of modulating the store-operated calcium (SOC) channel comprising contacting the SOC channel complex, or part thereof, with a compound or composition of the application. In one aspect, the SOC channel complex is calcium-release activated calcium (CRAC) channel complex. In one aspect, the contacting occurs in vitro. In another aspect, the contacting occurs in vivo.

In one aspect, the present application relates to a method of modulating store-operated calcium (SOC) channel activity comprising contacting the store-operated calcium (SOC) channel complex, or part thereof, with a compound of the application, or pharmaceutically acceptable salt, solvate, prodrug thereof. In one aspect, the contacting occurs in vitro. In another aspect, the contacting occurs in vivo. In one aspect, the contacting occurs ex vivo. In one aspect, a compound of the application, modulates an interaction of, or modulates the level of, or binds to, or interacts with at least one part of the store-operated calcium channel complex, including but not limited to a stromal interaction molecule (STIM) or Orai family of protein. In one aspect, a compound of the application modulates an activity of, modulates an interaction of, or modulates the level of, or binds to, or interacts with at least one part of STIM1 or STIM2. In another aspect, the compound of the application modulates an activity of, modulates an interaction of, or modulates the level of, or binds to, or interacts with at least one part of Orai1. In one aspect, modulating store-operated calcium (SOC) channel activity with a compound of the application modulates store-operated calcium entry (SOCE). In another aspect, the store-operated calcium channel complex is calcium-release activated calcium (CRAC) channel complex. In one aspect, modulating CRAC activity with a compound of the application, modulates the electrophysiological current ($I_{CRAC}$) directly associated with activated CRAC channels. In one aspect, a compound of the application may bind to the CRAC channel. In one aspect, a compound of the application may bind to Orai1. In another aspect, a compound of the application may bind to or influence the activity of one or more additional proteins (other than STIM or Orai) directly involved in regulating SOCE.

In one aspect, the present application relates to a method of modulating store-operated calcium entry (SOCE) activation of nuclear factor of activated T cells (NFAT) in a subject comprising administering a compound of the application, or a pharmaceutically acceptable salt, solvate, or prodrug thereof.

In one aspect, the present application relates to a method of modulating cytokine expression by modulating the store-operated calcium entry activation of NFAT in a subject comprising administering a compound of the application, or a pharmaceutically acceptable salt, solvate, or prodrug thereof. In one aspect, the cytokine is selected from IL-2, IL-3, IL-4, IL-5, IL-6, IL-7, IL-8, IL-9, IL-10, IL-11, IL-12, IL-13, IL-15, IL-16, IL-17, IL-18, IL-1α, IL-1 β, IL-I RA, granulocyte colony stimulating factor (G-CSF), granulocyte-macrophage colony stimulating factor (GM-CSF), oncostatin M, erythropoietin, leukemia inhibitory factor (LIF), interferons, gamma-interferon (γ-IFN), B7-1 (CD80), B7-2 (B70, CD86), TNF-α, TNF-β, LT-β, CD40 ligand, Fas ligand, CD27 ligand, CD30 ligand, 4-1 BBL, Trail, beta-hexosaminidase, and migration inhibitory factor (MIF).

SOC plays an important role in the regulation of calcium levels in cells. Many diseases are linked to calcium dysregulation, for example, immune disorders, inflammatory disorders, and allergic disorders. Examples of immune disorders include e.g., multiple sclerosis, myasthenia gravis, Guillain-Barre, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, psoriasis, dermatitis herpetiformis, pemphigus vulgaris, vitiligo, Crohn's disease, ulcerative colitis, primary biliary cirrhosis, autoimmune hepatitis, Type 1 diabetes mellitus, immune-mediated diabetes mellitus, Grave's disease, Hashimoto's thyroiditis, autoimmune oophoritis disorder of the adrenal gland, orchitis, autoimmune disorder of the adrenal gland, rheumatoid arthritis, systemic lupus erythematosus, scleroderma, polymyositis, dermatomyositis, ankylosing spondylitis, and Sjogren's syndrome.

Inflammatory disorders may include e.g., from transplant rejection, skin graft rejection, arthritis, rheumatoid arthritis, osteoarthritis, bone diseases associated with increased bone resorption, inflammatory bowel disease, ileitis, ulcerative colitis, Barrett's syndrome, Crohn's disease, asthma, adult respiratory distress syndrome, chronic obstructive airway disease, corneal dystrophy, trachoma, onchocerciasis, uveitis, sympathetic ophthalmitis, endophthalmitis, gingivitis, periodontitis, tuberculosis, leprosy, uremic complications, glomerulonephritis, nephrosis, sclerodermatitis, psoriasis, eczema, chronic demyelinating diseases of the nervous system, multiple sclerosis, AIDS-related neurodegeneration, Alzheimer's disease, infectious meningitis, encephalomyelitis, Parkinson's disease, Huntington's disease, amyotrophic lateral sclerosis, viral encephalitis, autoimmune encephalitis, autoimmune disorders, immune-complex vasculitis, systemic lupus erythematosus (SLE), cardiomyopathy, ischemic heart disease, hypercholesterolemia, atherosclerosis, preeclampsia, chronic liver failure, brain trauma, spinal cord trauma, and cancer.

Allergic disorders may include e.g., allergic rhinitis, sinusitis, rhinosinusitis, chronic otitis media, recurrent otitis media, drug reactions, insect sting reactions, latex reactions, conjunctivitis, urticaria, anaphylaxis reactions, anaphylactoid reactions, atopic dermatitis, asthma, or food allergies.

Store-Operated Calcium Channels

Clinical studies demonstrate that the CRAC channel, a type of SOC channel, is required for the activation of genes underlying the T cell response to antigen (Partiseti et al., J Biol. Chem., 269, 32327-32335, 1994; Feske et al., Curr. Biol. 15, 1235-1241, 2005). In one aspect, store-operated calcium entry (SOCE) may contribute directly to the elevation of cytosolic calcium levels in T lymphocytes, where CRAC channels generate the sustained calcium signals needed to drive gene expression underlying T cell activation by antigen. Sustained calcium entry is needed for lymphocyte activation and adpative immune response. Calcium entry into lymphocytes occurs primarily through the CRAC channels. Increased calcium levels lead to NFAT activation and to expression of cytokines required for immune response.

The CRAC channel has a distinctive biophysical fingerprint, quantifiable store-dependence, and essential function in multiple cell types of the immune system. Studies have shown that active CRAC channels are formed from two component proteins. The two functional components are comprised of a STIM family member (STIM1 or STIM2) and an Orai family member (Orai1, Orai2, or Orai3). Specifically, STIM1 (stromal interaction molecule 1) was identified as the mammalian ER calcium sensor; and Orai1 was identified as a component of the mammalian CRAC channel.

STIM1 is the sensor of calcium levels within ER calcium stores, and redistributes in response to store depletion into ER puncta close to the plasma membrane. Orai1 is a pore forming CRAC channel subunit in the plasma membrane. The two membrane proteins STIM1 and Orai1 have each been shown to be essential for the activation of CRAC channels.

Expression of both STIM1 and Orai1 in human embryonic kidney 293 cells (HEK293 cells) reconstitute functional CRAC channels. Expression of Orai1 alone reduces SOCE in HEK293 cells and the calcium release-activated calcium current ($I_{CRAC}$) in rat basophilic leukemia cells. However, when co-expressed with the store-sensing STIM1 protein, Orai1 causes a massive increase in SOCE, enhancing the rate of calcium entry by up to 103-fold. This entry is entirely store dependent since the same coexpression causes no measurable store-independent calcium entry. This entry can be blocked by the store-operated channel blocker, 2-aminoethoxydiphenylborate.

4. Definitions

For convenience, certain terms used in the specification, examples and appended claims are collected here.

"Treating", includes any effect, e.g., lessening, reducing, modulating, or eliminating, that results in the improvement of the condition, disease, disorder, etc. "Treating" or "treatment" of a disease state includes: (1) inhibiting the disease state, i.e., arresting the development of the disease state or its clinical symptoms; (2) relieving the disease state, i.e., causing temporary or permanent regression of the disease state or its clinical symptoms; or (3) reducing or lessening the symptoms of the disease state.

"Preventing", refers to causing the clinical symptoms of the disease state not to develop in a subject that may be exposed to or predisposed to the disease state, but does not yet experience or display symptoms of the disease state.

An "effective amount" of a compound of the disclosed is the quantity which, when administered to a subject having a disease or disorder, results in regression of the disease or disorder in the subject. The amount of the disclosed compound to be administered to a subject will depend on the particular disorder, the mode of administration, co-administered compounds, if any, and the characteristics of the subject, such as general health, other diseases, age, sex, genotype, body weight and tolerance to drugs. The skilled artisan will be able to determine appropriate dosages depending on these and other factors.

As used herein, the term "effective amount" refers to an amount of a compound, or a combination of compounds, of the present application effective when administered alone or in combination with one or more agents. For example, an effective amount refers to an amount of the compound present in a formulation or on a medical device given to a recipient patient or subject sufficient to elicit biological activity. The combination of compounds optionally is a synergistic combination. Synergy, as described, for example, by Chou and Talalay, *Adv. Enzyme Regul.* vol. 22, pp. 27-55 (1984), occurs when the effect of the compounds when administered in combination is greater than the additive effect of the compounds when administered alone as a single agent. In general, a synergistic effect is most clearly demonstrated at sub-optimal concentrations of the compounds.

Synergy can be in terms of lower cytotoxicity, or increased biological activity, or some other beneficial effect of the combination compared with the individual components.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

The present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When any variable (e.g., $R^1$) occurs more than one time in any constituent or formula for a compound, its definition at each occurrence is independent of its definition at every other occurrence. Thus, for example, if a group is shown to be substituted with 0-2 $R^1$ moieties, then the group may optionally be substituted with up to two $R^1$ moieties and $R^1$ at each occurrence is selected independently from the definition of $R^1$. Also, combinations of substituents and/or variables are permissible, but only if such combinations result in stable compounds.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

Compounds of the present application that contain nitrogens can be converted to N-oxides by treatment with an oxidizing agent (e.g., 3-chloroperoxybenzoic acid (m-CPBA) and/or hydrogen peroxides) to afford other compounds of the present application. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present application can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_{1-6}$ alkyl, $C_{1-6}$ alkenyl, $C_{1-6}$ alkynyl, $C_{3-14}$ carbocycle, or 3-14-membered heterocycle) derivatives.

When an atom or chemical moiety is followed by a subscripted numeric range (e.g., $C_{1-6}$), the application is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

As used herein, "alkyl" is intended to include both branched and straight-chain saturated aliphatic hydrocarbon groups having the specified number of carbon atoms. For example, $C_{1-6}$ alkyl is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, s-pentyl, and n-hexyl. When "alkyl" further includes alkyl groups that have oxygen, nitrogen, sulfur or phosphorous atoms replacing one or more hydrocarbon backbone carbon atoms, these are also known as heteroalkyl. In certain embodiments, a straight chain or branched chain alkyl has six or fewer carbon atoms in its backbone (e.g., $C_1$-$C_6$ for straight chain, $C_3$-$C_6$ for branched chain), and in another embodiment, a straight chain or branched chain alkyl has four or fewer carbon atoms. Likewise, cycloalkyls have from three to eight carbon atoms in their ring structure, and in another embodiment, cycloalkyls have five or six carbons in the ring structure.

"Substituted alkyls" refers to alkyl moieties having substituents replacing one or more hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, acylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can also be substituted, e.g., with the substituents described above. An "alkylaryl" or an "aralkyl" moiety is an alkyl substituted with an aryl (e.g., phenylmethyl (benzyl)).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. "Alkenyl" can include alkenyl groups, which include oxygen, nitrogen, sulfur or phosphorous atoms replacing one or more hydrocarbon backbone carbons. These are also known as heteroalkenyl. In certain embodiments, a straight chain or branched chain alkenyl group has six or fewer carbon atoms in its backbone (e.g., $C_2$-$C_6$ for straight chain, $C_3$-$C_6$ for branched chain). Cycloalkenyl groups may have from three to eight carbon atoms in their ring structure, and in one embodiment, cycloalkenyl groups have five or six carbons in the ring structure. The term "$C_2$-$C_6$" includes alkenyl groups containing two to six carbon atoms. The term "$C_3$-$C_6$" includes alkenyl groups containing three to six carbon atoms.

"Substituted alkenyls" refers to alkenyl moieties having substituents replacing one or more hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups. When "alkynyl" includes alkynyl groups having oxygen, nitrogen, sulfur or phosphorous atoms replacing one or more hydrocarbon backbone carbons, these are also known as heteroalkynyl. In certain embodiments, a straight chain or branched chain alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

"Substituted alkynyls" refers to alkynyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted (e.g., "substituted aryl") at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "halo" or "halogen" refers to fluoro, chloro, bromo, and iodo. The term "perhalogenated" generally refers to a moiety wherein all hydrogens are replaced by halogen atoms.

The term "haloalkyl" refers to both branched and straight-chain saturated aliphatic hydrocarbon groups having the specified number of carbon atoms, substituted with 1 or more halogen (for example —$C_vF_w$ wherein v=1 to 3 and w=1 to (2v+1)). Examples of haloalkyl include, but are not limited to, trifluoromethyl, trichloromethyl, pentafluoroethyl, and pentachloroethyl.

The term "non-hydrogen substituent" refers to substituents other than hydrogen. Non-limiting examples include alkyl groups, alkoxy groups, halogen groups, hydroxyl groups, aryl groups, etc.

As used herein, "carbocycle" or "carbocyclic ring" is intended to mean any stable monocyclic, bicyclic, or tricyclic ring having the specified number of carbons, any of which may be saturated, unsaturated, or aromatic. For example a $C_{3-14}$ carbocycle is intended to mean a mono-, bi-, or tricyclic ring having 3, 4, 5, 6, 7, 8, 9, 10, 11, 12, 13, or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl, and tetrahydronaphthyl. Bridged rings are also included in the definition of carbocycle, including, for example, [3.3.0]bicyclooctane, [4.3.0]bicyclononane, [4.4.0]bicyclodecane, and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl and tetrahydronaphthyl) and spiro rings are also included.

A carbocycle can be substituted (e.g., "substituted carbocycle") at one or more ring positions with one or more substituents, for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "heterocycle" or "heterocyclic" is intended to mean any stable monocyclic, bicyclic, or tricyclic ring which is saturated, unsaturated, or aromatic and comprises carbon atoms and one or more ring heteroatoms, e.g., 1 or 1-2 or 1-3 or 1-4 or 1-5 or 1-6 heteroatoms, independently selected from the group consisting of nitrogen, oxygen, and sulfur. A bicyclic or tricyclic heterocycle may have one or more heteroatoms located in one ring, or the heteroatoms may be located in more than one ring. The nitrogen and sulfur heteroatoms may optionally be oxidized (i.e., N→O and $S(O)_p$, where p=1 or 2). When a nitrogen atom is included in the ring it is either N or NH, depending on whether or not it is attached to a double bond in the ring (i.e., a hydrogen is present if needed to maintain the trivalency of the nitrogen atom). The nitrogen atom may be substituted or unsubstituted (i.e., N or NR wherein R is H or another substituent, as defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. In one embodiment, when the total number of S and O atoms in the heterocycle exceeds 1, then these heteroatoms are not adjacent to one another. Bridged rings are also included in the definition of heterocycle. A bridged ring occurs when one or more atoms (i.e., C, O, N, or S) link two non-adjacent carbon or nitrogen atoms. Bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. Spiro and fused rings are also included.

A heterocycle can be substituted (e.g., "substituted heterocycle") at one or more ring positions with one or more substituents, for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "aromatic heterocycle" or "heteroaryl" is intended to mean a stable 5, 6, or 7-membered monocyclic or bicyclic aromatic heterocyclic ring or 7, 8, 9, 10, 11, or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen, and sulfur. In the case of bicyclic heterocyclic aromatic rings, only one of the two rings needs to be aromatic (e.g., 2,3-dihydroindole), though both may be (e.g., quinoline). The second ring can also be fused or bridged as defined above for heterocycles. The nitrogen atom may be substituted or unsubstituted (i.e., N or NR wherein R is H or another substituent, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

A heteroaryl can be substituted (e.g., "substituted heteroaryl") at one or more ring positions with one or more substituents, for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "hydroxy" or "hydroxyl" includes groups with an —OH or —O⁻.

Additionally, the compounds of the present application, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Tautomers" refers to compounds whose structures differ markedly in arrangement of atoms, but which exist in easy and rapid equilibrium. It is to be understood that the compounds of the application may be depicted as different tautomers. It should also be understood that when compounds have tautomeric forms, all tautomeric forms are intended to be within the scope of the application, and the naming of the compounds does not exclude any tautomer form.

Some compounds of the present application can exist in a tautomeric form which are also intended to be encompassed within the scope of the present application.

The compounds, salts and prodrugs of the present application can exist in several tautomeric forms, including the enol and imine form, and the keto and enamine form and geometric isomers and mixtures thereof. All such tautomeric forms are included within the scope of the present application. Tautomers exist as mixtures of a tautomeric set in solution. In solid form, usually one tautomer predominates. Even though one tautomer may be described, the present application includes all tautomers of the present compounds A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertible by tautomerizations is called tautomerism.

A "pharmaceutical composition" is a formulation containing the disclosed compounds in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salt, hydrate, solvate, or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this application include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In one embodiment, the subject is human.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The compounds of the application are capable of further forming salts. All of these forms are also contemplated within the scope of the application.

"Pharmaceutically acceptable salt" of a compound means a salt that is pharmaceutically acceptable and that possesses the desired pharmacological activity of the parent compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The application also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The pharmaceutically acceptable salts of the present application can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; non-aqueous media like ether, ethyl acetate, ethanol, isopropanol, or acetonitrile can be used. Lists of suitable salts are found in *Remington's Pharmaceutical Sciences*, 18th ed. (Mack Publishing Company, 1990). For example, salts can include, but are not limited to, the hydrochloride and acetate salts of the aliphatic amine-containing, hydroxyl amine-containing, and imine-containing compounds of the present application.

The compounds of the present application can also be prepared as esters, for example pharmaceutically acceptable esters. For example a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds of the present application can also be prepared as prodrugs, for example pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.) the compounds of the present application can be delivered in prodrug form. Thus, the present application is intended to cover prodrugs of the presently claimed compounds, methods of delivering the same and compositions containing the same. "Prodrugs" are also intended to include any covalently bonded carriers that release an active parent drug of the present application in vivo when such prodrug is administered to a subject. Prodrugs the present application are prepared by modifying functional groups present in the compound in such a way that the modifications are cleaved, either in routine manipulation or in vivo, to the parent compound. Prodrugs include compounds of the present application wherein a hydroxy, amino, sulfhydryl, carboxy, or carbonyl group is bonded to any group that, may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p. 1-92, Elesevier, N.Y.-Oxford (1985).

The term "compounds of the application" or "a compound of the application" refers to a compound according to formula I, II, III, IVa, IVb, IVc, IVd, or V, or a compound of Table 1.

The term "cytokine" refers to small soluble proteins secreted by cells that can alter the behavior or properties of the secreting cell or another cell. Cytokines bind to cytokine receptors and trigger a behavior or property within the cell, for example, cell proliferation, death or differentiation. Exemplary cytokines include, but are not limited to, interleukins (e.g., IL-2, IL-3, IL-4, IL-5, IL-6, IL-7, IL-8, IL-9, IL-10, IL-11, IL-12, IL-13, IL-15, IL-16, IL-17, IL-18, IL-1α, IL-1β, and IL-1 RA), granulocyte colony stimulating factor (G-CSF), granulocyte-macrophage colony stimulating factor (GM-CSF), oncostatin M, erythropoietin, leukemia inhibitory factor (LIF), interferons, B7-1 (also known as CD80), B7-2 (also known as B70, CD86), TNF family members (TNF-α, TNF-β, LT-β, CD40 ligand, Fas ligand, CD27 ligand, CD30 ligand, 4-1BBL, Trail), and MIF.

5. General Synthesis of Compounds of the Application

Compounds of the application may be synthesized according to methods known in the art. For example, compounds of the application may be synthesized according to Scheme 1.

Scheme 1

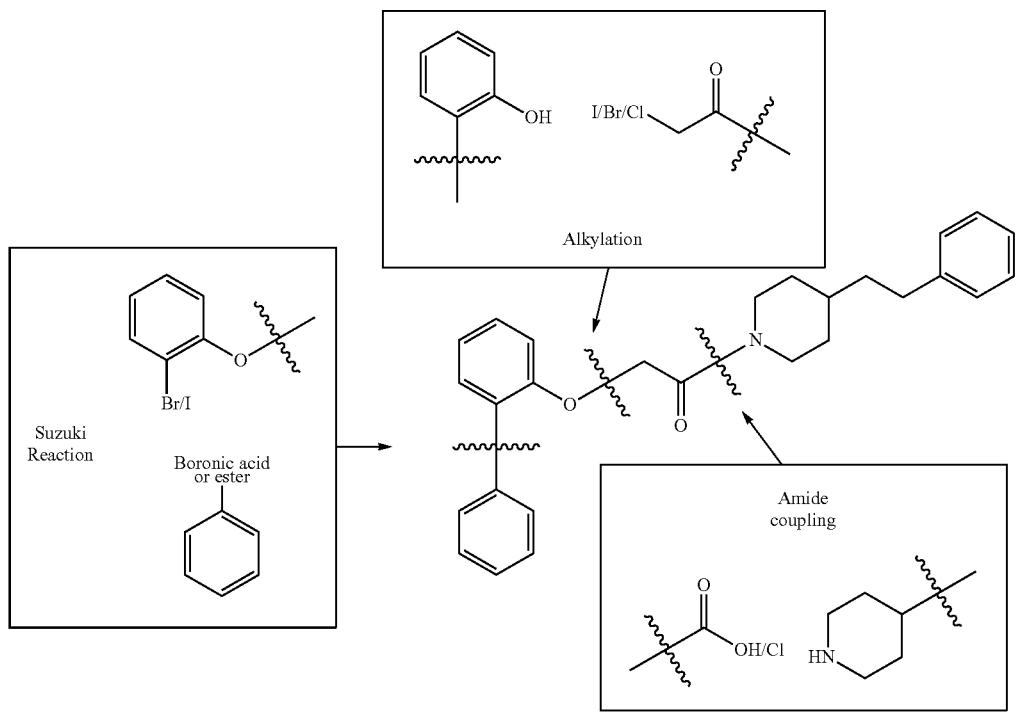

Scheme 1 illustrates the primary bond-forming reactions employed in the synthesis of the compounds of the application. The order in which these bonds are created varies from compound to compound but the general experimental execution of each of these steps may be similar regardless of the order.

The Suzuki reaction may be used to form the biaryl portion of the compounds of the application from an aryl bromide or aryl iodide and an arylboronic acid or ester. This is a well-established synthetic transformation. The Suzuki reactions employed in the synthesis of the compounds of the application may employ a palladium catalyst, for example, tetrakis(triphenylphosphine)palladium, palladium acetate with added tri-ortho-tolylphosphine, or a resin-bound palladium catalyst like FibreCat®. The reaction must also include a base, for example, sodium carbonate, sodium bicarbonate, potassium carbonate, or cesium carbonate, which may be used either neat or as a 2M aqueous solution. The reaction solvent may be, for example, 1,2-dimethoxyethane, 1,4-dioxane, toluene, N,N-dimethylformamide, ethanol, and water or combinations thereof. The reaction may be heated between 80° C. to 120° C. induced by either conventional or microwave heating. High purity desired products may be obtained in good yield (>50%) by extraction and silica gel chromatography or reverse phase HPLC.

The alkylation reaction may involve the reaction between a phenol and a halo-alkane heated under basic conditions to form an ether. This is a well-established synthetic transformation. Reaction conditions used for the synthesis of the claimed compounds may involve using a base, for example, potassium carbonate, cesium carbonate, or sodium carbonate in 3-5 fold molar excess relative to the phenol. The reaction solvent may be acetone, acetonitrile, or 1,4-dioxane heated between 40° C. to reflux temperature of the solvent. Reaction times may be 1 hour to 24 hours. The desired products may be isolated by extraction followed by silica gel chromatography of reverse phase HPLC.

The amide coupling reaction may involve reacting a carboxylic acid derivative with a piperidine derivative to form an amide bond. For example, when a carboxylic acid chloride is used, the reaction may be performed by making a cooled (e.g., 0° C.) solution of the piperidine derivative in a reaction solvent (e.g., dichloromethane or 1,2-dichloroethane) in the presence of an organic base (e.g., diisopropylethylamine) to which a solution of the acid chloride in the same solvent may be added slowly to prevent the reaction from heating excessively. This reaction may proceed quickly (e.g., less than 6 hours) and the desired products may be isolated by extraction followed by silica gel chromatography or reverse-phase HPLC. Isolated product may afford yields greater than 50%.

Most Amide coupling reactions involve reacting a carboxylic acid with the piperidine derivative to form the amide. Standard amide coupling agent such as diisopropylcarbodiimide/hydroxybenzotriazole or 1-[Bis(dimethylamino)methylene]-1H-1,2,3-triazolo[4,5-b]pyridinium-3-oxid hexafluorophosphate (HATU) may be employed. The reaction solvent may be N,N-dimethylformamide or dichloromethane. The base used in the reaction may be diisopropylethylamine or triethylamine. Reactions may be carried out at room temperature for 10 minutes to 24 hours. The desired products may be isolated by extraction followed by silica gel chromatography or reverse phase HPLC.

Phenethyl Piperidine Syntheses

In one embodiment, compounds of the application may be synthesized according to the Scheme below.

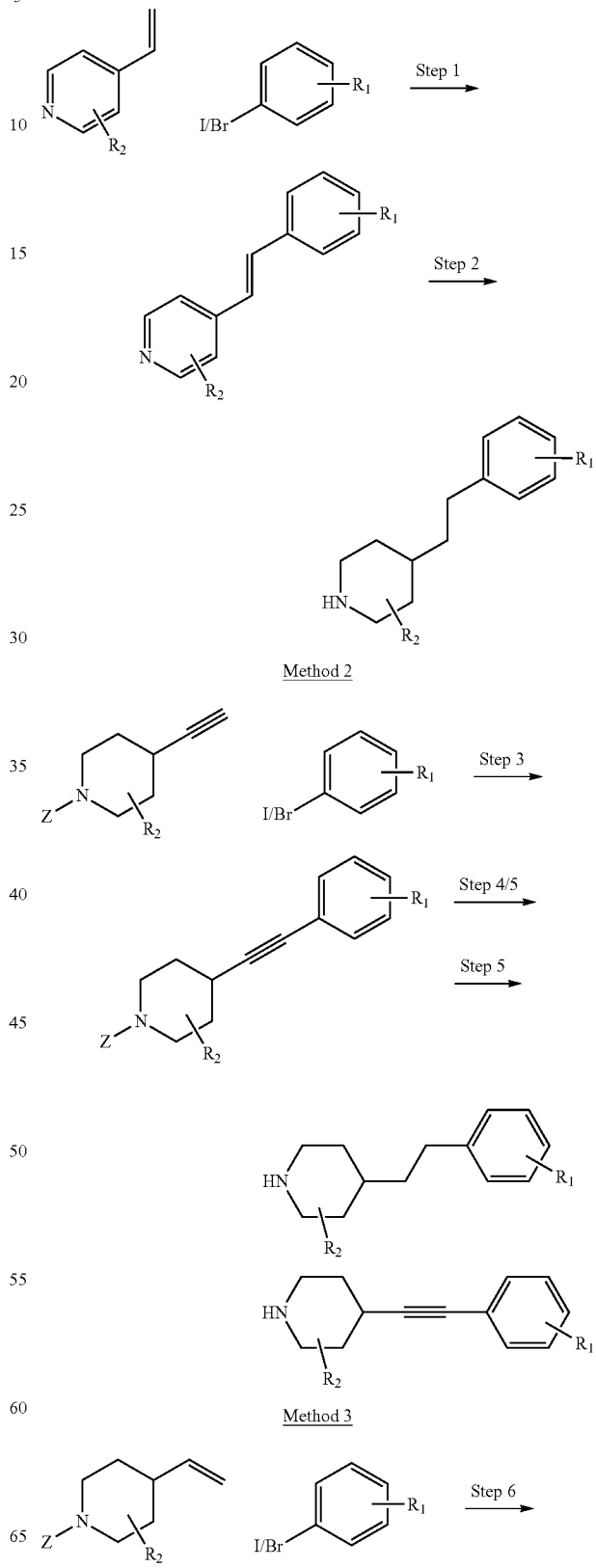

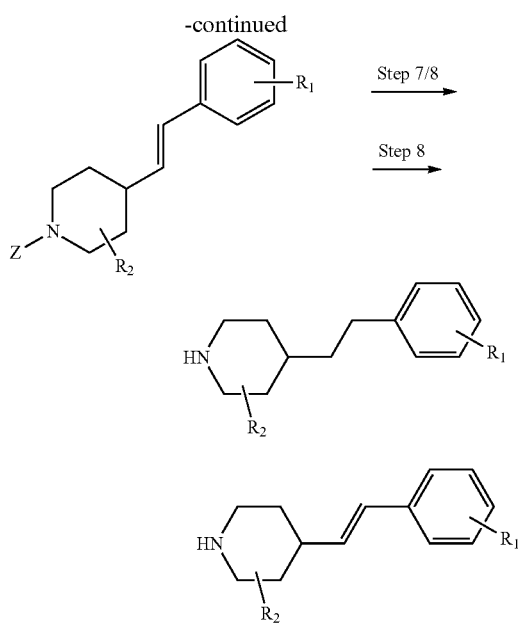

Variables $R_1$ and $R_2$ in the scheme are not the same as those in the claims, and they are used in this scheme for purposes of this particular description. The phenethylpiperidine portion of the compounds may be synthesized in one of three ways.

Method 1

Method 1 illustrates how 4-vinylpyridine can be reacted with an aryl bromide or iodide (Step 1) to provide a trans-aryl-vinylpyridine. This transformation, known as a Heck reaction, involves using a palladium catalyst such as palladium acetate, a phosphine ligand such as triphenylphosphine or tri-ortho-tolylphosphine, and a base such as sodium carbonate, sodium bicarbonate, potassium carbonate, potassium acetate, triethylamine, or cesium carbonate all of which are combined and heated in a reaction solvent composition chosen from 1,4-dioxane, toluene, 1,2-dimethoxyethane, acetonitrile, and/or water. The reaction may use a 2-4 fold molar excess of the vinyl pyridine to drive the reaction to completion with reaction temperatures of 80° C. to 120° C. induced by either conventional or microwave heating. High purity desired products may be obtained in good yield (>50%) by extraction and silica gel chromatography or reverse phase HPLC. Step 2 involves the reduction of the alkene and the pyridine ring to alkane and piperidine, respectively. This transformation may be performed by catalytic hydrogenation over a platinum(IV)oxide hydrate catalyst commonly known as Adam's catalyst. This reduction is conducted in the presence of acetic acid from 10% to 100% (v/v) in combination with another solvent such as methanol or ethanol. The hydrogen atmosphere is typically in the range of 35 to 60 psi on a Parr Hydrogen apparatus. Vigorous shaking or stirring may be needed and gentle heating (40° C. to 50° C.) accelerates the reaction without generating any other detectable side products. Reaction time may varies from 12 to 72 hours. The desired products may be obtained in good yield (>75%) by alkaline extraction and silica gel chromatography or reverse phase HPLC.

Method 2

Method 2 illustrates an alternative version of the phenethylpiperidine synthesis and a route to provide aryl-alkynylpiperidine derivatives. This approach also may be used when the substituents ($R_1$) on the aryl ring are not compatible with the reduction conditions in Step 2. For example, protected (Z=t-butyl carbamate or benzyl carbamate) 4-alkynylpiperidine may be reacted with an aryl bromide or iodide in a Sonogashira reaction to provide the aryl-alkynylpiperidine. This specific transformation involves using a palladium catalyst such as palladium bis-triphenylphosphine dichloride or palladium [1,1'-bis(diphenylphosphino)ferrocene]dichloride as well as a copper co-catalyst, typically copper(I)iodide. The reaction may also include a base, for example triethylamine. In one aspect, triethylamine may be used as the reaction solvent but on occasion other co-solvents such as dimethylformamide, N-methyl pyrolidone, or toluene may be used along with the triethylamine. The reactions may be heated to 80° C. to 120° C. by either conventional or microwave heating for times extending from 10 minutes to 48 hours. High purity desired products may be obtained in good yield (>50%) by extraction and silica gel chromatography or reverse phase HPLC. Step 4 represents a catalytic hydrogenation reduction of the alkyne and Step 5 represents deprotection of the piperidine. In cases where the aryl-alkynylpiperidine is desired, Step 4 is omitted. In cases where the phenethylpiperidine is desired, Steps 4 and 5 are both conducted.

Step 4, the catalytic reduction, may be conducted under a hydrogen atmosphere (from atmospheric pressure to 50 psi) over a palladium on carbon catalyst. The solvent used may be methanol, ethanol, or ethyl acetate. The reactions may be completed within 8 hours. The desired products may be obtained by filtering off the heterogeneous catalyst and in some cases silica gel chromatography may be needed. In instances where the Z-protecting group is a benzyloxycarbamate, these reaction conditions may serve to deprotect the piperidine in addition to reducing the alkyne to the alkane. In these instances the products may be obtained by reverse-phase HPLC.

Step 5 represents the deprotection of the piperidine when the Z-protecting group is a t-butylcarbamate. This conversion is very common and may be performed in acidic organic media. Specific conditions may be trifluoroacetic acid:dichloromethane (e.g., 1:1, v/v), hydrochloric acid in methanol (2-3M), or hydrochloric acid in 1,4-dioxane (2-3M). Initially the reaction temperature may be 0° C. which is allowed to warm to room temperature over the course of the reaction (1-8 hours). The desired products may be obtained by neutralization and extraction. In some cases reverse phase HPLC may be employed to further purify the desired compounds.

Method 3

Method 3 illustrates an alternative version of the phenethylpiperidine synthesis. This method may also be used when the aryl-alkenylpiperidine is desired. Step 6 is a Heck reaction identical to Step 1 described above. Step 7 represents a catalytic hydrogenation reduction of the alkene, and Step 8 represents deprotection of the piperidine. In cases where the aryl-alkenylpiperidine is desired Step 7 is omitted.

Step 7, the catalytic reduction, is typically conducted under a hydrogen atmosphere (from atmospheric pressure to 50 psi) over a palladium on carbon or platinum (Adam's) catalyst. The solvent used may be methanol, ethanol, or ethyl acetate. The reactions may be completed within 8 hours. The desired products may be obtained by filtering off the heterogeneous catalyst and in some cases additional purification by silica gel chromatography may be needed. In instances where the Z-protecting group is a benzyloxycarbamate, these reaction conditions served to deprotect the piperidine in addition to reducing the alkene to the alkane. In these instances, the products may be obtained by reverse-phase HPLC.

Step 8 represents the deprotection of the piperidine when the Z-protecting group is a t-butylcarbamate. This conversion is common and may be performed in acidic organic media. Specific conditions may be trifluoroacetic acid:dichloromethane (typically 1:1 v/v), hydrochloric acid in methanol (2-3M), or hydrochloric acid in 1,4-dioxane (2-3M). Initially the reaction temperature may be 0° C., which is allowed to warm to room temperature over the course of the reaction (e.g., 1-8 hours). The desired products may be obtained by neutralization and extraction and in some cases reverse phase HPLC may be employed.

6. Characterization of Compounds of the Application by LCMS

A Thermo MSQPlus LCMS may be used to characterize the purity and molecular weight of the claimed compounds. A Thermo Hypersil gold C18 column (100×2.1 mm, 3 um) may be used. The binary solvent gradient program may be used as shown below. The MS detector may include electrospray ionization with a probe temperature of 500° C., and a cone voltage of 75V. The MS may be set to detect positive and negative ions. An in line photodiode array detector may be used and all compounds may be verified to have certain spectral purity by UV at 254 nm.

| Time (minutes) | Relative % of 0.1% acetic acid in water | Relative % of 0.1% acetic acid in acetonitrile | Flow rate (uL/min) |
|---|---|---|---|
| 0.00 | 95 | 5 | 500 |
| 0.25 | 95 | 5 | 500 |
| 2.50 | 5 | 95 | 500 |
| 4.25 | 5 | 95 | 500 |
| 4.30 | 95 | 5 | 500 |
| 6.00 | 95 | 5 | 500 |

7. General Assays

The efficacy of the compounds of the application may be evaluated using methods known in the art.

Evaluation of Calcium Entry-Mediated Events

Evaluation of calcium-entry mediated events may be used to monitor intracellular calcium and may be used in screening assays described herein to monitor the effects of compounds of the application. Examples of assays include but are not limited to assays which detect, or determine the presence, levels, alteration of levels, production, modification (such as phosphorylation and dephosphorylation), translocation, degradation and activity of compounds of the application involved in calcium-entry mediated events (Trevillyan et al. (2001) J. Biol. Chem. 276:48118-26). The assays described herein may be used with cells that have been treated with or contacted with a compound of the application, or that express an altered amount of a compound of the application, or with control cells. The assays may also be conducted in cells that have been stimulated with a physiological activator (e.g., $IP_3$) or nonphysiological activator (e.g., thapsigargin, cyclopiazonic acid (CPA), ionomycin or 1,2-bis(2-amino-phenoxy)ethane-N,N,N,N'-tetraacetic acid (BAPTA)), or in unstimulated cells. The following are representative assays and are meant to be exemplary only. Other assays can also be employed in any of the screening and/or modulation methods described herein.

β-Hexosaminidase Release

In mast cells, calcium influx results in degranulation and release of inflammatory mediators such as heparin, histamine and enzymes such as β-hexosaminidase. Detecting and/or measuring release of such molecules may be used to monitor intracellular calcium. For example, media from mast cells may be collected. A suitable substrate for β-hexosaminidase (e.g. p-nitrophenyl-acetyl-glucosamide) may then be added and the absorbance of the resulting mixture assessed to measure the relative amount of β-hexosaminidase activity in the samples (see e.g., Funaba et al. (2003) Cell Biol. International 27:879-85).

Calcium/Calmodulin-Dependent CaN Phosphatase Activity

The phosphatase calcineurin (CaN) dephosphorylates various proteins, affecting their activity and localization. CaN activity may be assessed by incubating purified CaN and a CaN substrate, for example a radiolabeled peptide corresponding to a sequence in the RII subunit of cAMP-dependent kinase, either with or without a compound of the application (see, Trevillyan et al. (2001) J. Biol. Chem 276:48118-26). The level of radiolabeled peptide and/or the amount of free inorganic phosphate released may be measured to assess CaN dephosphorylation activity.

NFAT Transcriptional Activity

The NFAT (nuclear factor of activated T cells) transcription factor regulates a number of genes in response to intracellular calcium levels. For example, NFAT proteins regulate the transcription of cytokine genes involved in the immune response. Promoters from NFAT-regulated genes, and/or regulatory regions and elements from these genes, may be used to monitor NFAT regulated expression and thereby monitor intracellular calcium. Reporter gene fusions can be constructed with NFAT regulated promoters or NFAT-regulated elements operably linked to a reporter gene such as luciferase, β-galactosidase, green fluorescent protein (GFP) or any other known reporter in the art (see for example, Published U.S. Application no. 2002-0034728). The amount of reporter protein or activity is a measure of NFAT activity.

NFAT Phosphorylation

NFAT activation is regulated primarily through its phosphorylation, which in turn regulates its subcellular localization. In unstimulated cells, NFAT is a hyperphosphorylated cytosolic protein. An elevation in intracellular calcium, induced by a variety of mechanisms, increases the activity of the $Ca^{2+}$-calmodulin-dependent phosphatase, calcineurin. Activated calcineurin dephosphorylates multiple serine residues within the regulatory region of the NFAT molecule. NFAT is rephosphorylated in response to decreases in $Ca^{2+}$ levels or CaN inhibition.

The phosphorylation state of NFAT may be monitored for example, by expressing a detectably tagged NFAT protein in cells, such as a $His_6$ tagged-NFAT. Tagged NFAT may be purified from cells using $Ni^{2+}$ chromatography and subjected to gel electrophoresis and staining or western blotting. More highly phosphorylated forms of NFAT may be distinguished by their slower migration. The state of phosphorylated NFAT may be used as a measure of NFAT activation (see, Trevillyan et al. (2001) J. Biol. Chem. 276:48118-26).

NFAT Nuclear Localization

NFAT localization between the cytoplasm and nucleus is regulated by the phosphorylation state of NFAT. Phosphorylation of NFAT prevents nuclear localization by masking the nuclear localization sequence. NFAT nuclear localization may be monitored, for example, by expressing fluorescently tagged NFAT, for example, GFP-NFAT, in cells. Confocal microscopy may be used to monitor nuclear localization of the tagged NFAT (see, Trevillyan et al (2001) J. Biol. Chem 276:48118-26).

Cytokine Secretion

Cytokine secretion, such as IL-2 secretion, may be monitored using protein detection assays. For example, supernatant may be collected from immune cells. An ELISA assay or other suitable format with IL-2 antibodies may be used to detect and/or measure the amount of IL-2 secreted as compared to control cells. Secretion of other cytokines, for example, TNFα, can also be detected in similar assays.

Cytokine Expression

Expression of cytokines, such as IL-2, may be assessed either directly or indirectly in cells. For example, in indirect methods, an IL-2 promoter may be operably linked to a reporter gene such as luciferase or β-galactosidase, and the reporter construct introduced into cells. Reporter gene expression may be monitored and compared to gene expression in control cells (see, Trevillyan et al. (2001) J. Biol. Chem. 276:48118-26). Alternatively, expression of endogenous or recombinant IL-2 mRNA or protein may be assessed. As another example, the number of cells positive for intracellular expression of a given cytokine may be determined by flow cytometry.

T Cell Proliferation

Cytokines such as IL-2 are necessary for T-cell proliferation in response to mitogen or alloantigen stimulation, and thus T-cell proliferation is altered by changes in cytokine expression or secretion. T cells may be induced, such as with concanavalin A or alloreactive lymphocytes and T cell proliferation measured, for example, by subjecting cells to a pulse of 3H-thymidine and measuring 3H-thymidine incorporation (see, Trevillyan et al. (2001) J. Biol. Chem 276: 48118-26).

Cell Activation and Cytokine Analysis

Cells to be tested may include, but are not limited to, a) Jurkat (a transformed human T cell leukemia), b) whole blood isolated from human or rodent sources, c) peripheral blood mononuclear cells (PBMC) freshly isolated from human or rodent whole blood, or d) purified fractions of PBMC (e.g., CD4 T cells). Cells are plated in 96-well plates at a final density of $1.0-2.0 \times 10^6$ cells/ml in 150 ul of assay medium (RPMI+0.5% fetal calf serum). Test compounds are included at a final concentration of ≤20 uM and generally pre-incubated with cells for 30 minutes prior to stimulation. An appropriate stimulus is added, including but not limited to, a) phytohemagglutinin (PHA), b) phorbol myristate acetate (PMA) and ionomycin, or c) stimulatory antibodies to the T cell receptor (TCR) complex (e.g., anti-CD3ε) and CD28. Cell cultures are stimulated for 24-48 hours in a humidified incubator (37 degrees C./5% $CO_2$). A fraction of the culture supernatant is than harvested from each well and assayed for the presence of appropriate cytokine using standard ELISA. Cytokines to be analyzed may include IL-2, IL-4, IL-10, IL-17, IL-22, IFNγ, and/or TNFα. If required, the number of cytokine producing cells can be determined using intracellular staining and flow cytometry.

Luciferase-based Reporter Assays

Jurkat T cells are transiently transfected with a DNA plasmid encoding Firefly luciferase under the transcriptional control of an appropriate regulatory element that may include multimerized NFAT, AP-1, NFκB, or CREB binding sites. Cells are co-transfected with a DNA plasmid encoding Renilla luciferase under the transcriptional control of a constitutive regulatory element (e.g., HSV-TK promoter). 24 hours following transfection, cells are collected and re-seeded in 96-well plates at a final density of $1.0 \times 10^6$ cells/ml in 150 ul assay medium. Test compounds may be included at a final concentration of ≤20 uM and generally pre-incubated with cells for 30 minutes prior to stimulation. An appropriate stimulus is added, including but not limited to, a) phorbol myristate acetate (PMA) and ionomycin, or b) stimulatory antibodies to the TCR complex (e.g., anti-CD3ε) and CD28. Cell cultures are stimulated for 4-6 hours in a humidified incubator (37 degrees C./5% $CO_2$). Cells are than lysed and the level of Firefly luciferase and Renilla Luciferase activity is determined using a standard assay (e.g., Promega's Dual Luciferase Reporter Assay System) and plate-reading luminometer. The ratio obtained by dividing activation induced Firefly luciferase activity by the constitutive Renilla luciferase activity is calculated and used as a quantitative measurement of cell activation.

Monitoring Intracellular Calcium Levels

Cells (e.g., Jurkat, RBL-1, HEK-293) are incubated with an appropriate calcium sensitive dye (e.g., Fluo-4) for 30 minutes in an appropriate buffer (e.g., HBSS) minus calcium and magnesium ions at 37 degrees C. (5% CO2). Test compounds are added (≤20 uM) and the cells are incubated for an additional 30 minutes at room temperature. Baseline fluorescence is established using a fluorescence plate reader (e.g., BioTek's Synergy 4 multi-mode plate reader) by monitoring fluorescence for a period of 3 minutes. An appropriate stimulus is added (e.g., the SERCA pump inhibitor thapsigargin) to deplete intracellular calcium stores and fluorescence is read for a period of 8-10 minutes. Finally, extracellular calcium levels are restored to 0.5-2.0 uM and fluorescence is read for an additional 10-12 minutes (calcium entry phase). In all cases, individual fluorescence levels in each well are measured at 30-45 second intervals.

EXAMPLES

Example 1: Synthesis of Compounds of the Application

Scheme 3: Compound 291 synthesis

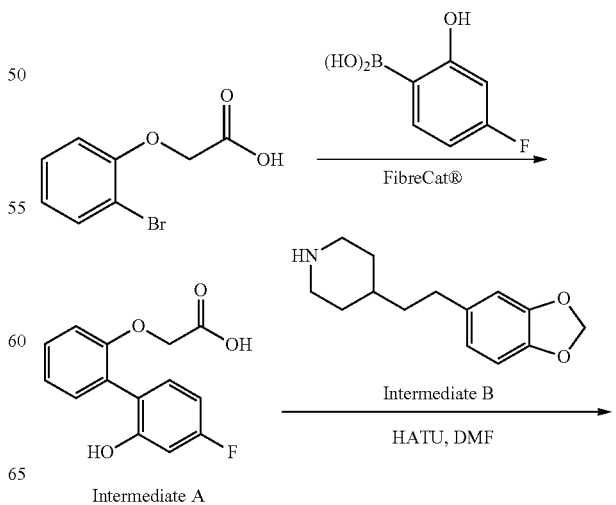

Intermediate A

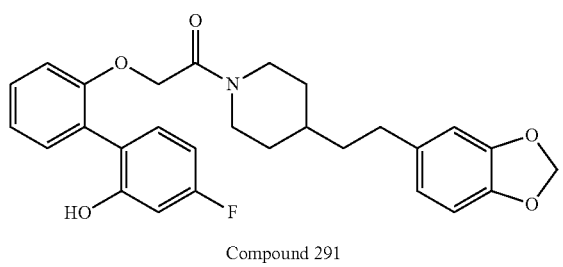

Compound 291

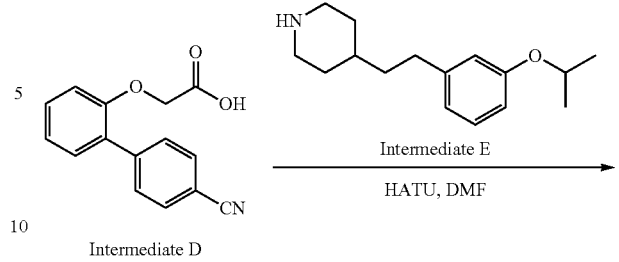

Intermediate D

Synthesis of Intermediate A

A mixture of 2-bromophenoxyacetic acid (300 mg, 1.0 equiv), 4-fluoro-2-hydroxyphenylboronic acid (405 mg, 2.0 equiv), FibreCat® (60 mg), and $K_2CO_3$ (720 mg, 4.0 equiv) in EtOH (6 mL) was microwaved at 100° C. for 30 min. The reaction mixture was diluted with EtOH, filtered through a syringe filter, and concentrated in vacuo. The crude residue was diluted with acetonitrile, added 400 µL of 10% aqueous TFA, and purified by reversed phase HPLC (25-100% acetonitrile/$H_2O$ (0.1% TFA) over 15 minutes) to afford Intermediate A (110 mg, 32%) as a brown viscous liquid.

Synthesis of Compound 291

To a mixture of Intermediate A (95 mg, 1.0 equiv) and Intermediate B (112 mg, 1.3 equiv) in anhydrous DCM (4 mL) was added HOBt.$H_2O$ (50 mg, 1.0 equiv) followed by EDCI.HCl (139 mg, 2.0 equiv) and $Et_3N$ (0.22 mL, 4.0 equiv). The reaction mixture was stirred at room temperature. Additional 139 mg (2.0 equiv) of EDCI.HCl was added after 15 minutes and stirring was continued for another 15 minutes. The reaction was quenched by adding 10% aqueous HCl (1 mL). The organic layer was separated, washed with brine, dried over $Na_2SO_4$, filtered, and concentrated. The crude product was purified by column chromatography on silica gel with EtOAc/heptane (0-30%) and then EtOAc/DCM (0-10%) as eluents to afford Compound 291 as a white solid (120 mg, 69%).

Scheme 4: Compound 403 synthesis

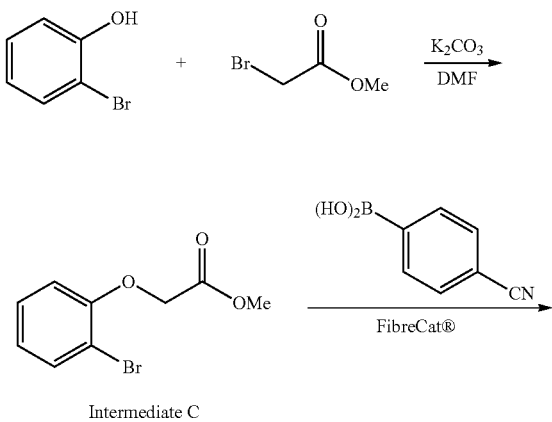

Intermediate C

Compound 403

Synthesis of Intermediate C

Methyl bromoacetate (0.96 mL, 1.2 equiv) was slowly added to a mixture of 2-bromophenol (0.9 mL, 1.0 equiv) and $K_2CO_3$ (3.50 g, 3.0 equiv) in anhydrous DMF (10 mL). Reaction mixture was stirred at room temperature overnight. Water-brine (3:1, 30 mL) was added, and the resulting solution was extracted with EtOAc. The organic layer was washed with brine (2×), dried over $Na_2SO_4$, filtered, concentrated, and the crude residue obtained was purified by column chromatography on silica gel with DCM as an eluent to give Intermediate C (1.980 g, 96%) as a colorless oil.

Synthesis of Intermediate D

A mixture of Intermediate C (406 mg, 1.0 equiv), 4-cyanophenylboronic acid (487 mg, 2.0 equiv), FibreCat® (40 mg), and $K_2CO_3$ (916 mg, 4.0 equiv) in EtOH (6 mL) was microwaved at 100° C. for 30 min. The reaction mixture was diluted with EtOH, filtered through a syringe filter, and concentrated in vacuo. The crude residue was diluted with acetonitrile, added 400 µL of 10% aqueous TFA, and purified by reversed phase HPLC (25-100% acetonitrile/$H_2O$ (0.1% TFA) over 15 minutes) to afford Intermediate D (200 mg, 48%) as a white solid.

Synthesis of Compound 403

To a mixture of Intermediate D (30 mg, 1.0 equiv) and Intermediate E (35 mg, 1.2 equiv) in anhydrous DMF (1 mL) was added HATU (45 mg, 1.0 equiv) followed by i-$Pr_2NEt$ (80 µL, 4.0 equiv). The reaction mixture was stirred for 10 min at room temperature. The reaction was diluted with acetonitrile and added 200 µL of 10% aqueous TFA. The crude product was purified by reversed phase HPLC (25-100% acetonitrile/$H_2O$ (0.1% TFA) over 15 minutes) to provide Compound 403 as a viscous semi-solid (35.3 mg, 62%).

Scheme 5: Synthesis of Compound 418
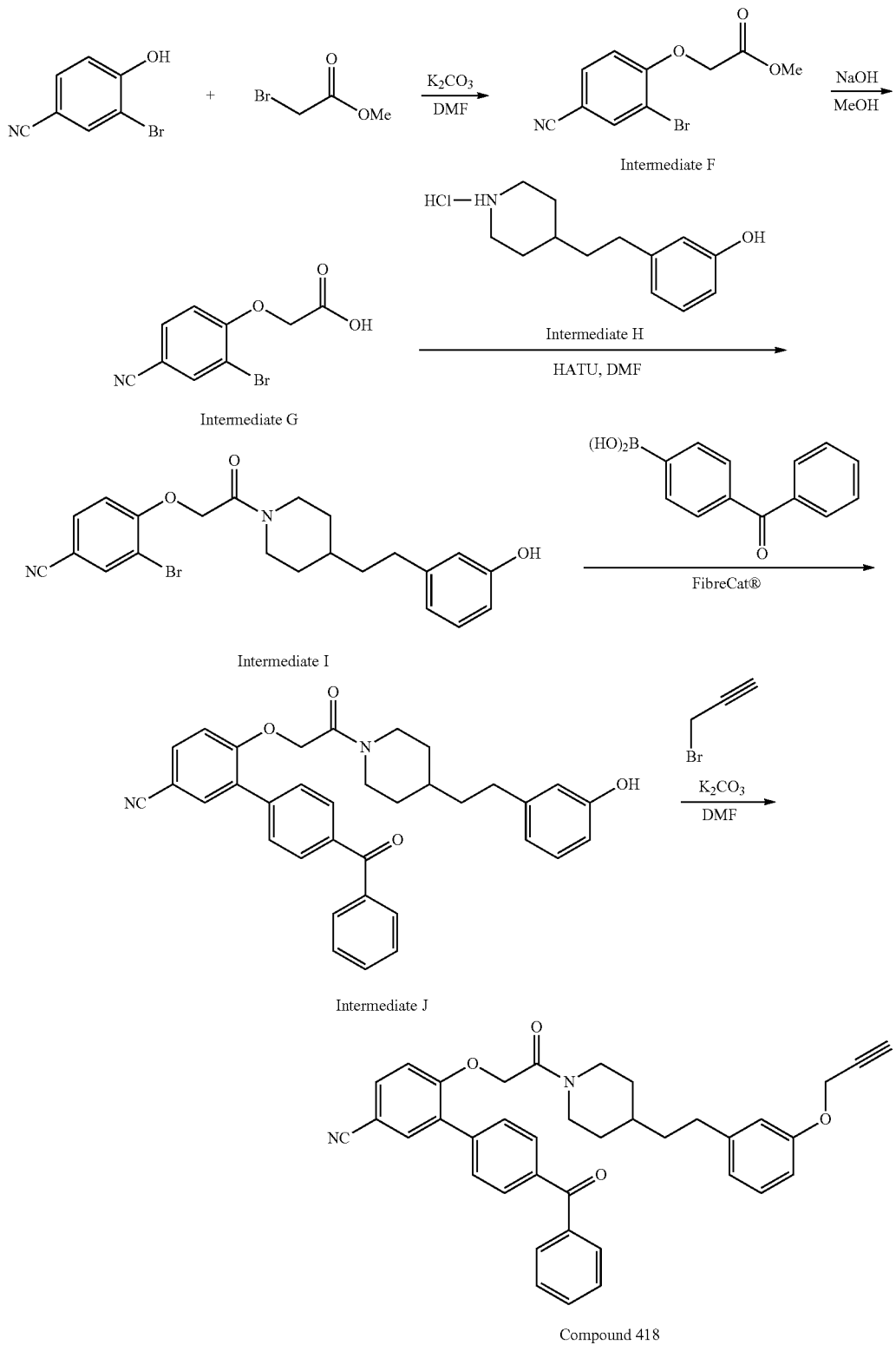
Synthesis of Intermediate F
Methyl bromoacetate (1.05 mL, 1.1 equiv) was slowly added to a mixture of 2-bromo-4-cyanophenol (2.0 g, 1.0 equiv) and K₂CO₃ (2.10 g, 1.5 equiv) in anhydrous DMF (12 mL). Reaction mixture was stirred at room temperature overnight. Water-brine (3:1, 30 mL) was added, and the resulting solution was extracted with EtOAc. The organic layer was washed with brine (2×), dried over Na$_2$SO$_4$, filtered, concentrated, and the crude residue obtained was purified by column chromatography on silica gel with MeOH/DCM (0-5%) as an eluent. The desired fractions were collected and concentrated in vacuo. The product was recrystallized from DCM/heptanes to afford Intermediate F (2.411 g, 88%) as a white solid.

Synthesis of Intermediate G

A solution of 1N aqueous NaOH (6.1 mL, 5.2 equiv) was added to a solution of Intermediate F (0.316 g, 1.0 equiv) in MeOH (4 mL). The reaction mixture was stirred at room temperature for 1 h. Then, the reaction was acidified to pH~3 with 1M aqueous HCl and extracted with EtOAc (2×). The combined organic layers were dried over Na$_2$SO$_4$, filtered, concentrated, and the residue obtained was recrystallized from EtOAc/heptane to provide Intermediate G (235 mg, 79%) as a white solid.

Synthesis of Intermediate I

To a mixture of Intermediate G (100 mg, 1.0 equiv) and Intermediate H (114 mg, 1.2 equiv) in anhydrous DMF (3 mL) was added HATU (149 mg, 1.0 equiv) followed by i-Pr$_2$NEt (260 μL, 4.0 equiv). The reaction mixture was stirred for 15 min at room temperature. Water-brine (3:1, 10 mL) was added, and the resulting solution was extracted with EtOAc. The organic layer was washed with brine (2×), dried over Na$_2$SO$_4$, filtered, concentrated, and the crude residue obtained was purified by column chromatography on silica gel MeOH/DCM (0-5%) as an eluent to afford Intermediate I (127 mg, 73%) as a viscous oil.

Synthesis of Intermediate J

A mixture of Intermediate I (50 mg, 1.0 equiv), 4-benzoylphenylboronic acid (51 mg, 2.0 equiv), FibreCat® (10 mg), and K$_2$CO$_3$ (63 mg, 4.0 equiv) in EtOH (4 mL) was microwaved at 100° C. for 30 min. The reaction mixture was diluted with EtOH, filtered through a syringe filter, and concentrated in vacuo. The crude residue was diluted with acetonitrile and added 400 μL of 10% aqueous TFA, and purified by reversed phase HPLC (25-100% acetonitrile/ H$_2$O (0.1% TFA) over 15 minutes) to afford Intermediate J (42.3 mg, 69%) as a white solid.

Synthesis of Compound 418

Propargyl bromide (15 μL, 1.5 equiv, 80% wt in toluene) was added to a mixture of Intermediate J (15.5 mg, 1.0 equiv) and K$_2$CO$_3$ (10 mg, 1.5 equiv) in anhydrous DMF (1 mL). The reaction mixture was stirred for 4 h at room temperature. The reaction was diluted with acetonitrile and added 50 μL of 10% aqueous TFA. The crude product was purified by reversed phase HPLC (25-100% acetonitrile/ H$_2$O (0.1% TFA) over 15 minutes) to yield Compound 418 (12.8 mg, 78%) as a white solid.

Scheme 6: Intermediate B synthesis

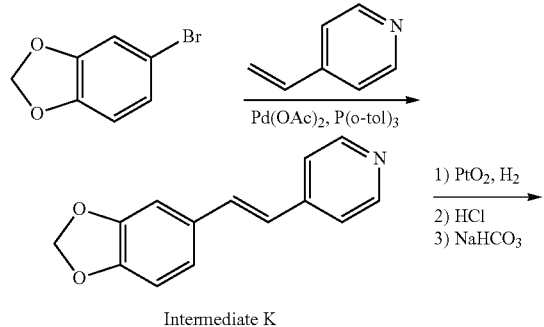

Intermediate K

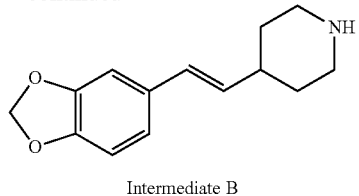

Intermediate B

Synthesis of Intermediate K

A mixture of 1-bromo-3,4-(methylenedioxy)benzene (2 mL, 1.0 equiv), N-Boc-4-vinylpyridine (2.7 mL, 1.5 equiv), Pd(OAc)$_2$ (300 mg, 0.08 equiv), and P(o-tol)$_3$ (1.213 g, 0.24 equiv) in CH$_3$CN-Et$_3$N (1:1, 40 mL) was heated at 85° C. for 4 h. After cooling to room temperature, the volatiles were removed in vacuo. To the residue, water was added and extracted with DCM (3×). The combined organic layers were washed with saturated aqueous NaHCO$_3$, water, brine, dried over Na$_2$SO$_4$, filtered, and concentrated. The crude product was purified by column chromatography on silica gel with MeOH/DCM (0-10%) as an eluent to give the product which was recrystallized from DCM/heptanes providing Intermediate K (2.050 g, 55%) as a yellow solid.

Synthesis of Intermediate B

To a solution of the Intermediate K (1.466 g) in MeOH—AcOH (2:1, 60 mL) under N$_2$ was added 186 mg of PtO$_2$. The reaction flask was degassed and the atmosphere was replaced with H$_2$ (balloon). This process was repeated 2 times. The suspension was stirred for 24 h at 67° C. and then at 86° C. for additional 24 h under H$_2$ atmosphere. The reaction mixture was filtered through a celite plug using MeOH and DCM. The solvent was removed and the residue was diluted with DCM, washed with saturated aqueous NaHCO$_3$ (2×). The aqueous layer was extracted (8×) with DCM/i-PrOH while saturating the aqueous layer with NH$_4$Cl. The organic layers were combined, dried over Na$_2$SO$_4$, filtered, and concentrated to give a residue which was triturated with DCM/heptanes to afford the Intermediate B in 1.10 g (72%) as a light grey liquid.

Scheme 7: Intermediate E synthesis

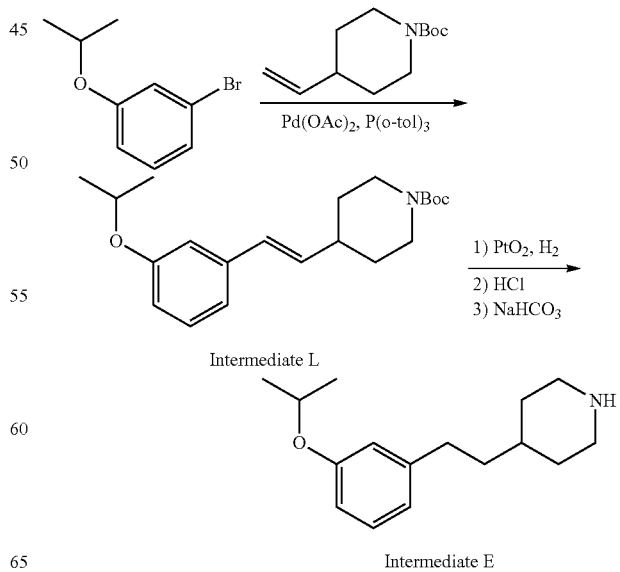

Intermediate E

Synthesis of Intermediate L

A mixture of 3-isopropoxy-bromobenzene (1.997 g, 1.0 equiv), N-Boc-4-vinylpiperidine (2.943 g, 1.5 equiv), Pd(OAc)$_2$ (167 mg, 0.08 equiv), and P(o-tol)$_3$ (680 mg, 0.24 equiv) in CH$_3$CN-Et$_3$N (1:1, 16 mL) was heated at 98° C. for 6 h in a sealed vial. After cooling to room temperature, the volatiles were removed in vacuo. To the residue, DCM was added, washed with water, brine, dried over Na$_2$SO$_4$, filtered, and concentrated. The crude product was purified by column chromatography on silica gel with EtOAc/heptane (0-20%) as an eluent to give 3.1622 g (99%) of Intermediate L as a yellow oil.

Synthesis of Intermediate E

To a solution of the Intermediate L (3.1622 g) in MeOH—AcOH (3:1, 40 mL) under N$_2$ was added 310 mg of PtO$_2$. The reaction flask was degassed and the atmosphere was replaced with H$_2$ (balloon). This process was repeated 3 times. The suspension was stirred overnight at room temperature under H$_2$ atmosphere. The reaction mixture was filtered through a celite plug using MeOH and DCM. The solvent was removed and the crude residue obtained was used in the next step without further purification. The residue was dissolved in DCM (15 mL) and added 9.1 mL (4.0 equiv) of a 4M HCl solution in dioxane and stirred at room temperature overnight. The reaction mixture was concentrated in vacuo and then diluted with DCM, washed with saturated aqueous NaHCO$_3$, brine, dried over Na$_2$SO$_4$, filtered, and concentrated to afford the Intermediate E in 1.950 g (86%) as a light yellow viscous liquid.

Scheme 8: Intermediate H synthesis

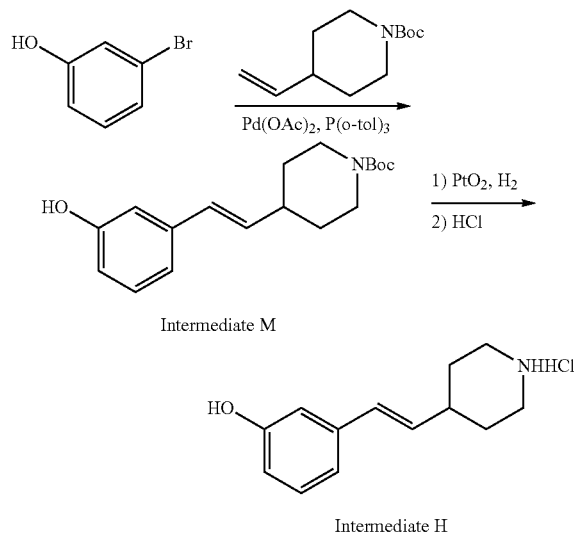

Intermediate M

Intermediate H

Synthesis of Intermediate M

A mixture of 3-bromophenol (1.2 g, 1.0 equiv), N-Boc-4-vinylpiperidine (2.2 g, 1.5 equiv), Pd(OAc)$_2$ (125 mg, 0.08 equiv), and P(o-tol)$_3$ (507 mg, 0.24 equiv) in CH$_3$CN-Et$_3$N (1:1, 16 mL) was heated at 98° C. for 16 h in a sealed vial. After cooling to room temperature, the volatiles were removed in vacuo. To the residue, DCM was added, washed with water, brine, dried over Na$_2$SO$_4$, filtered, and concentrated. The crude product was purified by column chromatography on silica gel with MeOH/DCM (0-5%) as an eluent to give 2.0 g (95%) of Intermediate M as a yellow oil.

Synthesis of Intermediate H

To a solution of the Intermediate M (2.0 g) in MeOH—AcOH (2:1, 30 mL) under N$_2$ was added 280 mg of PtO$_2$. The reaction flask was degassed and the atmosphere was replaced with H$_2$ (balloon). This process was repeated 3 times. The suspension was stirred overnight at room temperature under H$_2$ atmosphere. The reaction mixture was filtered through a celite plug using MeOH and DCM. The solvent was removed and the crude residue obtained was used in the next step without further purification. The residue (700 mg) was dissolved in DCM (10 mL) and added 5.1 mL (9.0 equiv) of a 4M HCl solution in dioxane and stirred at room temperature overnight. The reaction mixture was concentrated in vacuo and the residue obtained was triturated with DCM/heptanes to afford the Intermediate H in 525 mg (95%) as a white solid.

Example 2: Cell Activation and Cytokine Analysis

Jurkat (a transformed human T cell leukemia) cells were plated in 96-well plates at a final density of 1.0-2.0×10$^6$ cells/ml in 150 ul of assay medium (RPMI+0.5% fetal calf serum). Compounds 403 and 413 were included at a final concentration of ≤20 uM and pre-incubated with cells for 30 minutes prior to stimulation. Mitogens PMA and ionomycin were added to the T cell receptor (TCR) complex (e.g., anti-CD3c) and CD28. Cell cultures were stimulated for 24-48 hours in a humidified incubator (37 degrees C./5% CO$_2$). A fraction of the culture supernatant was then harvested from each well and assayed for the presence of appropriate cytokine using standard ELISA. Cytokines analyzed was IL-2. If required, the number of cytokine producing cells can be determined using intracellular staining and flow cytometry.

More specifically, Jurkat T cells were stimulated with the mitogens PMA and ionomycin in the presence of varying concentrations of compound 403 or compound 413. Supernatants were harvested at 20 hours and analyzed for IL-2 content by ELISA. IL-2 values obtained from vehicle (DMSO) treated control wells (~2800 pg/ml) were assigned a value of 100% and used to calculate the % inhibition achieved for each compound. The concentrations required to achieve 50% inhibition (IC$_{50}$) are 68 nM for compound 403 and 18 nM for compound 413.

Example 3: Luciferase-Based Reporter Assays

Jurkat T cells were transiently transfected with a DNA plasmid encoding Firefly luciferase under the transcriptional control of an appropriate regulatory element that may include multimerized NFAT, AP-1, NFκB, or CREB binding sites. Cells were co-transfected with a DNA plasmid encoding Renilla luciferase under the transcriptional control of a constitutive regulatory element (e.g., HSV-TK promoter). 24 hours following transfection, cells were collected and re-seeded in 96-well plates at a final density of 1.0×10$^6$ cells/ml in 150 ul assay medium. Compound 413 was included at a final concentration of ≤20 uM and pre-incubated with cells for 30 minutes prior to stimulation. Mitogens PMA and ionomycin were added. Cell cultures were stimulated for 4-6 hours in a humidified incubator (37° C./5% CO$_2$). Cells were then lysed and the level of Firefly luciferase and Renilla Luciferase activity was determined using a standard assay (e.g., Promega's Dual Luciferase Reporter Assay System) and plate-reading luminometer. The ratio obtained by dividing activation induced Firefly luciferase activity by the constitutive Renilla luciferase activity was calculated and used as a quantitative measurement of cell activation.

More specifically, Jurkat T cells were co-transfected with a NFAT-dependent Firefly Luciferase reporter plasmid and a control *Renilla* Luciferase reporter plasmid. 24 hours later, cells were seeded into 96 well plates in the presence of compounds of the application. Cells were stimulated with the mitogens PMA and ionomycin for 6 hours. Lysates were prepared and analyzed for luciferase activity using the Dual Luciferase Reporter Assay System (Promega). Luciferase values obtained from vehicle (DMSO) treated control wells were assigned a value of 100% and used to calculate the % inhibition achieved for each compound. The concentration required to achieve 50% inhibition ($IC_{50}$) is 9 nM for compound 413.

Example 4: Monitoring Intracellular Calcium Levels

Cells (e.g., Jurkat, RBL-1, HEK-293) were incubated with an appropriate calcium sensitive dye (e.g., Fluo-4) for 30 minutes in an appropriate buffer (e.g., HBSS) minus calcium and magnesium ions at 37° C. (5% $CO_2$). Compound 403 was added (≤20 uM) and the cells were incubated for an additional 30 minutes at room temperature. Baseline fluorescence was established using a fluorescence plate reader (e.g., BioTek's Synergy 4 multi-mode plate reader) by monitoring fluorescence for a period of 3 minutes. An appropriate stimulus was added (e.g., the SERCA pump inhibitor thapsigargin) to deplete intracellular calcium stores and fluorescence was read for a period of 8-10 minutes. Finally, extracellular calcium levels were restored to 0.5-2.0 uM and fluorescence was read for an additional 10-12 minutes (calcium entry phase). In all cases, individual fluorescence levels in each well were measured at 30-45 second intervals. Results obtained using Fluo-4 as a calcium sensitive indicator are shown in FIG. 1. FIG. 1 is graph showing the fluorescence reading at various time intervals. Jurkat T cells were loaded with the calcium sensitive dye Fluo-4 prior in calcium free HBSS prior to analysis. Cells were maintained in calcium free HBSS and baseline fluorescence established over a period of 3 minutes. Thapsigargin was added (Arrow a) and readings continued for an additional 8 minutes. External calcium was restored to 2 mM (Arrow b) and fluorescence reading continued for an additional 10 minutes. Compound 403 (1 uM final) was added during the last 30 minutes of pre-incubation with Fluo-4.

The biological assay data are provided in the table below.
50% inhibition at concentrations between 50 uM and 10 uM="+"
50% inhibition at concentrations less than 10 uM and greater than 1 uM="++"
50% inhibition at concentrations of less than 1 uM="+++"

TABLE 2

| Compound no | PHA-IL2 | TCR-NFAT |
| --- | --- | --- |
| 100 | +++ | ++ |
| 101 | +++ | +++ |
| 102 |  | ++ |
| 103 |  | ++ |
| 104 |  | ++ |
| 105 | +++ | ++ |
| 106 |  | ++ |
| 107 |  | + |
| 108 |  | ++ |
| 109 |  | ++ |
| 110 |  | + |
| 111 | ++ | ++ |
| 112 |  | ++ |
| 113 |  | ++ |
| 114 | +++ | ++ |
| 115 |  | ++ |
| 116 |  | + |
| 117 | +++ |  |
| 118 | ++ | + |
| 119 |  | ++ |
| 120 | +++ |  |
| 121 |  | + |
| 122 |  | + |
| 123 |  | + |
| 124 | +++ | + |
| 125 |  | + |
| 126 | ++ |  |
| 127 |  | + |
| 128 |  | + |
| 129 |  | + |
| 130 |  | + |
| 131 |  | + |
| 132 |  | + |
| 133 |  | + |
| 134 |  | + |
| 135 |  | + |
| 136 |  | + |
| 137 |  | + |
| 138 |  | ++ |
| 139 |  | + |
| 140 |  | + |
| 141 | ++ | + |
| 142 |  | ++ |
| 143 |  | + |
| 144 |  | ++ |
| 145 |  | ++ |
| 146 |  | ++ |
| 147 |  | ++ |
| 148 | ++ | ++ |
| 149 |  | ++ |
| 150 |  | + |
| 151 |  | + |
| 152 |  | + |
| 153 | + |  |
| 154 | + |  |
| 155 | ++ |  |
| 156 | ++ |  |
| 157 | + |  |
| 158 | + |  |
| 159 | ++ |  |
| 160 | ++ |  |
| 161 | ++ |  |
| 162 | ++ |  |
| 163 | ++ |  |
| 164 | ++ |  |
| 165 | +++ |  |
| 166 | +++ |  |
| 167 | ++ |  |
| 168 | ++ |  |
| 169 | +++ | +++ |
| 170 | ++ |  |
| 171 | + |  |
| 172 | + |  |
| 173 | ++ |  |
| 174 | ++ |  |
| 175 | + |  |
| 176 | + |  |
| 177 | ++ |  |
| 178 | ++ |  |
| 179 | ++ |  |
| 180 | ++ |  |
| 181 | + |  |
| 182 | + |  |
| 183 | + |  |
| 184 | + |  |
| 185 | + |  |
| 186 | ++ |  |
| 187 | ++ |  |
| 188 | +++ |  |

TABLE 2-continued

| Compound no | PHA-IL2 | TCR-NFAT |
|---|---|---|
| 189 | ++ | |
| 190 | +++ | |
| 191 | ++ | |
| 192 | ++ | |
| 193 | +++ | |
| 194 | ++ | |
| 195 | + | |
| 196 | + | |
| 197 | +++ | |
| 198 | +++ | |
| 199 | +++ | |
| 200 | +++ | |
| 201 | +++ | |
| 202 | ++ | |
| 203 | +++ | |
| 204 | +++ | |
| 205 | ++ | |
| 206 | +++ | |
| 207 | +++ | |
| 208 | +++ | |
| 209 | +++ | |
| 210 | +++ | |
| 211 | ++ | |
| 213 | + | |
| 216 | +++ | |
| 217 | ++ | |
| 218 | ++ | |
| 219 | + | |
| 220 | + | |
| 221 | + | |
| 222 | ++ | |
| 223 | ++ | |
| 224 | ++ | |
| 225 | ++ | |
| 226 | ++ | |
| 227 | ++ | |
| 228 | ++ | |
| 229 | ++ | |
| 230 | +++ | |
| 231 | +++ | |
| 232 | +++ | |
| 233 | +++ | |
| 234 | ++ | |
| 235 | +++ | |
| 236 | + | |
| 237 | +++ | |
| 238 | +++ | |
| 239 | +++ | |
| 240 | ++ | |
| 241 | +++ | |
| 242 | ++ | |
| 243 | ++ | |
| 244 | ++ | |
| 245 | ++ | |
| 246 | ++ | |
| 247 | ++ | |
| 248 | + | |
| 249 | +++ | |
| 250 | +++ | |
| 251 | +++ | |
| 252 | + | |
| 253 | +++ | |
| 254 | ++ | |
| 255 | ++ | |
| 256 | +++ | |
| 257 | ++ | |
| 258 | ++ | |
| 259 | +++ | |
| 260 | +++ | |
| 261 | ++ | |
| 262 | ++ | |
| 263 | +++ | |
| 264 | +++ | |
| 265 | +++ | |
| 266 | +++ | |
| 267 | +++ | |
| 268 | +++ | |
| 269 | +++ | |
| 270 | ++ | |
| 271 | +++ | |
| 272 | +++ | |
| 273 | ++ | |
| 274 | ++ | |
| 275 | ++ | |
| 276 | +++ | |
| 277 | +++ | |
| 278 | +++ | |
| 279 | +++ | |
| 280 | +++ | |
| 281 | +++ | |
| 282 | +++ | |
| 283 | +++ | |
| 284 | +++ | |
| 285 | ++ | |
| 286 | ++ | |
| 287 | ++ | |
| 288 | +++ | |
| 289 | +++ | |
| 290 | +++ | |
| 291 | +++ | |
| 292 | ++ | |
| 293 | +++ | |
| 294 | ++ | |
| 295 | ++ | |
| 296 | +++ | |
| 297 | +++ | |
| 298 | +++ | |
| 299 | +++ | |
| 300 | +++ | |
| 301 | +++ | |
| 302 | +++ | |
| 303 | ++ | |
| 304 | +++ | |
| 305 | +++ | |
| 306 | +++ | |
| 307 | ++ | |
| 308 | +++ | |
| 309 | +++ | |
| 310 | +++ | |
| 311 | +++ | |
| 312 | + | |
| 313 | + | |
| 314 | +++ | |
| 315 | ++ | |
| 316 | ++ | |
| 317 | +++ | |
| 318 | ++ | |
| 319 | + | |
| 320 | +++ | |
| 321 | ++ | |
| 322 | ++ | |
| 323 | ++ | |
| 324 | ++ | |
| 325 | ++ | |
| 326 | ++ | |
| 327 | + | |
| 328 | ++ | |
| 329 | + | |
| 330 | ++ | |
| 331 | + | |
| 332 | ++ | |
| 333 | + | |
| 334 | ++ | |
| 335 | ++ | |
| 336 | + | |
| 337 | +++ | |
| 338 | ++ | |
| 339 | ++ | |
| 340 | ++ | |
| 341 | ++ | |
| 342 | + | |
| 343 | + | |
| 344 | ++ | |
| 345 | +++ | |

TABLE 2-continued

| Compound no | PHA-IL2 | TCR-NFAT |
|---|---|---|
| 346 | +++ | |
| 347 | +++ | |
| 348 | +++ | |
| 349 | ++ | |
| 350 | +++ | |
| 351 | +++ | |
| 352 | +++ | |
| 353 | +++ | |
| 354 | ++ | |
| 355 | ++ | |
| 356 | ++ | |
| 357 | +++ | |
| 358 | ++ | |
| 359 | ++ | |
| 360 | ++ | |
| 361 | ++ | |
| 362 | ++ | |
| 363 | ++ | |
| 364 | ++ | |
| 365 | ++ | |
| 366 | +++ | |
| 367 | ++ | |
| 368 | ++ | |
| 369 | ++ | |
| 370 | ++ | |
| 371 | +++ | |
| 372 | ++ | |
| 373 | ++ | |
| 374 | + | |
| 375 | ++ | |
| 376 | ++ | |
| 377 | ++ | |
| 378 | ++ | |
| 379 | ++ | |
| 380 | ++ | |
| 381 | + | |
| 382 | ++ | |
| 383 | ++ | |
| 384 | ++ | |
| 385 | ++ | |
| 386 | ++ | |
| 387 | ++ | |
| 388 | +++ | |
| 389 | ++ | |
| 390 | ++ | |
| 391 | ++ | |
| 392 | ++ | |
| 393 | ++ | |
| 396 | ++ | |
| 397 | ++ | |
| 398 | +++ | |
| 399 | +++ | |
| 400 | +++ | |
| 401 | +++ | |
| 402 | +++ | |
| 403 | +++ | |
| 404 | +++ | |
| 405 | +++ | |
| 406 | +++ | |
| 407 | +++ | |
| 408 | +++ | |
| 409 | +++ | |
| 410 | +++ | |
| 411 | +++ | |
| 412 | ++ | |
| 413 | +++ | |
| 414 | +++ | |
| 415 | +++ | |
| 416 | ++ | |
| 417 | +++ | |
| 418 | +++ | |
| 419 | ++ | |
| 420 | +++ | |
| 421 | ++ | |
| 422 | +++ | |
| 423 | ++ | |
| 424 | ++ | |
| 425 | ++ | |
| 426 | ++ | |
| 427 | +++ | |
| 428 | ++ | |
| 429 | ++ | |
| 430 | +++ | |
| 431 | +++ | |
| 432 | +++ | |
| 433 | +++ | |
| 434 | +++ | |
| 435 | +++ | |
| 436 | +++ | |
| 437 | +++ | |
| 438 | +++ | |
| 439 | +++ | |
| 440 | +++ | |
| 441 | +++ | |
| 442 | +++ | |
| 443 | +++ | |
| 444 | +++ | |

INCORPORATION BY REFERENCE

The entire disclosure of each of the patent documents and scientific articles referred to herein is incorporated by reference for all purposes.

Other Embodiments

While the application has been described in conjunction with the detailed description thereof, the foregoing description is intended to illustrate and not limit the scope of the application, which is defined by the scope of the appended claims. Other aspects, advantages, and modifications are within the scope of the following claims. It will be understood by those skilled in the art that various changes in form and details may be made therein without departing from the scope of the application encompassed by the appended claims.

Should read:
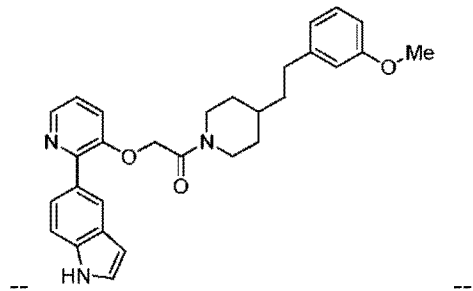
At Column 429, Claim number 14, Compound No. 378:
" 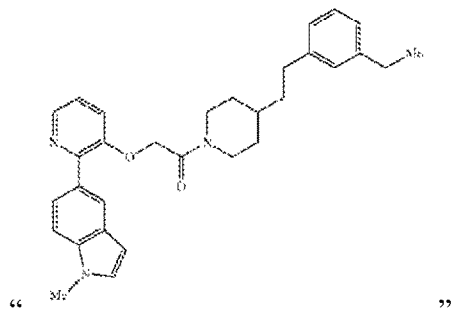 "
Should read:
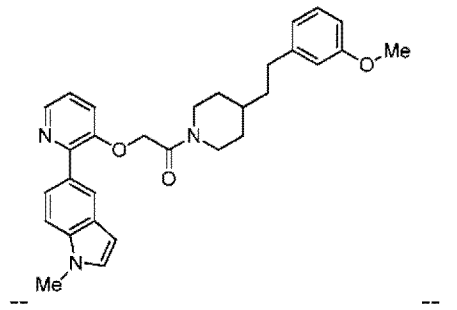

The invention claimed is:

1. A method of treating an immune disorder associated with T cell activation in a subject comprising administering to the subject an effective amount of a compound of formula (I):

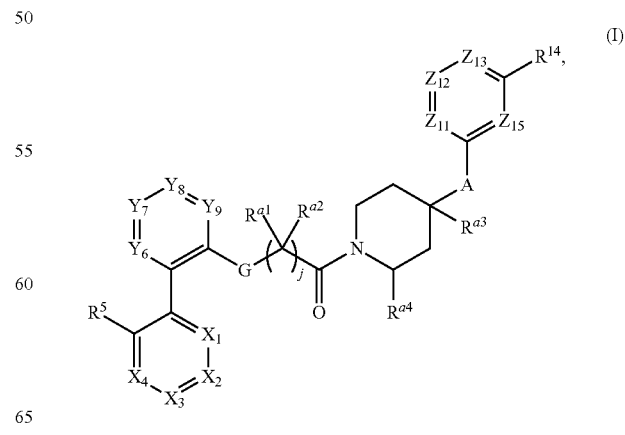

or a pharmaceutically acceptable salt thereof, wherein
- $X_1$ is selected from $CR^1$, N, and N—O;
- $X_2$ is selected from $CR^2$, N, and N—O;
- $X_3$ is selected from $CR^3$, N, and N—O;
- $X_4$ is selected from $CR^4$, N, and N—O;
- $R^1$, $R^2$, $R^3$, $R^4$, and $R^5$ are independently selected from hydrogen; halogen; $C_1$-$C_6$ alkyl; $C_2$-$C_6$ alkenyl; $C_2$-$C_6$ alkynyl; $C_1$-$C_6$ haloalkyl; ($C_1$-$C_6$ alkyl)-$OR^{20}$; OH; $O(C_1$-$C_6$ alkyl); $OCF_3$; $OCF_2H$; $OCFH_2$; CN; $N_3$; $NO_2$; $NH_2$; $NH(C_1$-$C_6$ alkyl); $N(C_1$-$C_6$ alkyl)$_2$; $NR^{20}C(O)R^{20}$; $C(O)NR^{20}R^{20}$; $COR^{20}$; $CO(C_1$-$C_6$ alkyl); $S(O)_pR^{20}$; $NR^{20}S(O)_pR^{20}$; $S(O)_pNR^{20}R^{20}$; $SR^{20}$, $SCF_3$; $COOR^{20}$; $OR^{20}$; ($C_1$-$C_6$ alkyl)-$R^{20}$; 3-7 membered saturated, partially saturated, or unsaturated carbocycle; and 3-7 membered saturated, partially saturated, or unsaturated heterocycle containing one or more heteroatoms selected from the group consisting of nitrogen, oxygen, and sulfur;
- alternatively, two substituents selected from $R^1$, $R^2$, $R^3$, $R^4$, and $R^5$ on two adjacent carbon atoms taken together form a 3-7 membered saturated, partially saturated, or unsaturated carbocycle; or a 3-7 membered saturated, partially saturated, or unsaturated heterocycle containing one or more heteroatoms selected from the group consisting of nitrogen, oxygen, and sulfur; where the carbocycle or heterocycle is optionally substituted with one or more $R^{20}$;
- $R^{20}$ is independently selected from hydrogen; $C_1$-$C_6$ alkyl; CN; ($C_1$-$C_6$ alkyl)-$NR^{21}R^{21}$; ($C_1$-$C_6$ alkyl)-$OR^{21}$; 3-7 membered saturated, partially saturated, or unsaturated carbocycle; 3-7 membered saturated, partially saturated, or unsaturated heterocycle containing one or more heteroatoms selected from the group consisting of nitrogen, oxygen, and sulfur; ($C_1$-$C_6$ alkyl)-3-7 membered saturated, partially saturated, or unsaturated carbocycle; ($C_1$-$C_6$ alkyl)-3-7 membered saturated, partially saturated, or unsaturated heterocycle containing one or more heteroatoms selected from the group consisting of nitrogen, oxygen, and sulfur; where the carbocycle or heterocycle is optionally substituted with one or more $R^{21}$;
- or two $R^{20}$ taken together with the carbon atom to which they are attached form a carbonyl;
- $R^{21}$ is independently selected from hydrogen, $C_1$-$C_6$ alkyl, $C_2$-$C_6$ alkenyl, $C_2$-$C_6$ alkynyl; OH, O—($C_1$-$C_6$ alkyl), O—($C_2$-$C_6$ alkenyl), and O—($C_2$-$C_6$ alkynyl);
- $Y_6$ is independently selected from $CR^6$, N, and N—O;
- $Y_7$ is independently selected from $CR^7$, N, and N—O;
- $Y_8$ is independently selected from $CR^8$, N, and N—O;
- $Y_9$ is independently selected from $CR^9$, N, and N—O;
- $R^6$, $R^7$, $R^8$, and $R^9$ are independently selected from hydrogen; halogen; $C_1$-$C_6$ alkyl; $C_2$-$C_6$ alkenyl; $C_2$-$C_6$ alkynyl; $C_1$-$C_6$ haloalkyl; ($C_1$-$C_6$ alkyl)-$R^{30}$; ($C_1$-$C_6$ alkyl)-$OR^{30}$; OH; $O(C_1$-$C_6$ alkyl); $OCF_3$; $OCF_2H$; $OCFH_2$; CN; $N_3$; $NO_2$; $NH_2$; $NH(C_1$-$C_6$ alkyl); $N(C_1$-$C_6$ alkyl)$_2$; $NR^{30}C(O)R^{30}$; $C(O)NR^{30}R^{30}$; $COR^{30}$; $CO(C_1$-$C_6$ alkyl); $S(O)_qR^{30}$; $NR^{30}S(O)_qR^{30}$; $S(O)_qNR^{30}R^{30}$; $SR^{30}$; $SCF_3$; and $COOR^{30}$;
- alternatively, two substituents selected from $R^6$, $R^7$, $R^8$, and $R^9$ on two adjacent carbon atoms taken together form a 3-7 membered saturated, partially saturated, or unsaturated carbocycle; or a 3-7 membered saturated, partially saturated, or unsaturated heterocycle containing one or more heteroatoms selected from the group consisting of nitrogen, oxygen, and sulfur; where the carbocycle or heterocycle is optionally substituted with one or more $R^{30}$;
- $R^{30}$ is independently selected from hydrogen; $C_1$-$C_6$ alkyl; ($C_1$-$C_6$ alkyl)-$R^{31}$; ($C_1$-$C_6$ alkyl)-$OR^{31}$; ($C_1$-$C_6$ alkyl)-$NR^{31}R^{31}$; 3-7 membered saturated, partially saturated, or unsaturated carbocycle; and 3-7 membered saturated, partially saturated, or unsaturated heterocycle containing one or more heteroatoms selected from the group consisting of nitrogen, oxygen, and sulfur; where the carbocycle or heterocycle is optionally substituted with one or more $R^{31}$;
- $R^{31}$ is independently selected from hydrogen; $C_1$-$C_6$ alkyl; 3-7 membered saturated, partially saturated, or unsaturated carbocycle; and 3-7 membered saturated, partially saturated, or unsaturated heterocycle containing one or more heteroatoms selected from the group consisting of nitrogen, oxygen, and sulfur;
- G is selected from a bond, O, S, S(O), $S(O)_2$, $CH_2$, $CH_2CH_2$, and CHCH;
- alternatively, G and $R^{a1}$ together form a 3-7 membered saturated, partially saturated, or unsaturated carbocycle; or a 3-7 membered saturated, partially saturated, or unsaturated heterocycle containing one or more heteroatoms selected from the group consisting of nitrogen, oxygen, and sulfur;
- A is selected from a bond, $CH_2$, $CH_2CH_2$, $CH_2CH_2CH_2$, CHCH, and C≡C;
- $R^{a1}$ and $R^{a2}$ are independently selected from hydrogen; halogen; $C_1$-$C_6$ alkyl; $C_2$-$C_6$ alkenyl; $C_2$-$C_6$ alkynyl; $C_1$-$C_6$ haloalkyl; OH; $O(C_1$-$C_6$ alkyl); ($C_1$-$C_6$ alkyl)-OH; ($C_1$-$C_6$ alkyl)-$O(C_1$-$C_6$ alkyl); ($C_1$-$C_6$ alkyl)-3-7 membered saturated, partially saturated, or unsaturated carbocycle; and ($C_1$-$C_6$ alkyl)-3-7 membered saturated, partially saturated, or unsaturated heterocycle containing one or more heteroatoms selected from the group consisting of nitrogen, oxygen, and sulfur;
- $R^{a3}$ is selected from hydrogen, halogen, OH, $O(C_1$-$C_6$ alkyl), and $C_1$-$C_6$ alkyl;
- $R^{a4}$ is selected from hydrogen, halogen, and $C_1$-$C_6$ alkyl;
- $Z_{11}$ is selected from $CR^{11}$, N, and N—O;
- $Z_{12}$ is selected from $CR^{12}$, N, and N—O;
- $Z_{13}$ is selected from $CR^{13}$, N, and N—O;
- $Z_{15}$ is selected from $CR^{15}$, N, and N—O;
- $R^{11}$, $R^{12}$, $R^{13}$, $R^{14}$, and $R^{15}$ are independently selected from hydrogen, halogen, $C_1$-$C_6$ alkyl, $C_2$-$C_6$ alkenyl, $C_2$-$C_6$ alkynyl, $C_1$-$C_6$ haloalkyl, ($C_1$-$C_6$ alkyl)-$OR^{40}$, OH, $O(C_1$-$C_6$ alkyl), $OCF_3$, $OCF_2H$, $OCFH_2$, CN, $N_3$, $NO_2$, $NH_2$, $NH(C_1$-$C_6$ alkyl), $N(C_1$-$C_6$ alkyl)$_2$, $NR^{40}C(O)R^{40}$, $C(O)NR^{40}R^{40}$, COH, $CO(C_1$-$C_6$ alkyl), $S(O)_rR^{40}$, $NR^{40}S(O)_rR^{40}$, $S(O)_rNR^{40}R^{40}$, $SR^{40}$, $SCF_3$, $COOR^{40}$, $COR^{40}$, and $OR^{40}$; 3-7 membered saturated, partially saturated, or unsaturated carbocycle; and 3-7 membered saturated, partially saturated, or unsaturated heterocycle containing one or more heteroatoms selected from the group consisting of nitrogen, oxygen, and sulfur;
- alternatively, two substituents selected from $R^{11}$, $R^{12}$, $R^{13}$, $R^{14}$, and $R^{15}$ on two adjacent carbon atoms taken together form a 3-7 membered saturated, partially saturated, or unsaturated carbocycle; or a 3-7 membered saturated, partially saturated, or unsaturated heterocycle containing one or more heteroatoms selected from the group consisting of nitrogen, oxygen, and sulfur; where the carbocycle or heterocycle is optionally substituted with one or more $R^{40}$;

$R^{40}$ is independently selected from hydrogen; halogen; $C_1$-$C_6$ alkyl; $C_2$-$C_6$ alkenyl, $C_2$-$C_6$ alkynyl; 3-7 membered saturated, partially saturated, or unsaturated carbocycle; 3-7 membered saturated, partially saturated, or unsaturated heterocycle containing one or more heteroatoms selected from the group consisting of nitrogen, oxygen, and sulfur; ($C_1$-$C_6$ alkyl)-3-7 membered saturated, partially saturated, or unsaturated carbocycle; and ($C_1$-$C_6$ alkyl)-3-7 membered saturated, partially saturated, or unsaturated heterocycle containing one or more heteroatoms selected from the group consisting of nitrogen, oxygen, and sulfur;

or two $R^{40}$ taken together with the carbon atom to which they are attached form a carbonyl;

j is 0, 1, or 2;
p is 0, 1, or 2;
q is 0, 1, or 2; and
t is 0, 1, or 2.

2. The method according to claim 1, wherein the compound is of formula (II):

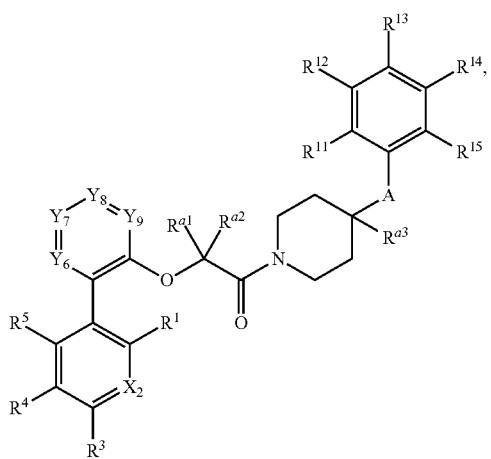

(II)

or a pharmaceutically acceptable salt thereof.

3. The method according to claim 1, wherein the compound is of formula (III):

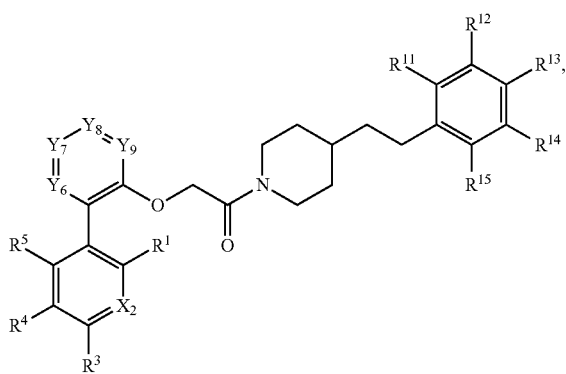

(III)

or a pharmaceutically acceptable salt thereof.

4. The method according to claim 1, wherein the compound is of a formula selected from:

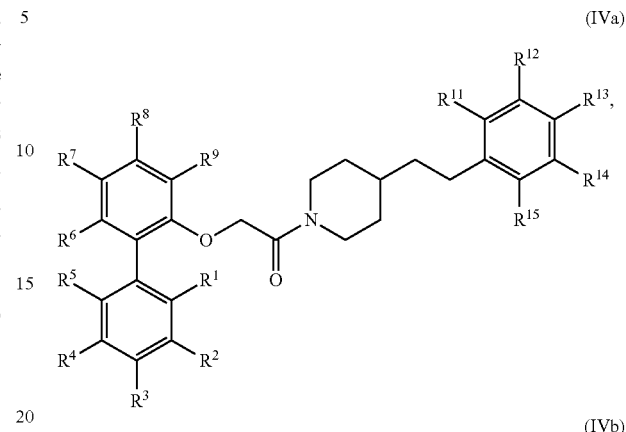

(IVa)

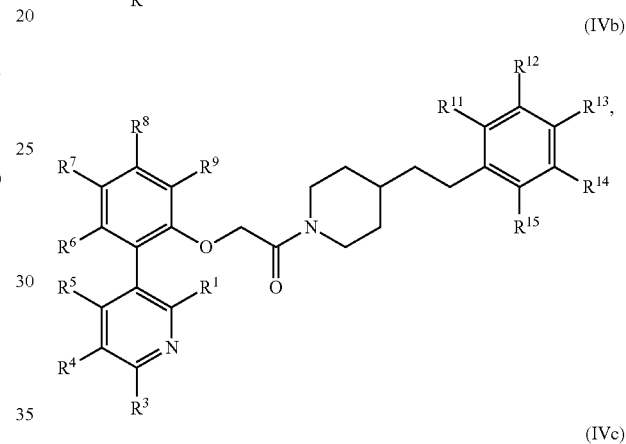

(IVb)

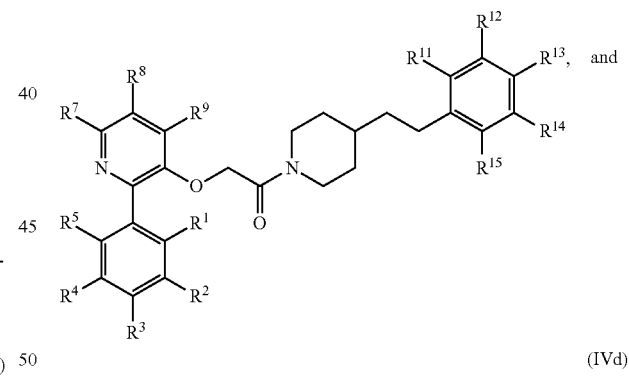

(IVc)

and

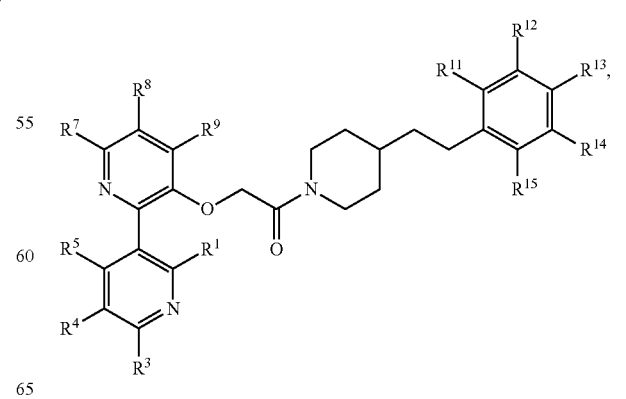

(IVd)

or a pharmaceutically acceptable salt thereof.

5. The method according to claim 1, wherein the compound is of formula (V):

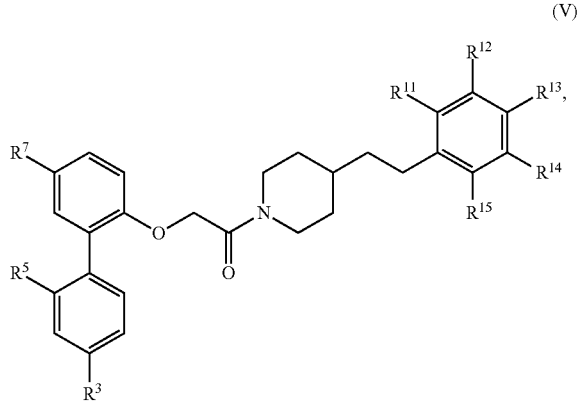

or a pharmaceutically acceptable salt thereof.

6. The method according to claim 1, wherein $R^3$ is selected from hydrogen, halogen, $C_1$-$C_6$ alkyl, $C_1$-$C_6$ haloalkyl, OH, O($C_1$-$C_6$ alkyl), $OCF_3$, $OCF_2H$, $OCFH_2$, CN, $N_3$, $NO_2$, $NH_2$, NH($C_1$-$C_6$ alkyl), and N($C_1$-$C_6$ alkyl)$_2$.

7. The method according to claim 6, wherein $R^3$ is selected from hydrogen, halogen, and CN.

8. The method according to claim 1, wherein $R^5$ is selected from hydrogen, halogen, $C_1$-$C_6$ alkyl, $C_1$-$C_6$ haloalkyl, OH, O($C_1$-$C_6$ alkyl), $OCF_3$, $OCF_2H$, $OCFH_2$, CN, $NH_2$, NH($C_1$-$C_6$ alkyl), and N($C_1$-$C_6$ alkyl)$_2$.

9. The method according to claim 8, wherein $R^5$ is selected from hydrogen, halogen, $C_1$-$C_6$ alkyl, OH, and O($C_1$-$C_6$ alkyl).

10. The method according to claim 1, wherein $R^7$ is selected from hydrogen, halogen, $C_1$-$C_6$ alkyl, $C_1$-$C_6$ haloalkyl, OH, O($C_1$-$C_6$ alkyl), $OCF_3$, $OCF_2H$, $OCFH_2$, CN, $NH_2$, NH($C_1$-$C_6$ alkyl), N($C_1$-$C_6$ alkyl)$_2$, $S(O)_qNR^{30}R^{30}$, $C(O)NR^{30}R^{30}$, $COR^{30}$, and $COOR^{30}$.

11. The method according to claim 10, wherein $R^7$ is selected from hydrogen, halogen, $C_1$-$C_6$ alkyl, $C_1$-$C_6$ haloalkyl, OH, O($C_1$-$C_6$ alkyl), CN, $S(O)_qNR^{30}R^{30}$, $C(O)NR^{30}R^{30}$, $COR^{30}$, and $COOR^{30}$.

12. The method according to claim 11, wherein $R^7$ is selected from hydrogen, $CF_3$, OH, CN, $S(O)_2NR^{30}R^{30}$, and $C(O)NR^{30}R^{30}$.

13. The method according to claim 1, wherein the compound is of the following structure:

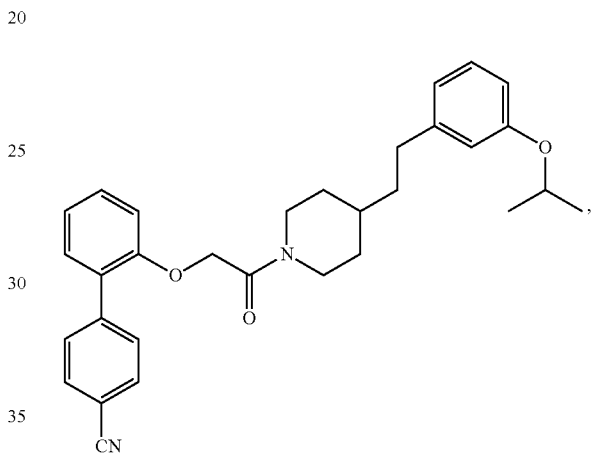

or a pharmaceutically acceptable salt thereof.

14. A method of treating an immune disorder associated with T cell activation in a subject comprising administering to the subject an effective amount of a compound selected from:

| Compound No. | Structure |
| --- | --- |
| 100 | ![structure] |

-continued
| Compound No. | Structure |
|---|---|
| 101 | 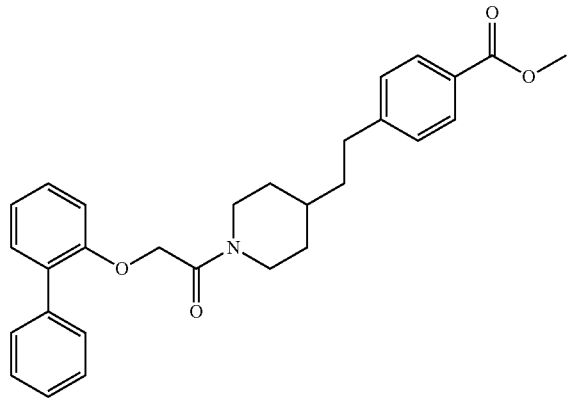 [SMILES: COC(=O)c1ccc(CCC2CCN(C(=O)COc3ccccc3-c3ccccc3)CC2)cc1] |
| 102 | 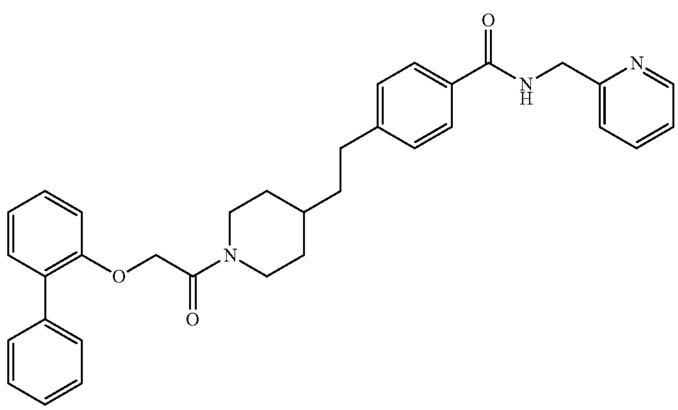 [SMILES: O=C(NCc1ccccn1)c1ccc(CCC2CCN(C(=O)COc3ccccc3-c3ccccc3)CC2)cc1] |
| 103 | 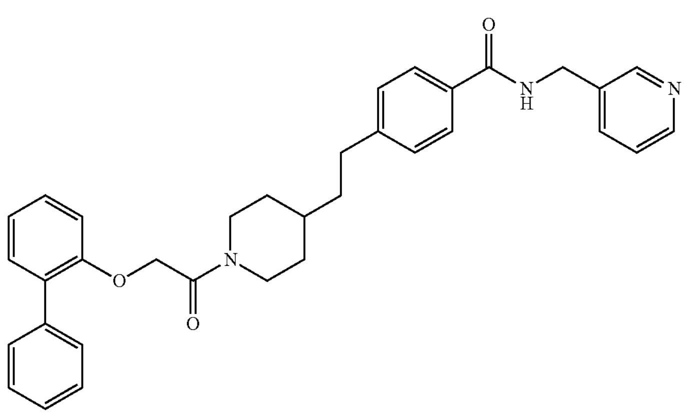 [SMILES: O=C(NCc1cccnc1)c1ccc(CCC2CCN(C(=O)COc3ccccc3-c3ccccc3)CC2)cc1] |

| Compound No. | Structure |
|---|---|
| 104 | 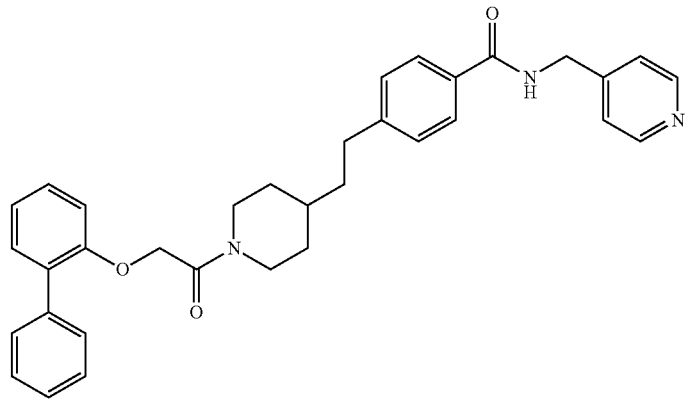 [SMILES: O=C(NCc1ccncc1)c1ccc(CCC2CCN(C(=O)COc3ccccc3-c3ccccc3)CC2)cc1] |
| 105 | 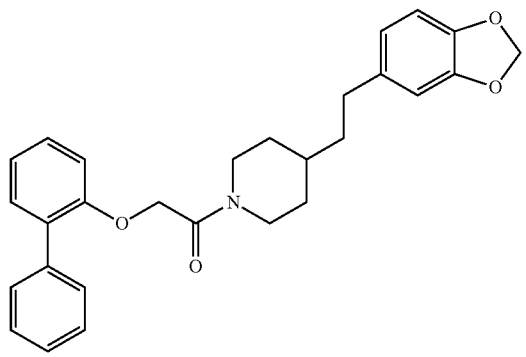 |
| 106 | 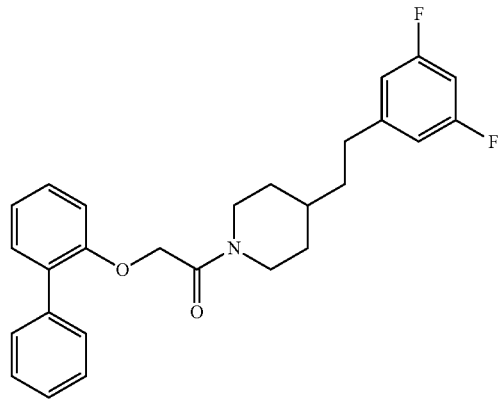 |
| 107 | 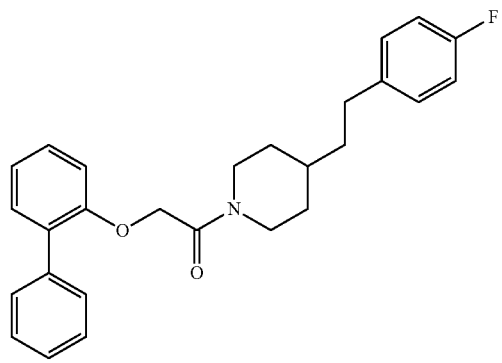 [SMILES: O=C(COc1ccccc1-c1ccccc1)N1CCC(CCc2ccc(F)cc2)CC1] |

| Compound No. | Structure |
|---|---|
| 108 | 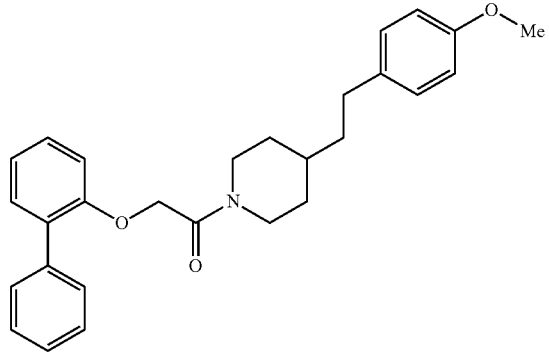 [SMILES: COc1ccc(CCC2CCN(C(=O)COc3ccccc3-c3ccccc3)CC2)cc1] |
| 109 | 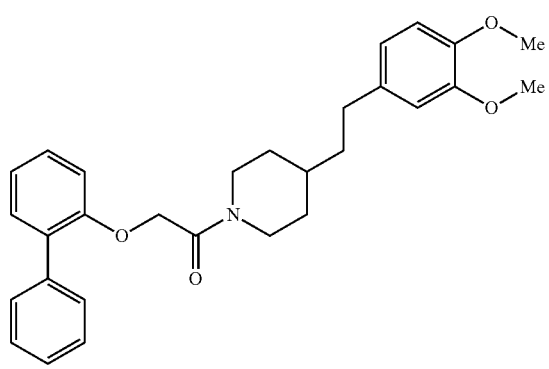 [SMILES: COc1ccc(CCC2CCN(C(=O)COc3ccccc3-c3ccccc3)CC2)cc1OC] |
| 110 | 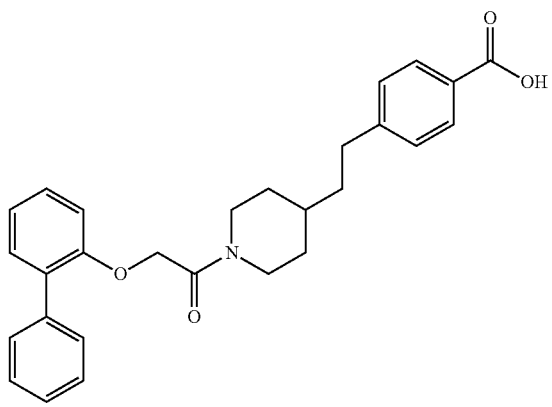 [SMILES: O=C(O)c1ccc(CCC2CCN(C(=O)COc3ccccc3-c3ccccc3)CC2)cc1] |
| 111 | 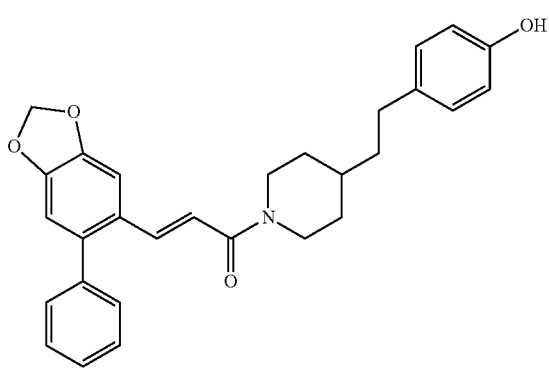 [SMILES: O=C(/C=C/c1cc2c(cc1-c1ccccc1)OCO2)N1CCC(CCc2ccc(O)cc2)CC1] |

-continued
| Compound No. | Structure |
|---|---|
| 112 | 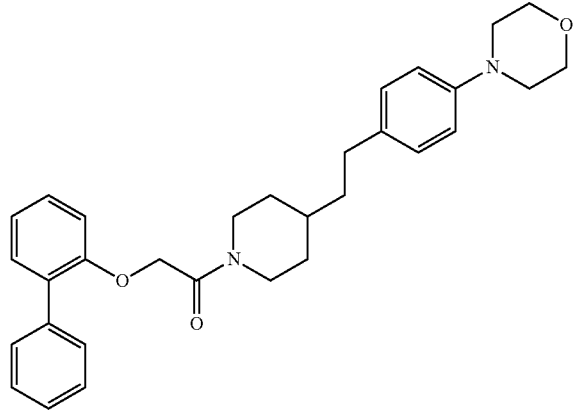 [SMILES: O=C(COc1ccccc1-c1ccccc1)N1CCC(CCc2ccc(N3CCOCC3)cc2)CC1] |
| 113 | 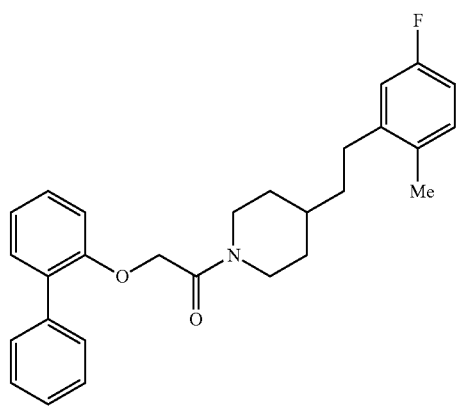 |
| 114 | 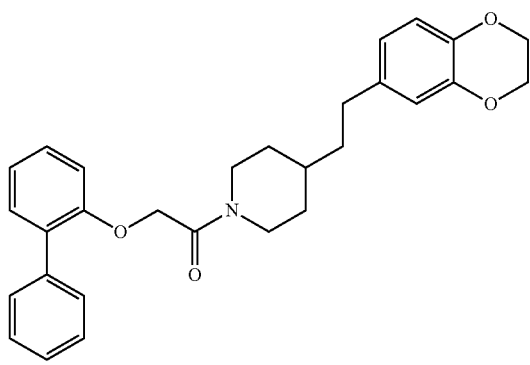 [SMILES: O=C(COc1ccccc1-c1ccccc1)N1CCC(CCc2ccc3c(c2)OCCO3)CC1] |
| 115 | 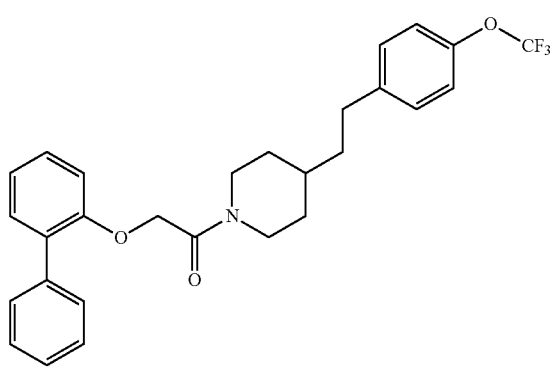 [SMILES: O=C(COc1ccccc1-c1ccccc1)N1CCC(CCc2ccc(OC(F)(F)F)cc2)CC1] |

-continued
| Compound No. | Structure |
| --- | --- |
| 116 | 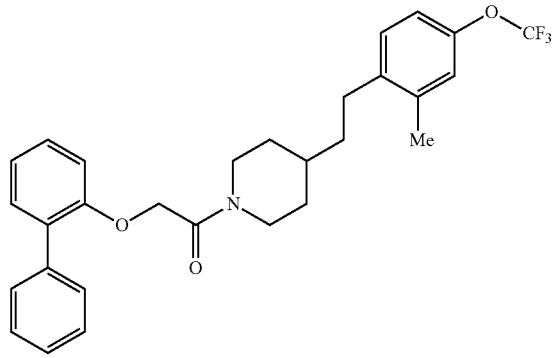 [SMILES: Cc1cc(OC(F)(F)F)ccc1CCC1CCN(C(=O)COc2ccccc2-c2ccccc2)CC1] |
| 117 | 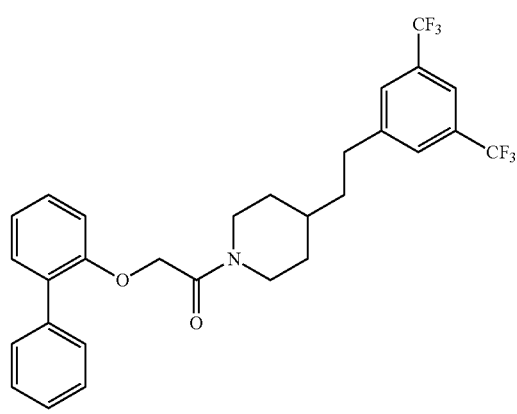 [SMILES: O=C(COc1ccccc1-c1ccccc1)N1CCC(CCc2cc(C(F)(F)F)cc(C(F)(F)F)c2)CC1] |
| 118 | 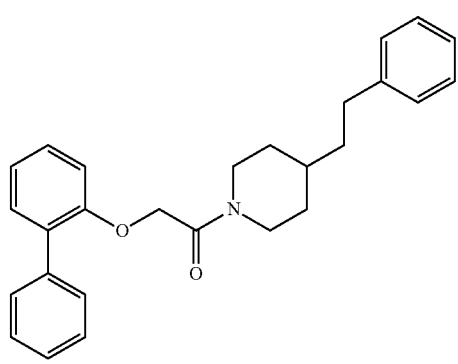 [SMILES: O=C(COc1ccccc1-c1ccccc1)N1CCC(CCc2ccccc2)CC1] |
| 119 | 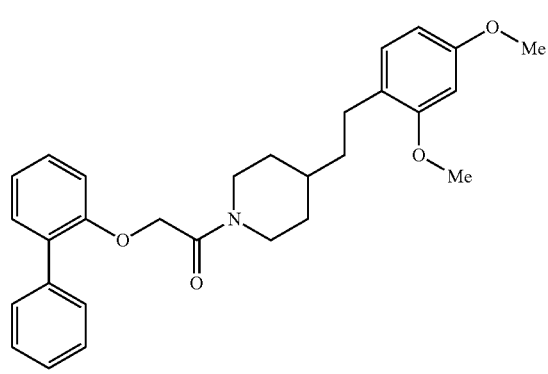 [SMILES: COc1ccc(CCC2CCN(C(=O)COc3ccccc3-c3ccccc3)CC2)c(OC)c1] |

-continued
| Compound No. | Structure |
|---|---|
| 120 | 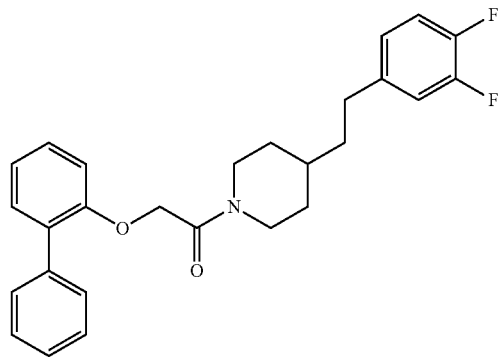 [SMILES: O=C(COc1ccccc1-c1ccccc1)N1CCC(CCc2ccc(F)c(F)c2)CC1] |
| 121 | 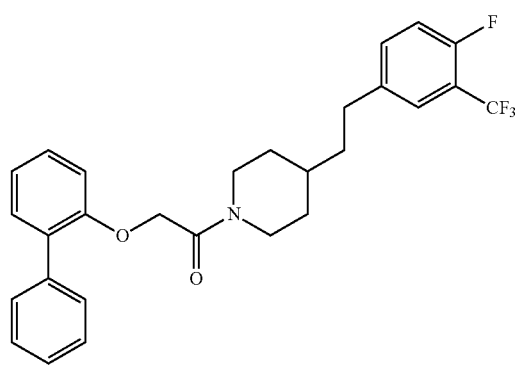 [SMILES: O=C(COc1ccccc1-c1ccccc1)N1CCC(CCc2ccc(F)c(C(F)(F)F)c2)CC1] |
| 122 | 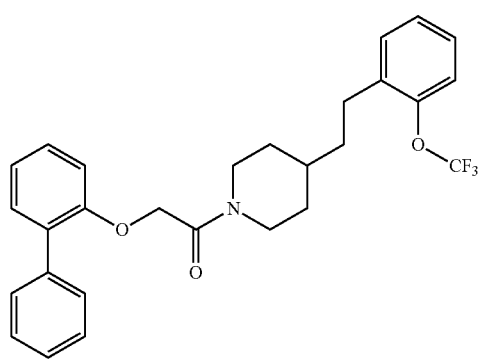 [SMILES: O=C(COc1ccccc1-c1ccccc1)N1CCC(CCc2ccccc2OC(F)(F)F)CC1] |
| 123 | 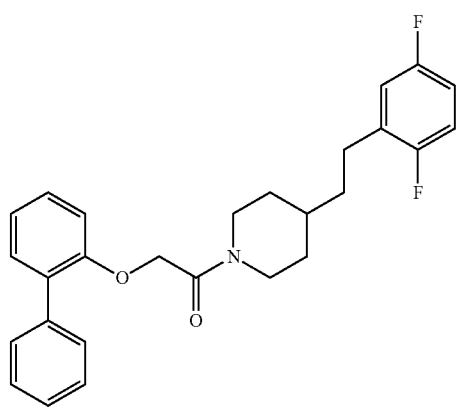 [SMILES: O=C(COc1ccccc1-c1ccccc1)N1CCC(CCc2cc(F)ccc2F)CC1] |

-continued
| Compound No. | Structure |
|---|---|
| 124 | 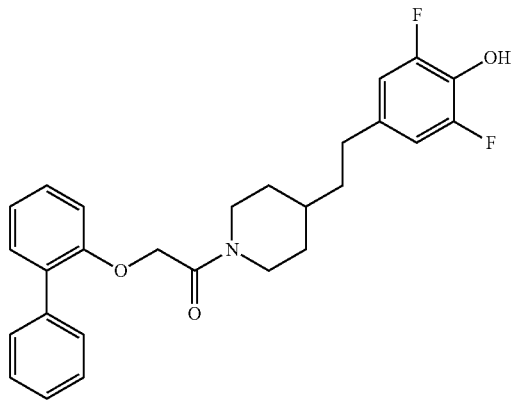 [SMILES: O=C(COc1ccccc1-c1ccccc1)N1CCC(CCc2cc(F)c(O)c(F)c2)CC1] |
| 125 | 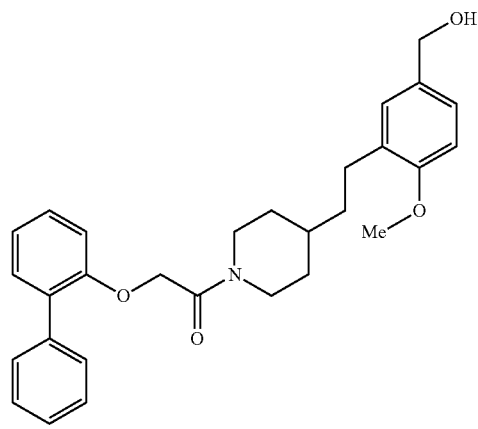 [SMILES: COc1ccc(CO)cc1CCC1CCN(C(=O)COc2ccccc2-c2ccccc2)CC1] |
| 126 | 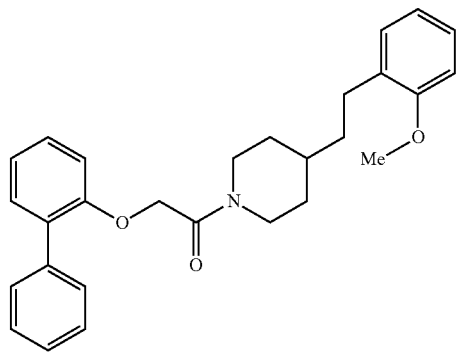 [SMILES: COc1ccccc1CCC1CCN(C(=O)COc2ccccc2-c2ccccc2)CC1] |
| 127 | 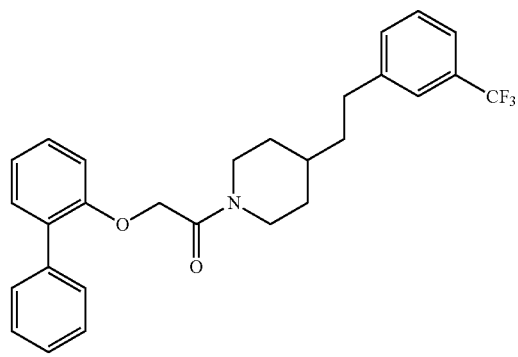 [SMILES: O=C(COc1ccccc1-c1ccccc1)N1CCC(CCc2cccc(C(F)(F)F)c2)CC1] |

| Compound No. | Structure |
|---|---|
| 128 | 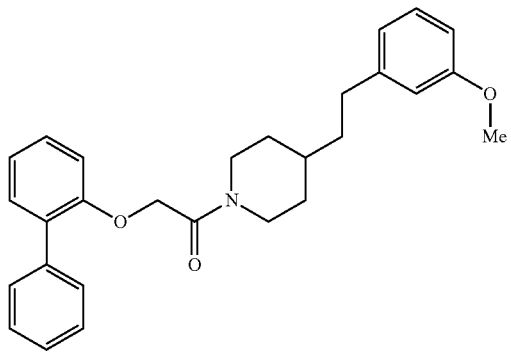 [SMILES: COc1cccc(CCC2CCN(C(=O)COc3ccccc3-c3ccccc3)CC2)c1] |
| 129 | 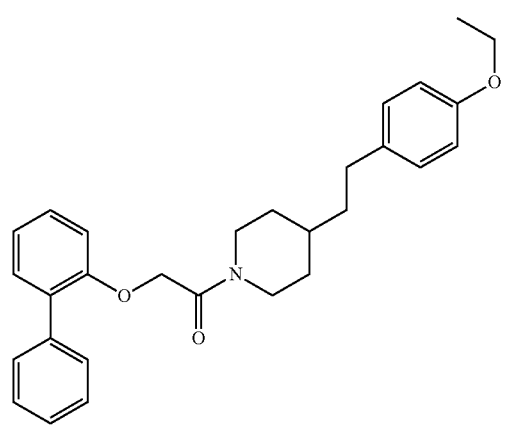 [SMILES: CCOc1ccc(CCC2CCN(C(=O)COc3ccccc3-c3ccccc3)CC2)cc1] |
| 130 | 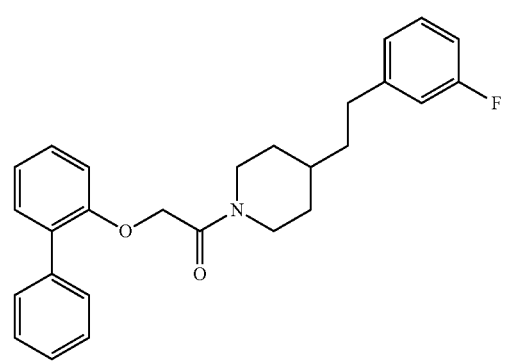 [SMILES: O=C(COc1ccccc1-c1ccccc1)N1CCC(CCc2cccc(F)c2)CC1] |
| 131 | 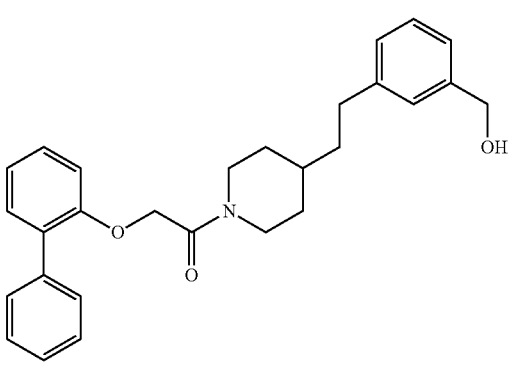 [SMILES: O=C(COc1ccccc1-c1ccccc1)N1CCC(CCc2cccc(CO)c2)CC1] |

-continued
| Compound No. | Structure |
|---|---|
| 132 | 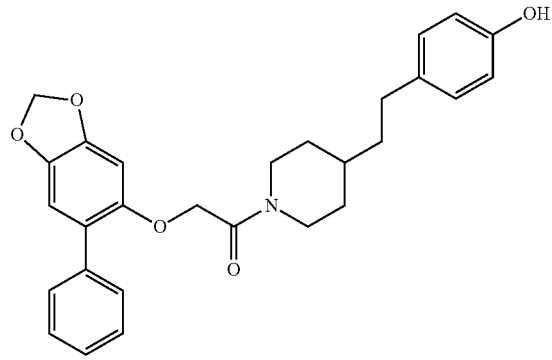 |
| 133 | 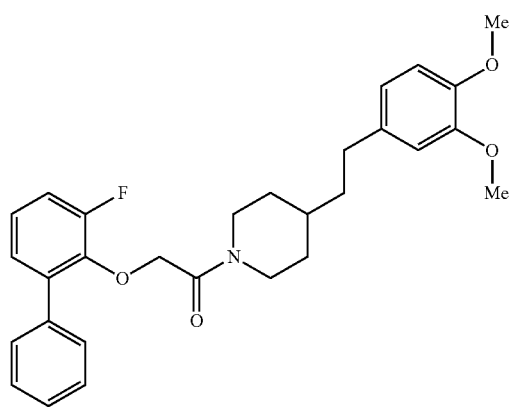 [SMILES: COc1ccc(CCC2CCN(C(=O)COc3c(F)cccc3-c3ccccc3)CC2)cc1OC] |
| 134 | 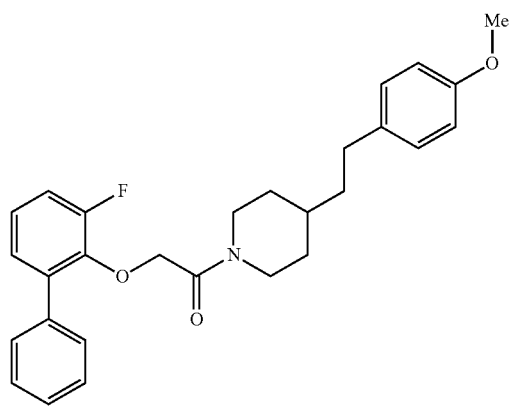 [SMILES: COc1ccc(CCC2CCN(C(=O)COc3c(F)cccc3-c3ccccc3)CC2)cc1] |

| Compound No. | Structure |
|---|---|
| 135 | 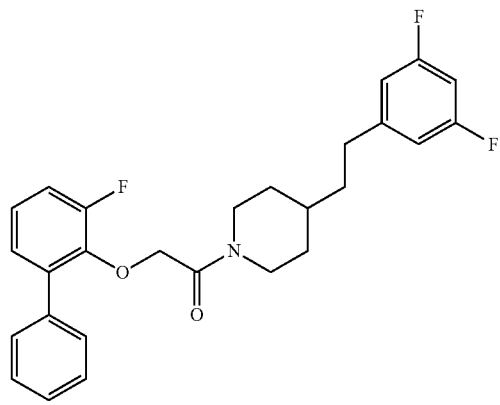 [SMILES: O=C(COc1c(F)cccc1-c1ccccc1)N1CCC(CCc2cc(F)cc(F)c2)CC1] |
| 136 | 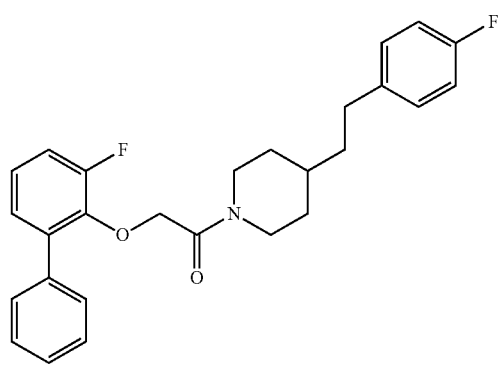 [SMILES: O=C(COc1c(F)cccc1-c1ccccc1)N1CCC(CCc2ccc(F)cc2)CC1] |
| 137 | 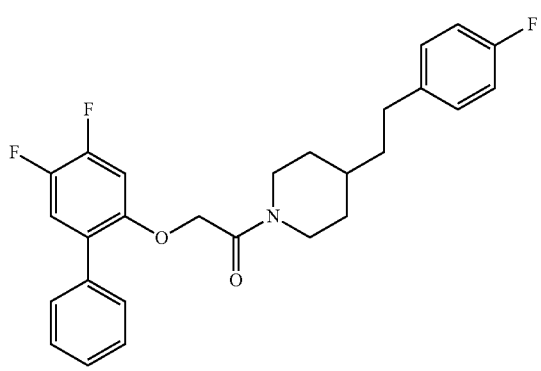 [SMILES: O=C(COc1cc(F)c(F)cc1-c1ccccc1)N1CCC(CCc2ccc(F)cc2)CC1] |
| 138 | 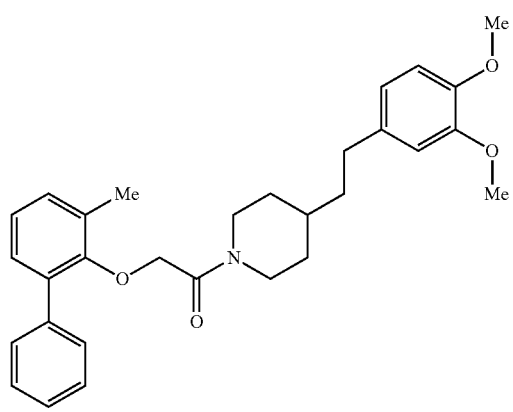 [SMILES: COc1ccc(CCC2CCN(C(=O)COc3c(C)cccc3-c3ccccc3)CC2)cc1OC] |

| Compound No. | Structure |
|---|---|
| 139 | 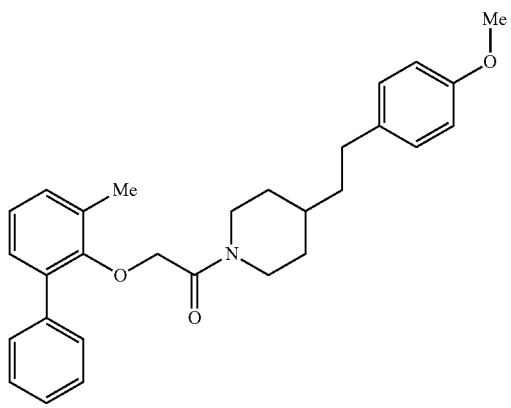 |
| 140 | 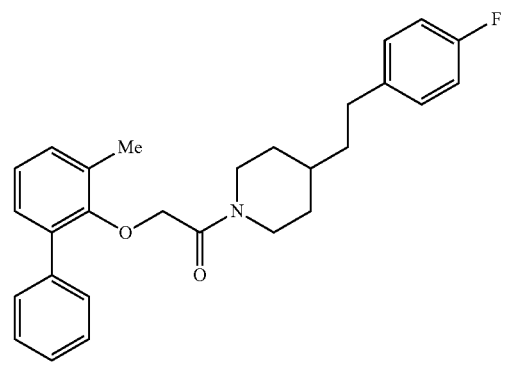 |
| 141 | 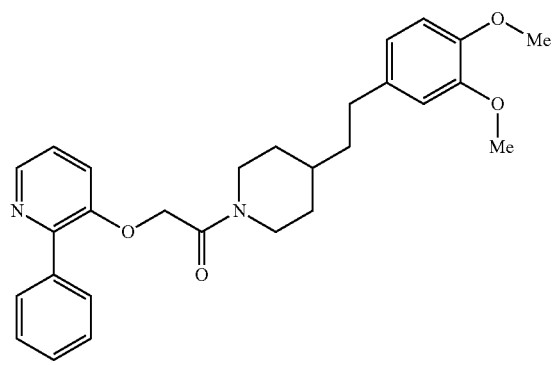 [SMILES: COc1ccc(CCC2CCN(C(=O)COc3cccnc3-c3ccccc3)CC2)cc1OC] |
| 142 | 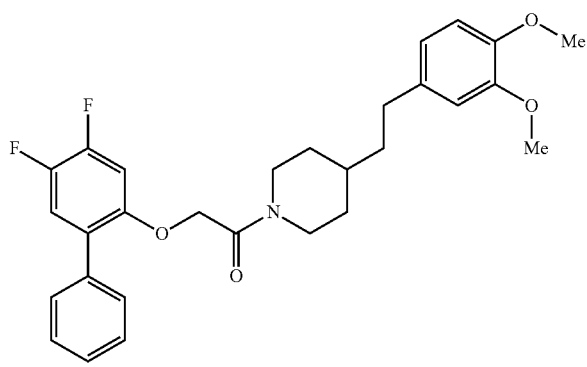 [SMILES: COc1ccc(CCC2CCN(C(=O)COc3cc(F)c(F)cc3-c3ccccc3)CC2)cc1OC] |

-continued
| Compound No. | Structure |
|---|---|
| 143 | 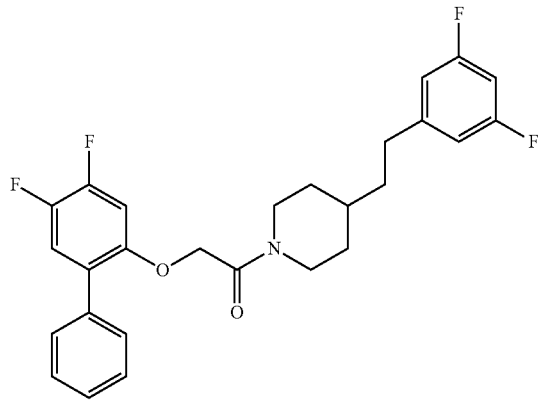 [SMILES: O=C(COc1cc(F)c(F)cc1-c1ccccc1)N1CCC(CCc2cc(F)cc(F)c2)CC1] |
| 144 | 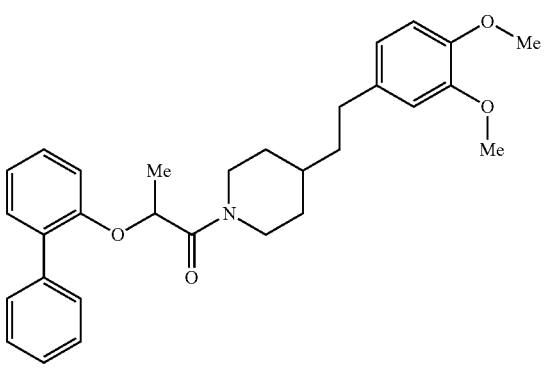 [SMILES: COc1ccc(CCC2CCN(C(=O)C(C)Oc3ccccc3-c3ccccc3)CC2)cc1OC] |
| 145 | 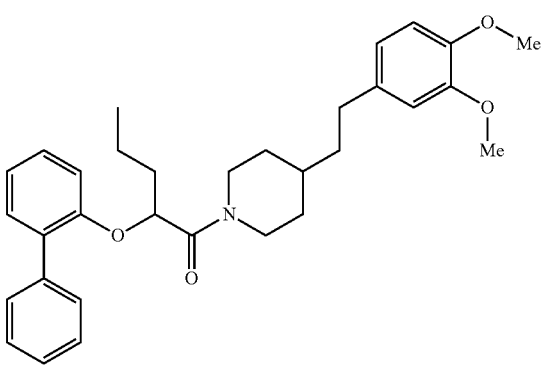 [SMILES: CCCC(Oc1ccccc1-c1ccccc1)C(=O)N1CCC(CCc2ccc(OC)c(OC)c2)CC1] |
| 146 | 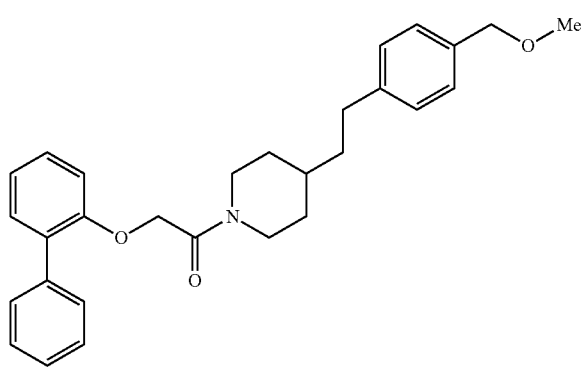 [SMILES: COCc1ccc(CCC2CCN(C(=O)COc3ccccc3-c3ccccc3)CC2)cc1] |

| Compound No. | Structure |
|---|---|
| 147 | 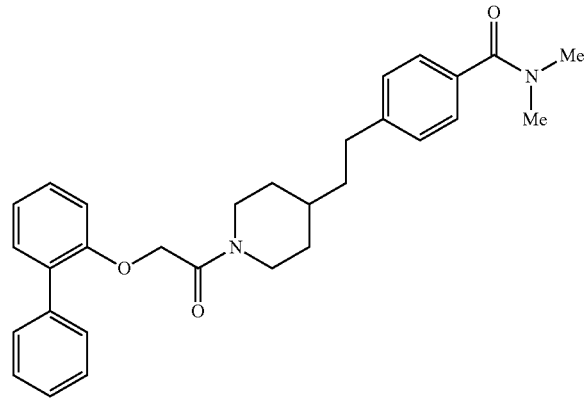 [SMILES: CN(C)C(=O)c1ccc(CCC2CCN(C(=O)COc3ccccc3-c3ccccc3)CC2)cc1] |
| 148 | 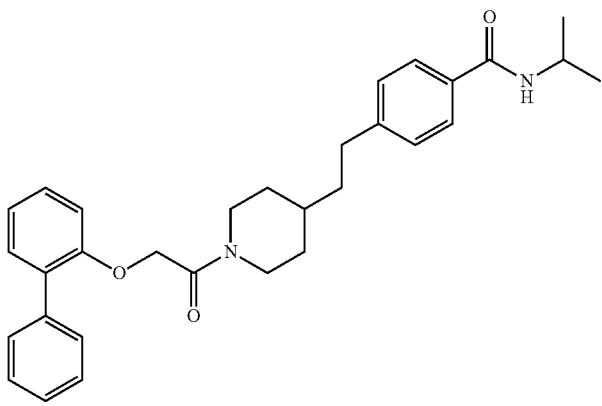 [SMILES: CC(C)NC(=O)c1ccc(CCC2CCN(C(=O)COc3ccccc3-c3ccccc3)CC2)cc1] |
| 149 | 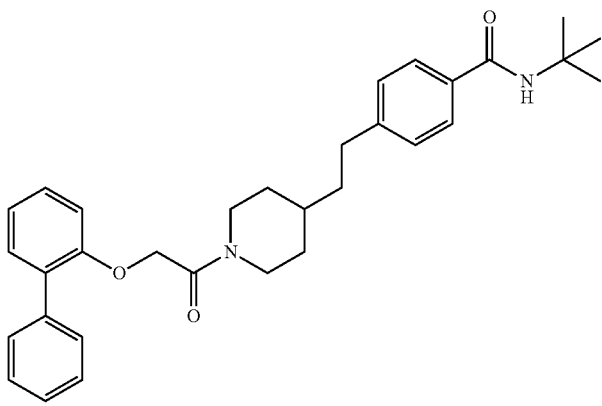 [SMILES: CC(C)(C)NC(=O)c1ccc(CCC2CCN(C(=O)COc3ccccc3-c3ccccc3)CC2)cc1] |

| Compound No. | Structure |
|---|---|
| 150 | 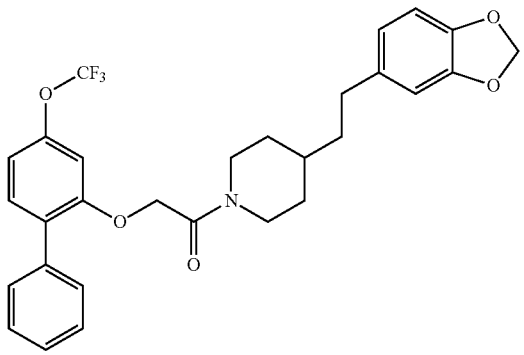 [SMILES: O=C(COc1cc(OC(F)(F)F)ccc1-c1ccccc1)N1CCC(CCc2ccc3c(c2)OCO3)CC1] |
| 151 | 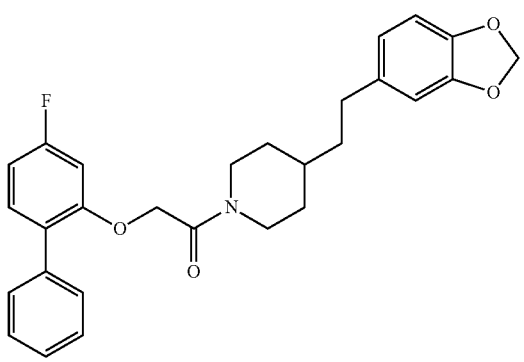 [SMILES: O=C(COc1cc(F)ccc1-c1ccccc1)N1CCC(CCc2ccc3c(c2)OCO3)CC1] |
| 152 | 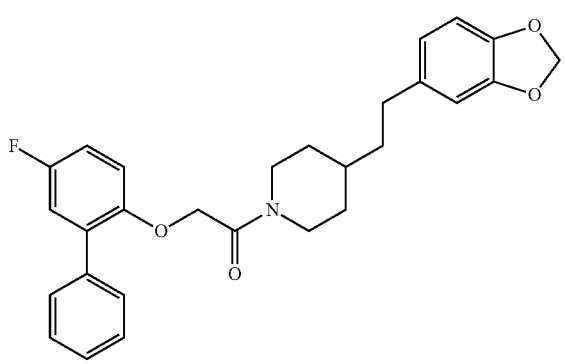 [SMILES: O=C(COc1ccc(F)cc1-c1ccccc1)N1CCC(CCc2ccc3c(c2)OCO3)CC1] |
| 153 | 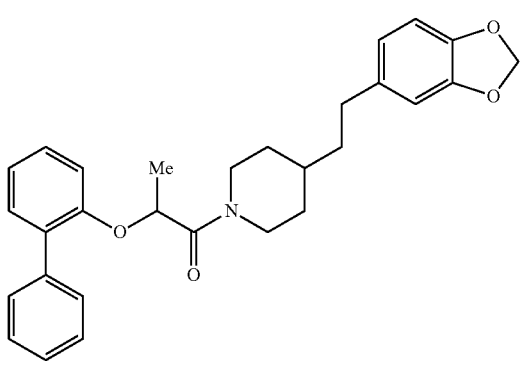 [SMILES: CC(Oc1ccccc1-c1ccccc1)C(=O)N1CCC(CCc2ccc3c(c2)OCO3)CC1] |

| Compound No. | Structure |
|---|---|
| 154 | 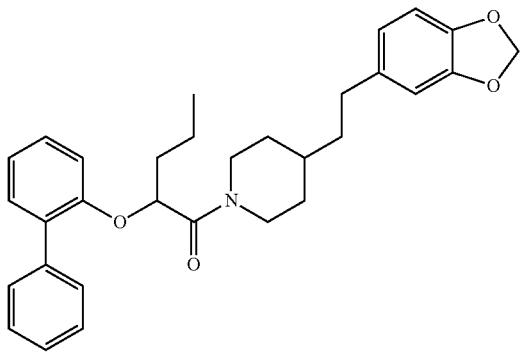 [SMILES: CCCC(Oc1ccccc1-c1ccccc1)C(=O)N1CCC(CCc2ccc3c(c2)OCO3)CC1] |
| 155 | 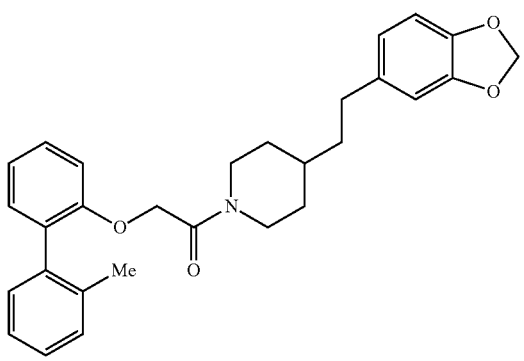 |
| 156 | 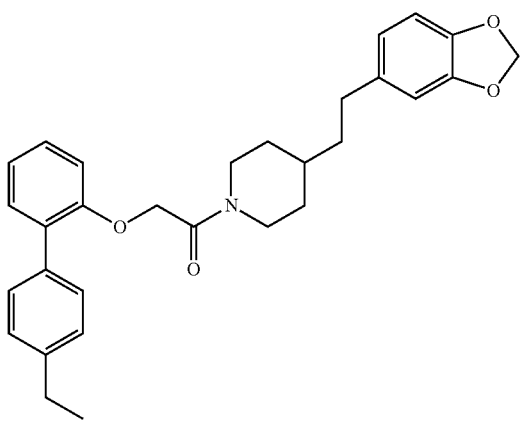 [SMILES: CCc1ccc(-c2ccccc2OCC(=O)N2CCC(CCc3ccc4c(c3)OCO4)CC2)cc1] |
| 157 | 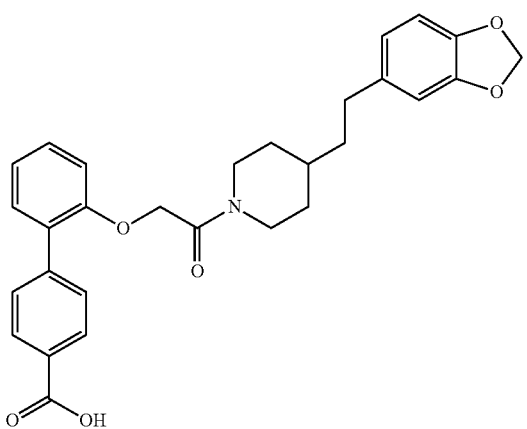 [SMILES: O=C(O)c1ccc(-c2ccccc2OCC(=O)N2CCC(CCc3ccc4c(c3)OCO4)CC2)cc1] |

| Compound No. | Structure |
|---|---|
| 158 | 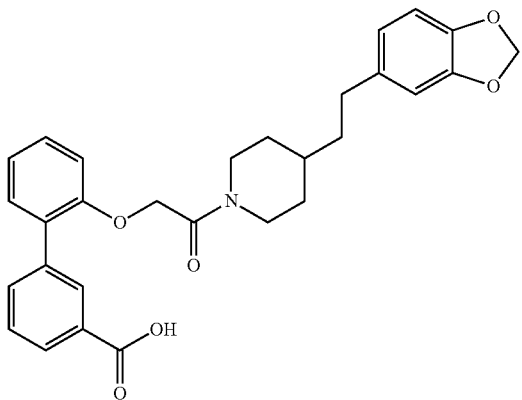 |
| 159 | 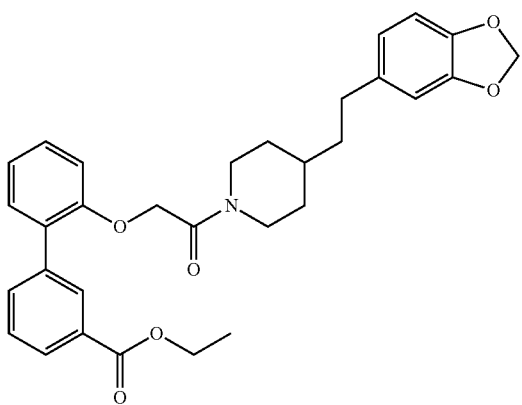 [SMILES: CCOC(=O)c1cccc(-c2ccccc2OCC(=O)N2CCC(CCc3ccc4c(c3)OCO4)CC2)c1] |
| 160 | 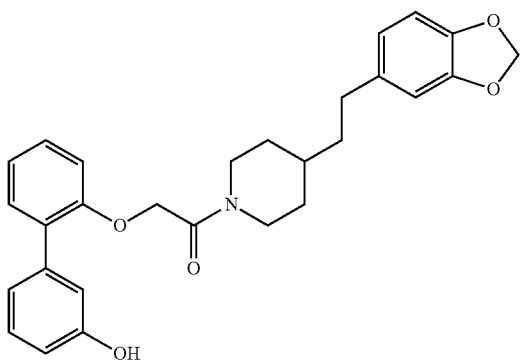 [SMILES: O=C(COc1ccccc1-c1cccc(O)c1)N1CCC(CCc2ccc3c(c2)OCO3)CC1] |

| Compound No. | Structure |
|---|---|
| 161 | 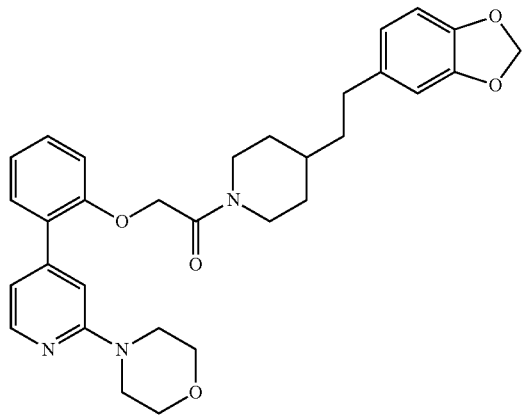 [SMILES: O=C(COc1ccccc1-c1ccnc(N2CCOCC2)c1)N1CCC(CCc2ccc3c(c2)OCO3)CC1] |
| 162 | 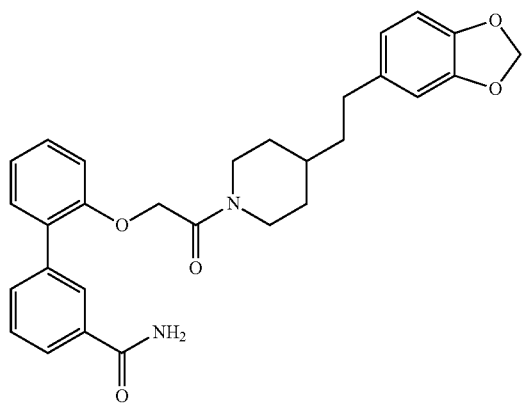 |
| 163 | 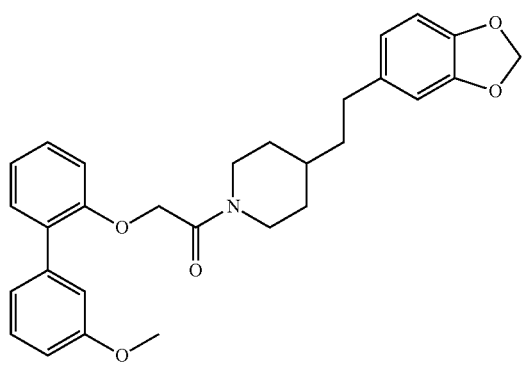 [SMILES: COc1cccc(-c2ccccc2OCC(=O)N2CCC(CCc3ccc4c(c3)OCO4)CC2)c1] |

| Compound No. | Structure |
|---|---|
| 164 | 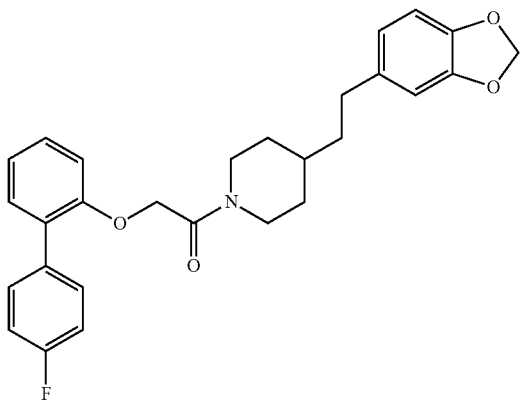 [SMILES: O=C(COc1ccccc1-c1ccc(F)cc1)N1CCC(CCc2ccc3c(c2)OCO3)CC1] |
| 165 | 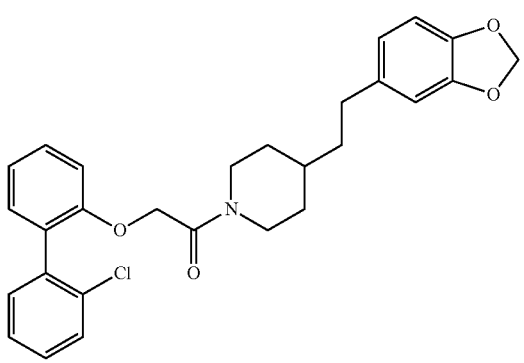 |
| 166 | 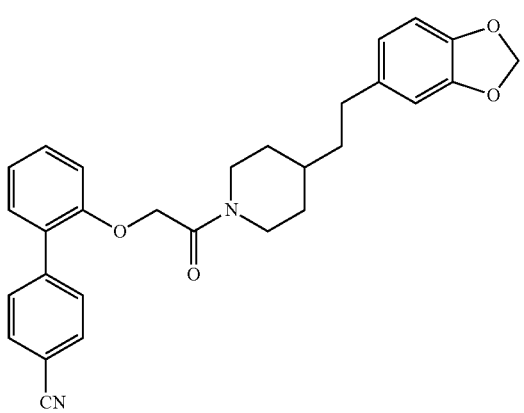 |
| 167 | 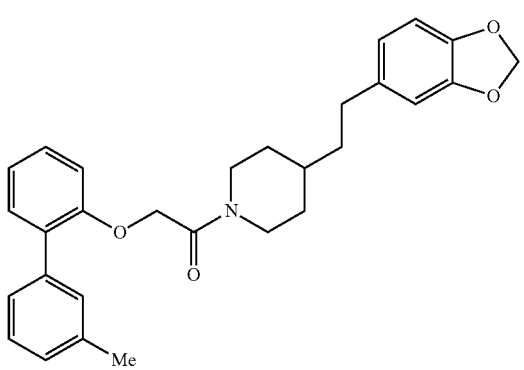 |

-continued
| Compound No. | Structure |
|---|---|
| 168 | 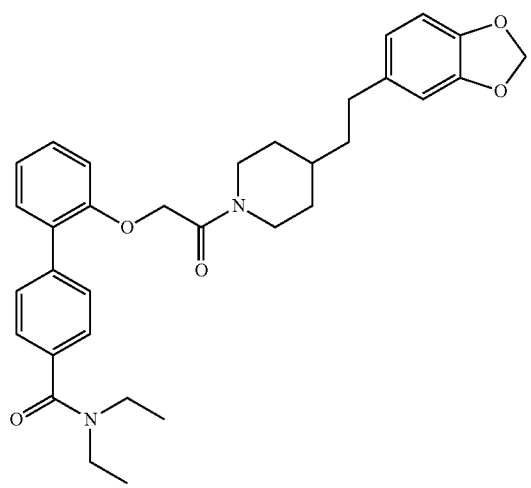 [SMILES: CCN(CC)C(=O)c1ccc(-c2ccccc2OCC(=O)N2CCC(CCc3ccc4c(c3)OCO4)CC2)cc1] |
| 169 | 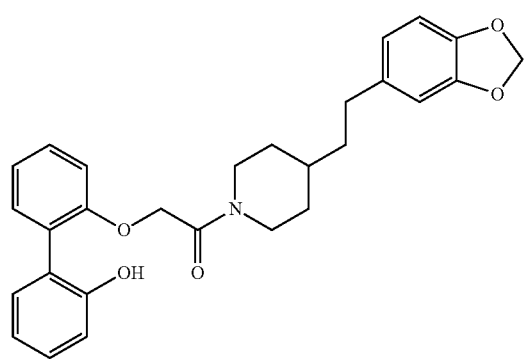 [SMILES: O=C(COc1ccccc1-c1ccccc1O)N1CCC(CCc2ccc3c(c2)OCO3)CC1] |
| 170 | 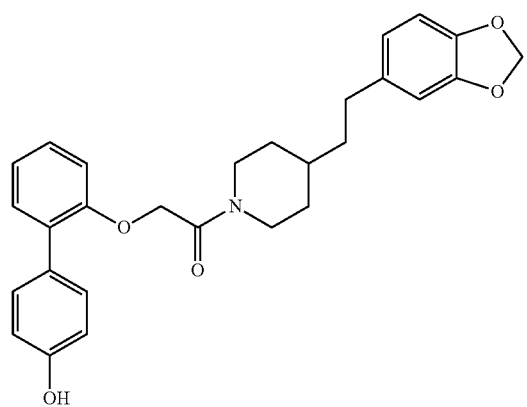 |

-continued
| Compound No. | Structure |
|---|---|
| 171 | 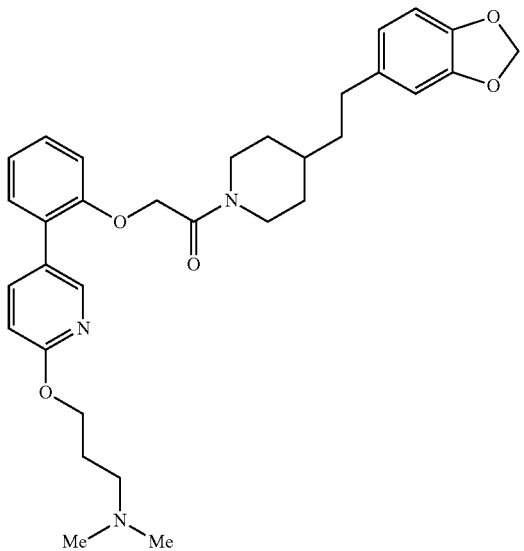 [SMILES: CN(C)CCCOc1ccc(-c2ccccc2OCC(=O)N2CCC(CCc3ccc4c(c3)OCO4)CC2)cn1] |
| 172 | 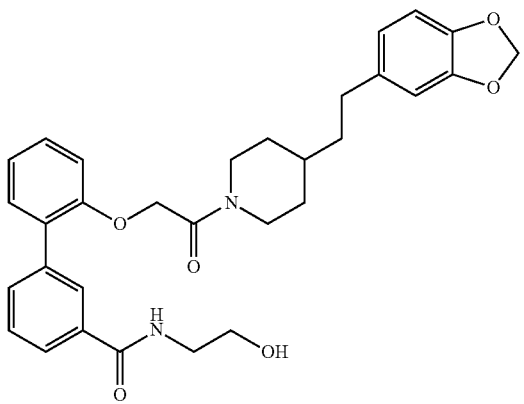 [SMILES: O=C(NCCO)c1cccc(-c2ccccc2OCC(=O)N2CCC(CCc3ccc4c(c3)OCO4)CC2)c1] |
| 173 | 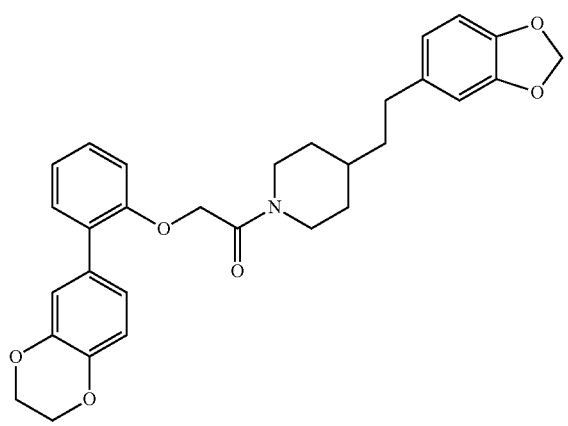 [SMILES: O=C(COc1ccccc1-c1ccc2c(c1)OCCO2)N1CCC(CCc2ccc3c(c2)OCO3)CC1] |

-continued
| Compound No. | Structure |
|---|---|
| 174 | 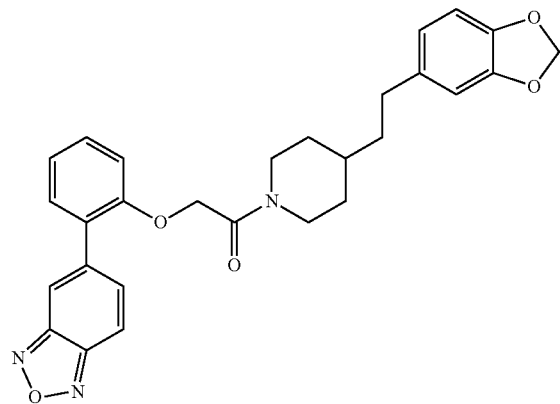 [SMILES: O=C(COc1ccccc1-c1ccc2nonc2c1)N1CCC(CCc2ccc3c(c2)OCO3)CC1] |
| 175 | 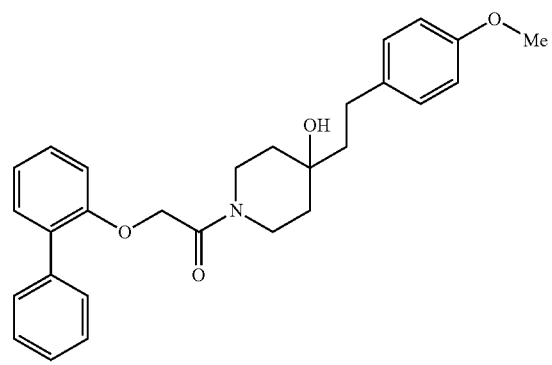 [SMILES: COc1ccc(CCC2(O)CCN(C(=O)COc3ccccc3-c3ccccc3)CC2)cc1] |
| 176 | 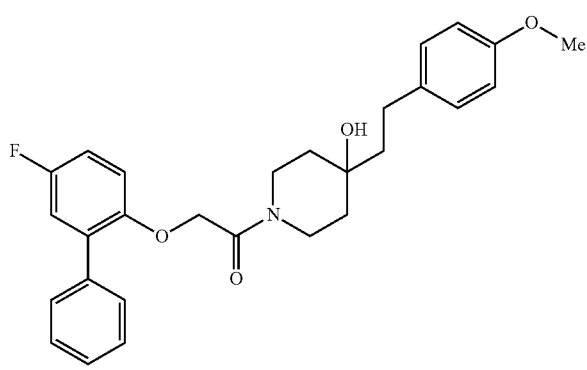 [SMILES: COc1ccc(CCC2(O)CCN(C(=O)COc3ccc(F)cc3-c3ccccc3)CC2)cc1] |
| 177 | 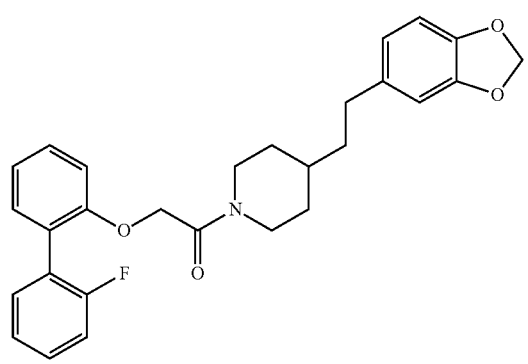 |

| Compound No. | Structure |
|---|---|
| 178 | 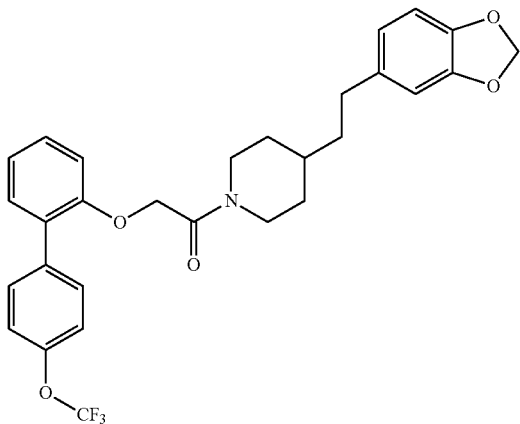 [SMILES: O=C(COc1ccccc1-c1ccc(OC(F)(F)F)cc1)N1CCC(CCc2ccc3c(c2)OCO3)CC1] |
| 179 | 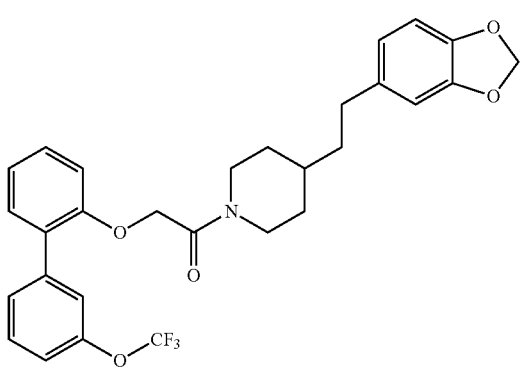 [SMILES: O=C(COc1ccccc1-c1cccc(OC(F)(F)F)c1)N1CCC(CCc2ccc3c(c2)OCO3)CC1] |
| 180 | 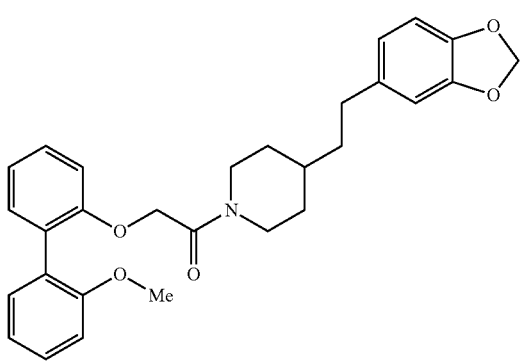 [SMILES: COc1ccccc1-c1ccccc1OCC(=O)N1CCC(CCc2ccc3c(c2)OCO3)CC1] |

| Compound No. | Structure |
|---|---|
| 181 | 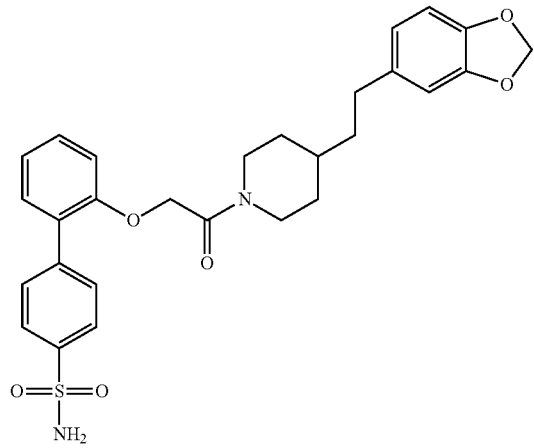 |
| 182 | 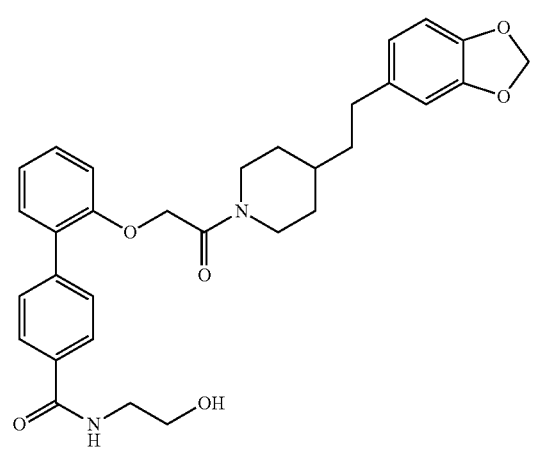 [SMILES: O=C(NCCO)c1ccc(-c2ccccc2OCC(=O)N2CCC(CCc3ccc4c(c3)OCO4)CC2)cc1] |
| 183 | 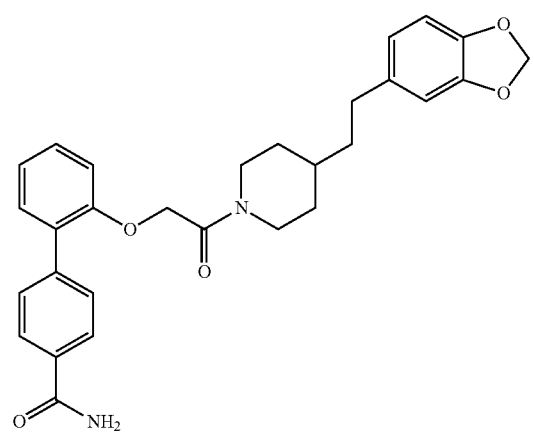 [SMILES: NC(=O)c1ccc(-c2ccccc2OCC(=O)N2CCC(CCc3ccc4c(c3)OCO4)CC2)cc1] |

| Compound No. | Structure |
|---|---|
| 184 | 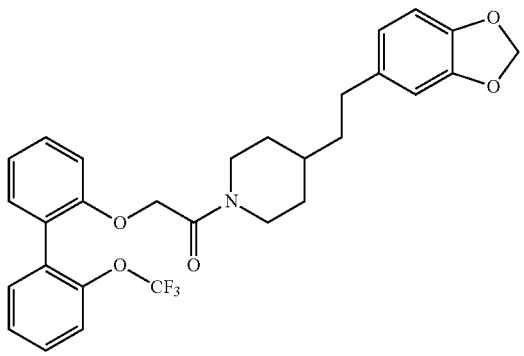 |
| 185 | 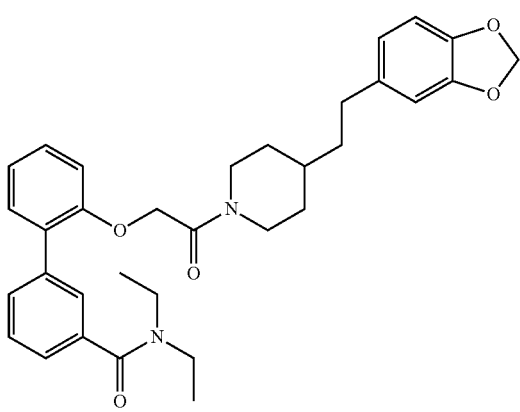 [SMILES: CCN(CC)C(=O)c1cccc(-c2ccccc2OCC(=O)N2CCC(CCc3ccc4c(c3)OCO4)CC2)c1] |
| 186 | 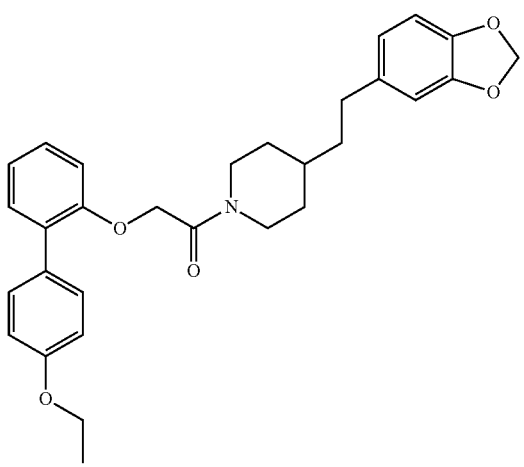 [SMILES: CCOc1ccc(-c2ccccc2OCC(=O)N2CCC(CCc3ccc4c(c3)OCO4)CC2)cc1] |

| Compound No. | Structure |
|---|---|
| 187 | 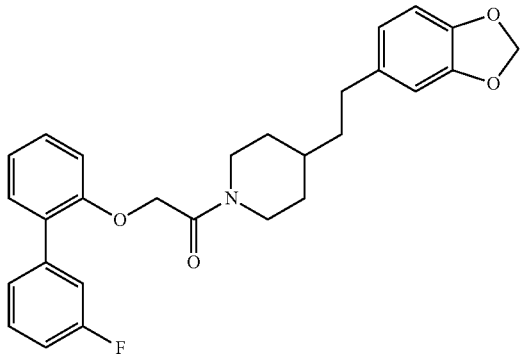 |
| 188 | 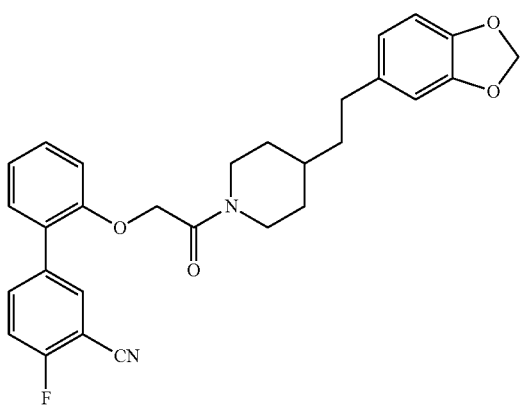 [SMILES: N#Cc1cc(-c2ccccc2OCC(=O)N2CCC(CCc3ccc4c(c3)OCO4)CC2)ccc1F] |
| 189 | 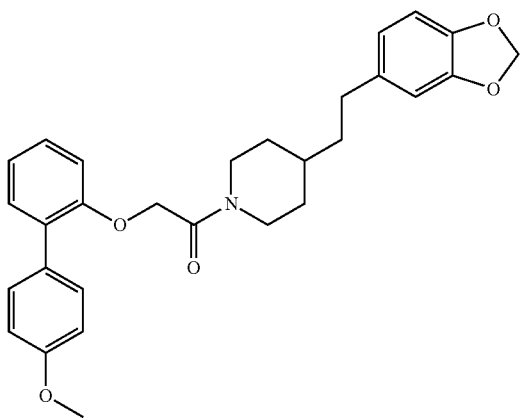 |

-continued
| Compound No. | Structure |
|---|---|
| 190 | 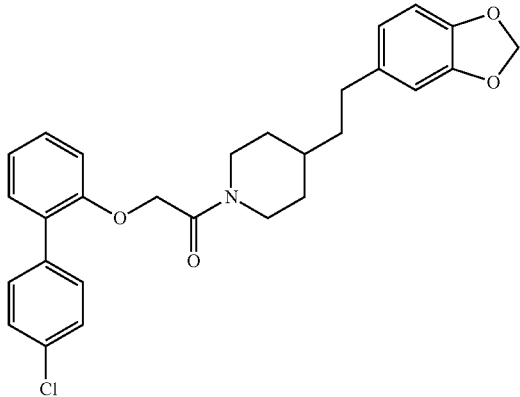 |
| 191 | 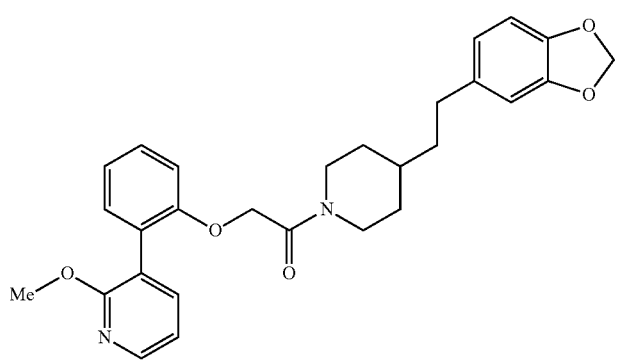 [SMILES: COc1ncccc1-c1ccccc1OCC(=O)N1CCC(CCc2ccc3c(c2)OCO3)CC1] |
| 192 | 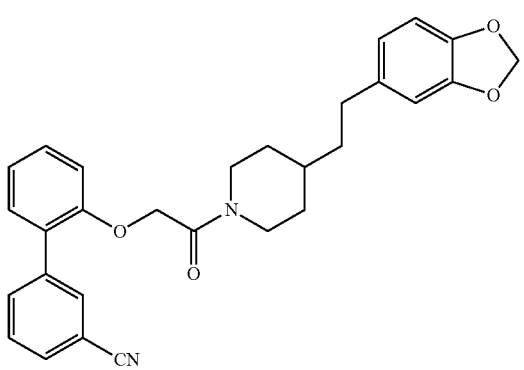 [SMILES: N#Cc1cccc(-c2ccccc2OCC(=O)N2CCC(CCc3ccc4c(c3)OCO4)CC2)c1] |
| 193 | 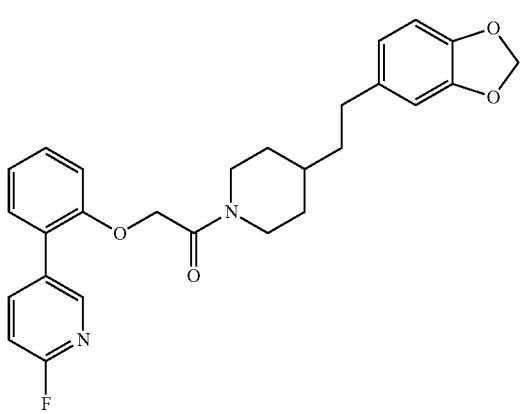 [SMILES: O=C(COc1ccccc1-c1ccc(F)nc1)N1CCC(CCc2ccc3c(c2)OCO3)CC1] |

-continued
| Compound No. | Structure |
|---|---|
| 194 | 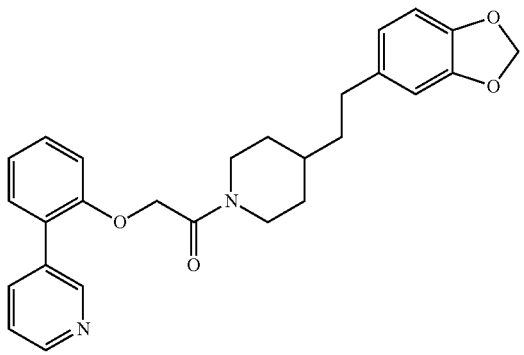 |
| 195 | 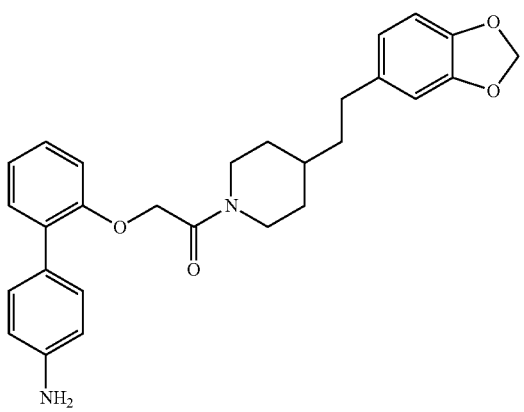 [SMILES: Nc1ccc(-c2ccccc2OCC(=O)N2CCC(CCc3ccc4c(c3)OCO4)CC2)cc1] |
| 196 | 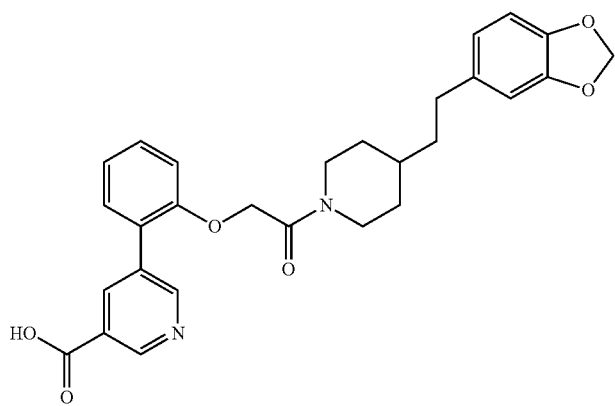 [SMILES: O=C(O)c1cncc(-c2ccccc2OCC(=O)N2CCC(CCc3ccc4c(c3)OCO4)CC2)c1] |

-continued
| Compound No. | Structure |
|---|---|
| 197 | 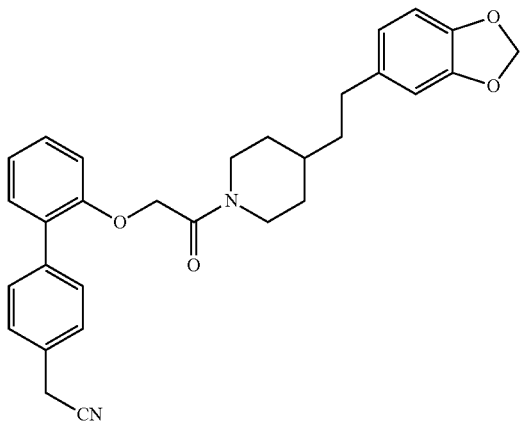 [SMILES: N#CCc1ccc(-c2ccccc2OCC(=O)N2CCC(CCc3ccc4c(c3)OCO4)CC2)cc1] |
| 198 | 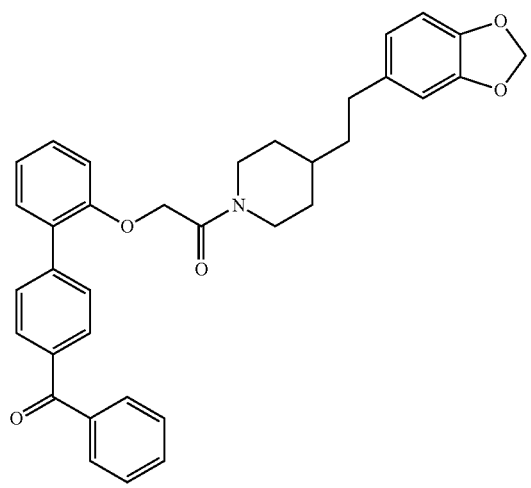 [SMILES: O=C(c1ccccc1)c1ccc(-c2ccccc2OCC(=O)N2CCC(CCc3ccc4c(c3)OCO4)CC2)cc1] |
| 199 | 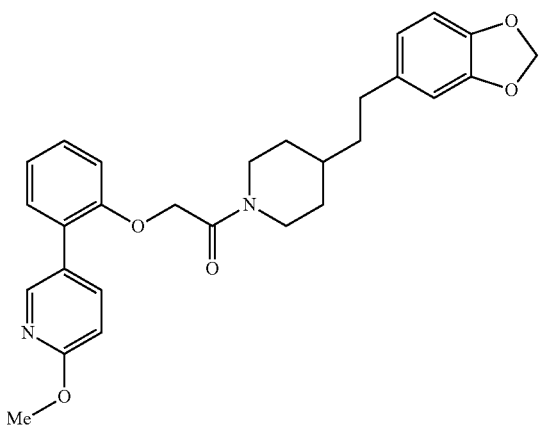 [SMILES: COc1ccc(-c2ccccc2OCC(=O)N2CCC(CCc3ccc4c(c3)OCO4)CC2)cn1] |

| Compound No. | Structure |
|---|---|
| 200 | 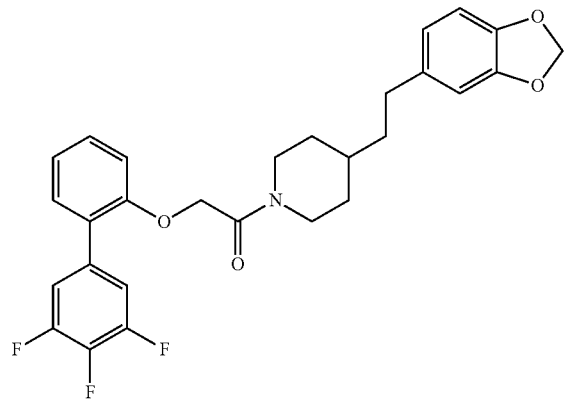 |
| 201 | 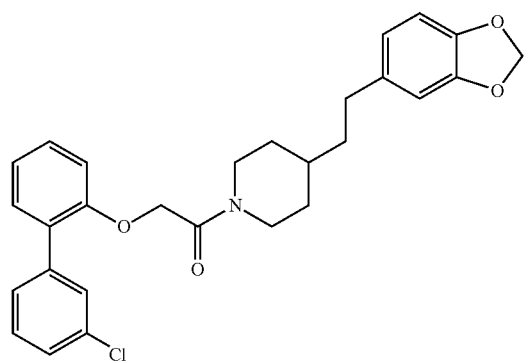 [SMILES: O=C(COc1ccccc1-c1cccc(Cl)c1)N1CCC(CCc2ccc3c(c2)OCO3)CC1] |
| 202 | 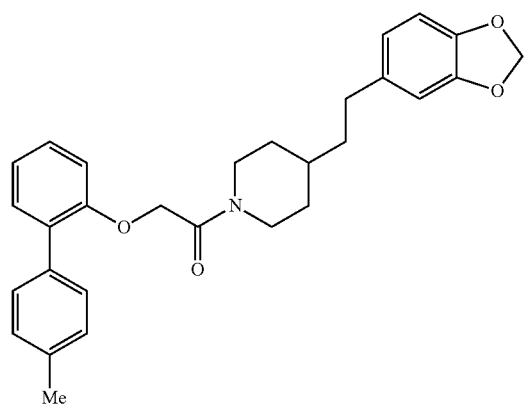 |

-continued
| Compound No. | Structure |
|---|---|
| 203 | 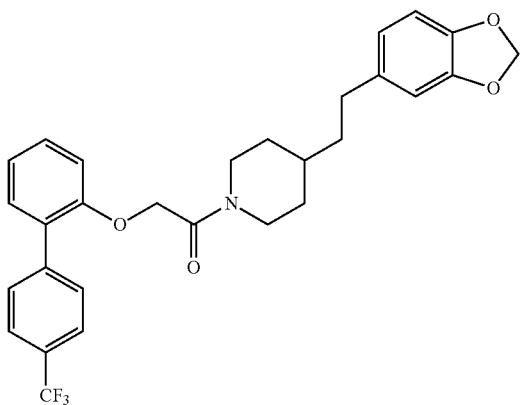 |
| 204 | 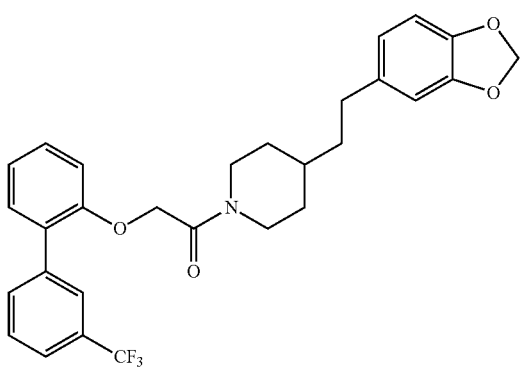 [SMILES: O=C(COc1ccccc1-c1cccc(C(F)(F)F)c1)N1CCC(CCc2ccc3c(c2)OCO3)CC1] |
| 205 | 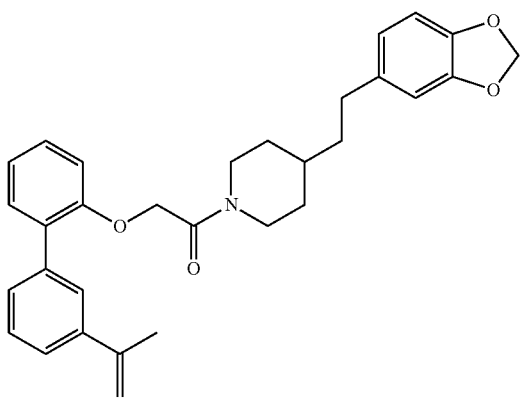 [SMILES: C=C(C)c1cccc(-c2ccccc2OCC(=O)N2CCC(CCc3ccc4c(c3)OCO4)CC2)c1] |
| 206 | 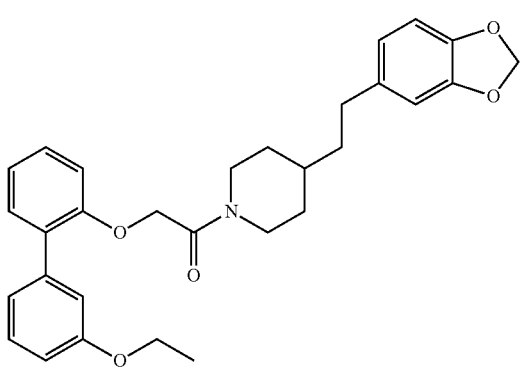 [SMILES: CCOc1cccc(-c2ccccc2OCC(=O)N2CCC(CCc3ccc4c(c3)OCO4)CC2)c1] |

| Compound No. | Structure |
|---|---|
| 207 | 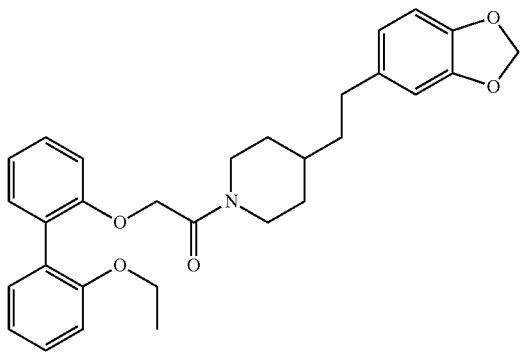 [SMILES: CCOc1ccccc1-c1ccccc1OCC(=O)N1CCC(CCc2ccc3c(c2)OCO3)CC1] |
| 208 | 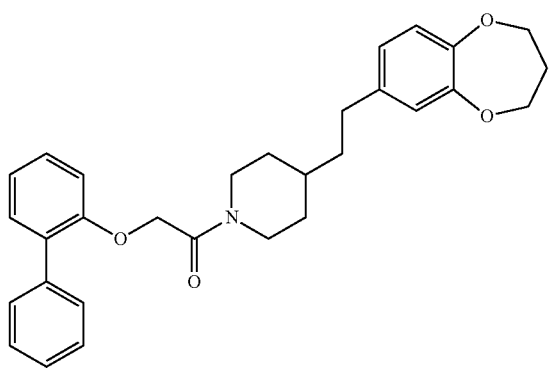 [SMILES: O=C(COc1ccccc1-c1ccccc1)N1CCC(CCc2ccc3c(c2)OCCCO3)CC1] |
| 209 | 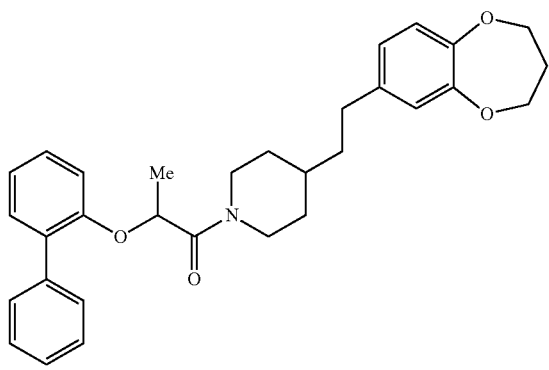 [SMILES: CC(Oc1ccccc1-c1ccccc1)C(=O)N1CCC(CCc2ccc3c(c2)OCCCO3)CC1] |
| 210 | 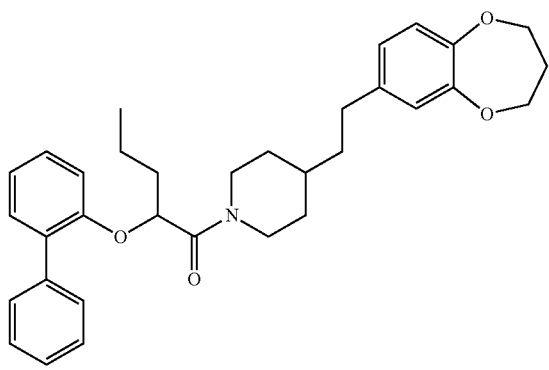 [SMILES: CCCC(Oc1ccccc1-c1ccccc1)C(=O)N1CCC(CCc2ccc3c(c2)OCCCO3)CC1] |

| Compound No. | Structure |
|---|---|
| 211 | 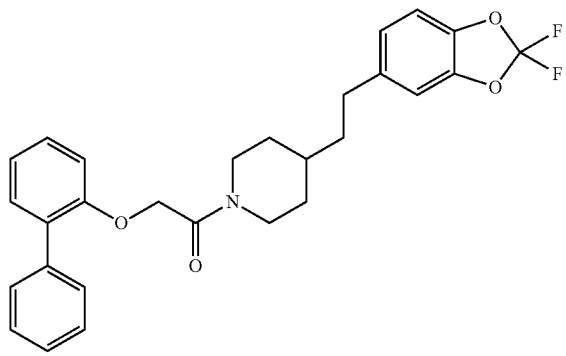 [SMILES: O=C(COc1ccccc1-c1ccccc1)N1CCC(CCc2ccc3c(c2)OC(F)(F)O3)CC1] |
| 213 | 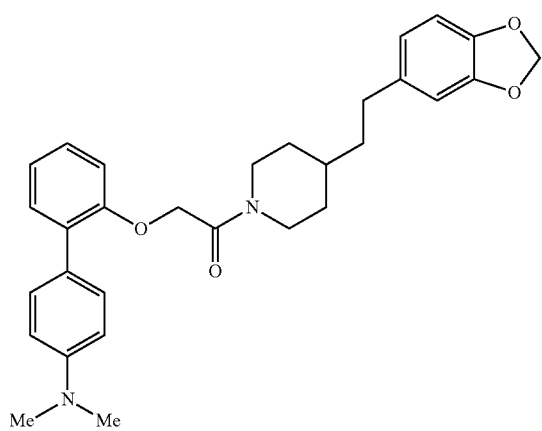 [SMILES: CN(C)c1ccc(-c2ccccc2OCC(=O)N2CCC(CCc3ccc4c(c3)OCO4)CC2)cc1] |
| 216 | 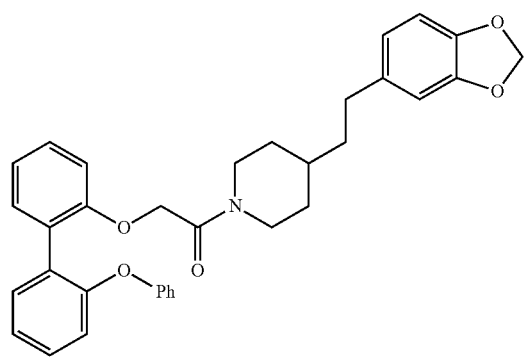 [SMILES: O=C(COc1ccccc1-c1ccccc1Oc1ccccc1)N1CCC(CCc2ccc3c(c2)OCO3)CC1] |

-continued
| Compound No. | Structure |
|---|---|
| 217 | 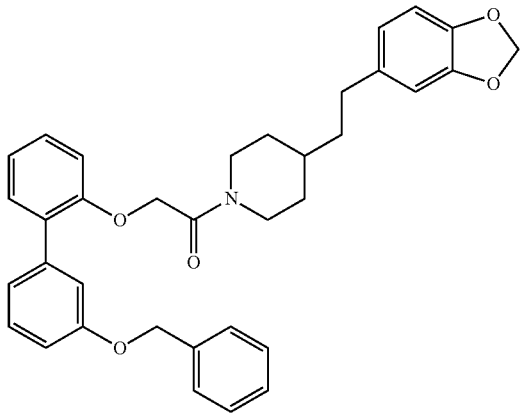 [SMILES: O=C(COc1ccccc1-c1cccc(OCc2ccccc2)c1)N1CCC(CCc2ccc3c(c2)OCO3)CC1] |
| 218 | 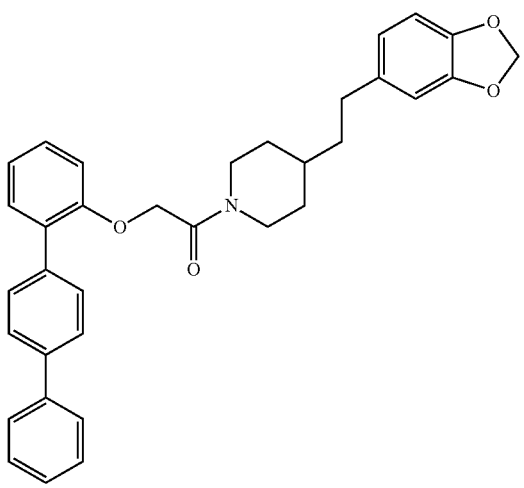 [SMILES: O=C(COc1ccccc1-c1ccc(-c2ccccc2)cc1)N1CCC(CCc2ccc3c(c2)OCO3)CC1] |
| 219 | 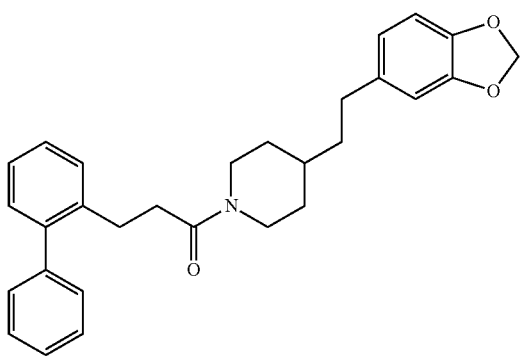 |

| Compound No. | Structure |
|---|---|
| 220 | 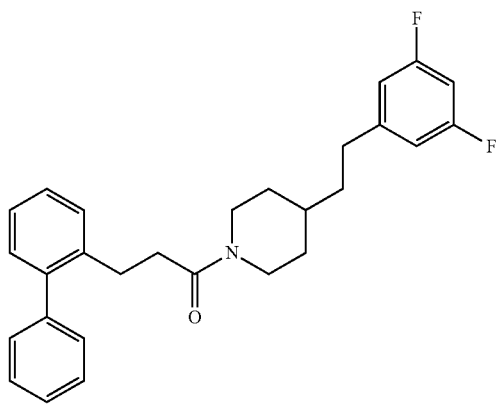 [SMILES: O=C(CCc1ccccc1-c1ccccc1)N1CCC(CCc2cc(F)cc(F)c2)CC1] |
| 221 | 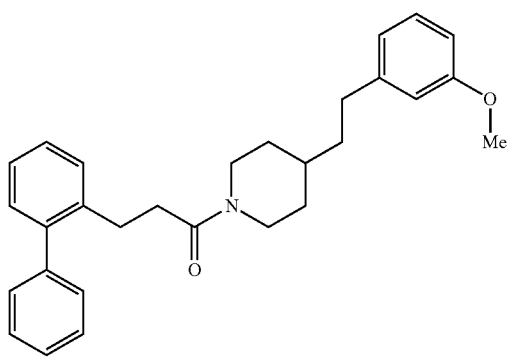 [SMILES: COc1cccc(CCC2CCN(C(=O)CCc3ccccc3-c3ccccc3)CC2)c1] |
| 222 | 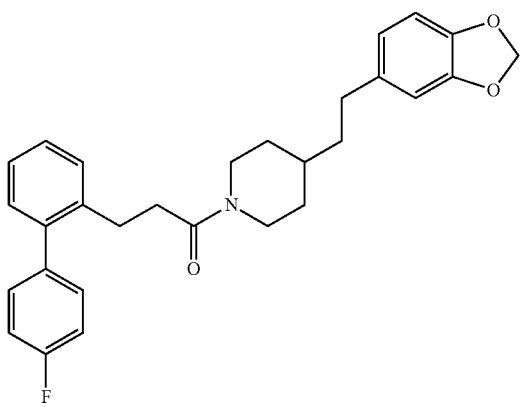 |

| Compound No. | Structure |
|---|---|
| 223 | 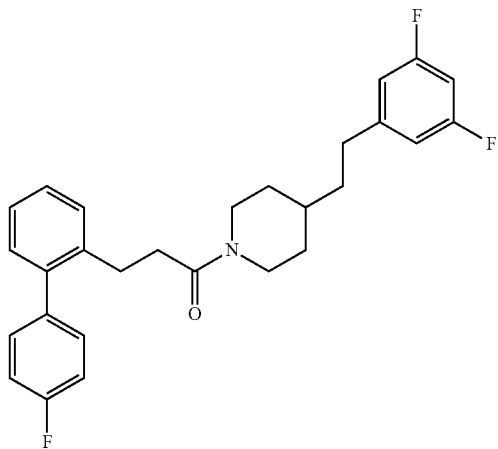 [SMILES: O=C(CCc1ccccc1-c1ccc(F)cc1)N1CCC(CCc2cc(F)cc(F)c2)CC1] |
| 224 | 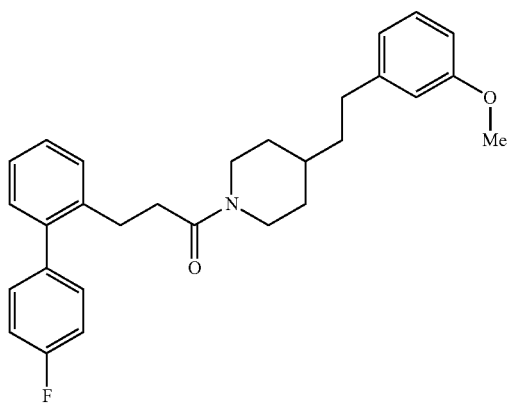 [SMILES: COc1cccc(CCC2CCN(C(=O)CCc3ccccc3-c3ccc(F)cc3)CC2)c1] |
| 225 | 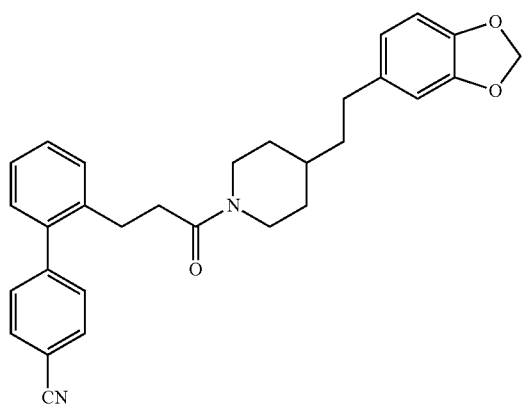 [SMILES: N#Cc1ccc(-c2ccccc2CCC(=O)N2CCC(CCc3ccc4c(c3)OCO4)CC2)cc1] |

-continued
| Compound No. | Structure |
|---|---|
| 226 | 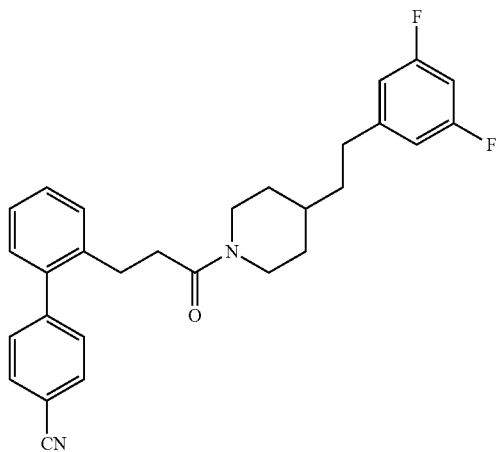 [SMILES: N#Cc1ccc(-c2ccccc2CCC(=O)N2CCC(CCc3cc(F)cc(F)c3)CC2)cc1] |
| 227 | 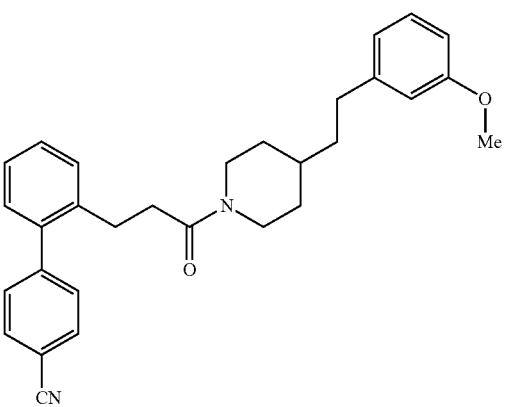 [SMILES: COc1cccc(CCC2CCN(C(=O)CCc3ccccc3-c3ccc(C#N)cc3)CC2)c1] |
| 228 | 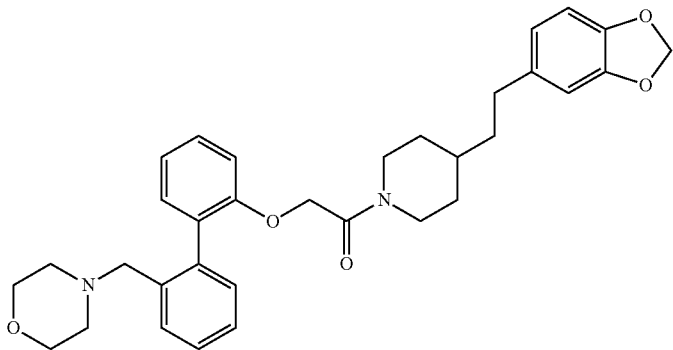 [SMILES: O=C(COc1ccccc1-c1ccccc1CN1CCOCC1)N1CCC(CCc2ccc3c(c2)OCO3)CC1] |

-continued
| Compound No. | Structure |
|---|---|
| 229 | 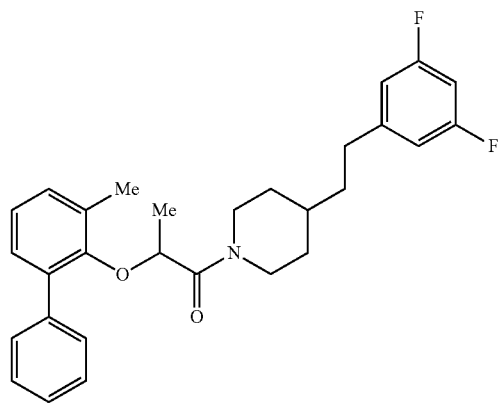 [SMILES: Cc1cccc(-c2ccccc2)c1OC(C)C(=O)N1CCC(CCc2cc(F)cc(F)c2)CC1] |
| 230 | 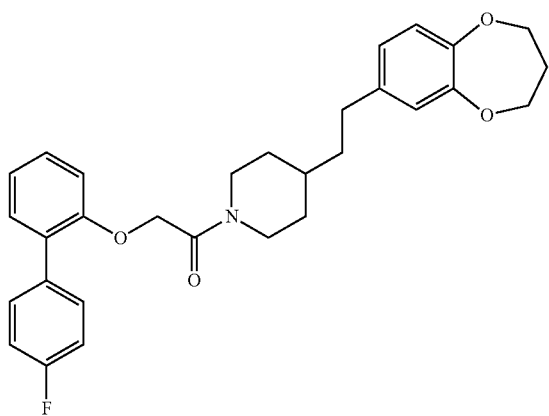 |
| 231 | 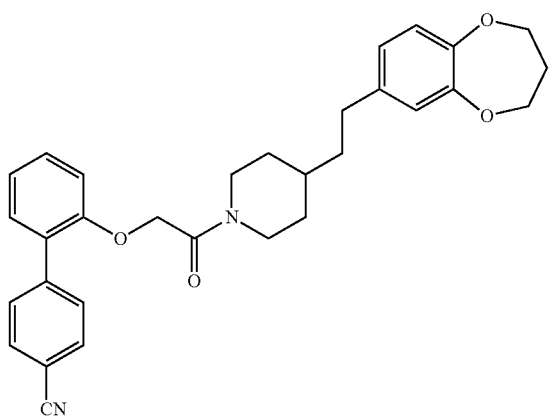 [SMILES: N#Cc1ccc(-c2ccccc2OCC(=O)N2CCC(CCc3ccc4c(c3)OCCCO4)CC2)cc1] |

| Compound No. | Structure |
|---|---|
| 232 | 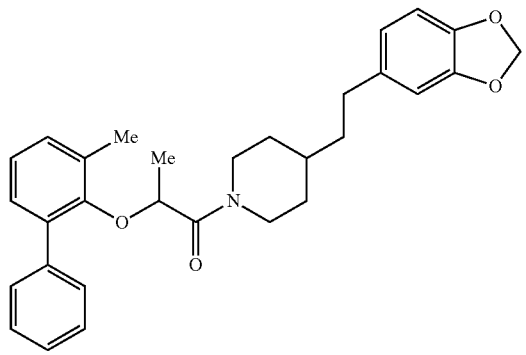 [SMILES: Cc1cccc(-c2ccccc2)c1OC(C)C(=O)N1CCC(CCc2ccc3c(c2)OCO3)CC1] |
| 233 | 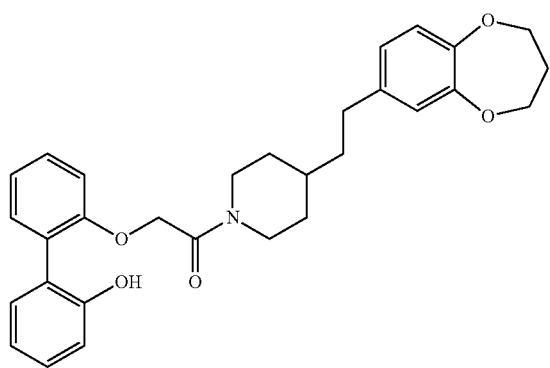 [SMILES: O=C(COc1ccccc1-c1ccccc1O)N1CCC(CCc2ccc3c(c2)OCCCO3)CC1] |
| 234 | 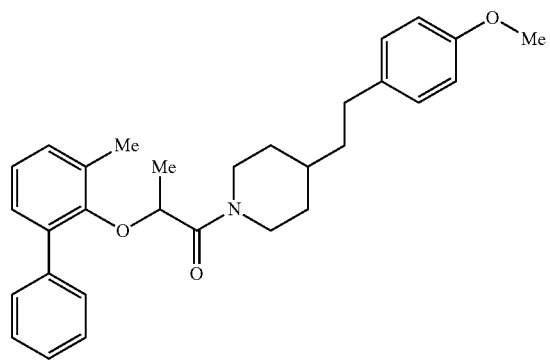 [SMILES: COc1ccc(CCC2CCN(C(=O)C(C)Oc3c(C)cccc3-c3ccccc3)CC2)cc1] |
| 235 | 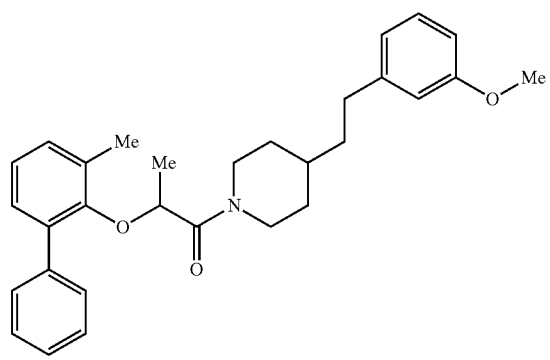 [SMILES: COc1cccc(CCC2CCN(C(=O)C(C)Oc3c(C)cccc3-c3ccccc3)CC2)c1] |

| Compound No. | Structure |
|---|---|
| 236 | 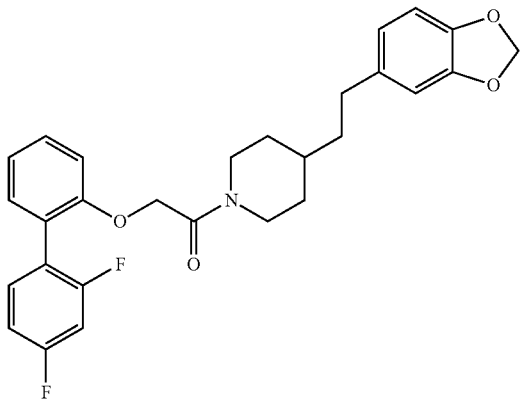 [SMILES: O=C(COc1ccccc1-c1ccc(F)cc1F)N1CCC(CCc2ccc3c(c2)OCO3)CC1] |
| 237 | 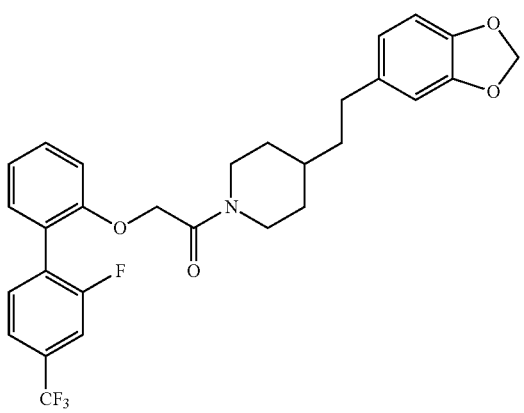 |
| 238 | 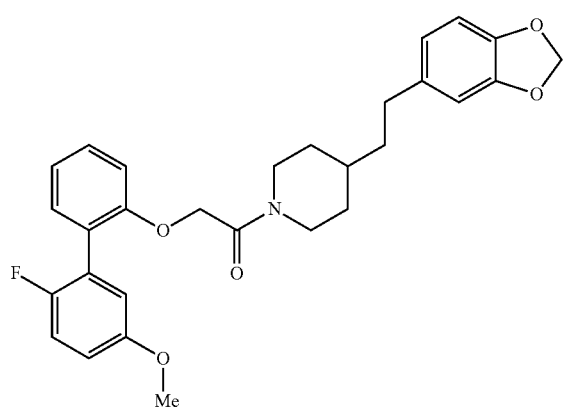 [SMILES: COc1ccc(F)c(-c2ccccc2OCC(=O)N2CCC(CCc3ccc4c(c3)OCO4)CC2)c1] |

| Compound No. | Structure |
|---|---|
| 239 | 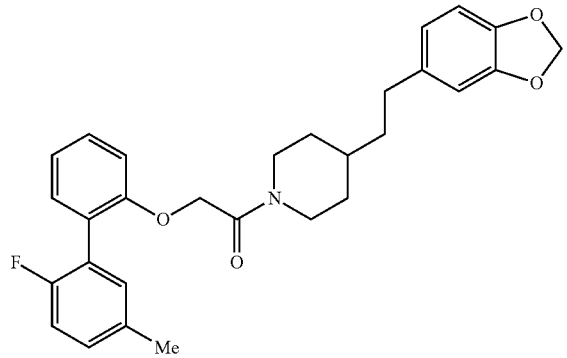 [SMILES: Cc1ccc(F)c(-c2ccccc2OCC(=O)N2CCC(CCc3ccc4c(c3)OCO4)CC2)c1] |
| 240 | 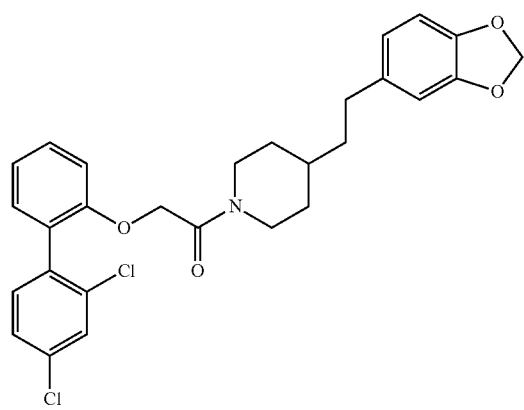 [SMILES: O=C(COc1ccccc1-c1ccc(Cl)cc1Cl)N1CCC(CCc2ccc3c(c2)OCO3)CC1] |
| 241 | 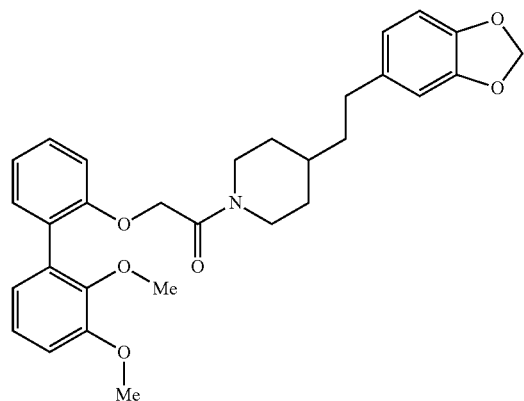 [SMILES: COc1cccc(-c2ccccc2OCC(=O)N2CCC(CCc3ccc4c(c3)OCO4)CC2)c1OC] |
| 242 | 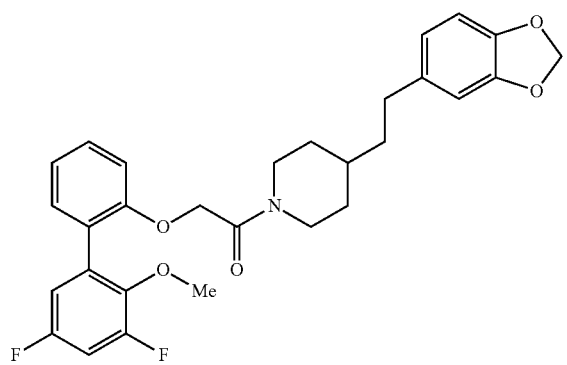 [SMILES: COc1c(F)cc(F)cc1-c1ccccc1OCC(=O)N1CCC(CCc2ccc3c(c2)OCO3)CC1] |

-continued
| Compound No. | Structure |
|---|---|
| 243 | 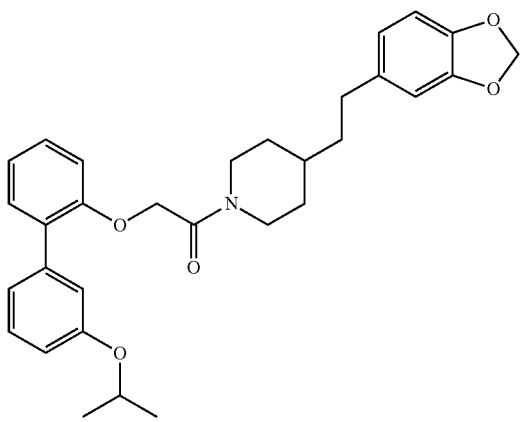 [SMILES: CC(C)Oc1cccc(-c2ccccc2OCC(=O)N2CCC(CCc3ccc4c(c3)OCO4)CC2)c1] |
| 244 | 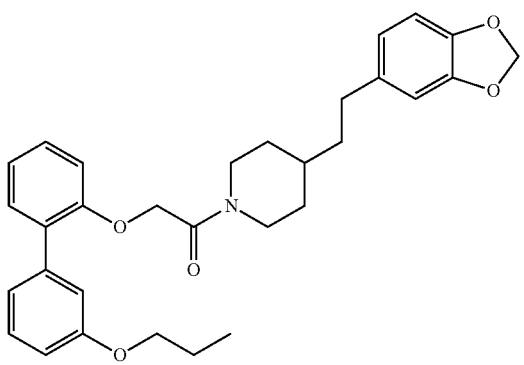 [SMILES: CCCOc1cccc(-c2ccccc2OCC(=O)N2CCC(CCc3ccc4c(c3)OCO4)CC2)c1] |
| 245 | 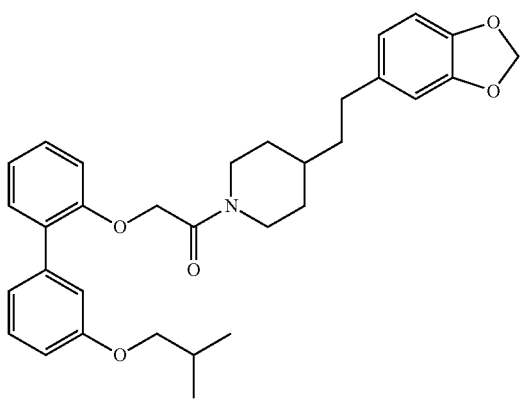 [SMILES: CC(C)COc1cccc(-c2ccccc2OCC(=O)N2CCC(CCc3ccc4c(c3)OCO4)CC2)c1] |
| 246 | 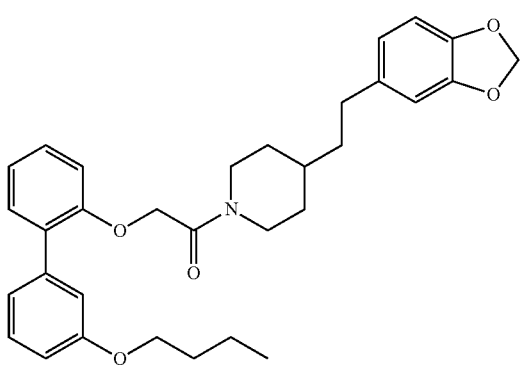 [SMILES: CCCCOc1cccc(-c2ccccc2OCC(=O)N2CCC(CCc3ccc4c(c3)OCO4)CC2)c1] |

| Compound No. | Structure |
|---|---|
| 247 | 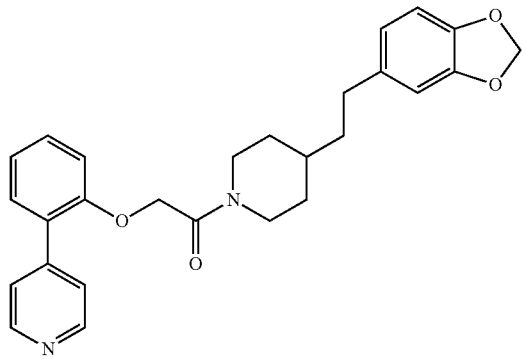 [SMILES: O=C(COc1ccccc1-c1ccncc1)N1CCC(CCc2ccc3c(c2)OCO3)CC1] |
| 248 | 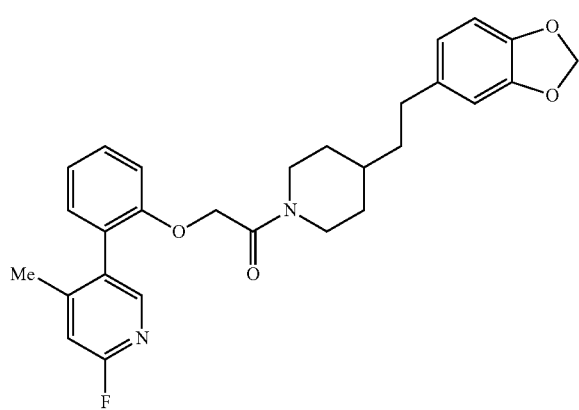 [SMILES: Cc1cc(F)ncc1-c1ccccc1OCC(=O)N1CCC(CCc2ccc3c(c2)OCO3)CC1] |
| 249 | 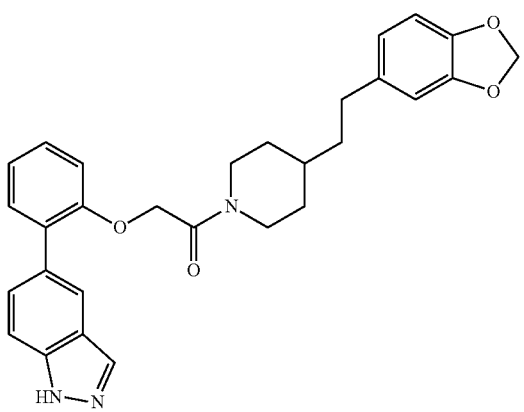 [SMILES: O=C(COc1ccccc1-c1ccc2[nH]ncc2c1)N1CCC(CCc2ccc3c(c2)OCO3)CC1] |

| Compound No. | Structure |
|---|---|
| 250 | 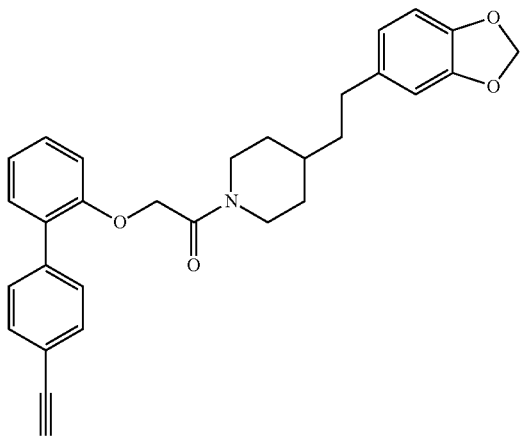 [SMILES: C#Cc1ccc(-c2ccccc2OCC(=O)N2CCC(CCc3ccc4c(c3)OCO4)CC2)cc1] |
| 251 | 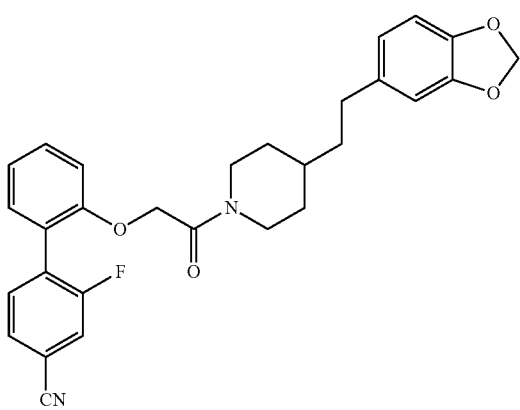 [SMILES: N#Cc1ccc(-c2ccccc2OCC(=O)N2CCC(CCc3ccc4c(c3)OCO4)CC2)c(F)c1] |
| 252 | 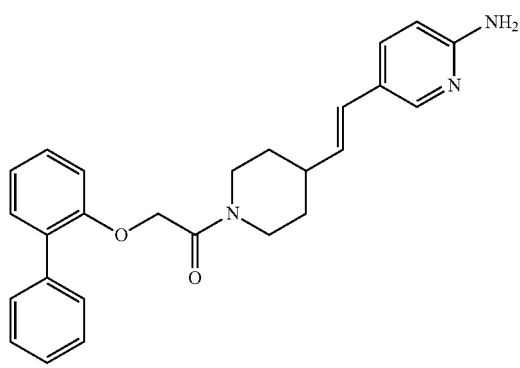 [SMILES: Nc1ccc(/C=C/C2CCN(C(=O)COc3ccccc3-c3ccccc3)CC2)cn1] |

-continued
| Compound No. | Structure |
|---|---|
| 253 | 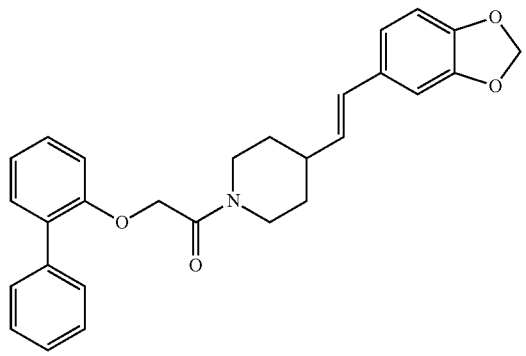 [SMILES: O=C(COc1ccccc1-c1ccccc1)N1CCC(/C=C/c2ccc3c(c2)OCO3)CC1] |
| 254 | 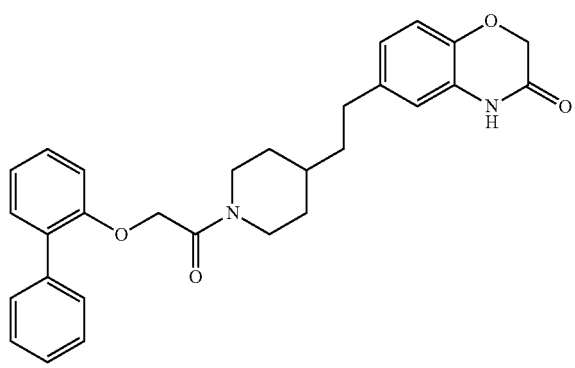 [SMILES: O=C1COc2ccc(CCC3CCN(C(=O)COc4ccccc4-c4ccccc4)CC3)cc2N1] |
| 255 | 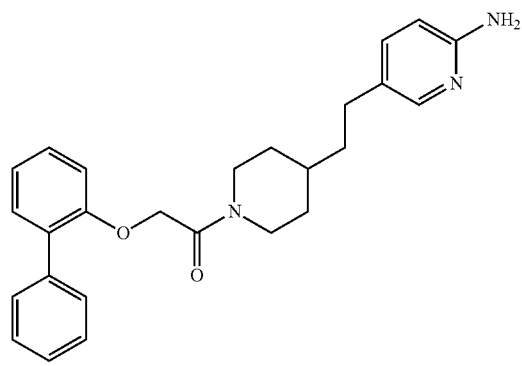 [SMILES: Nc1ccc(CCC2CCN(C(=O)COc3ccccc3-c3ccccc3)CC2)cn1] |
| 256 | 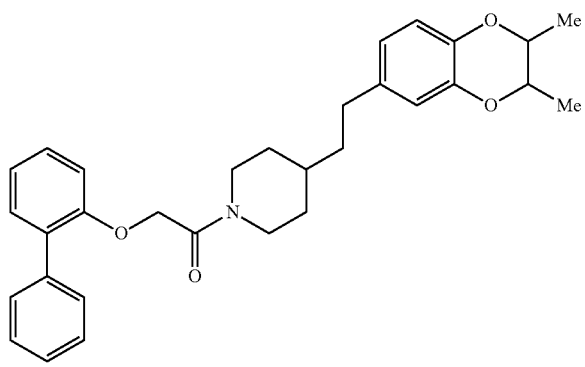 [SMILES: CC1Oc2ccc(CCC3CCN(C(=O)COc4ccccc4-c4ccccc4)CC3)cc2OC1C] |

-continued
| Compound No. | Structure |
|---|---|
| 257 | 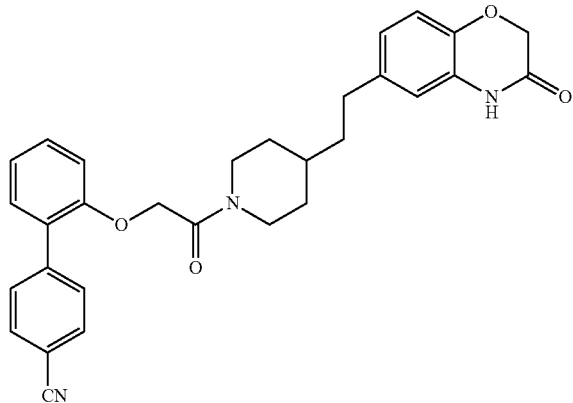 [SMILES: N#Cc1ccc(-c2ccccc2OCC(=O)N2CCC(CCc3ccc4c(c3)NC(=O)CO4)CC2)cc1] |
| 258 | 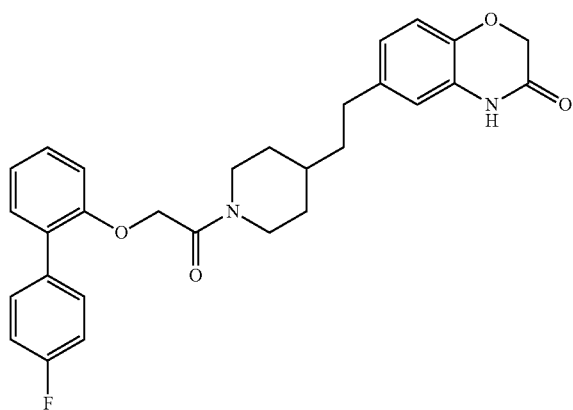 [SMILES: O=C1COc2ccc(CCC3CCN(C(=O)COc4ccccc4-c4ccc(F)cc4)CC3)cc2N1] |
| 259 | 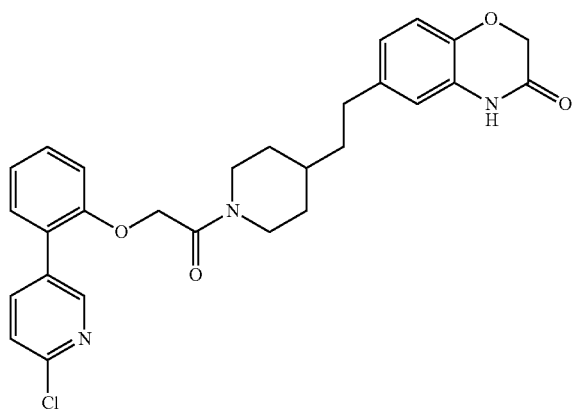 [SMILES: O=C1COc2ccc(CCC3CCN(C(=O)COc4ccccc4-c4ccc(Cl)nc4)CC3)cc2N1] |

US 10,899,747 B2
353 354
-continued
| Compound No. | Structure |
|---|---|
| 260 | 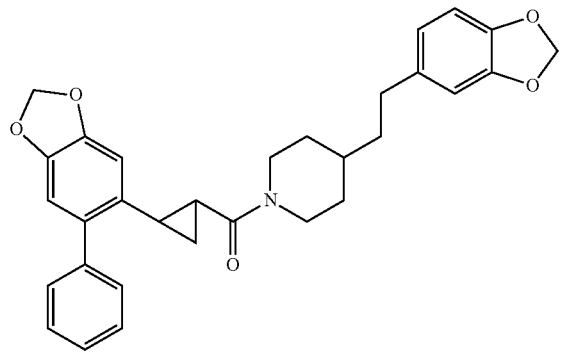 [SMILES: O=C(C1CC1c1cc2c(cc1-c1ccccc1)OCO2)N1CCC(CCc2ccc3c(c2)OCO3)CC1] |
| 261 | 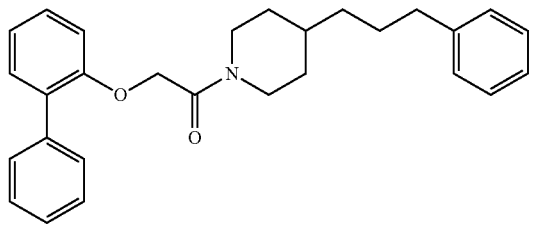 [SMILES: O=C(COc1ccccc1-c1ccccc1)N1CCC(CCCc2ccccc2)CC1] |
| 262 | 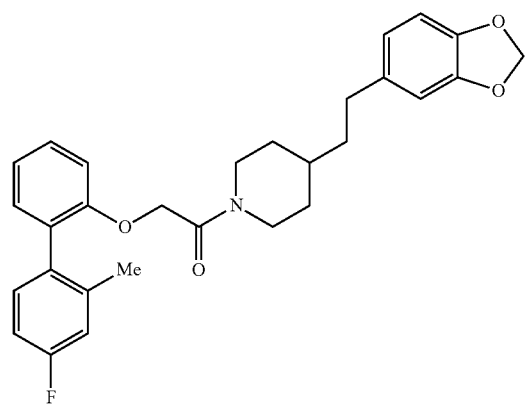 [SMILES: Cc1cc(F)ccc1-c1ccccc1OCC(=O)N1CCC(CCc2ccc3c(c2)OCO3)CC1] |
| 263 | 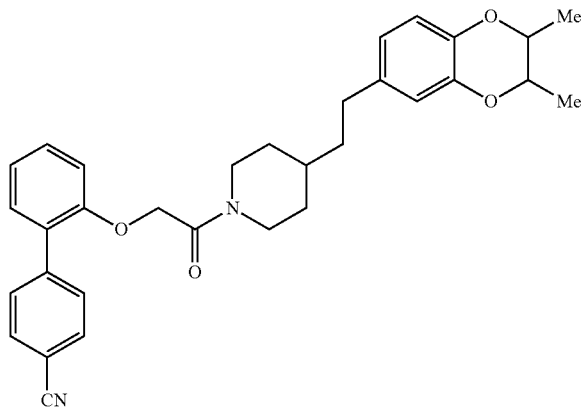 [SMILES: CC1Oc2ccc(CCC3CCN(C(=O)COc4ccccc4-c4ccc(C#N)cc4)CC3)cc2OC1C] |

-continued
| Compound No. | Structure |
|---|---|
| 264 | 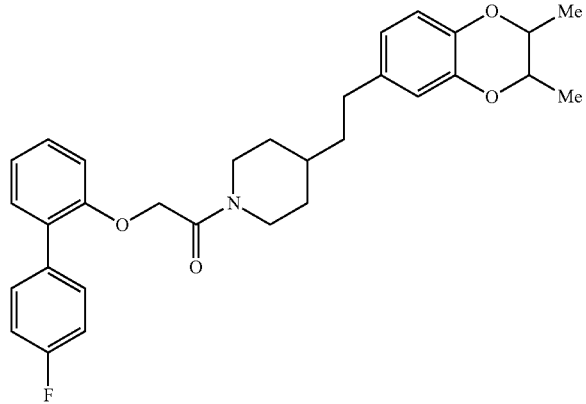 [SMILES: CC1Oc2ccc(CCC3CCN(C(=O)COc4ccccc4-c4ccc(F)cc4)CC3)cc2OC1C] |
| 265 | 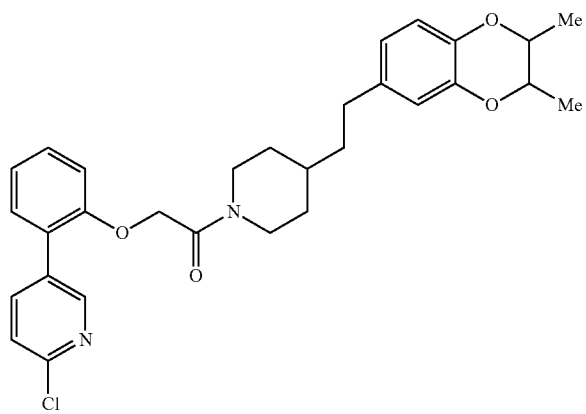 [SMILES: CC1Oc2ccc(CCC3CCN(C(=O)COc4ccccc4-c4ccc(Cl)nc4)CC3)cc2OC1C] |
| 266 | 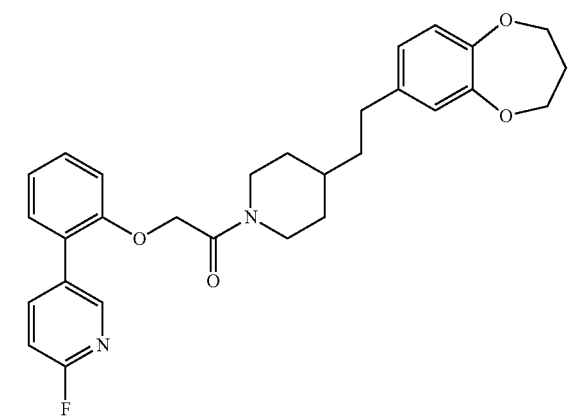 |

| Compound No. | Structure |
|---|---|
| 267 | 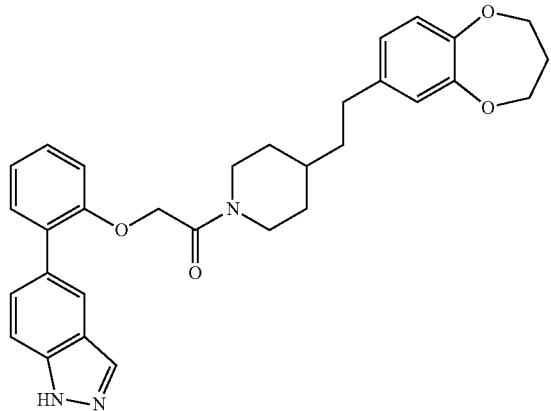 [SMILES: O=C(COc1ccccc1-c1ccc2[nH]ncc2c1)N1CCC(CCc2ccc3c(c2)OCCCO3)CC1] |
| 268 | 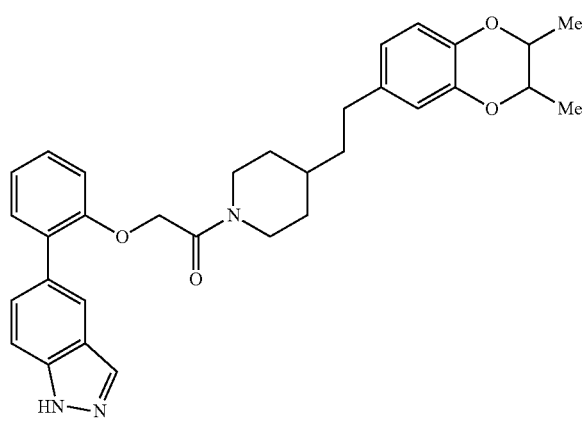 [SMILES: CC1Oc2ccc(CCC3CCN(C(=O)COc4ccccc4-c4ccc5[nH]ncc5c4)CC3)cc2OC1C] |
| 269 | 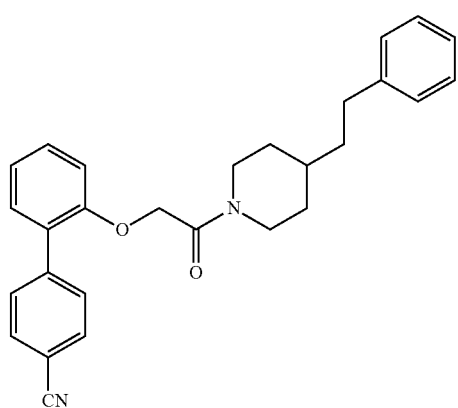 [SMILES: N#Cc1ccc(-c2ccccc2OCC(=O)N2CCC(CCc3ccccc3)CC2)cc1] |

-continued
| Compound No. | Structure |
|---|---|
| 270 | 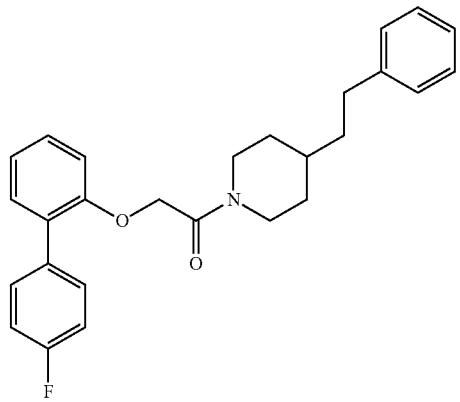 [SMILES: O=C(COc1ccccc1-c1ccc(F)cc1)N1CCC(CCc2ccccc2)CC1] |
| 271 | 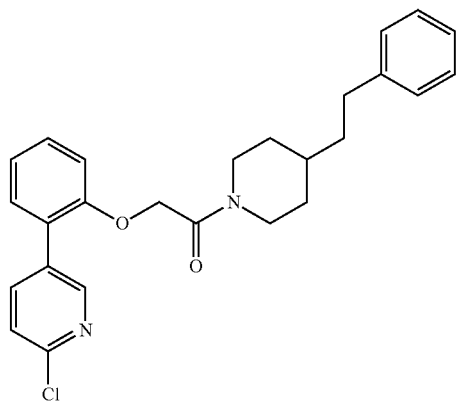 [SMILES: O=C(COc1ccccc1-c1ccc(Cl)nc1)N1CCC(CCc2ccccc2)CC1] |
| 272 | 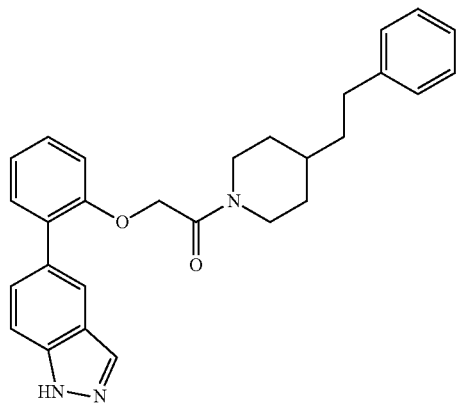 [SMILES: O=C(COc1ccccc1-c1ccc2[nH]ncc2c1)N1CCC(CCc2ccccc2)CC1] |

| Compound No. | Structure |
|---|---|
| 273 | 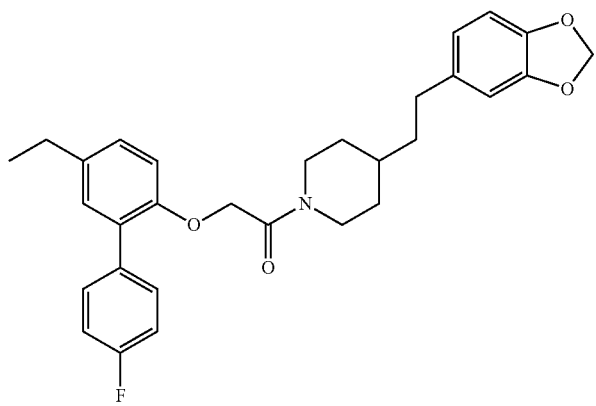 [SMILES: CCc1ccc(OCC(=O)N2CCC(CCc3ccc4c(c3)OCO4)CC2)c(-c2ccc(F)cc2)c1] |
| 274 | 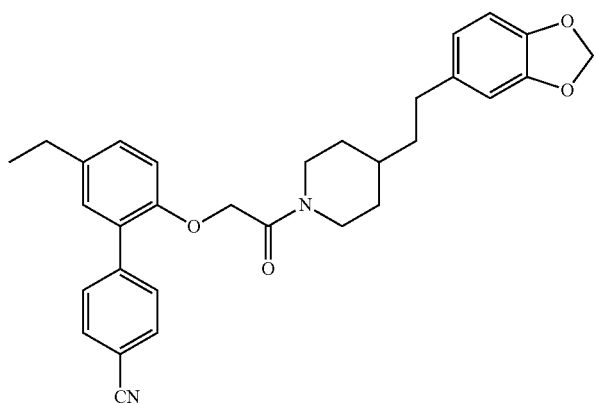 [SMILES: CCc1ccc(OCC(=O)N2CCC(CCc3ccc4c(c3)OCO4)CC2)c(-c2ccc(C#N)cc2)c1] |
| 275 | 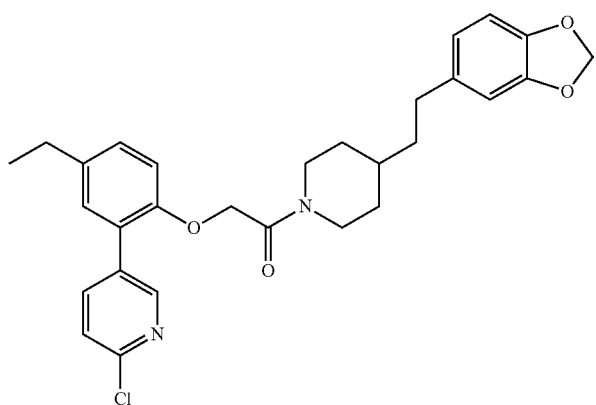 [SMILES: CCc1ccc(OCC(=O)N2CCC(CCc3ccc4c(c3)OCO4)CC2)c(-c2ccc(Cl)nc2)c1] |

| Compound No. | Structure |
|---|---|
| 276 | 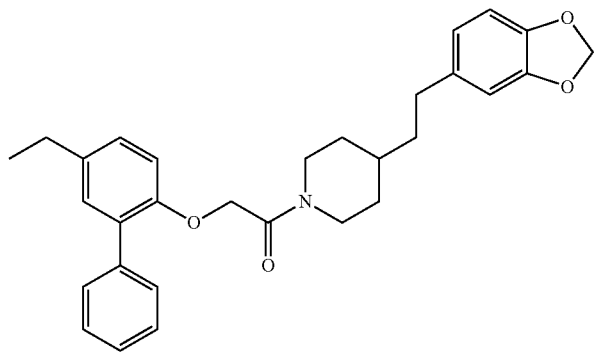 [SMILES: CCc1ccc(OCC(=O)N2CCC(CCc3ccc4c(c3)OCO4)CC2)c(-c2ccccc2)c1] |
| 277 | 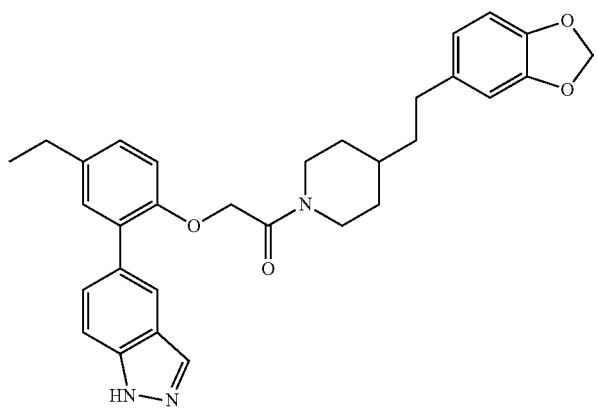 [SMILES: CCc1ccc(OCC(=O)N2CCC(CCc3ccc4c(c3)OCO4)CC2)c(-c2ccc3[nH]ncc3c2)c1] |
| 278 | 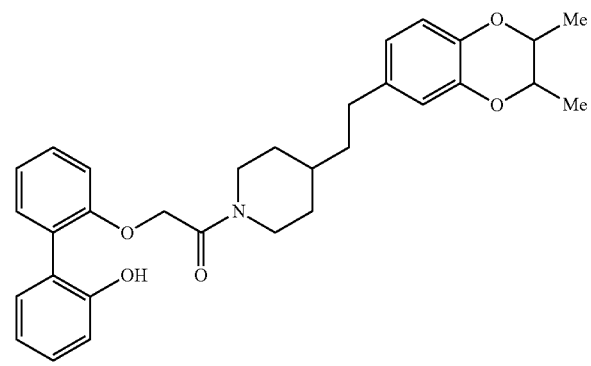 [SMILES: CC1Oc2ccc(CCC3CCN(C(=O)COc4ccccc4-c4ccccc4O)CC3)cc2OC1C] |
| 279 | 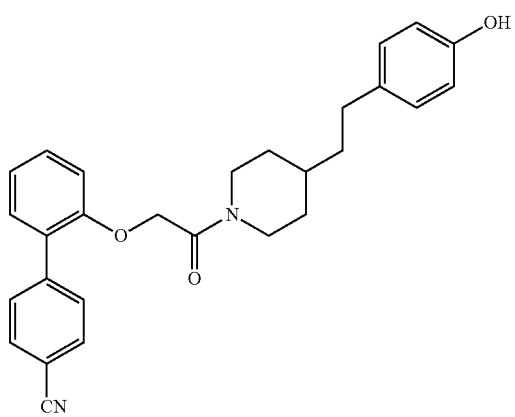 [SMILES: N#Cc1ccc(-c2ccccc2OCC(=O)N2CCC(CCc3ccc(O)cc3)CC2)cc1] |

| Compound No. | Structure |
|---|---|
| 280 | 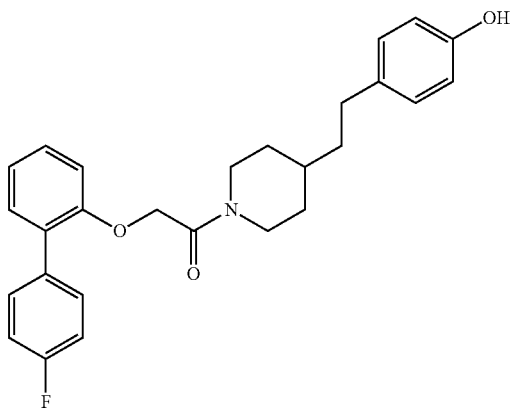 [SMILES: O=C(COc1ccccc1-c1ccc(F)cc1)N1CCC(CCc2ccc(O)cc2)CC1] |
| 281 | 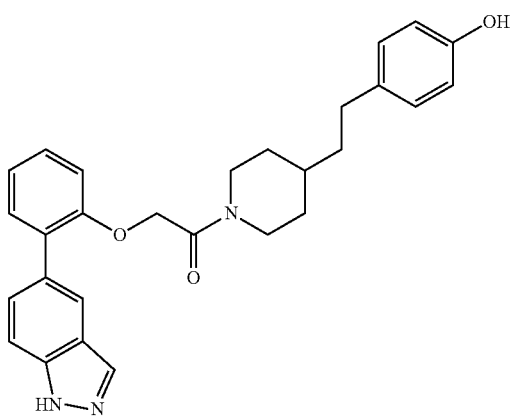 [SMILES: O=C(COc1ccccc1-c1ccc2[nH]ncc2c1)N1CCC(CCc2ccc(O)cc2)CC1] |
| 282 | 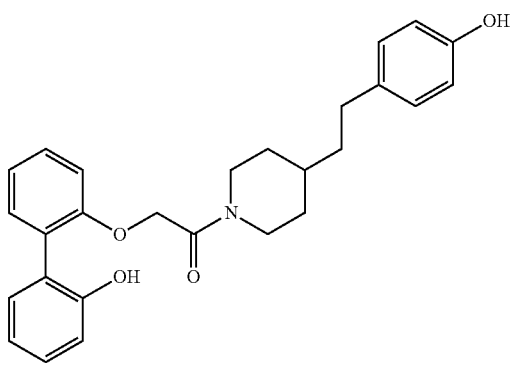 [SMILES: O=C(COc1ccccc1-c1ccccc1O)N1CCC(CCc2ccc(O)cc2)CC1] |

| Compound No. | Structure |
|---|---|
| 283 | 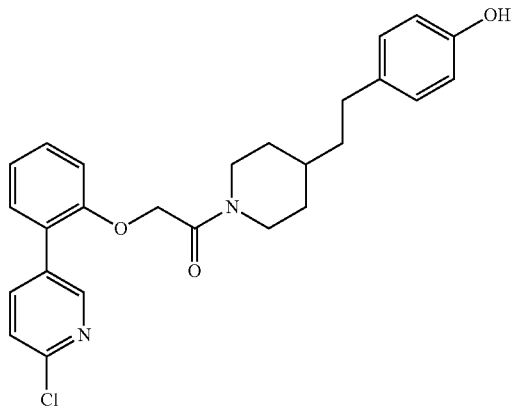 [SMILES: O=C(COc1ccccc1-c1ccc(Cl)nc1)N1CCC(CCc2ccc(O)cc2)CC1] |
| 284 | 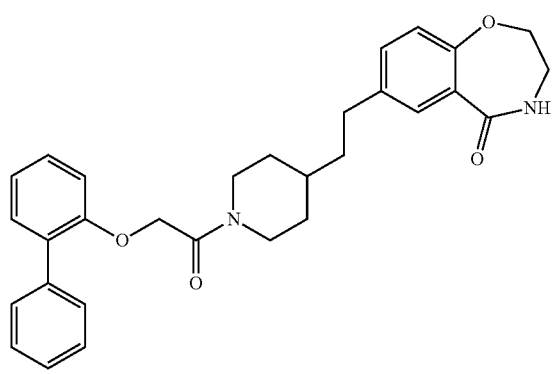 [SMILES: O=C1NCCOc2ccc(CCC3CCN(C(=O)COc4ccccc4-c4ccccc4)CC3)cc21] |
| 285 | 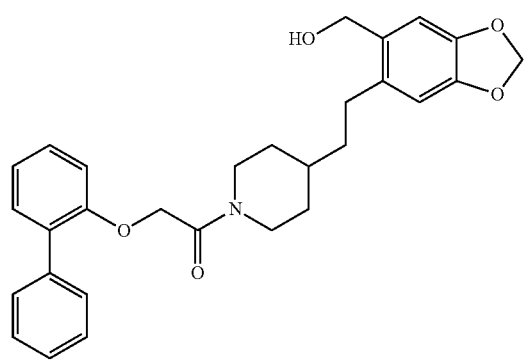 [SMILES: O=C(COc1ccccc1-c1ccccc1)N1CCC(CCc2cc3c(cc2CO)OCO3)CC1] |
| 286 | 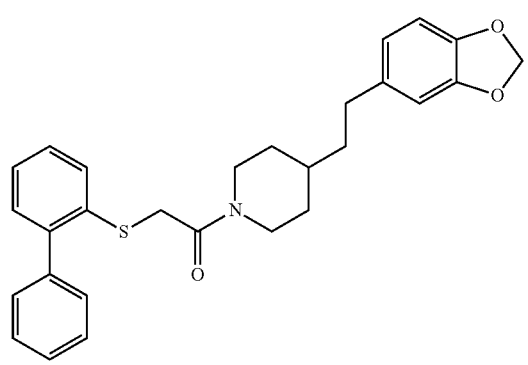 |

-continued
| Compound No. | Structure |
|---|---|
| 287 | 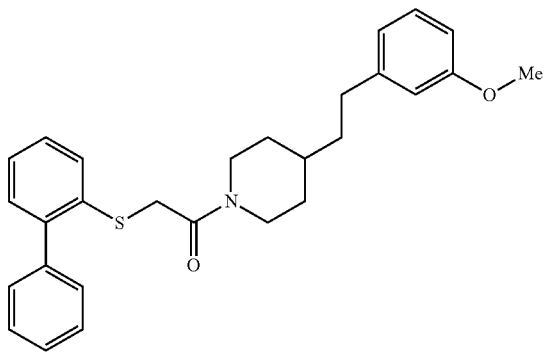 [SMILES: COc1cccc(CCC2CCN(C(=O)CSc3ccccc3-c3ccccc3)CC2)c1] |
| 288 | 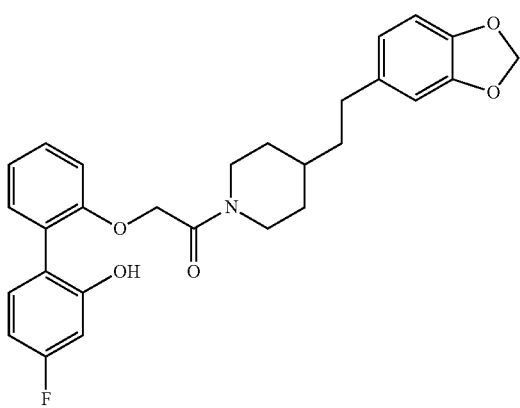 [SMILES: O=C(COc1ccccc1-c1ccc(F)cc1O)N1CCC(CCc2ccc3c(c2)OCO3)CC1] |
| 289 | 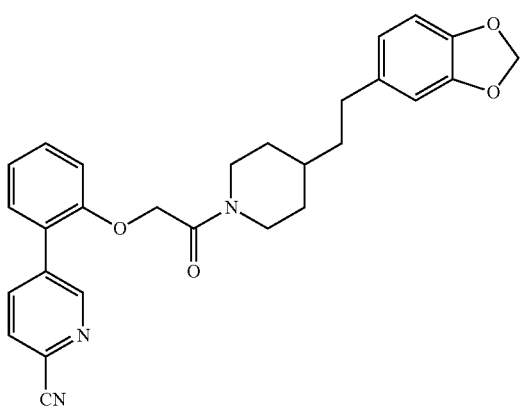 [SMILES: N#Cc1ccc(-c2ccccc2OCC(=O)N2CCC(CCc3ccc4c(c3)OCO4)CC2)cn1] |

| Compound No. | Structure |
|---|---|
| 290 | 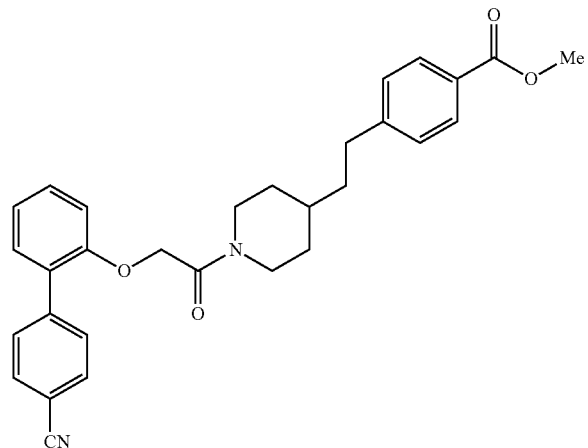 [SMILES: COC(=O)c1ccc(CCC2CCN(C(=O)COc3ccccc3-c3ccc(C#N)cc3)CC2)cc1] |
| 291 | 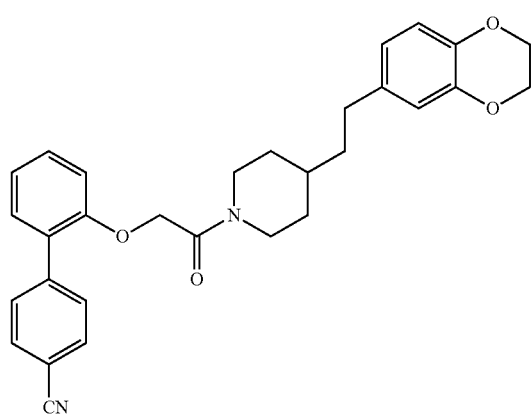 [SMILES: N#Cc1ccc(-c2ccccc2OCC(=O)N2CCC(CCc3ccc4c(c3)OCCO4)CC2)cc1] |
| 292 | 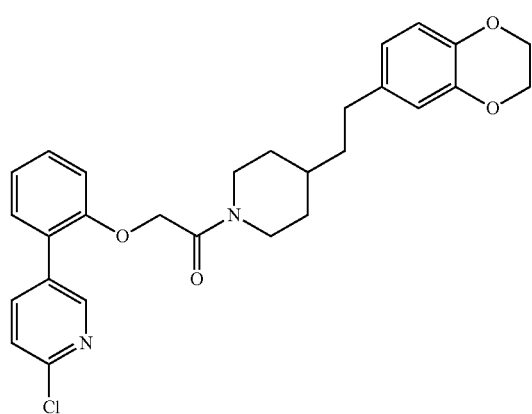 [SMILES: O=C(COc1ccccc1-c1ccc(Cl)nc1)N1CCC(CCc2ccc3c(c2)OCCO3)CC1] |

| Compound No. | Structure |
|---|---|
| 293 | 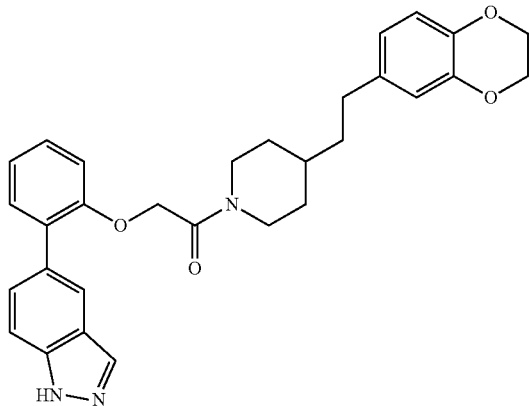 [SMILES: O=C(COc1ccccc1-c1ccc2[nH]ncc2c1)N1CCC(CCc2ccc3c(c2)OCCO3)CC1] |
| 294 | 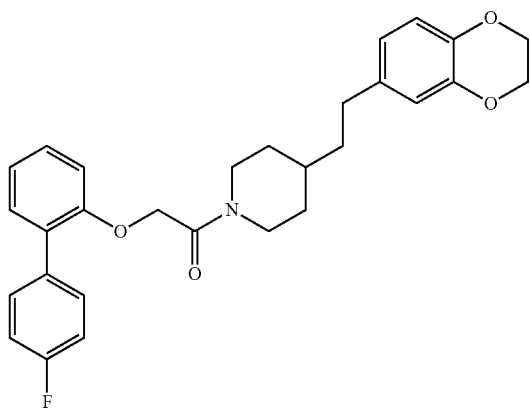 [SMILES: O=C(COc1ccccc1-c1ccc(F)cc1)N1CCC(CCc2ccc3c(c2)OCCO3)CC1] |
| 295 | 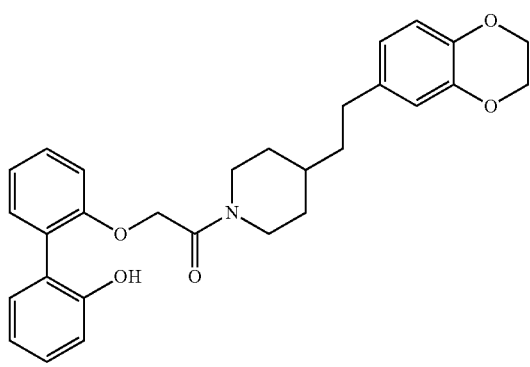 [SMILES: O=C(COc1ccccc1-c1ccccc1O)N1CCC(CCc2ccc3c(c2)OCCO3)CC1] |

-continued
| Compound No. | Structure |
|---|---|
| 296 | 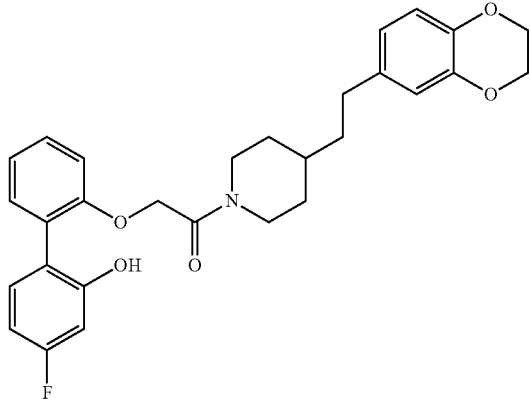 [SMILES: O=C(COc1ccccc1-c1ccc(F)cc1O)N1CCC(CCc2ccc3c(c2)OCCO3)CC1] |
| 297 | 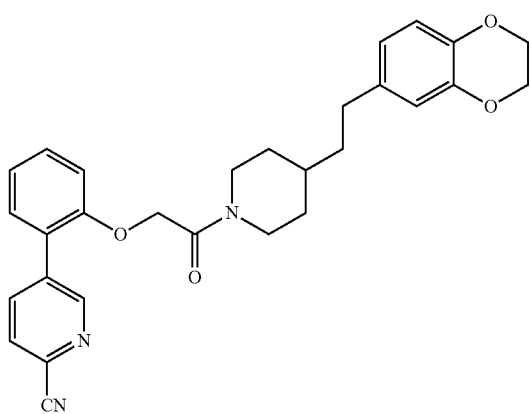 |
| 298 | 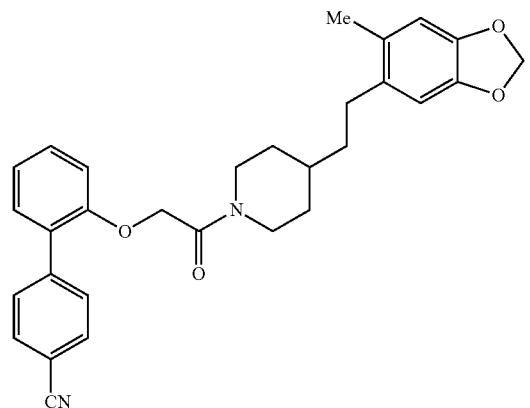 [SMILES: Cc1cc2c(cc1CCC1CCN(C(=O)COc3ccccc3-c3ccc(C#N)cc3)CC1)OCO2] |

-continued
| Compound No. | Structure |
|---|---|
| 299 | 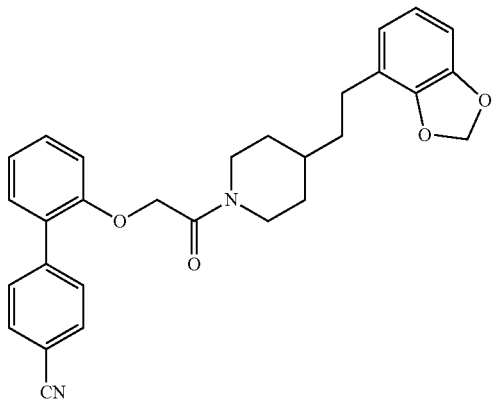 [SMILES: N#Cc1ccc(-c2ccccc2OCC(=O)N2CCC(CCc3cccc4c3OCO4)CC2)cc1] |
| 300 | 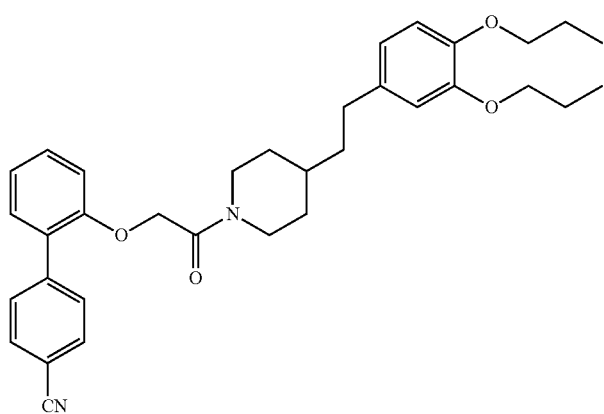 [SMILES: CCCOc1ccc(CCC2CCN(C(=O)COc3ccccc3-c3ccc(C#N)cc3)CC2)cc1OCCC] |
| 301 | 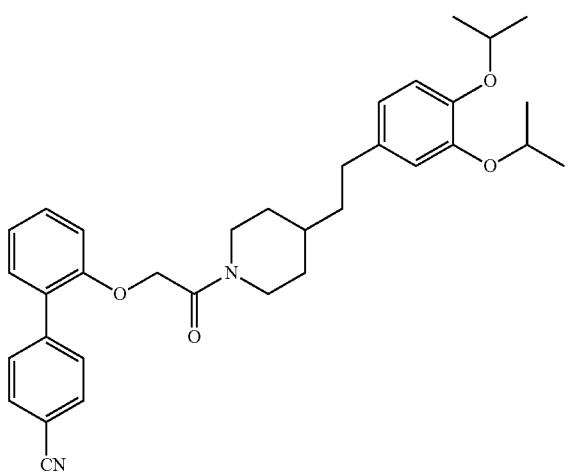 [SMILES: CC(C)Oc1ccc(CCC2CCN(C(=O)COc3ccccc3-c3ccc(C#N)cc3)CC2)cc1OC(C)C] |

| Compound No. | Structure |
|---|---|
| 302 | 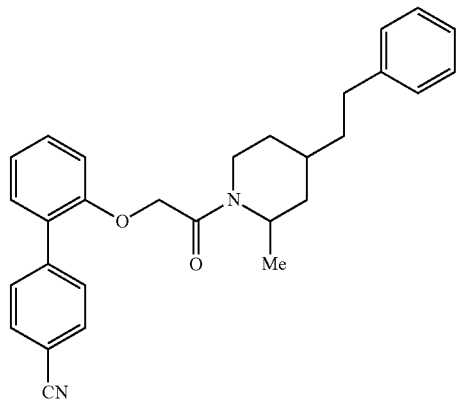 [SMILES: CC1CC(CCc2ccccc2)CCN1C(=O)COc1ccccc1-c1ccc(C#N)cc1] |
| 303 | 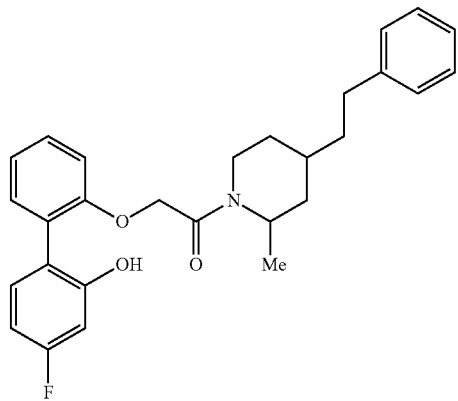 [SMILES: CC1CC(CCc2ccccc2)CCN1C(=O)COc1ccccc1-c1ccc(F)cc1O] |
| 304 | 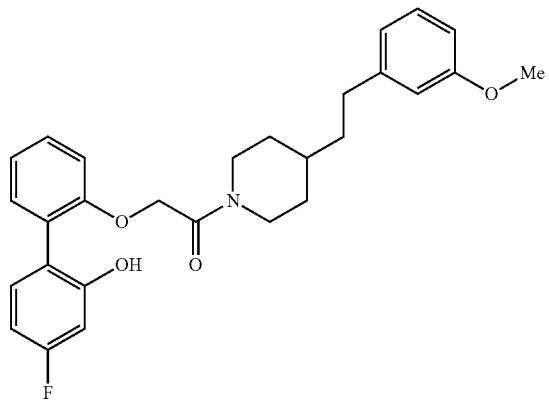 [SMILES: COc1cccc(CCC2CCN(C(=O)COc3ccccc3-c3ccc(F)cc3O)CC2)c1] |

| Compound No. | Structure |
---|---
305 | 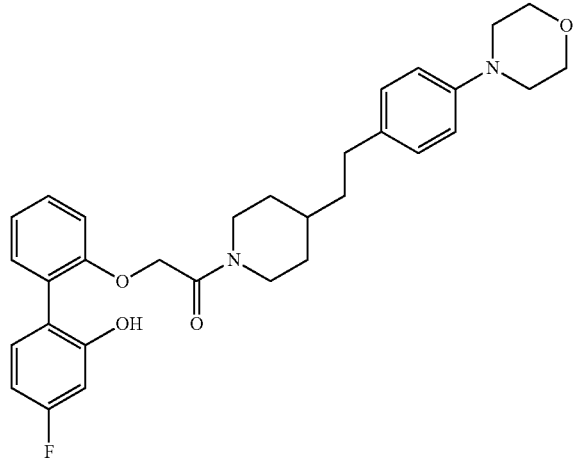 [SMILES: O=C(COc1ccccc1-c1ccc(F)cc1O)N1CCC(CCc2ccc(N3CCOCC3)cc2)CC1]
306 | 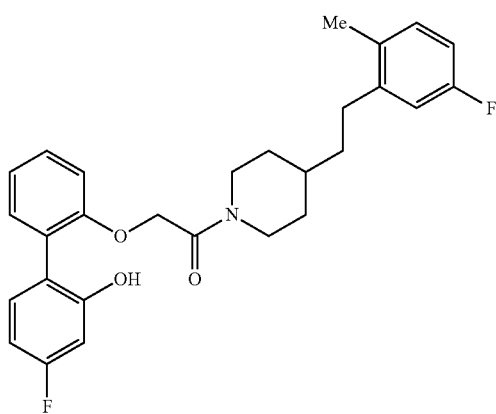 [SMILES: Cc1ccc(F)cc1CCC1CCN(C(=O)COc2ccccc2-c2ccc(F)cc2O)CC1]
307 | 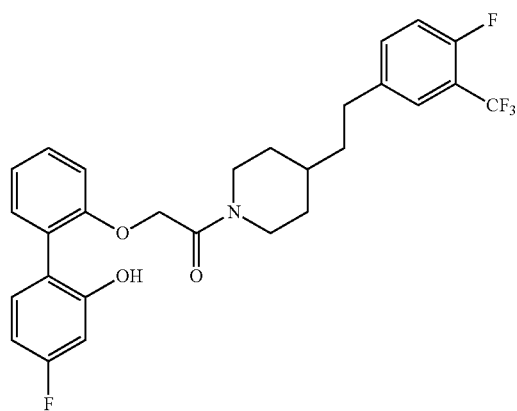 [SMILES: O=C(COc1ccccc1-c1ccc(F)cc1O)N1CCC(CCc2ccc(F)c(C(F)(F)F)c2)CC1]

| Compound No. | Structure |
|---|---|
| 308 | 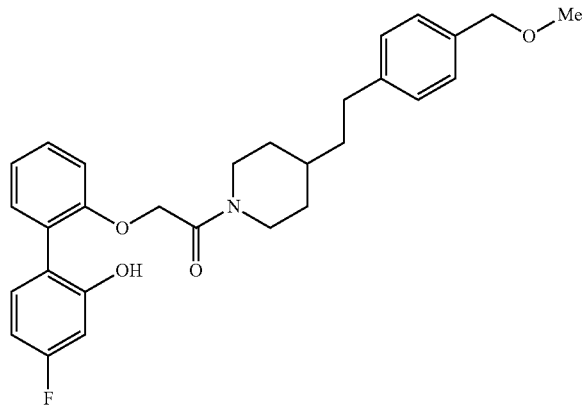 [SMILES: COCc1ccc(CCC2CCN(C(=O)COc3ccccc3-c3ccc(F)cc3O)CC2)cc1] |
| 309 | 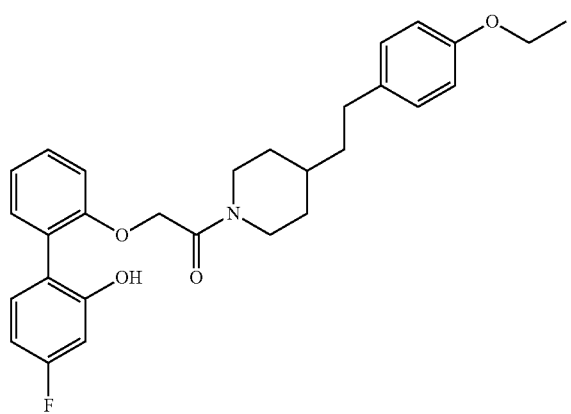 [SMILES: CCOc1ccc(CCC2CCN(C(=O)COc3ccccc3-c3ccc(F)cc3O)CC2)cc1] |
| 310 | 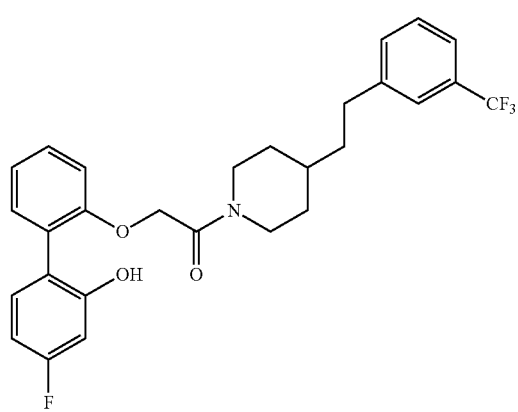 [SMILES: O=C(COc1ccccc1-c1ccc(F)cc1O)N1CCC(CCc2cccc(C(F)(F)F)c2)CC1] |

-continued
| Compound No. | Structure |
|---|---|
| 311 | 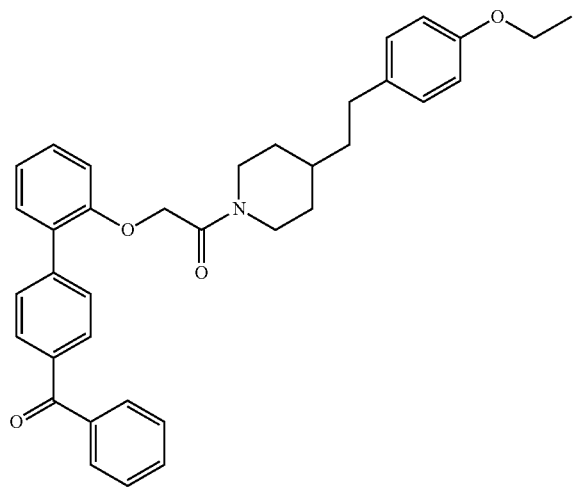 [SMILES: CCOc1ccc(CCC2CCN(C(=O)COc3ccccc3-c3ccc(C(=O)c4ccccc4)cc3)CC2)cc1] |
| 312 | 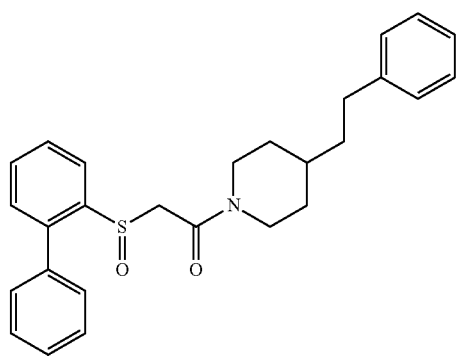 [SMILES: O=C(CS(=O)c1ccccc1-c1ccccc1)N1CCC(CCc2ccccc2)CC1] |
| 313 | 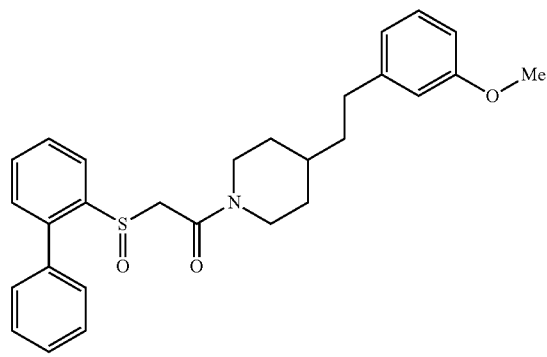 [SMILES: COc1cccc(CCC2CCN(C(=O)CS(=O)c3ccccc3-c3ccccc3)CC2)c1] |

| Compound No. | Structure |
|---|---|
| 314 | 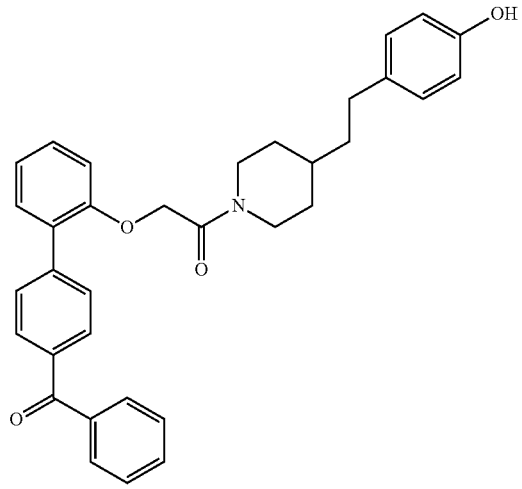 [SMILES: O=C(c1ccccc1)c1ccc(-c2ccccc2OCC(=O)N2CCC(CCc3ccc(O)cc3)CC2)cc1] |
| 315 | 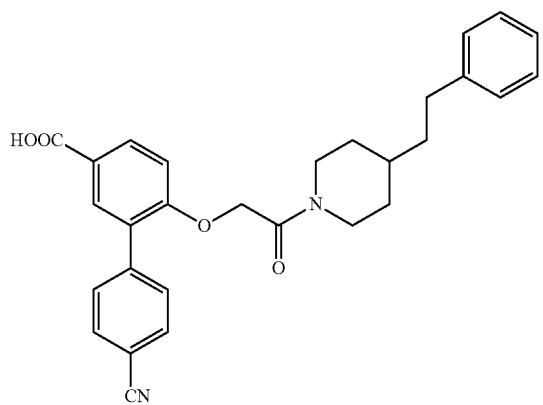 [SMILES: N#Cc1ccc(-c2cc(C(=O)O)ccc2OCC(=O)N2CCC(CCc3ccccc3)CC2)cc1] |
| 316 | 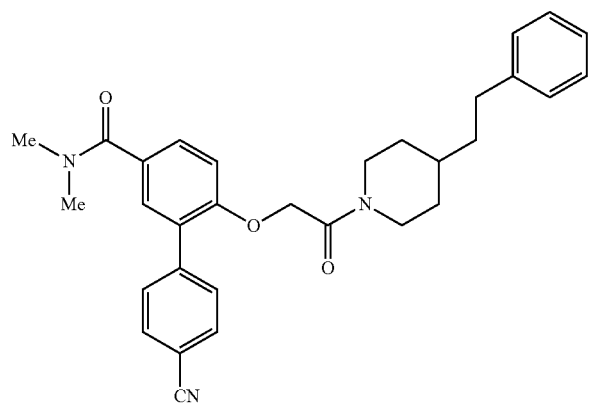 [SMILES: CN(C)C(=O)c1ccc(OCC(=O)N2CCC(CCc3ccccc3)CC2)c(-c2ccc(C#N)cc2)c1] |

| Compound No. | Structure |
|---|---|
| 317 | 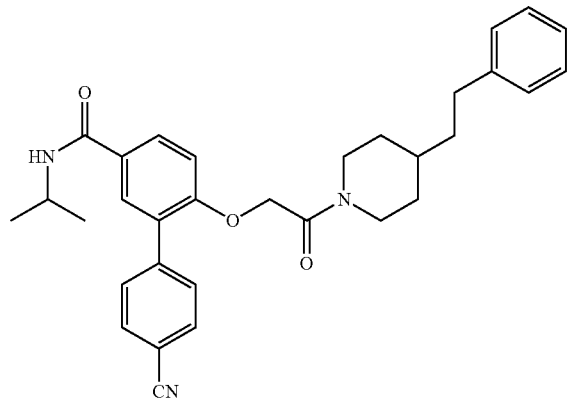 [SMILES: CC(C)NC(=O)c1ccc(OCC(=O)N2CCC(CCc3ccccc3)CC2)c(-c2ccc(C#N)cc2)c1] |
| 318 | 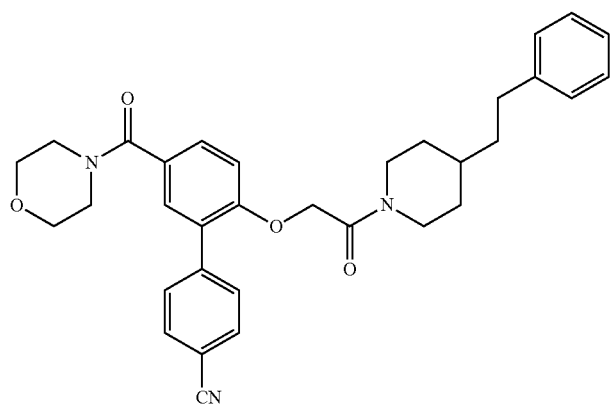 [SMILES: N#Cc1ccc(-c2cc(C(=O)N3CCOCC3)ccc2OCC(=O)N2CCC(CCc3ccccc3)CC2)cc1] |
| 319 | 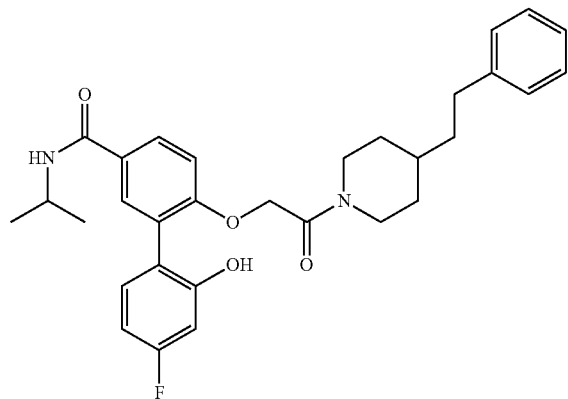 [SMILES: CC(C)NC(=O)c1ccc(OCC(=O)N2CCC(CCc3ccccc3)CC2)c(-c2ccc(F)cc2O)c1] |

| Compound No. | Structure |
|---|---|
| 320 | 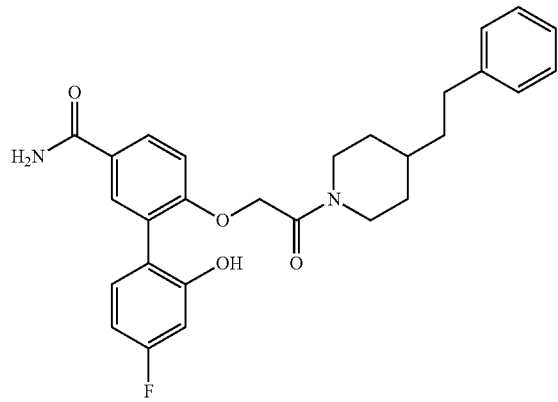 [SMILES: NC(=O)c1ccc(OCC(=O)N2CCC(CCc3ccccc3)CC2)c(-c2ccc(F)cc2O)c1] |
| 321 | 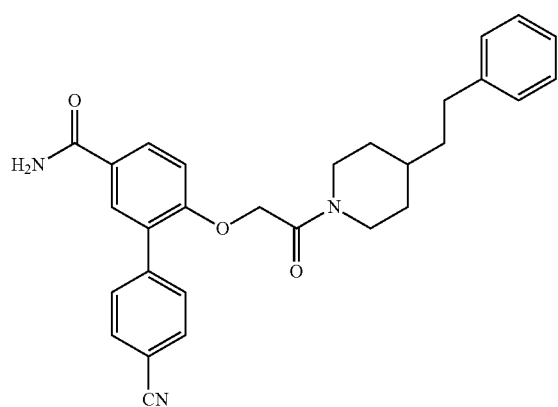 [SMILES: N#Cc1ccc(-c2cc(C(N)=O)ccc2OCC(=O)N2CCC(CCc3ccccc3)CC2)cc1] |
| 322 | 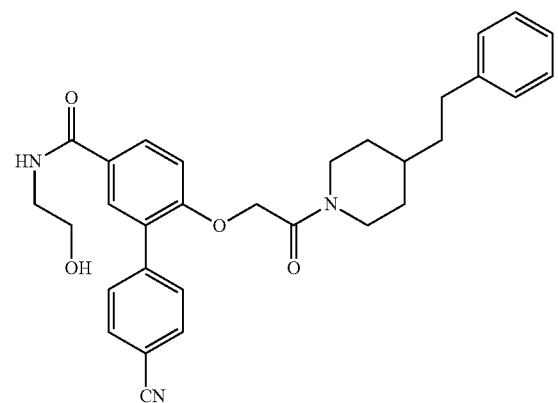 [SMILES: N#Cc1ccc(-c2cc(C(=O)NCCO)ccc2OCC(=O)N2CCC(CCc3ccccc3)CC2)cc1] |

| Compound No. | Structure |
|---|---|
| 323 | 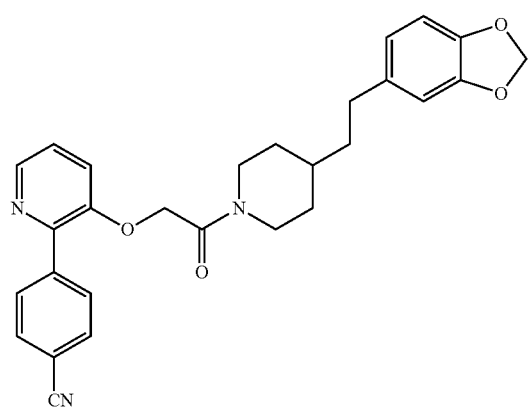 |
| 324 | 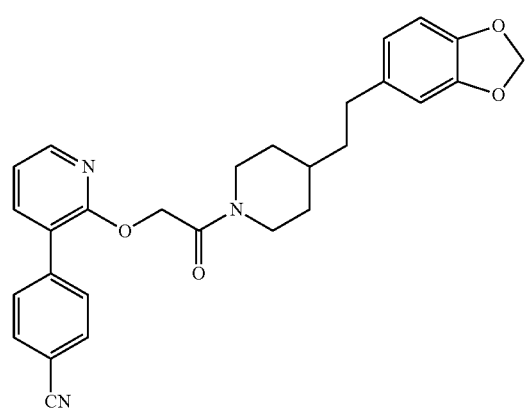 |
| 325 | 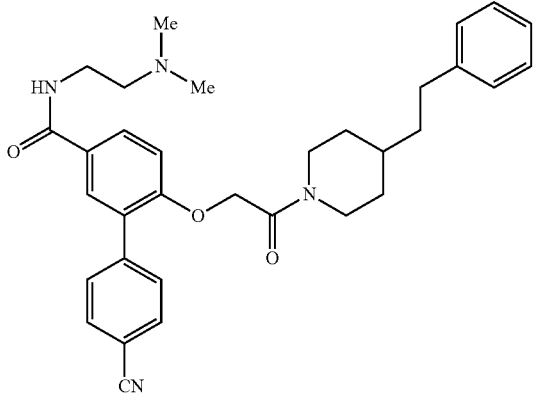 [SMILES: CN(C)CCNC(=O)c1ccc(OCC(=O)N2CCC(CCc3ccccc3)CC2)c(-c2ccc(C#N)cc2)c1] |

| Compound No. | Structure |
|---|---|
| 326 | 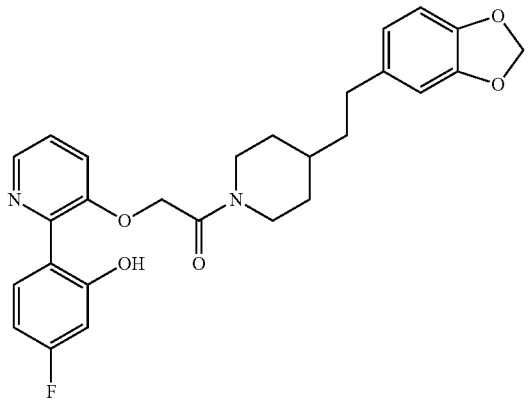 [SMILES: O=C(COc1cccnc1-c1ccc(F)cc1O)N1CCC(CCc2ccc3c(c2)OCO3)CC1] |
| 327 | 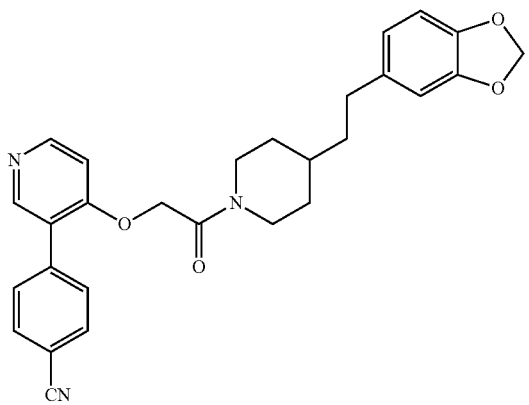 [SMILES: N#Cc1ccc(-c2cnccc2OCC(=O)N2CCC(CCc3ccc4c(c3)OCO4)CC2)cc1] |
| 328 | 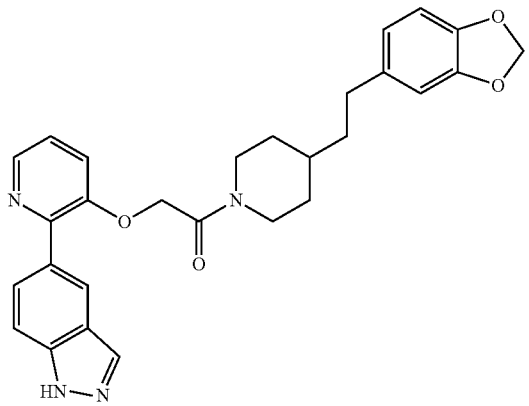 [SMILES: O=C(COc1cccnc1-c1ccc2[nH]ncc2c1)N1CCC(CCc2ccc3c(c2)OCO3)CC1] |

| Compound No. | Structure |
|---|---|
| 329 | 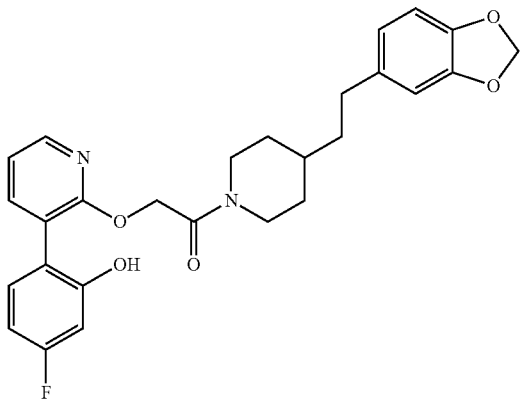 [SMILES: O=C(COc1ncccc1-c1ccc(F)cc1O)N1CCC(CCc2ccc3c(c2)OCO3)CC1] |
| 330 | 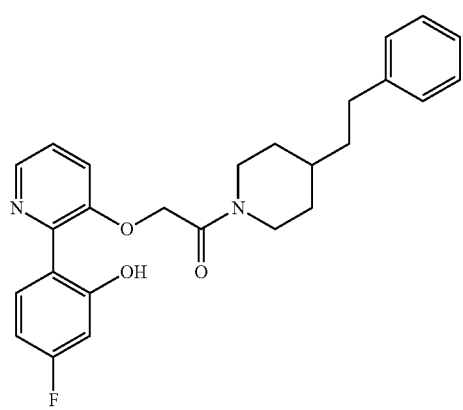 [SMILES: O=C(COc1cccnc1-c1ccc(F)cc1O)N1CCC(CCc2ccccc2)CC1] |
| 331 | 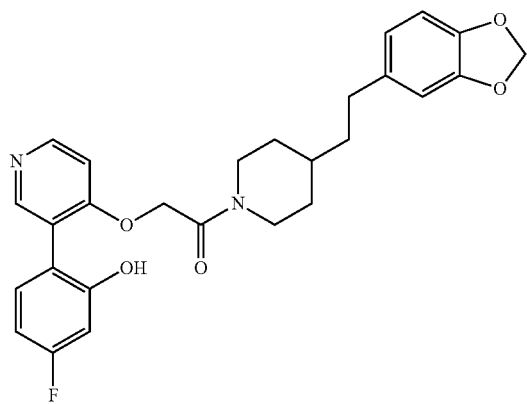 [SMILES: O=C(COc1ccncc1-c1ccc(F)cc1O)N1CCC(CCc2ccc3c(c2)OCO3)CC1] |

| Compound No. | Structure |
|---|---|
| 332 | 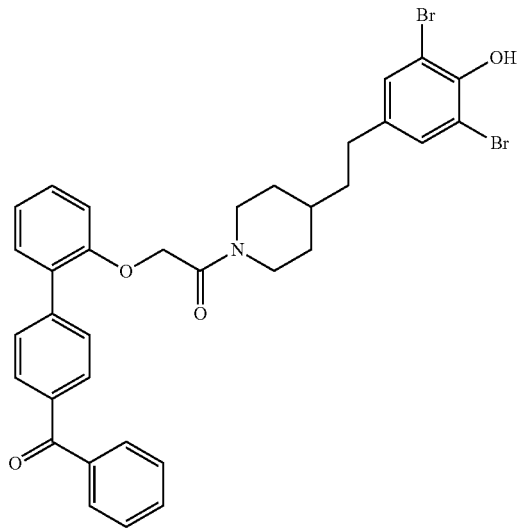 [SMILES: O=C(c1ccccc1)c1ccc(-c2ccccc2OCC(=O)N2CCC(CCc3cc(Br)c(O)c(Br)c3)CC2)cc1] |
| 333 | 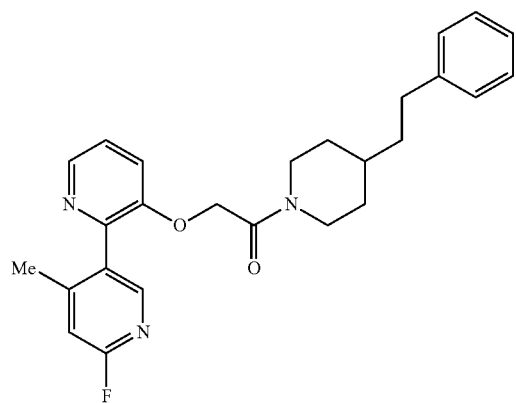 |
| 334 | 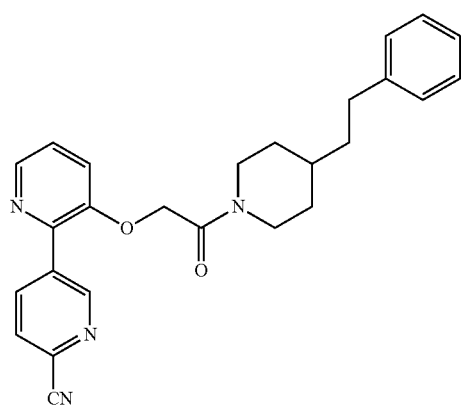 [SMILES: N#Cc1ccc(-c2ncccc2OCC(=O)N2CCC(CCc3ccccc3)CC2)cn1] |

| Compound No. | Structure |
|---|---|
| 335 | 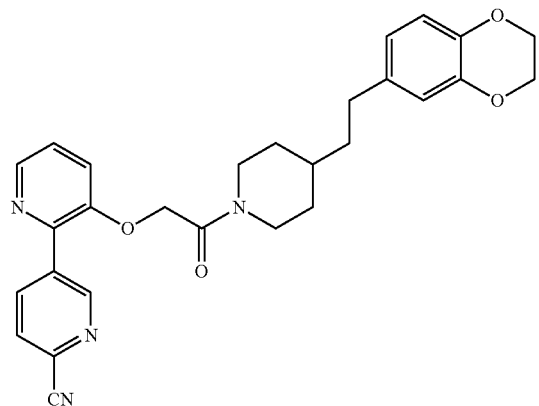 |
| 336 | 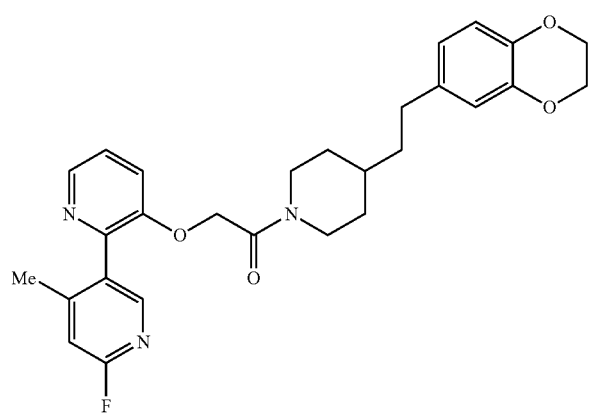 |
| 337 | 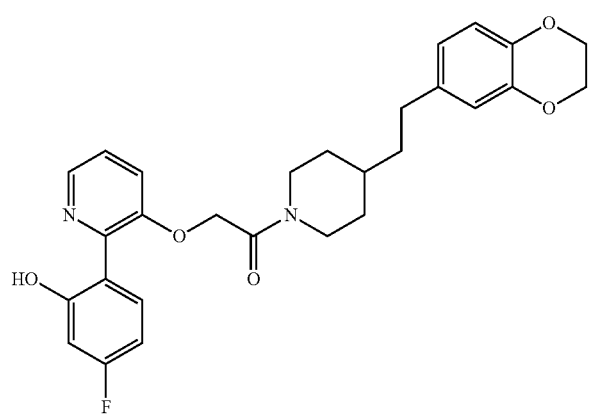 [SMILES: O=C(COc1cccnc1-c1ccc(F)cc1O)N1CCC(CCc2ccc3c(c2)OCCO3)CC1] |

| Compound No. | Structure |
|---|---|
| 338 | 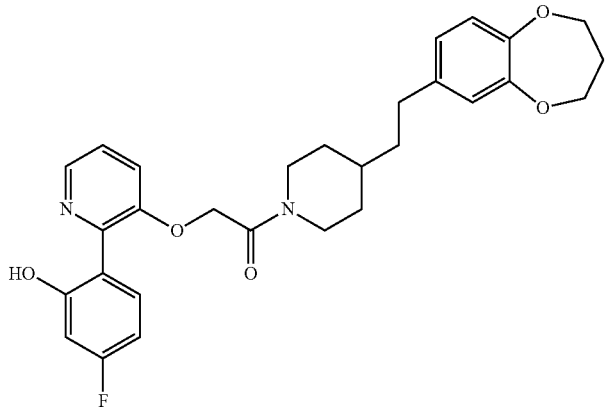 [SMILES: O=C(COc1cccnc1-c1ccc(F)cc1O)N1CCC(CCc2ccc3c(c2)OCCCO3)CC1] |
| 339 | 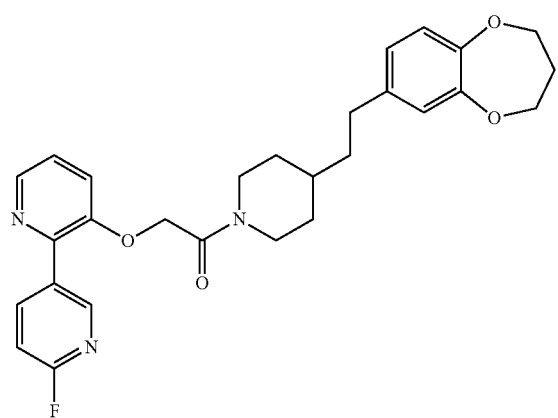 [SMILES: O=C(COc1cccnc1-c1ccc(F)nc1)N1CCC(CCc2ccc3c(c2)OCCCO3)CC1] |
| 340 | 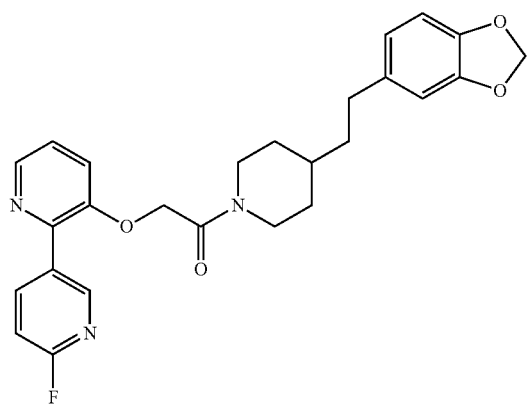 |

-continued
| Compound No. | Structure |
|---|---|
| 341 | 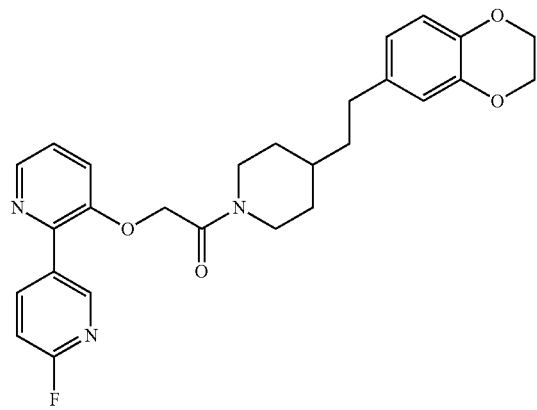 [SMILES: O=C(COc1cccnc1-c1ccc(F)nc1)N1CCC(CCc2ccc3c(c2)OCCO3)CC1] |
| 342 | 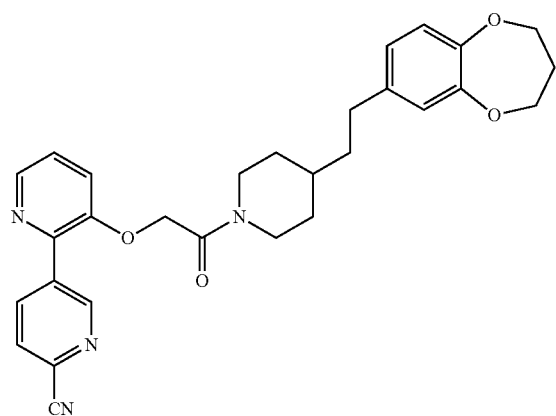 [SMILES: N#Cc1ccc(-c2ncccc2OCC(=O)N2CCC(CCc3ccc4c(c3)OCCCO4)CC2)cn1] |
| 343 | 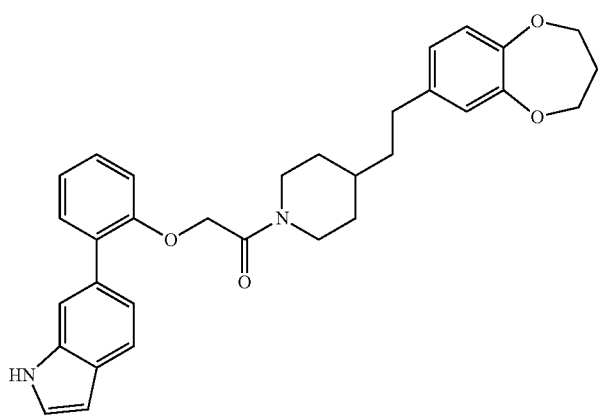 [SMILES: O=C(COc1ccccc1-c1ccc2cc[nH]c2c1)N1CCC(CCc2ccc3c(c2)OCCCO3)CC1] |

| Compound No. | Structure |
|---|---|
| 344 | 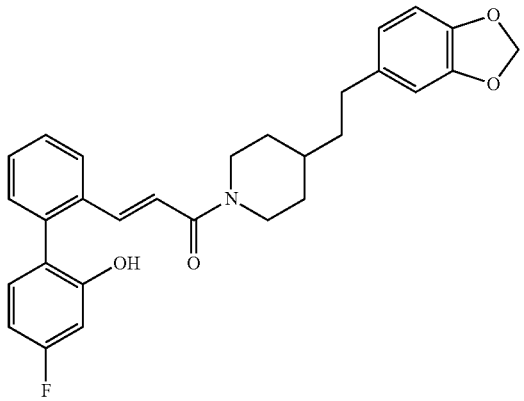 [SMILES: O=C(/C=C/c1ccccc1-c1ccc(F)cc1O)N1CCC(CCc2ccc3c(c2)OCO3)CC1] |
| 345 | 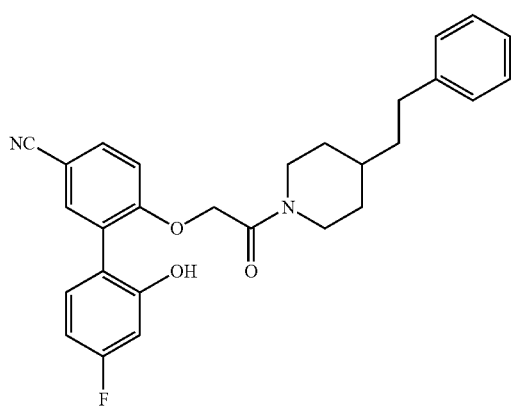 [SMILES: N#Cc1ccc(OCC(=O)N2CCC(CCc3ccccc3)CC2)c(-c2ccc(F)cc2O)c1] |
| 346 | 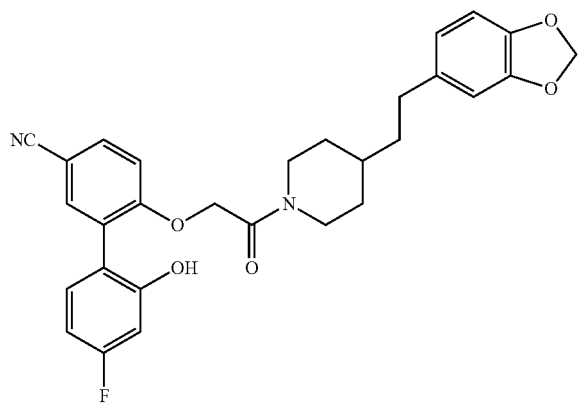 [SMILES: N#Cc1ccc(OCC(=O)N2CCC(CCc3ccc4c(c3)OCO4)CC2)c(-c2ccc(F)cc2O)c1] |

| Compound No. | Structure |
|---|---|
| 347 | 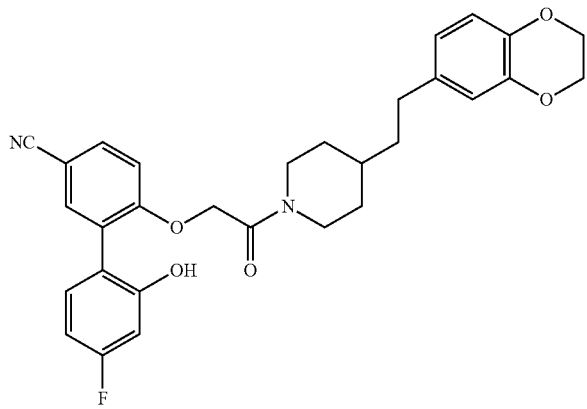 [SMILES: N#Cc1ccc(OCC(=O)N2CCC(CCc3ccc4c(c3)OCCO4)CC2)c(-c2ccc(F)cc2O)c1] |
| 348 | 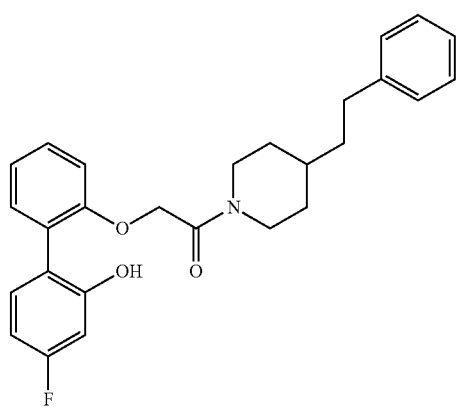 [SMILES: O=C(COc1ccccc1-c1ccc(F)cc1O)N1CCC(CCc2ccccc2)CC1] |
| 349 | 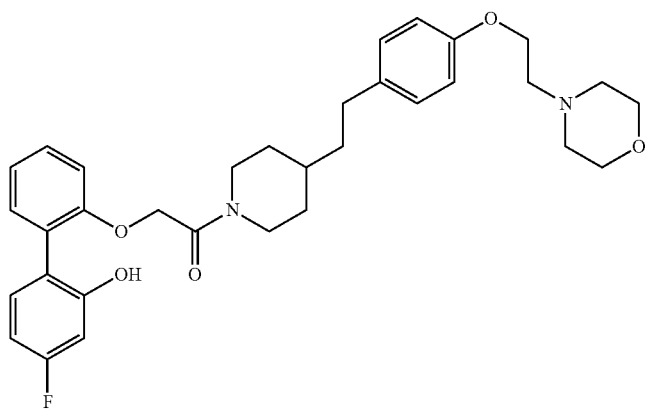 [SMILES: O=C(COc1ccccc1-c1ccc(F)cc1O)N1CCC(CCc2ccc(OCCN3CCOCC3)cc2)CC1] |

-continued
| Compound No. | Structure |
|---|---|
| 350 | 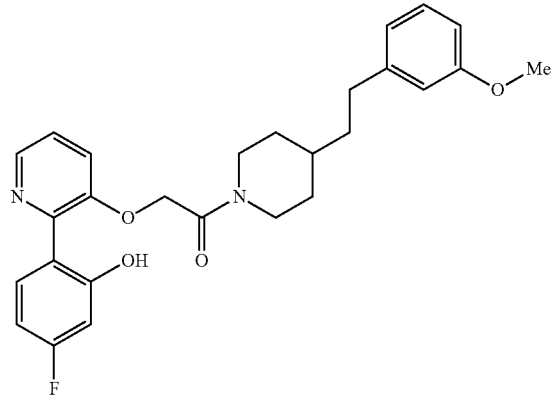 [SMILES: COc1cccc(CCC2CCN(C(=O)COc3cccnc3-c3ccc(F)cc3O)CC2)c1] |
| 351 | 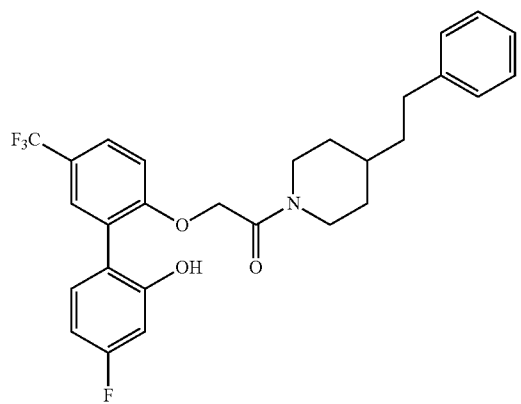 [SMILES: O=C(COc1ccc(C(F)(F)F)cc1-c1ccc(F)cc1O)N1CCC(CCc2ccccc2)CC1] |
| 352 | 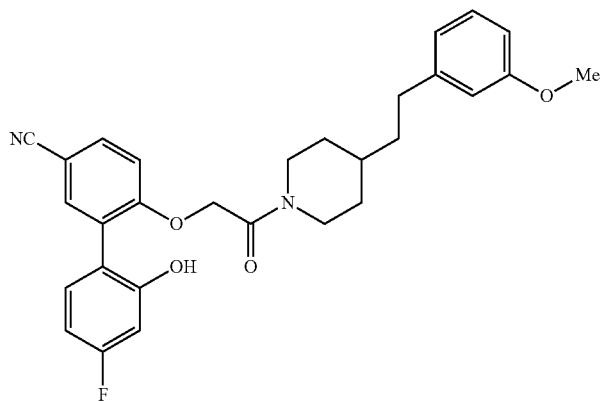 [SMILES: COc1cccc(CCC2CCN(C(=O)COc3ccc(C#N)cc3-c3ccc(F)cc3O)CC2)c1] |

| Compound No. | Structure |
|---|---|
| 353 | 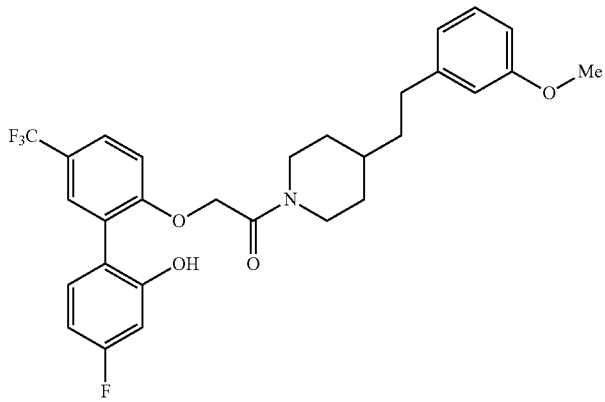 [SMILES: COc1cccc(CCC2CCN(C(=O)COc3ccc(C(F)(F)F)cc3-c3ccc(F)cc3O)CC2)c1] |
| 354 | 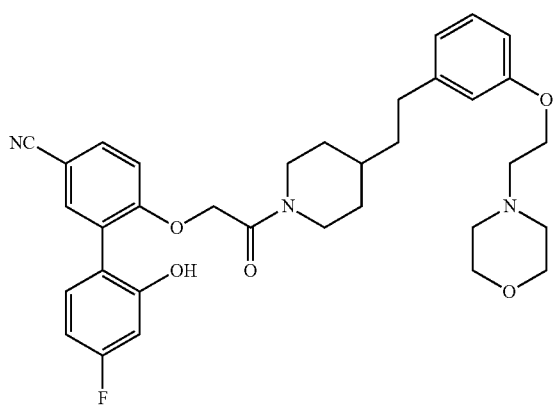 [SMILES: N#Cc1ccc(OCC(=O)N2CCC(CCc3cccc(OCCN4CCOCC4)c3)CC2)c(-c2ccc(F)cc2O)c1] |
| 355 | 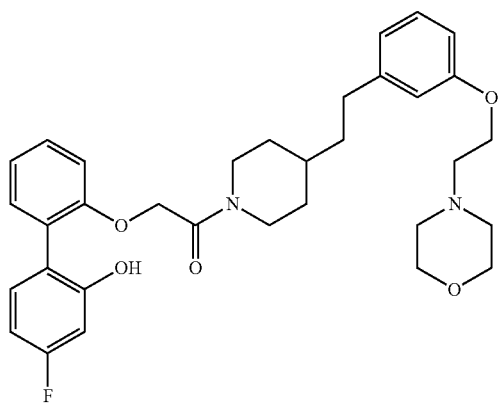 [SMILES: O=C(COc1ccccc1-c1ccc(F)cc1O)N1CCC(CCc2cccc(OCCN3CCOCC3)c2)CC1] |

| Compound No. | Structure |
|---|---|
| 356 | 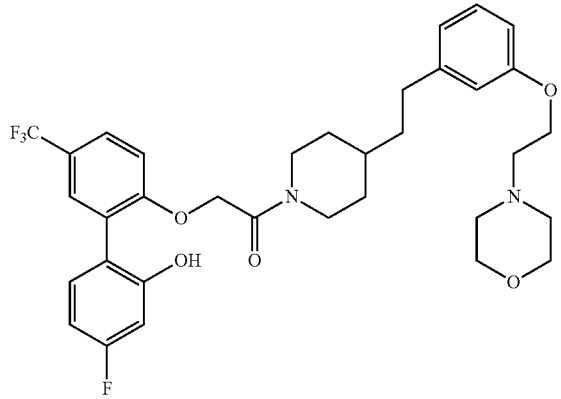 [SMILES: O=C(COc1ccc(C(F)(F)F)cc1-c1ccc(F)cc1O)N1CCC(CCc2cccc(OCCN3CCOCC3)c2)CC1] |
| 357 | 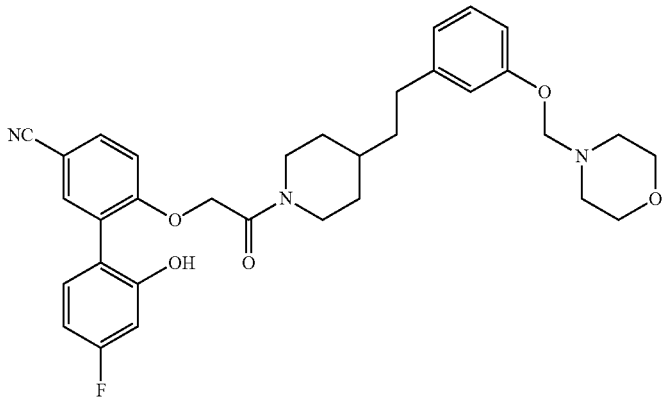 [SMILES: N#Cc1ccc(OCC(=O)N2CCC(CCc3cccc(OCN4CCOCC4)c3)CC2)c(-c2ccc(F)cc2O)c1] |
| 358 | 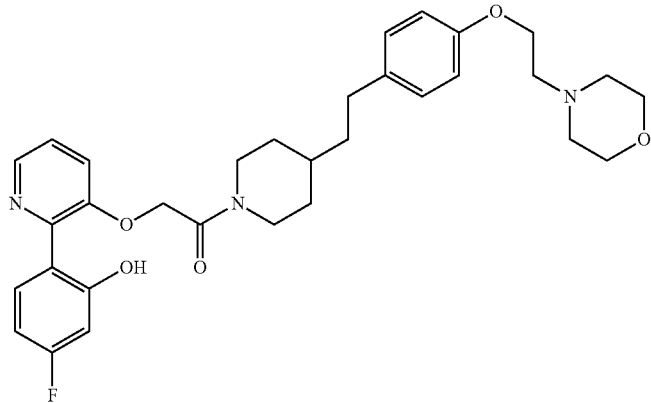 [SMILES: O=C(COc1cccnc1-c1ccc(F)cc1O)N1CCC(CCc2ccc(OCCN3CCOCC3)cc2)CC1] |

US 10,899,747 B2
417
418
-continued
| Compound No. | Structure |
|---|---|
| 359 | 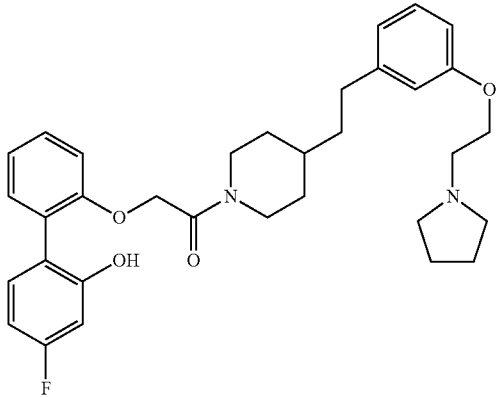 [SMILES: O=C(COc1ccccc1-c1ccc(F)cc1O)N1CCC(CCc2cccc(OCCN3CCCC3)c2)CC1] |
| 360 | 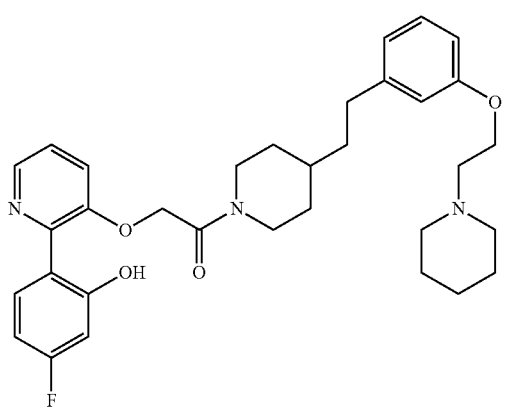 [SMILES: O=C(COc1cccnc1-c1ccc(F)cc1O)N1CCC(CCc2cccc(OCCN3CCCCC3)c2)CC1] |
| 361 | 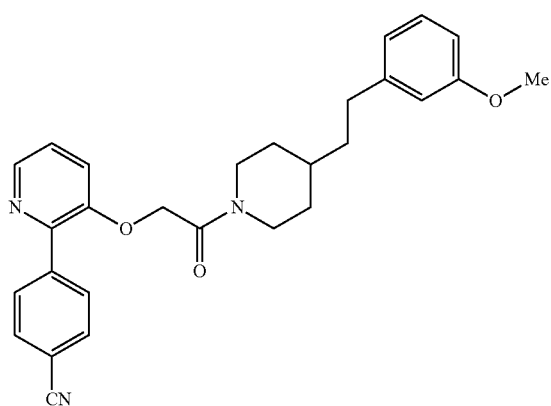 [SMILES: COc1cccc(CCC2CCN(C(=O)COc3cccnc3-c3ccc(C#N)cc3)CC2)c1] |

| Compound No. | Structure |
|---|---|
| 362 | 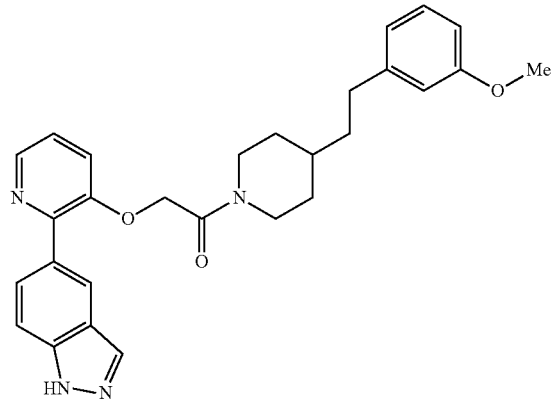 [SMILES: COc1cccc(CCC2CCN(C(=O)COc3cccnc3-c3ccc4[nH]ncc4c3)CC2)c1] |
| 363 | 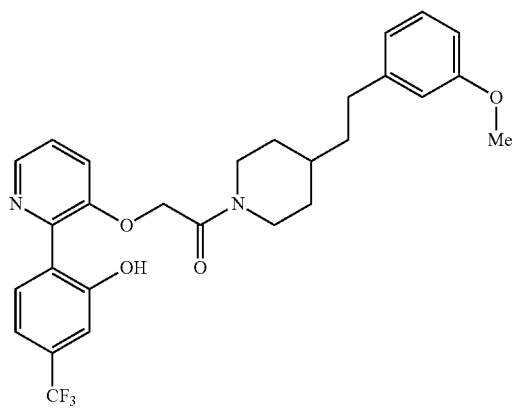 [SMILES: COc1cccc(CCC2CCN(C(=O)COc3cccnc3-c3ccc(C(F)(F)F)cc3O)CC2)c1] |
| 364 | 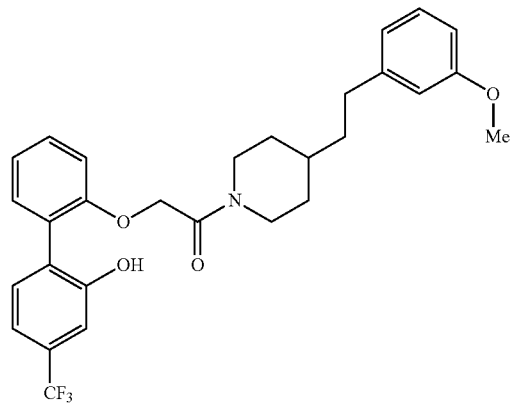 [SMILES: COc1cccc(CCC2CCN(C(=O)COc3ccccc3-c3ccc(C(F)(F)F)cc3O)CC2)c1] |

-continued
| Compound No. | Structure |
|---|---|
| 365 | 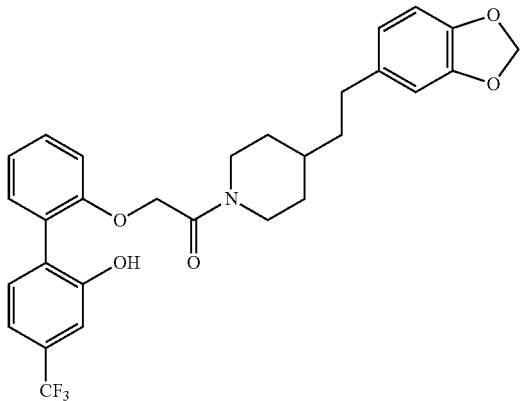 [SMILES: O=C(COc1ccccc1-c1ccc(C(F)(F)F)cc1O)N1CCC(CCc2ccc3c(c2)OCO3)CC1] |
| 366 | 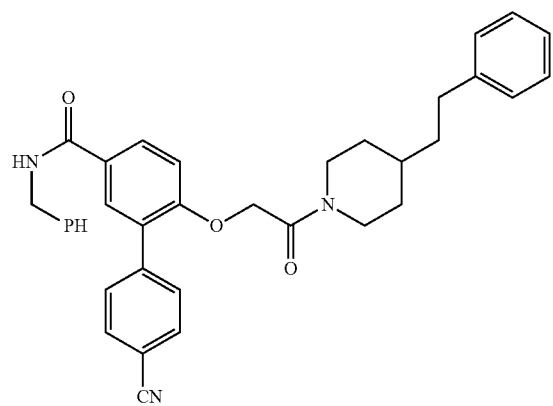 |
| 367 | 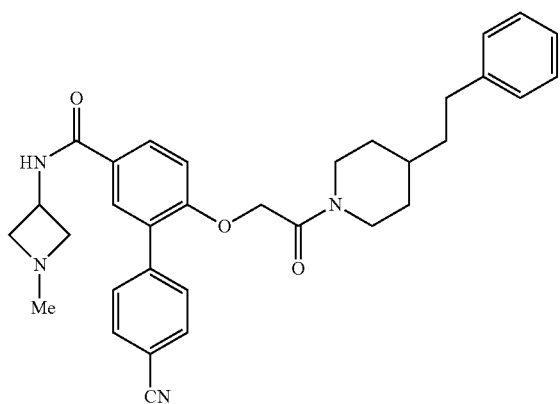 [SMILES: CN1CC(NC(=O)c2ccc(OCC(=O)N3CCC(CCc4ccccc4)CC3)c(-c3ccc(C#N)cc3)c2)C1] |

-continued
| Compound No. | Structure |
|---|---|
| 368 | 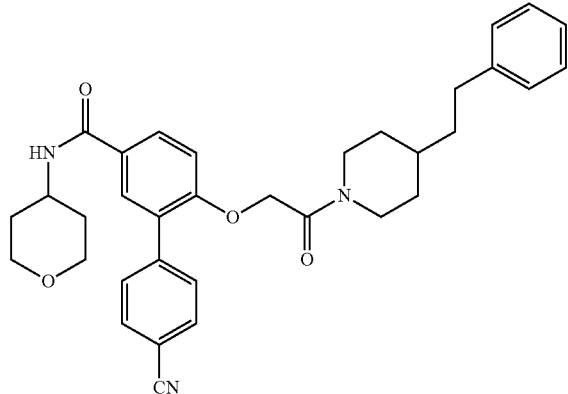 [SMILES: N#Cc1ccc(-c2cc(C(=O)NC3CCOCC3)ccc2OCC(=O)N2CCC(CCc3ccccc3)CC2)cc1] |
| 369 | 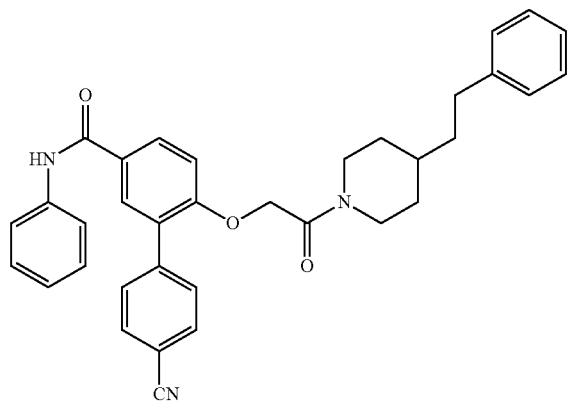 [SMILES: N#Cc1ccc(-c2cc(C(=O)Nc3ccccc3)ccc2OCC(=O)N2CCC(CCc3ccccc3)CC2)cc1] |
| 370 | 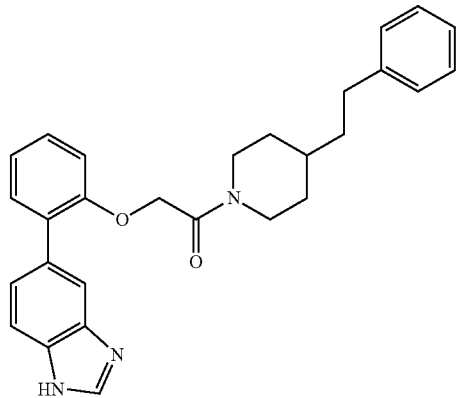 [SMILES: O=C(COc1ccccc1-c1ccc2[nH]cnc2c1)N1CCC(CCc2ccccc2)CC1] |

-continued
| Compound No. | Structure |
|---|---|
| 371 | 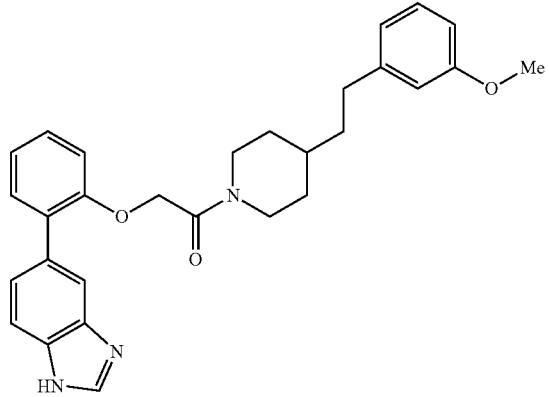 [SMILES: COc1cccc(CCC2CCN(C(=O)COc3ccccc3-c3ccc4[nH]cnc4c3)CC2)c1] |
| 372 | 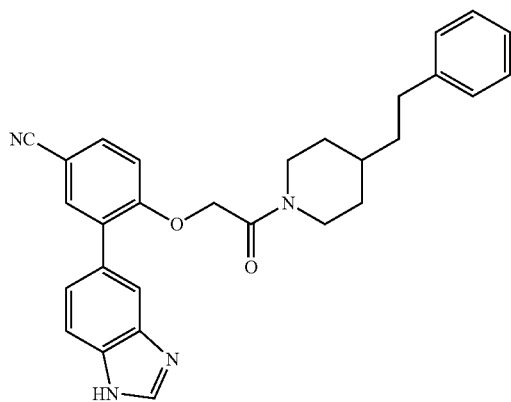 [SMILES: N#Cc1ccc(OCC(=O)N2CCC(CCc3ccccc3)CC2)c(-c2ccc3[nH]cnc3c2)c1] |
| 373 | 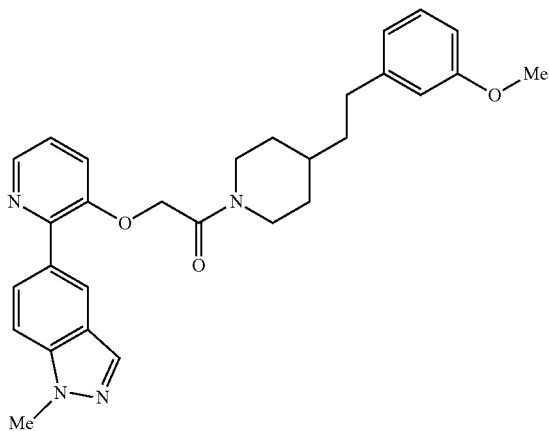 [SMILES: COc1cccc(CCC2CCN(C(=O)COc3cccnc3-c3ccc4c(cnn4C)c3)CC2)c1] |

| Compound No. | Structure |
|---|---|
| 374 | 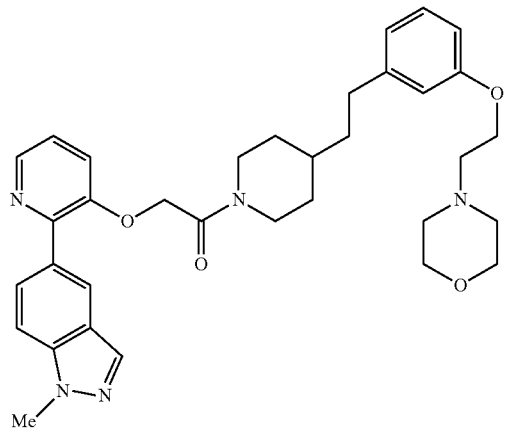 [SMILES: Cn1ncc2cc(-c3ncccc3OCC(=O)N3CCC(CCc4cccc(OCCN5CCOCC5)c4)CC3)ccc21] |
| 375 | 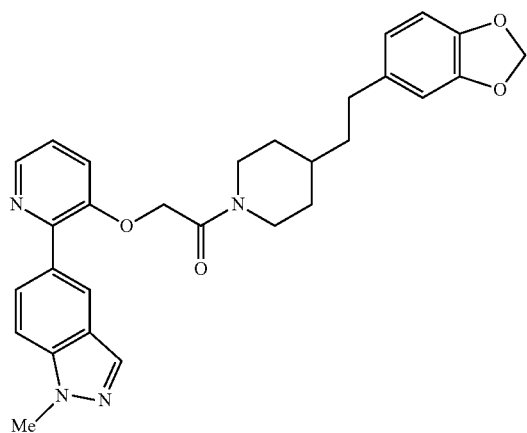 [SMILES: Cn1ncc2cc(-c3ncccc3OCC(=O)N3CCC(CCc4ccc5c(c4)OCO5)CC3)ccc21] |
| 376 | 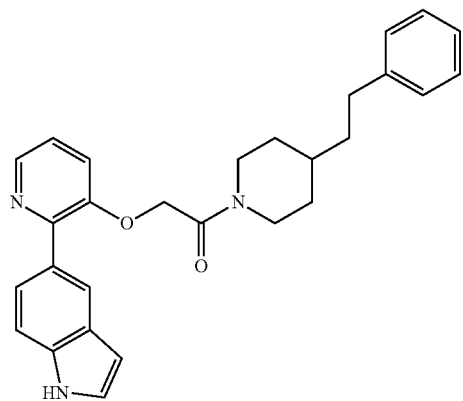 [SMILES: O=C(COc1cccnc1-c1ccc2[nH]ccc2c1)N1CCC(CCc2ccccc2)CC1] |

| Compound No. | Structure |
|---|---|
| 377 | 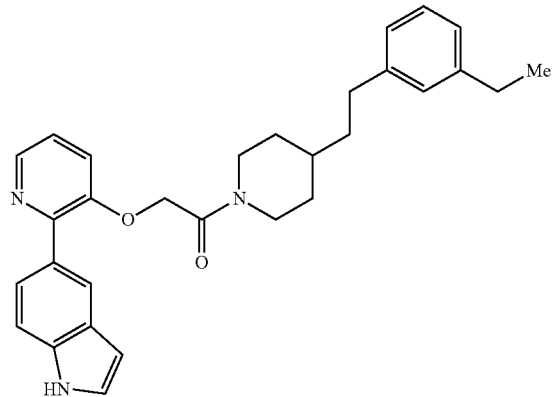 [SMILES: CCc1cccc(CCC2CCN(C(=O)COc3cccnc3-c3ccc4[nH]ccc4c3)CC2)c1] |
| 378 | 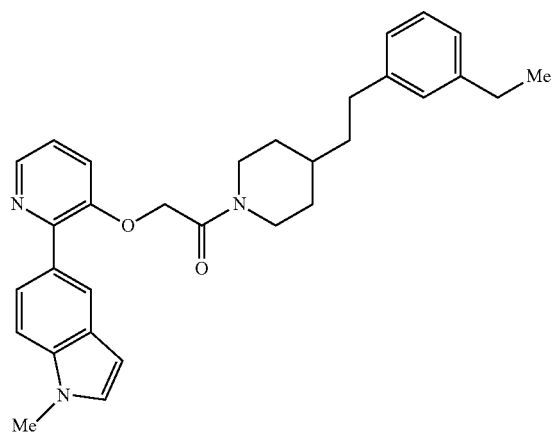 [SMILES: CCc1cccc(CCC2CCN(C(=O)COc3cccnc3-c3ccc4c(ccn4C)c3)CC2)c1] |
| 379 | 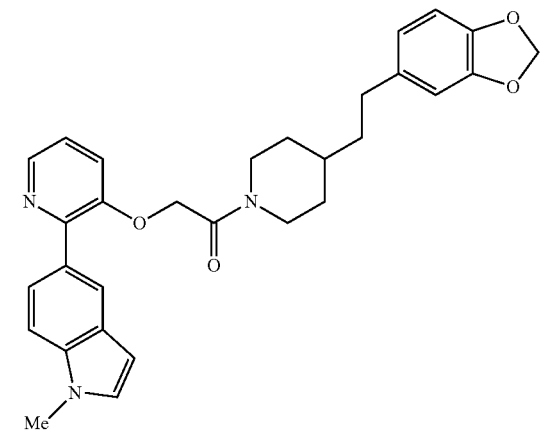 |

| Compound No. | Structure |
|---|---|
| 380 | 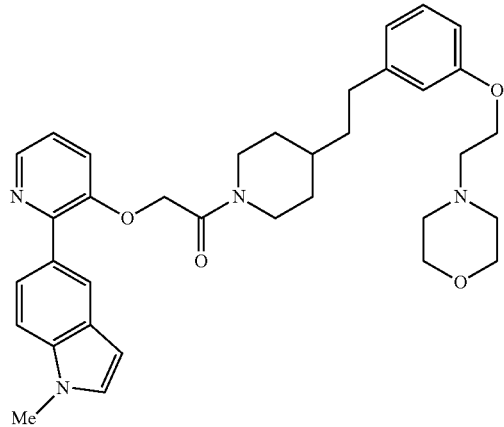 [SMILES: Cn1ccc2cc(-c3ncccc3OCC(=O)N3CCC(CCc4cccc(OCCN5CCOCC5)c4)CC3)ccc21] |
| 381 | 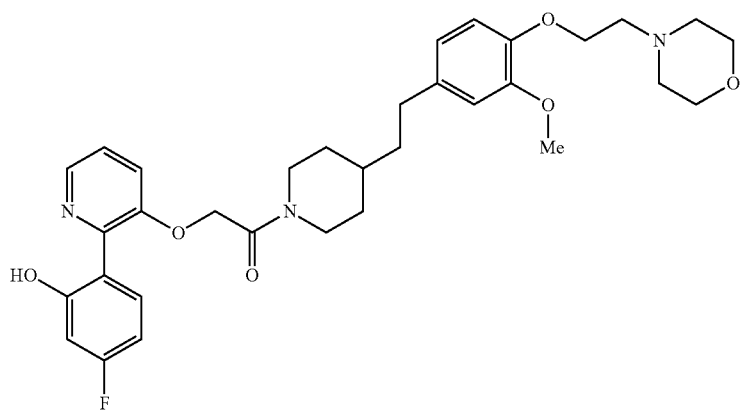 [SMILES: COc1cc(CCC2CCN(C(=O)COc3cccnc3-c3ccc(F)cc3O)CC2)ccc1OCCN1CCOCC1] |
| 382 | 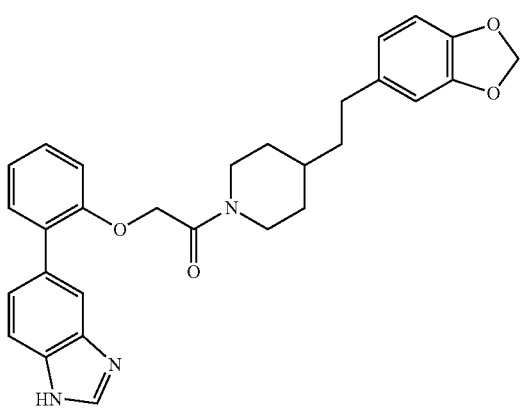 [SMILES: O=C(COc1ccccc1-c1ccc2[nH]cnc2c1)N1CCC(CCc2ccc3c(c2)OCO3)CC1] |

| Compound No. | Structure |
|---|---|
| 383 | 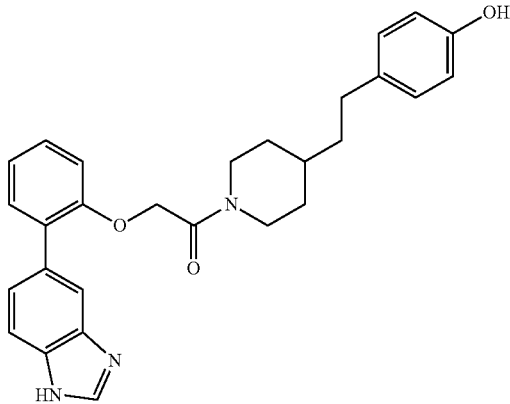 [SMILES: O=C(COc1ccccc1-c1ccc2[nH]cnc2c1)N1CCC(CCc2ccc(O)cc2)CC1] |
| 384 | 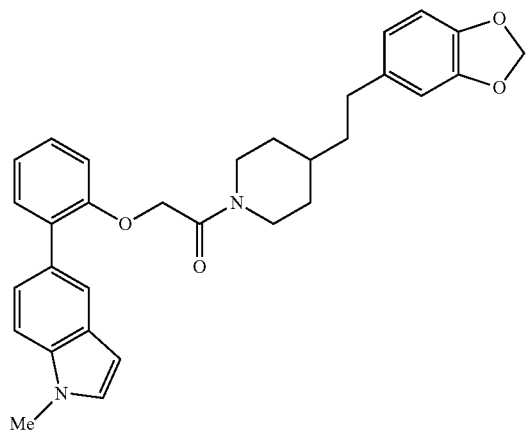 [SMILES: Cn1ccc2cc(-c3ccccc3OCC(=O)N3CCC(CCc4ccc5c(c4)OCO5)CC3)ccc21] |
| 385 | 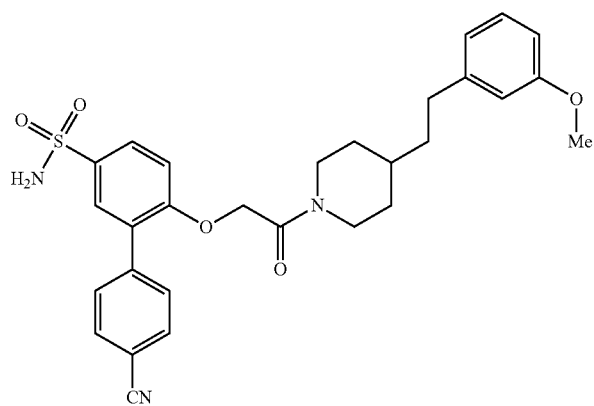 [SMILES: COc1cccc(CCC2CCN(C(=O)COc3ccc(S(N)(=O)=O)cc3-c3ccc(C#N)cc3)CC2)c1] |

| Compound No. | Structure |
|---|---|
| 386 | 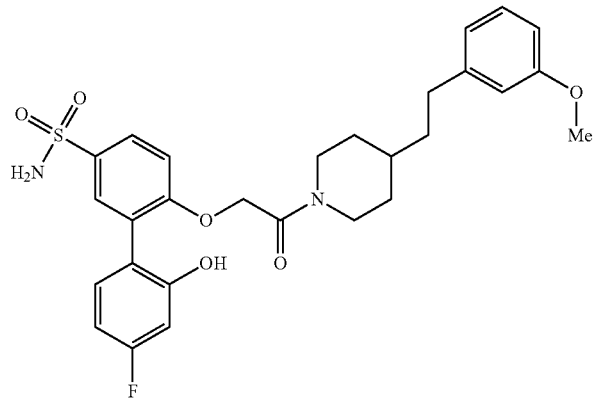 [SMILES: COc1cccc(CCC2CCN(C(=O)COc3ccc(S(N)(=O)=O)cc3-c3ccc(F)cc3O)CC2)c1] |
| 387 | 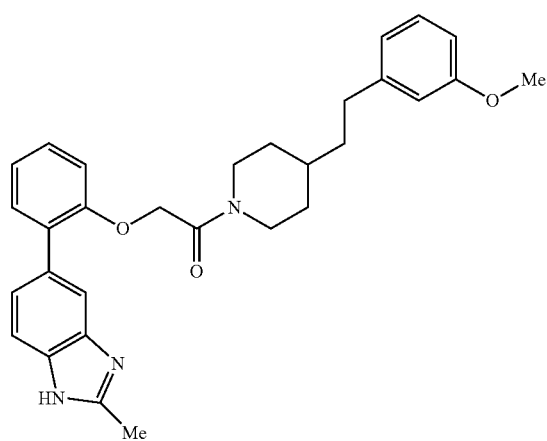 [SMILES: COc1cccc(CCC2CCN(C(=O)COc3ccccc3-c3ccc4[nH]c(C)nc4c3)CC2)c1] |
| 388 | 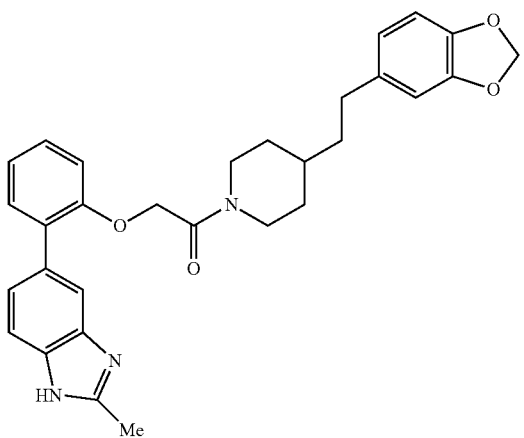 [SMILES: Cc1nc2cc(-c3ccccc3OCC(=O)N3CCC(CCc4ccc5c(c4)OCO5)CC3)ccc2[nH]1] |

| Compound No. | Structure |
|---|---|
| 389 | 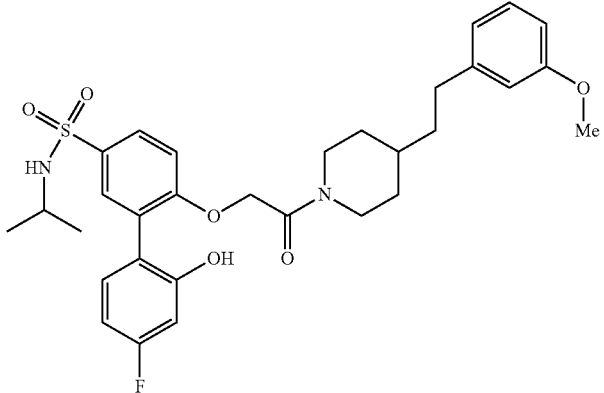 [SMILES: COc1cccc(CCC2CCN(C(=O)COc3ccc(S(=O)(=O)NC(C)C)cc3-c3ccc(F)cc3O)CC2)c1] |
| 390 | 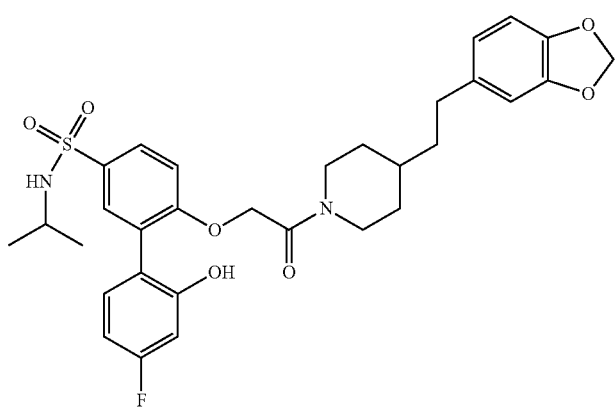 [SMILES: CC(C)NS(=O)(=O)c1ccc(OCC(=O)N2CCC(CCc3ccc4c(c3)OCO4)CC2)c(-c2ccc(F)cc2O)c1] |
| 391 | 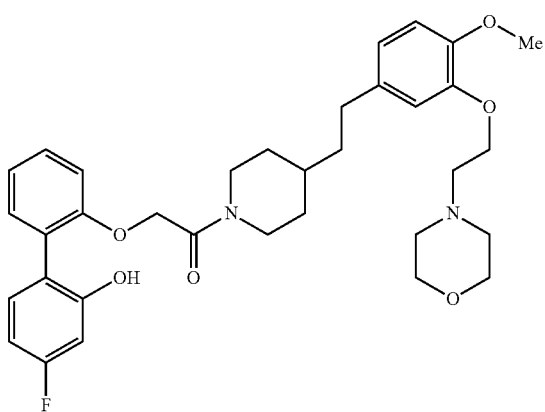 [SMILES: COc1ccc(CCC2CCN(C(=O)COc3ccccc3-c3ccc(F)cc3O)CC2)cc1OCCN1CCOCC1] |

-continued
| Compound No. | Structure |
|---|---|
| 392 | 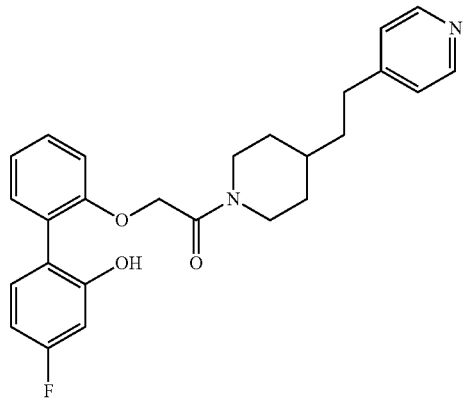 [SMILES: O=C(COc1ccccc1-c1ccc(F)cc1O)N1CCC(CCc2ccncc2)CC1] |
| 393 | 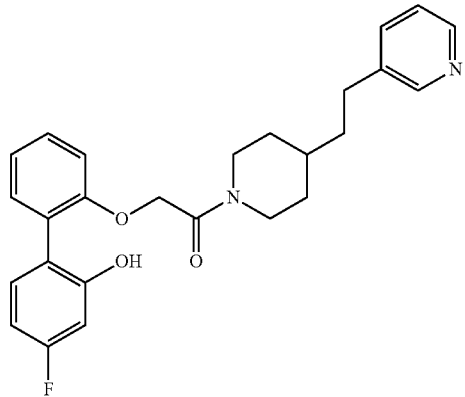 [SMILES: O=C(COc1ccccc1-c1ccc(F)cc1O)N1CCC(CCc2cccnc2)CC1] |
| 396 | 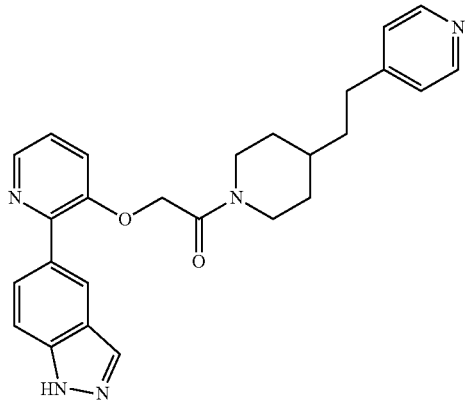 [SMILES: O=C(COc1cccnc1-c1ccc2[nH]ncc2c1)N1CCC(CCc2ccncc2)CC1] |

| Compound No. | Structure |
|---|---|
| 397 | 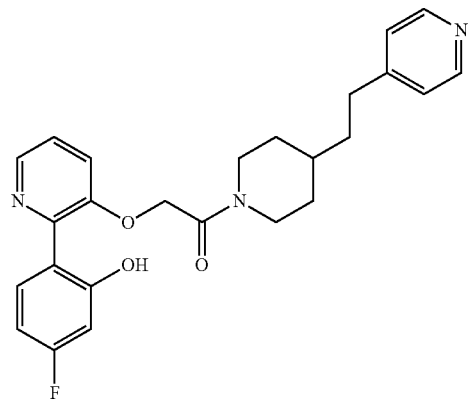 [SMILES: O=C(COc1cccnc1-c1ccc(F)cc1O)N1CCC(CCc2ccncc2)CC1] |
| 398 | 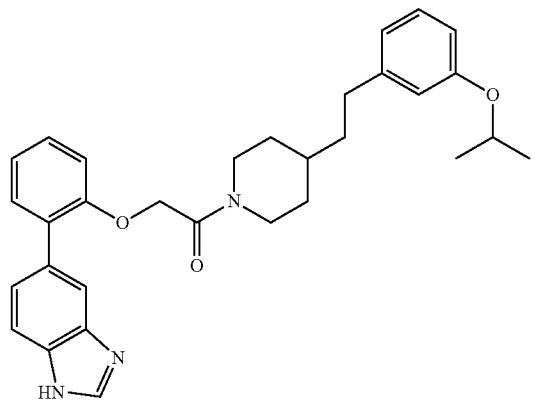 [SMILES: CC(C)Oc1cccc(CCC2CCN(C(=O)COc3ccccc3-c3ccc4[nH]cnc4c3)CC2)c1] |
| 399 | 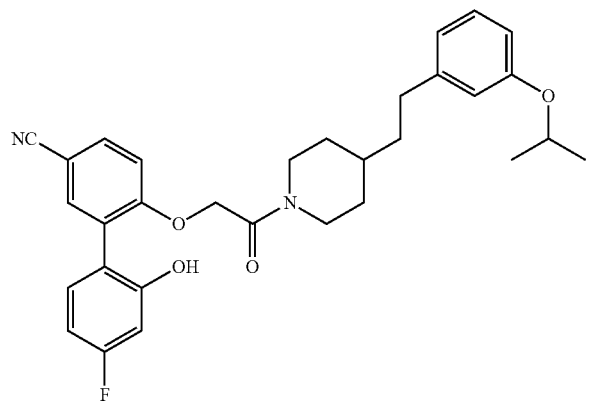 [SMILES: CC(C)Oc1cccc(CCC2CCN(C(=O)COc3ccc(C#N)cc3-c3ccc(F)cc3O)CC2)c1] |

| Compound No. | Structure |
|---|---|
| 400 | 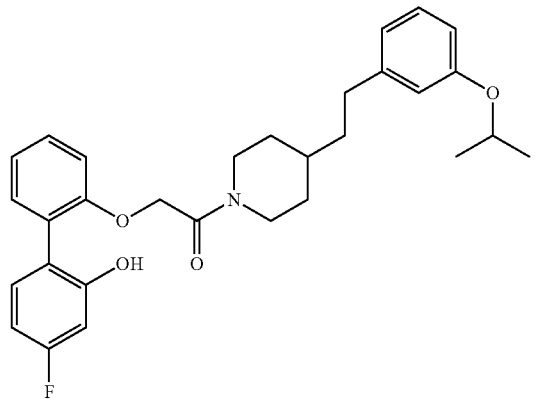 [SMILES: CC(C)Oc1cccc(CCC2CCN(C(=O)COc3ccccc3-c3ccc(F)cc3O)CC2)c1] |
| 401 | 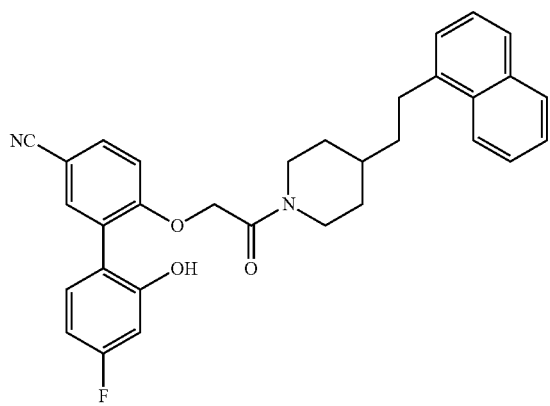 [SMILES: N#Cc1ccc(OCC(=O)N2CCC(CCc3cccc4ccccc34)CC2)c(-c2ccc(F)cc2O)c1] |
| 402 | 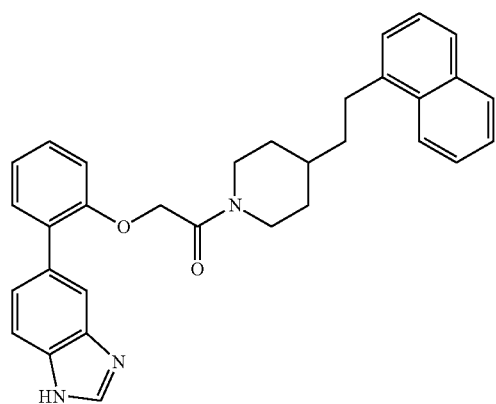 [SMILES: O=C(COc1ccccc1-c1ccc2[nH]cnc2c1)N1CCC(CCc2cccc3ccccc23)CC1] |

-continued
| Compound No. | Structure |
|---|---|
| 403 | 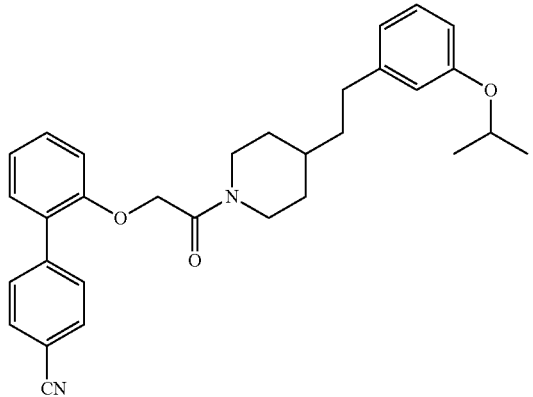 [SMILES: CC(C)Oc1cccc(CCC2CCN(C(=O)COc3ccccc3-c3ccc(C#N)cc3)CC2)c1] |
| 404 | 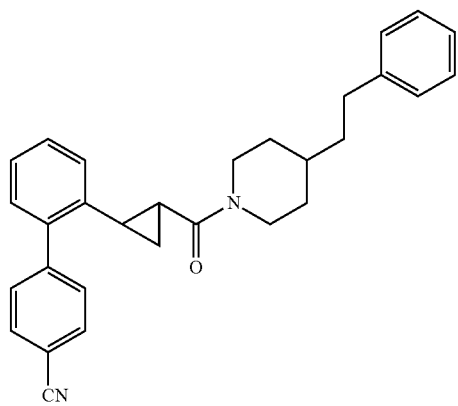 [SMILES: N#Cc1ccc(-c2ccccc2C2CC2C(=O)N2CCC(CCc3ccccc3)CC2)cc1] |
| 405 | 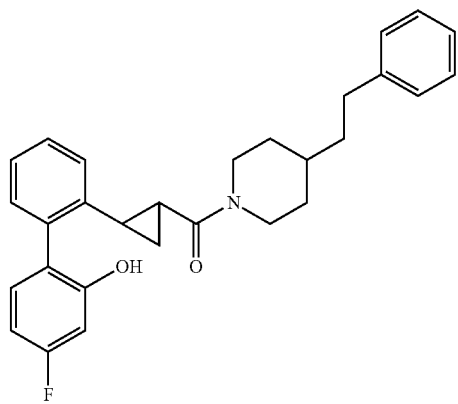 [SMILES: O=C(C1CC1c1ccccc1-c1ccc(F)cc1O)N1CCC(CCc2ccccc2)CC1] |

| Compound No. | Structure |
|---|---|
| 406 | 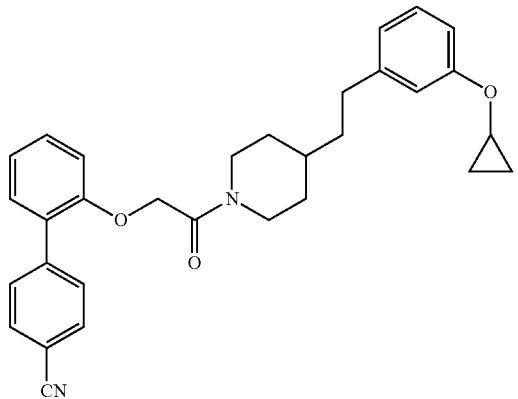 [SMILES: N#Cc1ccc(-c2ccccc2OCC(=O)N2CCC(CCc3cccc(OC4CC4)c3)CC2)cc1] |
| 407 | 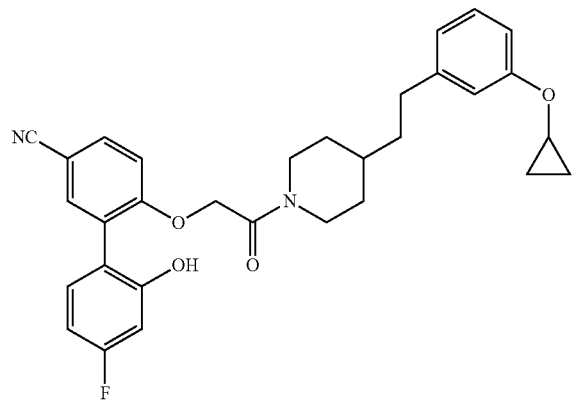 [SMILES: N#Cc1ccc(OCC(=O)N2CCC(CCc3cccc(OC4CC4)c3)CC2)c(-c2ccc(F)cc2O)c1] |
| 408 | 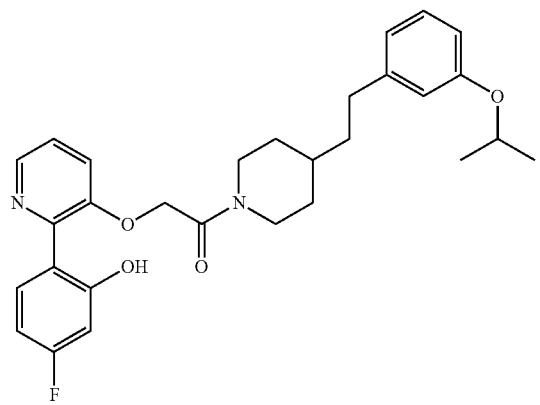 [SMILES: CC(C)Oc1cccc(CCC2CCN(C(=O)COc3cccnc3-c3ccc(F)cc3O)CC2)c1] |

-continued
| Compound No. | Structure |
|---|---|
| 409 | 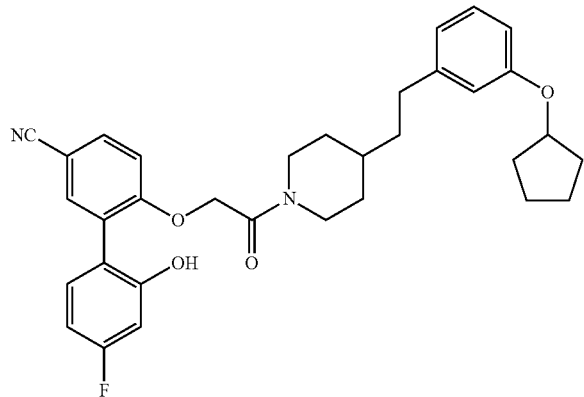 [SMILES: N#Cc1ccc(OCC(=O)N2CCC(CCc3cccc(OC4CCCC4)c3)CC2)c(-c2ccc(F)cc2O)c1] |
| 410 | 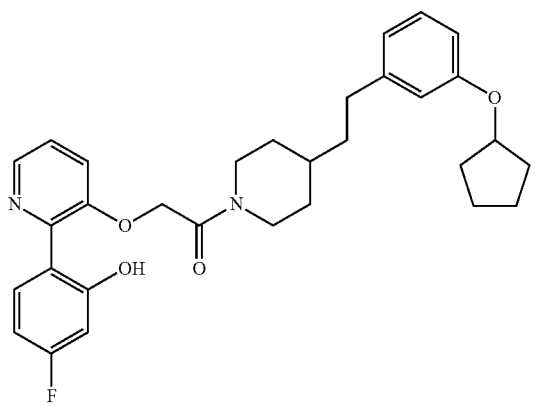 [SMILES: O=C(COc1cccnc1-c1ccc(F)cc1O)N1CCC(CCc2cccc(OC3CCCC3)c2)CC1] |
| 411 | 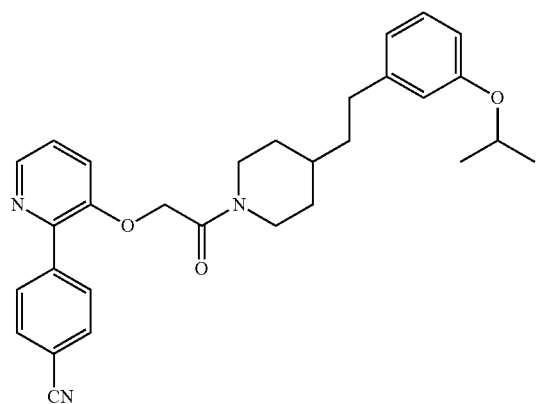 [SMILES: CC(C)Oc1cccc(CCC2CCN(C(=O)COc3cccnc3-c3ccc(C#N)cc3)CC2)c1] |

| Compound No. | Structure |
|---|---|
| 412 | 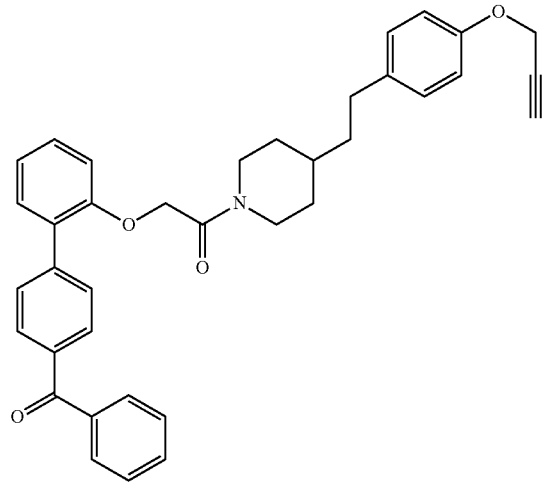 [SMILES: C#CCOc1ccc(CCC2CCN(C(=O)COc3ccccc3-c3ccc(C(=O)c4ccccc4)cc3)CC2)cc1] |
| 413 | 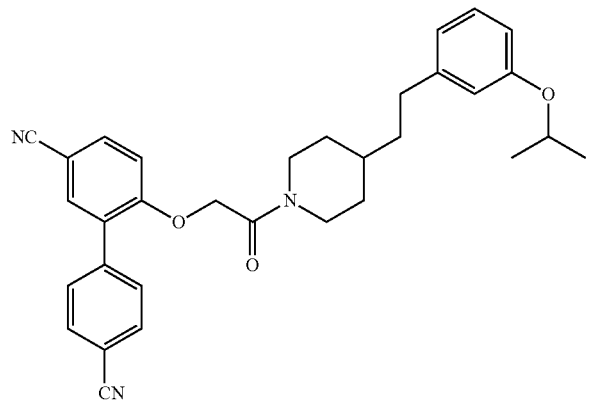 [SMILES: CC(C)Oc1cccc(CCC2CCN(C(=O)COc3ccc(C#N)cc3-c3ccc(C#N)cc3)CC2)c1] |
| 414 | 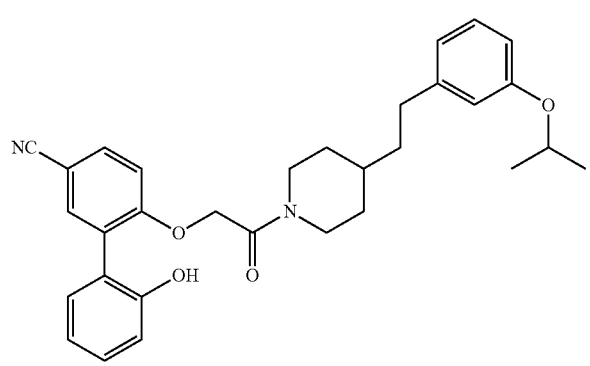 [SMILES: CC(C)Oc1cccc(CCC2CCN(C(=O)COc3ccc(C#N)cc3-c3ccccc3O)CC2)c1] |

| Compound No. | Structure |
|---|---|
| 415 | 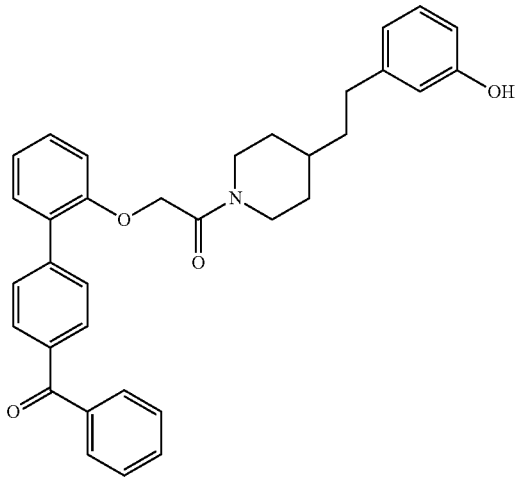 [SMILES: O=C(c1ccccc1)c1ccc(-c2ccccc2OCC(=O)N2CCC(CCc3cccc(O)c3)CC2)cc1] |
| 416 | 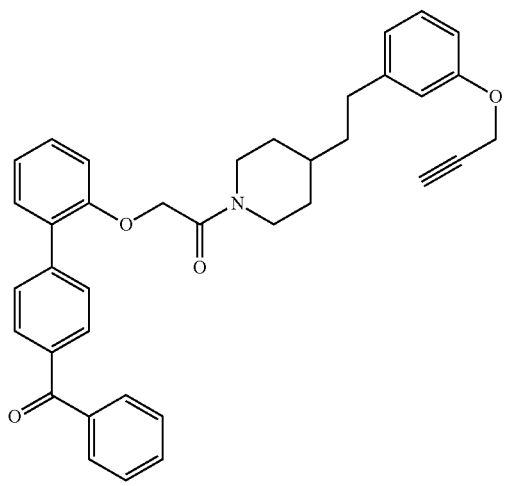 [SMILES: C#CCOc1cccc(CCC2CCN(C(=O)COc3ccccc3-c3ccc(C(=O)c4ccccc4)cc3)CC2)c1] |
| 417 | 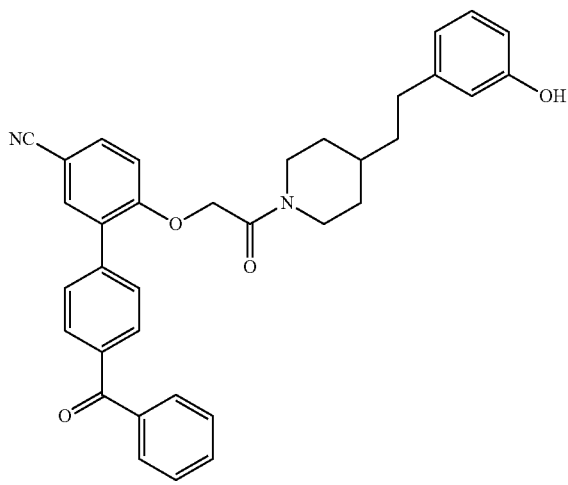 [SMILES: N#Cc1ccc(OCC(=O)N2CCC(CCc3cccc(O)c3)CC2)c(-c2ccc(C(=O)c3ccccc3)cc2)c1] |

-continued
| Compound No. | Structure |
|---|---|
| 418 | 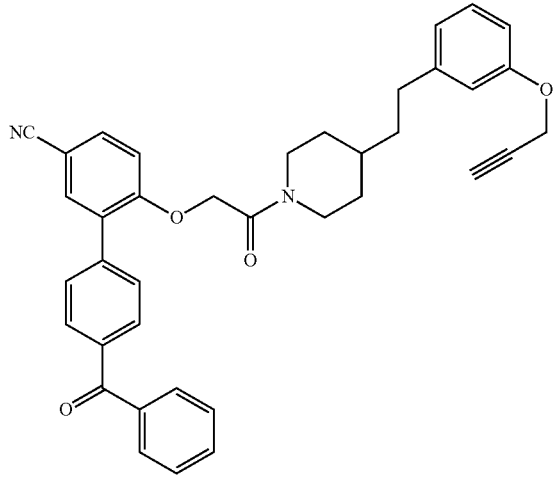 [SMILES: C#CCOc1cccc(CCC2CCN(C(=O)COc3ccc(C#N)cc3-c3ccc(C(=O)c4ccccc4)cc3)CC2)c1] |
| 419 | 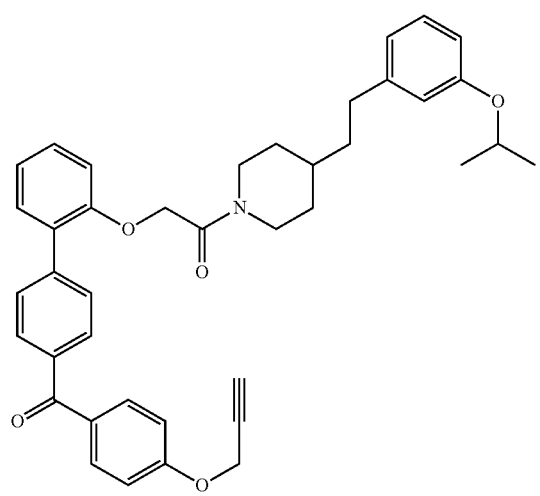 [SMILES: C#CCOc1ccc(C(=O)c2ccc(-c3ccccc3OCC(=O)N3CCC(CCc4cccc(OC(C)C)c4)CC3)cc2)cc1] |
| 420 | 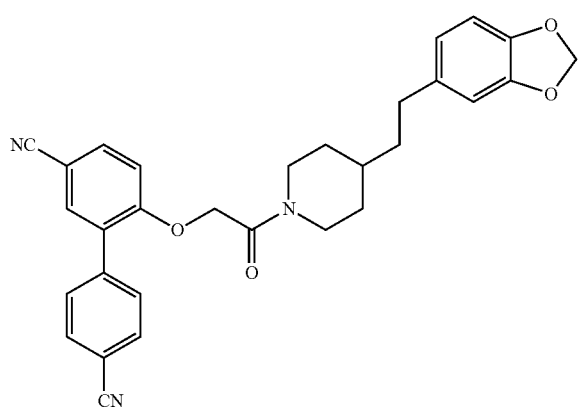 [SMILES: N#Cc1ccc(-c2cc(C#N)ccc2OCC(=O)N2CCC(CCc3ccc4c(c3)OCO4)CC2)cc1] |

| Compound No. | Structure |
|---|---|
| 421 | 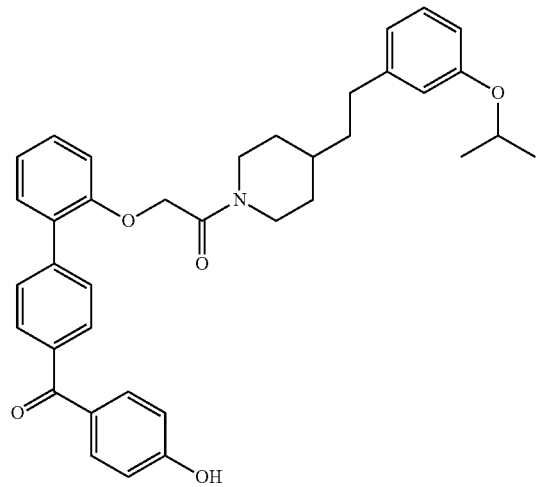 [SMILES: CC(C)Oc1cccc(CCC2CCN(C(=O)COc3ccccc3-c3ccc(C(=O)c4ccc(O)cc4)cc3)CC2)c1] |
| 422 | 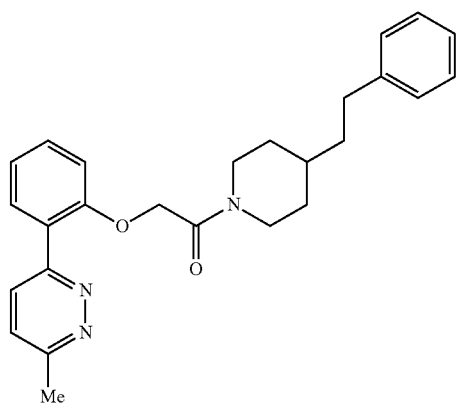 [SMILES: Cc1ccc(-c2ccccc2OCC(=O)N2CCC(CCc3ccccc3)CC2)nn1] |
| 423 | 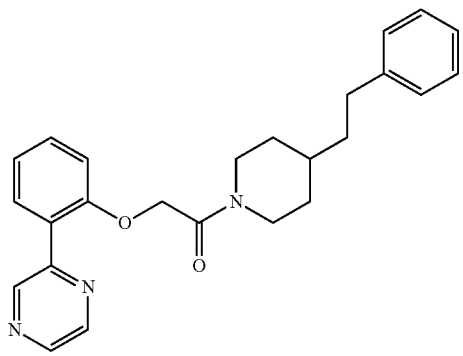 [SMILES: O=C(COc1ccccc1-c1cnccn1)N1CCC(CCc2ccccc2)CC1] |

| Compound No. | Structure |
|---|---|
| 424 | 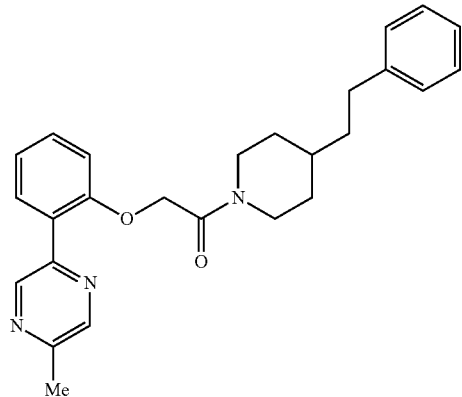 [SMILES: Cc1cnc(-c2ccccc2OCC(=O)N2CCC(CCc3ccccc3)CC2)cn1] |
| 425 | 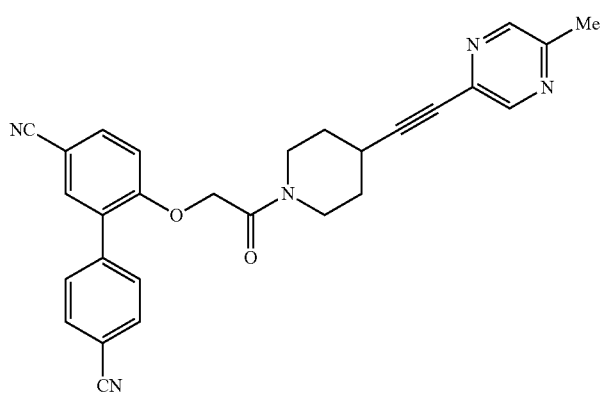 |
| 426 | 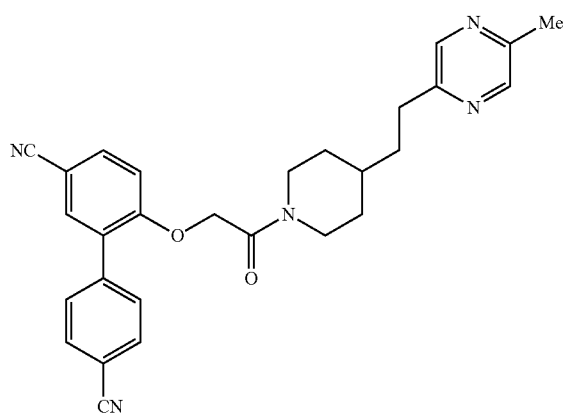 [SMILES: Cc1cnc(CCC2CCN(C(=O)COc3ccc(C#N)cc3-c3ccc(C#N)cc3)CC2)cn1] |

| Compound No. | Structure |
|---|---|
| 427 | 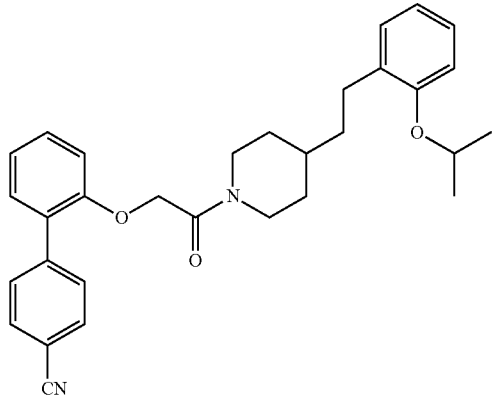 [SMILES: CC(C)Oc1ccccc1CCC1CCN(C(=O)COc2ccccc2-c2ccc(C#N)cc2)CC1] |
| 428 | 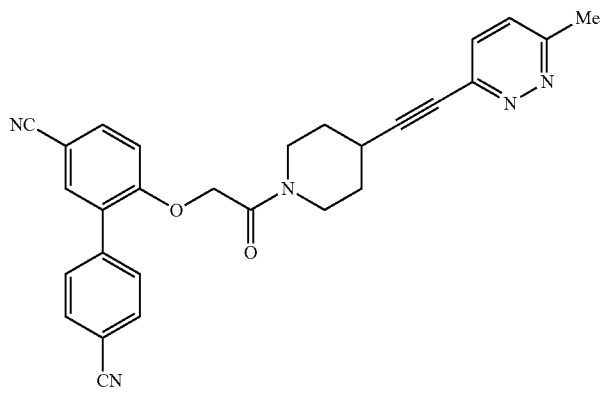 [SMILES: Cc1ccc(C#CC2CCN(C(=O)COc3ccc(C#N)cc3-c3ccc(C#N)cc3)CC2)nn1] |
| 429 | 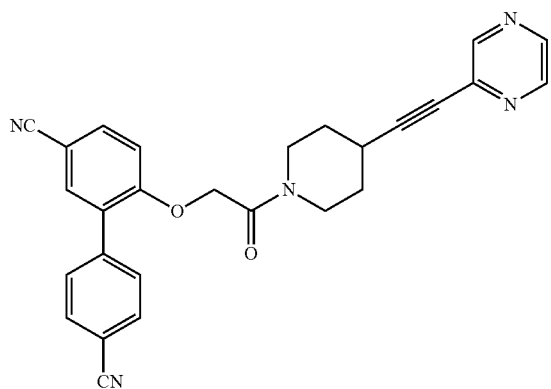 [SMILES: N#Cc1ccc(-c2cc(C#N)ccc2OCC(=O)N2CCC(C#Cc3cnccn3)CC2)cc1] |

| Compound No. | Structure |
|---|---|
| 430 | 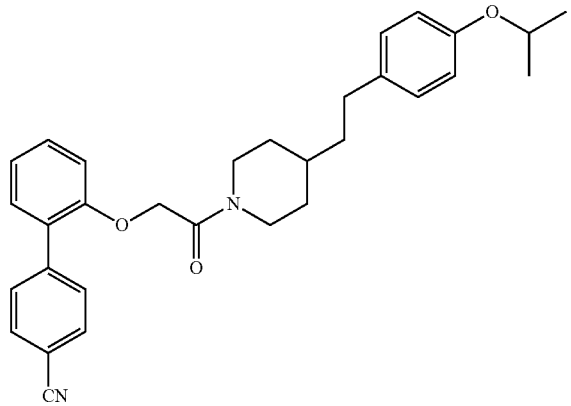 [SMILES: CC(C)Oc1ccc(CCC2CCN(C(=O)COc3ccccc3-c3ccc(C#N)cc3)CC2)cc1] |
| 431 | 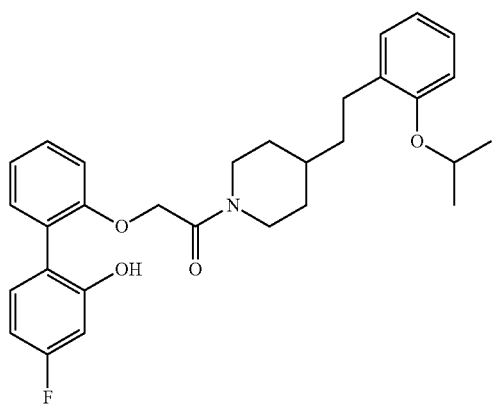 [SMILES: CC(C)Oc1ccccc1CCC1CCN(C(=O)COc2ccccc2-c2ccc(F)cc2O)CC1] |
| 432 | 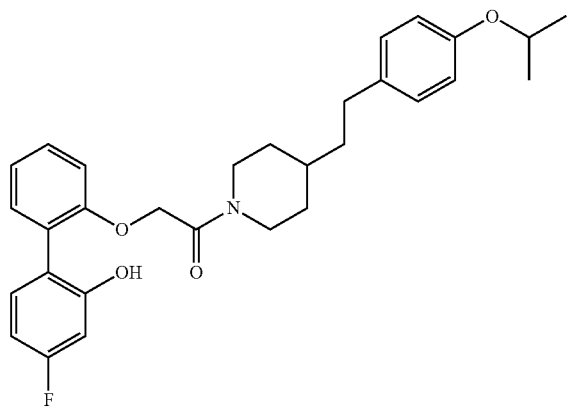 [SMILES: CC(C)Oc1ccc(CCC2CCN(C(=O)COc3ccccc3-c3ccc(F)cc3O)CC2)cc1] |

| Compound No. | Structure |
|---|---|
| 433 | 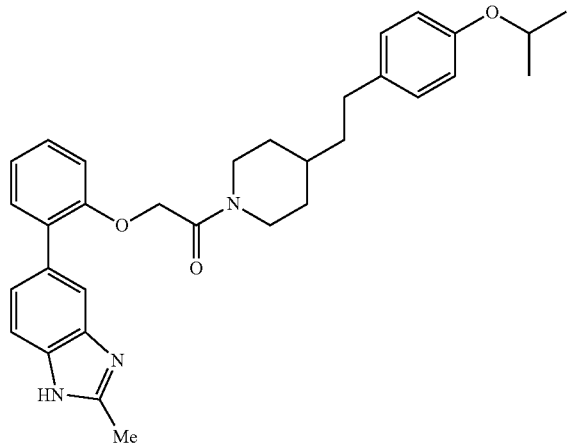 [SMILES: Cc1nc2cc(-c3ccccc3OCC(=O)N3CCC(CCc4ccc(OC(C)C)cc4)CC3)ccc2[nH]1] |
| 434 | 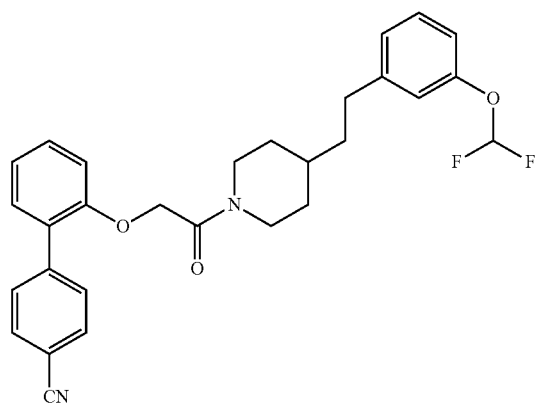 [SMILES: N#Cc1ccc(-c2ccccc2OCC(=O)N2CCC(CCc3cccc(OC(F)F)c3)CC2)cc1] |
| 435 | 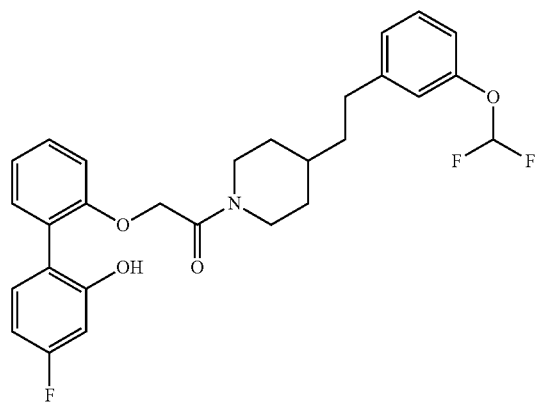 [SMILES: O=C(COc1ccccc1-c1ccc(F)cc1O)N1CCC(CCc2cccc(OC(F)F)c2)CC1] |

-continued
| Compound No. | Structure |
|---|---|
| 436 | 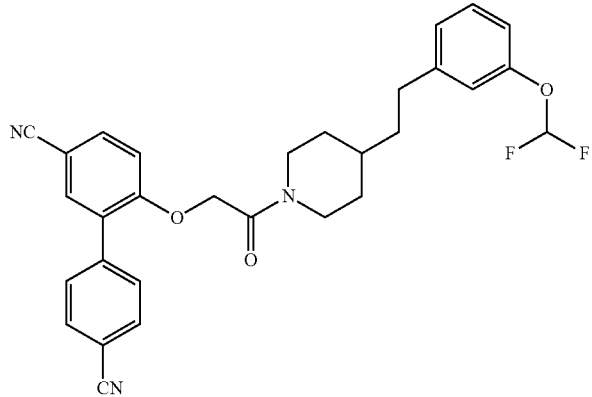 [SMILES: N#Cc1ccc(-c2cc(C#N)ccc2OCC(=O)N2CCC(CCc3cccc(OC(F)F)c3)CC2)cc1] |
| 437 | 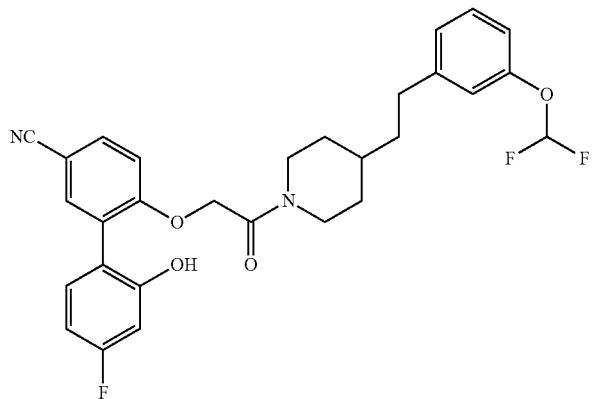 [SMILES: N#Cc1ccc(OCC(=O)N2CCC(CCc3cccc(OC(F)F)c3)CC2)c(-c2ccc(F)cc2O)c1] |
| 438 | 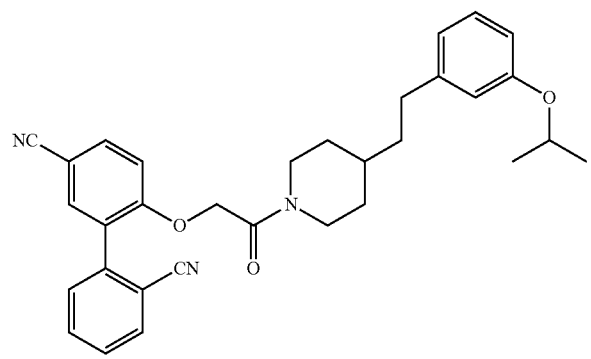 [SMILES: CC(C)Oc1cccc(CCC2CCN(C(=O)COc3ccc(C#N)cc3-c3ccccc3C#N)CC2)c1] |

| Compound No. | Structure |
|---|---|
| 439 | 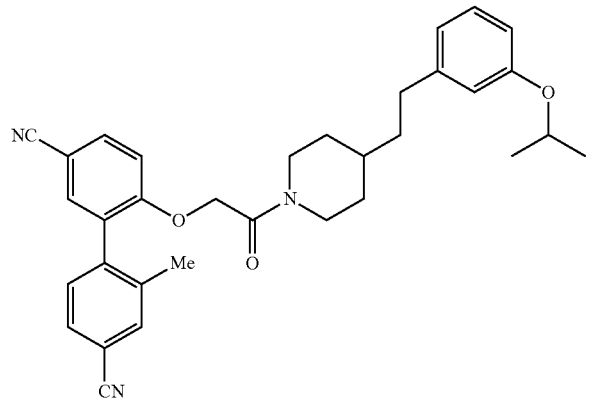 [SMILES: Cc1cc(C#N)ccc1-c1cc(C#N)ccc1OCC(=O)N1CCC(CCc2cccc(OC(C)C)c2)CC1] |
| 440 | 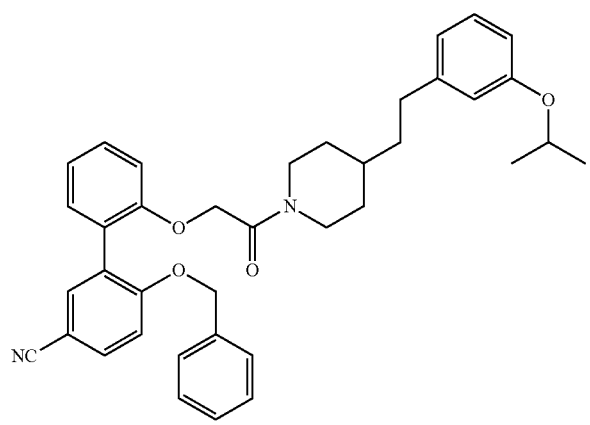 [SMILES: CC(C)Oc1cccc(CCC2CCN(C(=O)COc3ccccc3-c3cc(C#N)ccc3OCc3ccccc3)CC2)c1] |
| 441 | 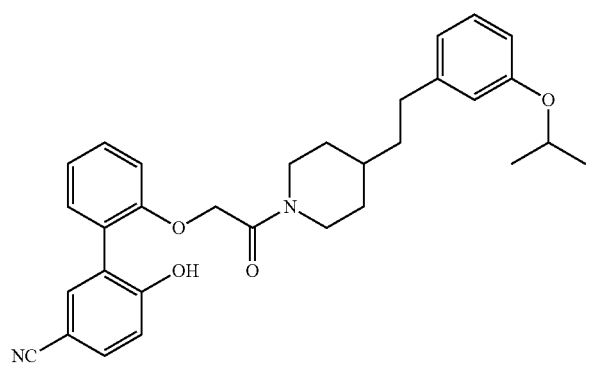 [SMILES: CC(C)Oc1cccc(CCC2CCN(C(=O)COc3ccccc3-c3cc(C#N)ccc3O)CC2)c1] |

| Compound No. | Structure |
|---|---|
| 442 | 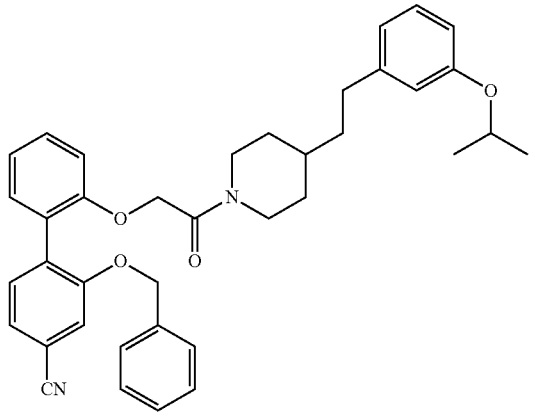 [SMILES: CC(C)Oc1cccc(CCC2CCN(C(=O)COc3ccccc3-c3ccc(C#N)cc3OCc3ccccc3)CC2)c1] |
| 443 | 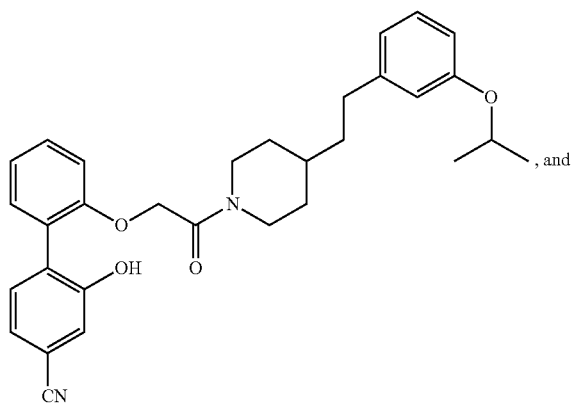 [SMILES: CC(C)Oc1cccc(CCC2CCN(C(=O)COc3ccccc3-c3ccc(C#N)cc3O)CC2)c1], and |
| 444 | 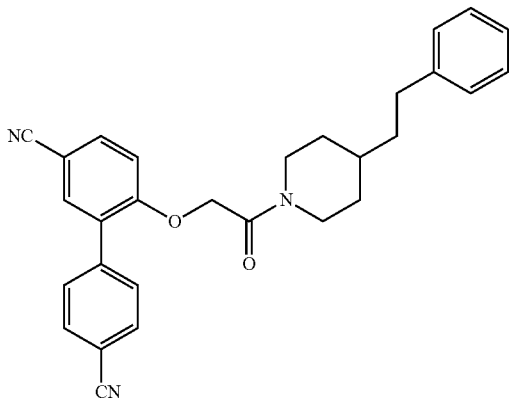 [SMILES: N#Cc1ccc(-c2cc(C#N)ccc2OCC(=O)N2CCC(CCc3ccccc3)CC2)cc1] | or a pharmaceutically acceptable salt thereof.

15. The method of claim 1, wherein the immune disorder is selected from rheumatoid arthritis, inflammatory bowel disease, and multiple sclerosis.

16. The method of claim 15, wherein the immune disorder is rheumatoid arthritis.

17. The method of claim 15, wherein the immune disorder is inflammatory bowel disease.

18. The method of claim 15, wherein the immune disorder is multiple sclerosis.

19. The method of claim 14, wherein the immune disorder is selected from rheumatoid arthritis, inflammatory bowel disease, and multiple sclerosis.

20. The method of claim 19, wherein the immune disorder is rheumatoid arthritis.

21. The method of claim 19, wherein the immune disorder is inflammatory bowel disease.

22. The method of claim 19, wherein the immune disorder is multiple sclerosis.

* * * * *

UNITED STATES PATENT AND TRADEMARK OFFICE
CERTIFICATE OF CORRECTION

PATENT NO. : 10,899,747 B2
APPLICATION NO. : 16/567300
DATED : January 26, 2021
INVENTOR(S) : Michael P. Smolinski et al.

It is certified that error appears in the above-identified patent and that said Letters Patent is hereby corrected as shown below:

On the Title Page

Second Column, (56) References Cited, Other Publications, Line number 24-27:
"Partiseti et al. "The Calcium Current Activated by T Cell Receptor and Store Depiction in Human Lymphocytes Is Absent in a Primary Immunodeficiency", The Journal of Biological Chemistry, vol. 269, No. 51, p. 32327-32335, 1994."

Should read:
-- Partiseti et al. "The Calcium Current Activated by T Cell Receptor and Store Depletion in Human Lymphocytes Is Absent in a Primary Immunodeficiency", The Journal of Biological Chemistry, vol. 269, No. 51, p. 32327-32335, 1994. --

In the Claims

At Column 279, Claim number 14, Compound No. 132:

" 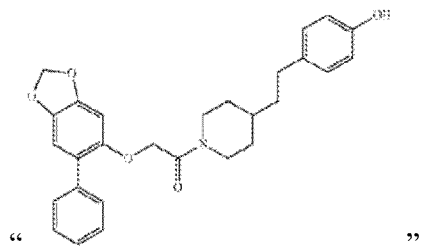 "

Signed and Sealed this
Thirteenth Day of July, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,899,747 B2

Should read:

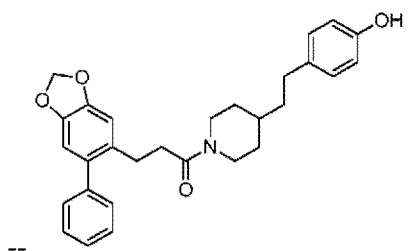

--  --

At Column 415, Claim number 14, Compound No. 357:

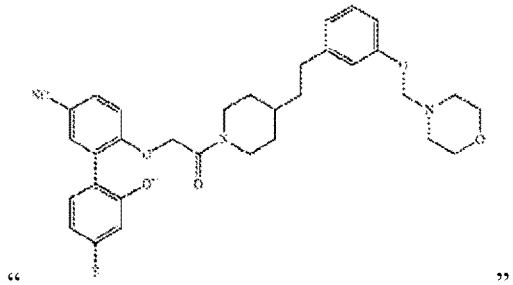

"  "

Should read:

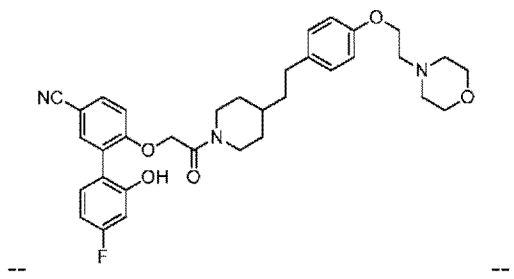

--  --

At Column 429, Claim number 14, Compound No. 377:

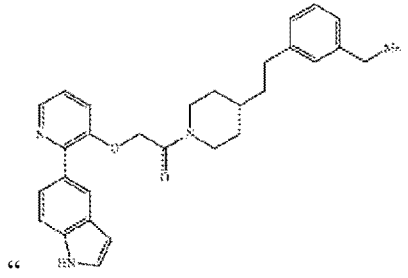

"  "